United States Patent
Filonov et al.

(10) Patent No.: US 12,338,484 B2
(45) Date of Patent: Jun. 24, 2025

(54) FRET BIOSENSOR FOR DETECTING AND REPORTING NAD+/NADH RATIO CHANGES

(71) Applicant: Sartorius BioAnalytical Instruments, Inc., Bohemia, NY (US)

(72) Inventors: Grigory Filonov, Ann Arbor, MI (US); Cicely Schramm, Ann Arbor, MI (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 0 days.

(21) Appl. No.: 17/812,030

(22) Filed: Jul. 12, 2022

(65) Prior Publication Data
US 2024/0026420 A1 Jan. 25, 2024

(51) Int. Cl.
*C12Q 1/48* (2006.01)
*G01N 33/542* (2006.01)

(52) U.S. Cl.
CPC .......... *C12Q 1/485* (2013.01); *G01N 33/542* (2013.01)

(58) Field of Classification Search
CPC ............... C07K 2319/00; C07K 14/00; G01N 33/57496; G01N 2021/6439; G01N 33/5005; C12Q 2563/107; C12Q 1/008; C12Q 1/6818; C12N 15/63; C40B 30/04
See application file for complete search history.

(56) References Cited

U.S. PATENT DOCUMENTS

| | | | |
|---|---|---|---|
| 9,606,121 | B2 | 3/2017 | Yang et al. |
| 9,945,860 | B2 | 4/2018 | Yang et al. |
| 2017/0198307 | A1 | 7/2017 | Marsischky et al. |
| 2018/0087083 | A1 | 3/2018 | Sallin et al. |
| 2021/0239615 | A1 | 8/2021 | Racowsky et al. |

FOREIGN PATENT DOCUMENTS

WO    WO 2021/081404    *  4/2021    ........... A61B 5/1455

OTHER PUBLICATIONS

Jing et al. Acc Chem Res. Sep. 20, 2011; 44(9): 784-792. (Year: 2011).*
Merriam-Webster, "Homodimer", Merriam Webster Dictionary, available online at https://www.merriam-webster.com/medical/homodimer, 2 pages (accessed on Oct. 24, 2023) at p. 1. (Year: 2023).*
Uniprot, "Redox-sensing transcriptional repressor Rex", UniProt, available online at https://www.uniprot.org/uniprotkb/Q9X2V5/entry, 7 pages (accessed on Oct. 24, 2023) at p. 1. (Year: 2023).*
Sickmier et al. Structure, vol. 13, (2005), 43-54 (Year: 2005).*
European Bioinformatics Institute, "Domain", EMBL—European Bioinformatics Institute, available online at https://www.ebi.ac.uk/training/online/courses/protein-classification-intro-ebi-resources/protein-classification/what-are-protein-domains/, 5 pages (accessed on Oct. 31, 2023) at p. 2. (Year: 2023).*
Miller et al., BioTechniques, vol. 26, (1999), 914-921 (Year: 1999).*
Bajar et al., Sensors, vol. 16, (2016), 1-26 (Year: 2016).*
Zapata-Hommer et al., BMC Biotechnology, vol. 3, (2003), 1-6 (Year: 2003).*
McLaughlin et al., Molecular Cell, vol. 38., (2010), 563-575 (Year: 2010).*
WO20211081404A1, Sequence Listing, (Year: 2021).*
Piatkevich et al., Methods Cell Biol. 2011; 102, pp. 431-461 (Year: 2011).*
UnitProt_Redox_Transcriptional_Represor, pp. 1-6 (Year: 2024).*
Hung et al., Cell Metabolism, vol. 14, (2011), 545-554. (Year: 2011)*
Supplemental Information, Cell Metabolism, vol. 14, (2011), 1-12. (Year: 2011)*
Bilan, et al., "Genetically encoded fluorescent indicator for imaging NAD+/NADH ratio changes in different cellular compartments." Biochim Biophys Acta. 1840(3): 951-957 (Mar. 2014).
Hung, et al., "Live cell imaging of cytosolic NADH-NAD+ redox state using a genetically encoded fluorescent biosensor." Methods Mol Biol. 1071: 83-95 (2014).
Zhao, et al., "SoNar, a Highly Responsive NAD+/NADH Sensor, Allows High-Throughput Metabolic Screening of Anti-tumor Agents." Cell Metabolism 21, 777-789 (May 2015).
Zhao, et al., "Genetically Encoded Fluorescent Sensors for Intracellular NADH Detection." Cell Metabolism 14, 555-566 (Oct. 2011).
Dey et al. "Repurposing an adenine riboswitch into a fluorogenic imaging and sensing tag". Nature Chemical Biology 18(2): 180-190, (2022).
International Search Report and Written Opinion of International Application No. PCT/US2023/069854, mailed Jan. 9, 2024.

\* cited by examiner

*Primary Examiner* — Lianko G Garyu
*Assistant Examiner* — Claudia Espinosa
(74) *Attorney, Agent, or Firm* — McDonnell Boehnen Hulbert & Berghoff

(57) ABSTRACT

FRET-based fusion protein biosensors and methods for their use in measuring an NAD+/NADH ratio change in live cells are provided.

15 Claims, 7 Drawing Sheets
Specification includes a Sequence Listing.

FRET BIOSENSOR FOR DETECTING AND REPORTING NAD+/NADH RATIO CHANGES

SEQUENCE LISTING STATEMENT

A computer readable form of the Sequence Listing is filed with this application by electronic submission and is incorporated into this application by reference in its entirety. The Sequence Listing is contained in the file created on Jul. 28, 2022 having the file name "22-0505-WO-SeqList.xml" and is 381 kb in size.

BACKGROUND

Nicotinamide adenine dinucleotide NAD(H) is a key cofactor for electron transfer in metabolism. Reactions utilizing NAD(H) as a cofactor are extremely important for glycolysis and mitochondrial metabolism and thus for cellular survival and normal functioning.

NAD(H) exists in two forms: oxidized NAD+ and reduced NADH. The ratio of free concentrations of oxidized and reduced forms of NAD(H) (NAD+/NADH) is an important indicator and regulator of cellular reduction-oxidation (redox) state. NAD+/NADH ratio has been reported to regulate embryonic development, gene expression, aging, and cell death. Additionally, NAD+/NADH ratio and thus cellular redox state has been implicated in development of a number of pathological conditions, such as cancer and diabetes.

Standard methods of assessing NAD+/NADH ratio changes in cells are end point assays which require cell lysis and often involve time-consuming sample preparation and/or assay workflows.

SUMMARY

In a first aspect, the disclosure provides fusion proteins, comprising the genus X1-B1-X2-B2-X3-B3-X4, wherein:
X1 comprises the amino acid sequence of a first Rex protein domain (RexA),
one of X2 and X4 comprises a fluorescence resonance energy transfer (FRET) acceptor polypeptide having an acceptor excitation wavelength and FRET emission wavelength, and the other of X2 and X4 comprises a FRET donor polypeptide having a donor excitation wavelength and a donor emission wavelength;
X3 comprises the amino acid sequence of a second Rex protein domain (RexB),
B1, B2, and B3 are independently absent or comprise an amino acid linker;
wherein the X1 and X3 domains are capable of forming a homodimer that can bind to either NADH or NAD+ and changing conformation of the fusion protein and causing interaction of the FRET acceptor polypeptide and the FRET donor polypeptide.

In one embodiment, X1 comprises an amino acid sequence at least 75%, 80%, 85%, 90%, 91%, 92%, 93%, 94%, 95%, 96%, 97%, 98%, 99%, or 100% to the amino acid sequence of SEQ ID NO:1 (RexA), wherein residues in parentheses are optional and may be present or absent

```
                                               (SEQ ID NO: 1)
(M)KVPEAAISRLITYLRILEELEAQGVHRTASEQLGELAQVTAFQVDK

DLSYFGSYGTDGVGYTVPVLKRELRHILGLNRKWGLCIVGMGRLGSALA
```

```
-continued
DWPGFGESFELRGFFDVDPGMVGRPVRGGVIEHVDLLPQRVPGRIEIAL

LTVPREAAQKAADLLVAAGIKGILNFAPVVLEVPKEVAVENVDILAGLT

RLSFAILNP;  and
```

X3 comprises an amino acid sequence at least 75%, 80%, 85%, 90%, 91%, 92%, 93%, 94%, 95%, 96%, 97%, 98%, 99%, or 100% to the amino acid sequence of SEQ ID NO:2 (RexB).

In another embodiment, the FRET acceptor polypeptide comprises an amino acid sequence at least 90%, 91%, 92%, 93%, 94% 95%, 96%, 97%, 98%, 99%, or 100% identical to the amino acid sequence of one or more of SEQ ID NOS: 3-5, and identical at the CYG chromophore. In a further embodiment, the FRET donor polypeptide comprises an amino acid sequence at least 85%, 87%, 90%, 91%, 92%, 93%, 94% 95%, 96%, 97%, 98%, 99%, or 100% identical to the amino acid sequence of SEQ ID NO: 6, 7, or 155, and identical at the TYG chromophore.

In one embodiment, the fusion protein comprises the genus X1-B1-X2-B2-X3-B3-X4, wherein:
one of X2 and X4 comprises an amino acid sequence at least 90%, 91%, 92%, 93%, 94% 95%, 96%, 97%, 98%, 99%, or 100% identical to the amino acid sequence of SEQ ID NO:6 or 7; and
the other of X2 and X4 comprises an amino acid sequence at least 90%, 91%, 92%, 93%, 94% 95%, 96%, 97%, 98%, 99%, or 100% identical to the amino acid sequence of SEQ ID NO:3, 4, or 5.

In one embodiment, X1 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:8 or 9 (RexA), wherein residues in parentheses are optional and may be present or absent

```
                                               (SEQ ID NO: 8)
(M)KVPEAAISRLITYLRILEELEAQGVHRTASEQLGELAQVTAFQVDK

DLSYFGSYGTDGVGYTVPVLKRELRHILGLNRKWGLCIVGMGRLGSALA

DWPGFGESFELRGFFDVDPGMVGRPVRGGVIEHVDLLPQRVPGRIEIAL

LTVPREAAQKAADLLVAAGIKGILNFAPVVLEVPKEVAVENVDILAGLT

RLSFAILNPT;
or
                                               (SEQ ID NO: 9)
(M)KVPEAAISRLITYLRILEELEAQGVHRTASEQLGELAQVTAFQVDK

DLSYFGSYGTDGVGYTVPVLKRELRHILGLNRKWGLCIVGMGRLGSALA

DWPGFGESFELRGFFDVDPGMVGRPVRGGVIEHVDLLPQRVPGRIEIAL

LTVPREAAQKAADLLVAAGIKGILNFAPVVLEVPKEVAVENVDILAGLT

RLSFAILNPTW
```

In another embodiment, X2 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:10.

In one embodiment, X3 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:11. In another embodiment, X4 comprises an amino acid sequence at least 90%, 91%, 92%, 93%, 94% 95%, 96%, 97%, 98%, 99%, or 100% identical to the amino acid sequence of SEQ ID NO:12.

In another embodiment, the fusion protein comprises the genus X1-B1-X2-B2-X3-B3-X4-X5, wherein X5 comprises the amino acid sequence MDELYK (SEQ ID NO: 156), EASMDELYK, (SEQ ID NO: 157)
or-

EASTSAWSHPQFEKGGGSGGGSGGSAWSHPQFEK. (SEQ ID NO: 158)

In various embodiments, the fusion protein comprises an amino acid sequence at least 90%, 91%, 92%, 93%, 94% 95%, 96%, 97%, 98%, 99%, or 100% identical to the amino acid sequence selected from the group consisting of SEQ ID NO:13-93, 95-154, and 191-193.

In a second aspect, the disclosure provides control fusion protein comprising the fusion protein of any embodiment of the first aspect, with the proviso that X1 and X3 comprises a mutation to confer non-responsiveness to changes in the ratio of NAD+/NADH. In one embodiment, the mutation comprises
(a) a G89A mutation in X1 relative to SEQ ID NO:1 residue numbering, and
(b) a G84A mutation in X3 relative to SEQ ID NO:2 residue numbering.

In another embodiment, the control fusion protein comprises the amino acid sequence selected from the group consisting of SEQ ID NO: 13-93, 95-154, and 191-193, but having a G89A mutation.

In other aspects, the disclosure provides a polynucleotide encoding the fusion protein or control fusion protein, expression vectors encoding the polynucleotide operatively linked to a promoter sequence capable of directing expression of the polynucleotide, host cells comprising the fusion protein, control fusion protein, polynucleotide, and/or expression vector, and kits comprising various combinations of the fusion proteins, control fusion proteins, polynucleotides, expression vectors, and host cells of the disclosure.

In a further aspect, the disclosure provides methods for determining an NAD+/NADH ratio change in a cell of interest, comprising of expressing a FRET biosensor in a cell that undergoes a detectable change upon binding of the FRET biosensor to NAD(H) in the cell, and performing live cell imaging to determine the ratio of NAD+/NADH inside living cells.

Proteins were expressed, purified, and treated with the mixture of NAD+ and NADH similarly as in the description above. To plot FRET ratios, the proteins were excited at 460 nm and emissions at 510 nm and 560 nm were collected. The FRET ratio was calculated as emission at 560 nm divided by emission at 510 nm, and the values were normalized to the FRET ratio value at the highest NAD+/NADH ratio. Normalized FRET ratio was measured for each protein at different NAD+/NADH ratios, ranging from 1 to 10,000. For each NAD+/NADH ratio final NAD+ concentration was kept constant at 80 uM and NADH concentration was varied.

Figure 4:
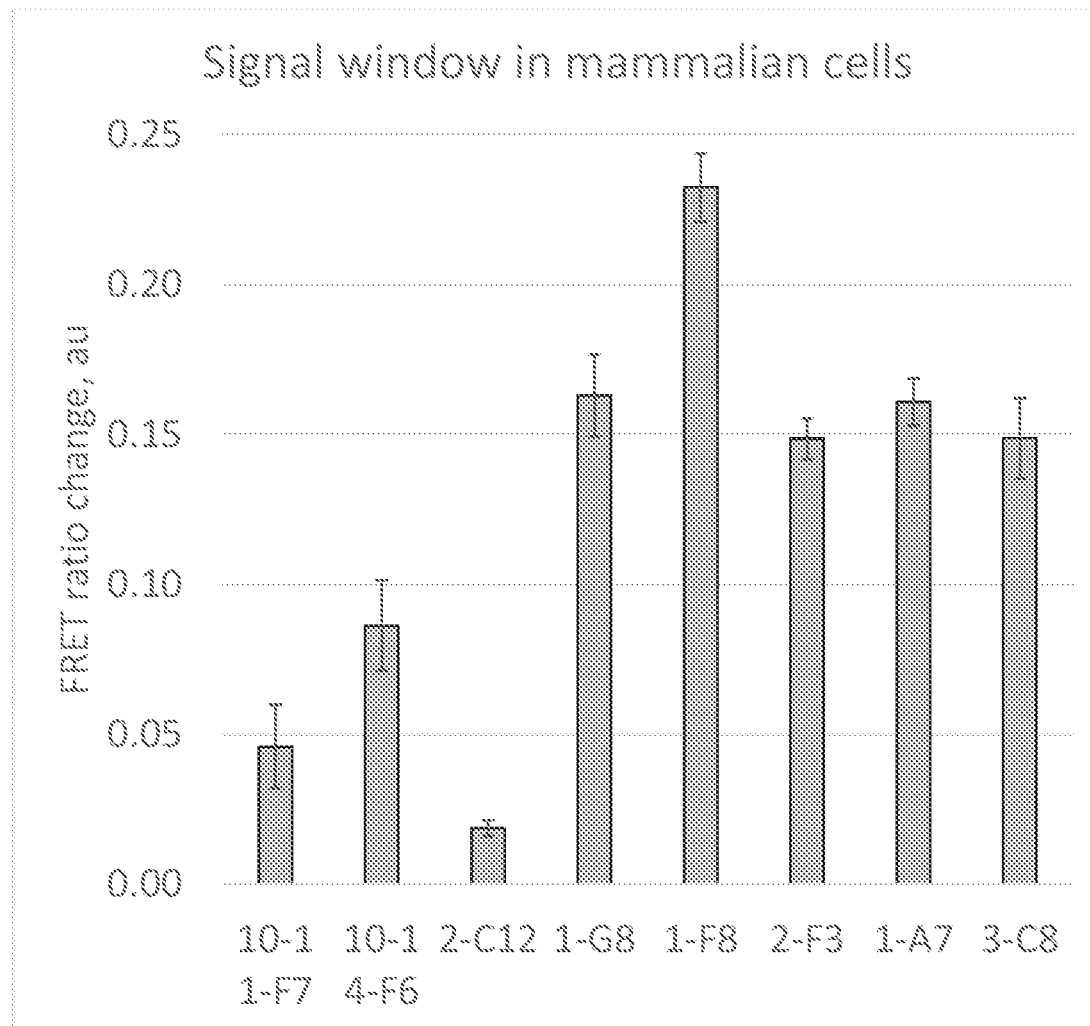

FIG. 4. Determining signal window in mammalian cells.

Proteins were expressed in HEK 293 mammalian cells following transient transfection with the plasmids encoding those proteins. Transfected cells were imaged using an Incucyte® SX5 equipped with a Metabolism Optical Module (Sartorius) and the data was processed using the built-in ATP analysis software module that allows quantification of average FRET ratio in all biosensor-expressing cells in the image. To measure signal window, cells were treated with either 10 mM lactate or 20 mM pyruvate. The former drives the NAD+/NADH ratio, and thus FRET signal down, and the latter drives the NAD+/NADH ratio, and thus FRET signal up. The difference between highest and lowest FRET ratios is the signal window in mammalian cells.

Figure 5:
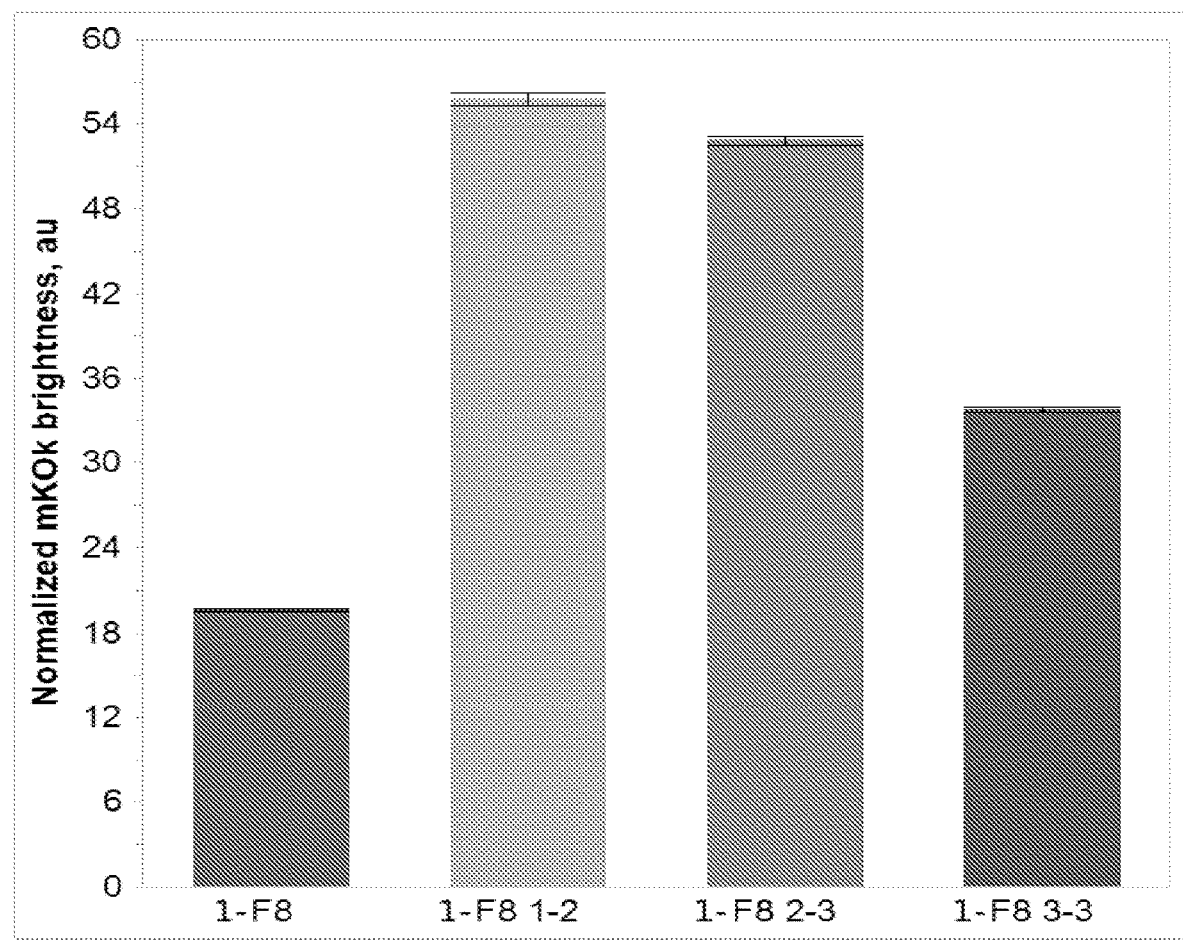

FIG. 5. Restoring the brightness of mKOk in clone 1-F8 in mammalian cells. HEK293 cells were transfected with the plasmids encoding the respective constructs. Following protein expression, cells were imaged using Incucyte® SX5 using orange and near-infrared imaging channels. The former channel was used to collect the signal from mKOk while the latter was used to collect emission from a near-infrared protein which came from another plasmid that was co-transfected into the same cells. This near-infrared protein's emission was used for the biosensor protein (mKOk) expression normalization purposes. Construct 1-F8 1-2 shows restoration of the mKOk brightness to the level expected for normally functioning mKOk.

Figure 6:
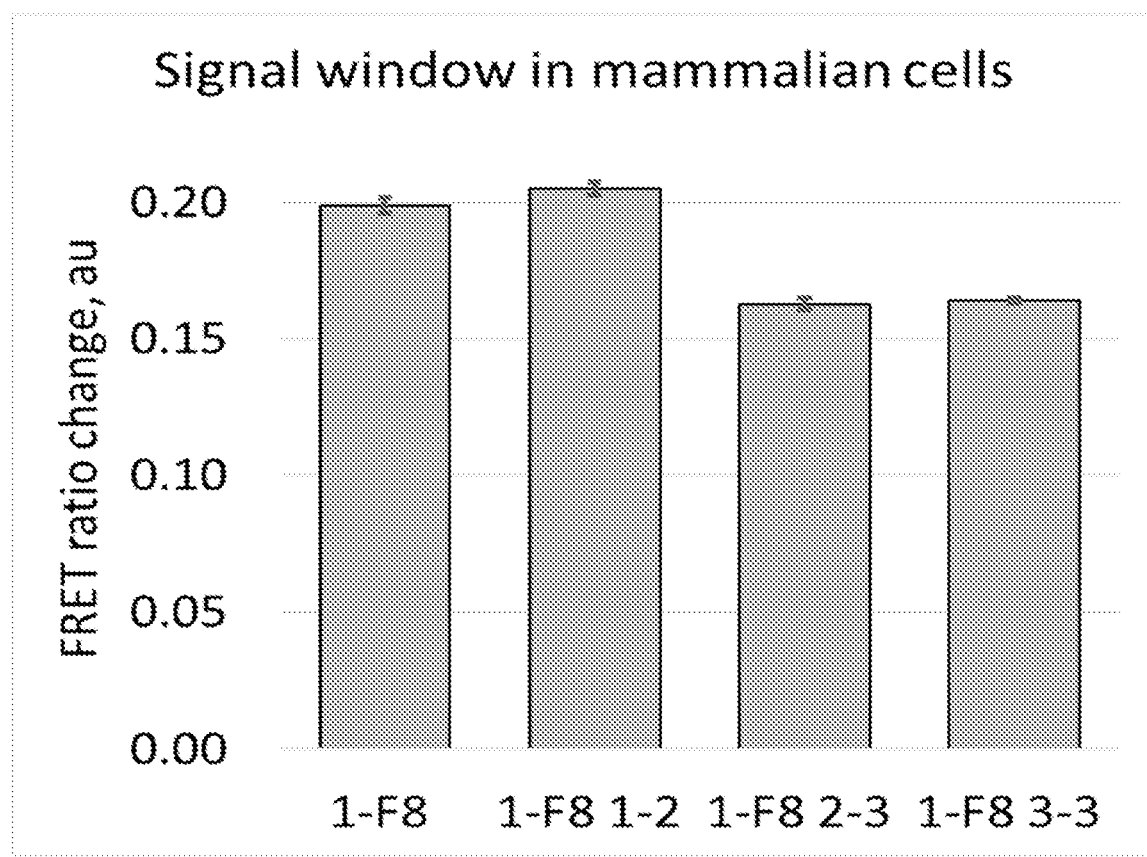

FIG. 6. Signal window of 1-F8 1-2 construct remained unchanged in mammalian cells compared to signal window of 1-F8. HEK293 cells were transfected with the plasmids encoding the respective constructs. Following protein expression, cells were treated with either mM lactate or 20 mM pyruvate and then imaged using an Incucyte® SX5 equipped with a Metabolism Optical Module (Sartorius). The data was processed using the built-in ATP analysis software module that allows quantification of average FRET ratio in all cells in the image. The difference between highest and lowest FRET ratios is the signal window in mammalian cells.

DETAILED DESCRIPTION

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; and Herdewijn, P. (Ed.), Oligonucleotide Synthesis: Methods and Applications, Methods in Molecular Biology, Humana Press, 2004.

The singular terms "a," "an," and "the" are not intended to be limiting and include plural referents unless explicitly stated otherwise or the context clearly indicates otherwise.

All embodiments disclosed herein can be combined unless the context clearly indicates otherwise.

In a first aspect, the disclosure provides fusion proteins, comprising the genus X1-B1-X2-B2-X3-B3-X4, wherein:
X1 comprises the amino acid sequence of a first Rex protein domain (RexA),
one of X2 and X4 comprises a fluorescence resonance energy transfer (FRET) acceptor polypeptide having an acceptor excitation wavelength and FRET emission wavelength, and the other of X2 and X4 comprises a FRET donor polypeptide having a donor excitation wavelength and a donor emission wavelength;
X3 comprises the amino acid sequence of a second Rex protein domain (RexB),
B1, B2, and B3 are independently absent or comprise an amino acid linker;
wherein the X1 and X3 domains are capable of forming a homodimer that can bind to either NADH or NAD+ and changing conformation of the fusion protein and causing interaction of the FRET acceptor polypeptide and the FRET donor polypeptide.

The fusion protein comprises two truncated subunits of Rex protein that are capable of forming a homodimer that can bind to either NADH or NAD+ and changing conformation of the fusion protein and causing interaction of the FRET acceptor polypeptide and the FRET donor polypeptide. The fusion proteins of this first aspect can be used, for example, to detect and measure NADH/NAD+ ratios in living cells, as detailed in the examples that follow.

In various embodiments, the first and second Rex protein domains may comprise truncated subunits of Rex proteins from *Thermus aquaticus* (NCBI GenBank AF061257.1), *Streptomyces coelicolor* (GenBank AL9391.1) or *Bacillus subtilis* (GenBank AL009126.1). In one embodiment, the first and second Rex protein domains may comprise truncated subunits of Rex proteins from *Thermus aquaticus* (T-Rex).

In some embodiments:
X1 comprises an amino acid sequence at least 75%, 80%, 85%, 90%, 91%, 92%, 93%, 94%, 95%, 96%, 97%, 98%, 99%, or 100% to the amino acid sequence of SEQ ID NO:1 (RexA), wherein residues in parentheses are optional and may be present or absent (M) KVPEAAISRLITYLRILEELEAQGVHRTASE-QLGELAQVTAFQVDKDLSYEGSY-GIDGVGYTVPVLKRELRHIL GLNRKWGL-CIVGMGRLGSALADWPGFGESFELRGFEDVDP GMVGRPVRGGVIEHVDLLPQRVPGRIE-IALLTVPREA AQKAADLLVAAGIKGILN-FAPVVLEVPKEVAVENVDILAGLTRLSFAILNP (SEQ ID NO: 1); and X3 comprises an amino acid sequence at least 75%, 80%, 85%, 90%, 91%, 92%, 93%, 94%, 95%, 96%, 97%, 98%, 99%, or 100% to the amino acid sequence of SEQ ID NO:2 (RexB)

(SEQ ID NO: 2)
AAISRLITYLRILEELEAQGVHRTASEQLGELAQVTAFQVDEDLSYFGS

YGTDGVGYTVPVLKRELRHILGLNRKWGLCIVGM<u>G</u>RLGSALADWPGFGE

SFELRGFFDVDPGMVGRPVRGGVIEHVDLLPQRVPGRIEIALLTVPREA

AQKAADLLVAAGIKGILNFAPVVLEVPKEVAVENVDFLAGLTRLSFAIL

NPKWRE.

FRET is non-radiative transfer of energy from an excited donor fluorophore to a suitable acceptor fluorophore in proximity to the donor. For selection of FRET fluorophore donor/acceptor polypeptide pairs for use in the fusion proteins of the disclosure, the absorption and emission wavelengths of each are considered. Based on the teachings herein, one of skill in the art can readily determine which of various fluorophores are to be used as FRET donor/acceptor polypeptide pairs in a particular application.

Any suitable polypeptide fluorophores may be used, including but not limited to, mKOk, mKO, mKO2, and truncations thereof and its derivatives; any of green fluorescent protein and derivatives such as BFP, EBFP, EBFP2, ECFP, RFP, and YFP; and other polypeptide fluorophores.

In one embodiment, X2 comprises a FRET acceptor polypeptide and X4 comprises a FRET donor polypeptide. In another embodiment, X2 comprises a FRET donor polypeptide and X4 comprises a FRET acceptor polypeptide.

In one embodiment, the FRET acceptor polypeptide has a maximal acceptor excitation wavelength in a range of 420 and 710 nm, or in a range of 500 to 560 nm and an acceptor maximal emission wavelength in a range of 460 nm and 720 nm, or a range of 530 to 580 nm.

In another embodiment, the FRET acceptor polypeptide comprises an amino acid sequence at least 90%, 91%, 92%, 93%, 94% 95%, 96%, 97%, 98%, 99%, or 100% identical to the amino acid sequence of one or more of SEQ ID NOS: 3-5, and identical at the CYG chromophore. Residues in parentheses are optional throughout. The CYG chromophore is highlighted.

mKOk
(SEQ ID NO: 3)
IKPEMKMRYYMDGSVNGHEFTIEGEGTGRPYEGHQEMTLRVTMAEGGPM

PFAFDLVSHVFCYGHRVFTKYPEEIPDYFKQAFPEGLSWERSLEFEDGG

SASVSAHISLRGNTFYHKSKFTGVNFPADGPIMQNQSVDWEPSTEKITA

SDGVLKGDVTMYLKLEGGGNHKCQFKTTYKAAKEILEMPGDHYIGHRLV

RKTEGNITEQVEDAVAHS

-continued mKO
(SEQ ID NO: 4)
(MSVIK)PEMKMRYYMDGSVNGHEFTIEGEGTGRPYEGHQEMTLRVTMA

KGGPMPFAFDLVSHVFCYGHRPFTKYPEEIPDYFKQAFPEGLSWERSLE

FEDGGSASVSAHISLRGNTFYHKSKFTGVNFPADGPIMQNSVDWEPST

EKITASDGVLKGDVTMYLKLEGGGNHKCQFKTTYKAAKKILKMPGSHYI

SHRLVRKTEGNITELVEDAVA (HS)

mKO2
(SEQ ID NO: 5)
(MVSVI)KPEMKMRYYMDGSVNGHEFTIEGEGTGRPYEGHQEMTLRVTM

AEGGPMPFAFDLVSHVFCYGHRVFTKYPEEIPDYFKQAFPEGLSWERSL

EFEDGGSASVSAHISLRGNTFYHKSKFTGVNFPADGPIMQNSVDWEPS

TEKITASDGVLKGDVTMYLKLEGGGNHKCQMKTTYKAAKEILEMPGDHY

IGHRLVRKTEGNITEQVEDAVA(HS)

In one embodiment, all optional amino acid residues in the FRET acceptor polypeptide are present.

In another embodiment, the FRET donor polypeptide has a maximal donor excitation wavelength in a range of 350 nm to 670 nm, or in a range of 450 to 500 nm and a maximal donor emission wavelength in a range of 420 nm to 700 nm, or in a range of 480 to 515 nm. In a further embodiment, the FRET donor polypeptide comprises an amino acid sequence at least 90%, 91%, 92%, 93%, 94% 95%, 96%, 97%, 98%, 99%, or 100% identical to the amino acid sequence of SEQ ID NO: 6, 7, or 155, and identical at the TYG chromophore.

mEGFP
(SEQ ID NO: 6)
LFTGVVPILVELDGDVNGHKFSVSGEGEGDATYGKLTLKFICTTGKLPV

PWPTLVTTLTYGVQCFSRYPDHMKQHDFFKSAMPEGYVQERTIFFKDDG

NYKTRAEVKFEGDTLVNRIELKGIDFKEDGNILGHKLEYNYNSHNVYIM

ADKQKNGIKVNFKIRHNIEDGSVQLADHYQQNTPIGDGPVLLPDNHYLS

TQSKLSKDPNEKRDHMVLLEFVTAAGITL

Circularly permuted (cpm) EGFP(173/174):
SEQ ID. NO: 7
(DG)SVQLADHYQQNTPIGDGPVLLPDNHYLSTQS(A/K)LSKDPNEKR

DHMVLLEFVTAAGITLGMDELYKGGSGGMVSKGEELFTGVVPILVELDG

DVNGHKESVSGEGEGDATYGKLTLKFICTTGKLPVPWPTLVTTLTYGVQ

CFSRYPDHMKQHDFFKSAMPEGYVQERTIFFKDDGNYKTRAEVKFEGDT

LVNRIELKGIDFKEDGNILGHKLEYNYNSHNVYIMADKQKNGIKVNFKI

RHNIE(EA)

cpmEGFP(145/146)
SEQ ID NO: 155
YNSHNVYIMADKQKNGIKVNFKIRHNIEDGSVQLADHYQQNTPIGDGPV

LLPDNHYLSTQSKLSKDPNEKRDHMVLLEFVTAAGITLGMDELYKGGSG

GMVSKGEELFTGVVPILVELDGDVNGHKESVSGEGEGDATYGKLTLKFI

CTTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYN

Exemplary FRET donor polypeptides having the requisite amino acid sequence identity to SEQ ID NO:7 and which can be used in the fusion proteins of the disclosure are listed in Table 1 below.

TABLE 1

| Name | % identity to SEQ ID NO: 7 | Database accession # |
|---|---|---|
| M1S2 protein [synthetic construct] | 97% | gi \| 400653667 \| AFP87541.1 |
| PKG#6 [synthetic construct] | 98% | gi \| 1033838710 \| ANH79566.1 |
| PKG#8 [synthetic construct] | 98% | gi \| 1033838714 \| ANH79568.1 |
| NES-YC3.6 [Binary expression vector NES-YC3.6] | 96% | gi \| 378792854 \| AFC41195.1 |
| yellow cameleon 2.60 [synthetic construct] | 96% | gi \| 50507914 \| BAD30083.1 |
| yellow cameleon 4.60 [synthetic construct] | 96% | gi \| 50507918 \| BAD30085.1 |
| yellow cameleon 3.60 [synthetic construct] | 96% | gi \| 50507916 \| BAD30084.1 |
| YC3.6 [Binary expression vector YC3.6-C] | 96% | gi \| 378792870 \| AFC41207.1 |
| yellow cameleon Nano50 [synthetic construct] | 96% | gi \| 302375510 \| ADL29888.1 |
| Fluorescent Mg2+ indicator [synthetic construct] | 96% | gi \| 1341117861 \| BBC69164.1 |
| calcium sensor cameleon D2cpv [synthetic construct] | 96% | gi \| 94471595 \| ABF21065.1 |
| yellow cameleon x 2.60 [synthetic construct] | 96% | gi \| 765098779 \| BAQ56021.1 |
| calcium sensor cameleon D3cpv [synthetic construct] | 96% | gi \| 94471597 \| ABF21066.1 |
| yellow cameleon Nano15 [synthetic construct] | 96% | gi \| 302375506 \| ADL29886.1 |
| yellow cameleon Nano30 [synthetic construct] | 96% | gi \| 302375508 \| ADL29887.1 |
| YC3.6 [Binary expression vector YC3.6-N] | 96% | gi \| 378792874 \| AFC41210.1 |
| NLS-YC3.6 [Binary expression vector NLS-YC3.6] | 96% | gi \| 378792858 \| AFC41198.1 |
| yellow cameleon Nano140 [synthetic construct] | 96% | gi \| 302375514 \| ADL29890.1 |
| yellow cameleon Nano65 [synthetic construct] | 96% | gi \| 302375512 \| ADL29889.1 |
| calcium sensor cameleon lynD3cpv [synthetic construct] | 96% | gi \| 94471601 \| ABF21068.1 |

TABLE 1-continued

| Name | % identity to SEQ ID NO: 7 | Database accession # |
|---|---|---|
| calcium sensor cameleon D4cpv [synthetic construct] | 96% | gi \| 94471599 \| ABF21067.1 |
| yellow cameleon Nano50 | 96% | gi \| 997831445 \| BAU51804.1 |
| yellow cameleon 3.60-pm [synthetic construct] | 96% | gi \| 50507920 \| BAD30086.1 |
| PKG#7 [synthetic construct] | 96% | gi \| 1033838712 \| ANH79567.1 |
| PKG#2 [synthetic construct] | 96% | gi \| 1033838702 \| ANH79562.1 |
| yellow cameleon Nano15 [Cloning vector pLN-YC Nano15] | 96% | gi \| 997831443 \| BAU51803.1 |
| TP-D3cpv [Binary expression vector TP-D3cpv] | 96% | gi \| 378792866 \| AFC41204.1 |
| PKG#4 [synthetic construct] | 96% | gi \| 1033838706 \| ANH79564.1 |
| photoactivatable calcium indicator PA-TNXL [ | 96% | gi \| 464095426 \| BAN00003.1 |
| PM-YC3.6-Lti6b [Binary expression vector PM-YC3.6-LTI6b] | 96% | gi \| 378792862 \| AFC41201.1 |
| mitochondrial calcium sensor cameleon 4mtD3cpv | 96% | gi \| 94471603 \| ABF21069.1 |
| 3× GFP [Cloning vector pGGC025] | 93% | gi \| 568816479 \| AHE38517.1 |
| SV40-3 × eGFP [Cloning vector pPLV04] | 97% | gi \| 334085767 \| AEG42740.1 |
| calcium indicator TN-XXL [synthetic construct] | 95% | gi \| 194716543 \| ACF93133.1 |
| three repeats of Citrine with GGSGGS linkers | 96% | gi \| 929652476 \| BAS49686.1 |
| PKG#3 [synthetic construct] | 95% | gi \| 1033838704 \| ANH79563.1 |
| Twitch-2B [synthetic construct] | 94% | gi \| 568402376 \| AHD25944.1 |
| mVenus(L68V)-mTurquoise [synthetic construct] | 91% | gi \| 341940080 \| AEL12177.1 |
| GEPRA-G [synthetic construct] | 93% | gi \| 478246796 \| BAN14786.1 |
| NLS-YFP-CFP [Yeast integrative vector pBS42] | 93% | gi \| 544370144 \| AGW21605.1 |
| NLS-YFP-Pro10-CFP [Yeast integrative vector pBS47] | 91% | gi \| 544370160 \| AGW21617.1 |
| ratiometric fluorescent temperature indicator | 87% | gi \| 1177648317 \| BAX25172.1 |
| NLS-YFP-Pro15-CFP [Yeast integrative vector pBS48] | 89% | gi \| 544370164 \| AGW21620.1 |
| NLS-YFP-Pro5-CFP [Yeast integrative vector pBS46] | 92% | gi \| 544370156 \| AGW21614.1 |
| NLS-YFP-Pro20-CFP [Yeast integrative vector pBS50] | 87% | gi \| 544370172 \| AGW21626.1 |
| NLS-YFP × CFP [Yeast integrative vector pBS42BN] | 92% | gi \| 544370148 \| AGW21608.1 |
| MT1-MMP FRET probe protein [synthetic construct] | 88% | gi \| 170791211 \| ACB38271.1 |
| ssrA-tagged green fluorescent protein [synthetic construct] | 93% | gi \| 339905310 \| AEK24782.1 |
| photoconvertible fluorescent protein Phamret | 90% | gi \| 187370622 \| BAG31927.1 |
| calcium-sensing GFP analog [synthetic construct] | 99% | gi \| 29150153 \| CAD79597.1 |
| MolyProbe protein [synthetic construct] | 96% | gi \| 457866284 \| BAM93494.1 |
| His-6-tagged G-CaMP1.6 [synthetic construct] | 98% | gi \| 94411311 \| ABF18599.1 |
| G-CaMP2 [synthetic construct] | 98% | gi \| 87248062 \| ABD36085.1 |
| GCaMP3 [synthetic construct] | 97% | gi \| 299818413 \| ADJ53338.1 |
| dLight1.4 [synthetic construct] | 97% | gi \| 1398286563 \| AWS21700.1 |
| GAP43-GCaMP6s [pAAV-hSyn1-FLEx-GAP43-GCaMP6s] | 97% | gi \| 1442830696 \| AXK50352.1 |
| GAP43-GCaMP6m [pAAV-hSyn1-GAP43-GCaMP6m] | 97% | gi \| 1442830702 \| AXK50356.1 |
| GAP43-GCaMP6f [Vector pAAV-hSyn1-GAP43-GCaMP6f] | 97% | gi \| 1442830699 \| AXK50354.1 |
| dLight1.5 [synthetic construct] | 97% | gi \| 1398286565 \| AWS21701.1 |
| 5htLight1.1 [synthetic construct] | 97% | gi \| 1398286577 \| AWS21707.1 |
| G-GECO1 [synthetic construct] | 96% | gi \| 345787073 \| AEO16868.1 |
| dLight1.1 [synthetic construct] | 97% | gi \| 1398286555 \| AWS21696.1 |
| dLight1.2 [synthetic construct] | 97% | gi \| 1398286557 \| AWS21697.1 |
| dLight1.3a [synthetic construct] | 97% | gi \| 1398286559 \| AWS21698.1 |
| dLight1.3b [synthetic construct] | 97% | gi \| 1398286561 \| AWS21699.1 |
| glutatmate sensor SF-iGluSnFR [synthetic construct] | 95% | gi \| 1488571045 \| AYH52532.1 |
| glutatmate sensor SF-iGluSnFR [synthetic construct] | 95% | gi \| 1488571043 \| AYH52531.1 |
| glutatmate sensor SF-iGluSnFR [synthetic construct] | 95% | gi \| 1488571041 \| AYH52530.1 |
| nLight3.1 [synthetic construct] | 97% | gi \| 1398286571 \| AWS21704.1 |
| GEX-GECO1 [synthetic construct] | 96% | gi \| 345786981 \| AEO16865.1 |

TABLE 1-continued

| Name | % identity to SEQ ID NO: 7 | Database accession # |
|---|---|---|
| iGABA sensor nFR [synthetic construct] | 95% | gi \| 1488571039 \| AYH52529.1 |
| kLight1.1 [synthetic construct] | 97% | gi \| 1398286573 \| AWS21705.1 |
| mtLight1.1 [synthetic construct] | 97% | gi \| 1398286579 \| AWS21708.1 |
| iGABA sensor nFR [synthetic construct] | 95% | gi \| 1488571035 \| AYH52527.1 |
| iGABA sensor nFR [synthetic construct] | 95% | gi \| 1488571037 \| AYH52528.1 |
| Crystal Structure Calcium Bound Dimeric Gcamp2 (#2) | 96% | gi \| 1209040728 \| 3EVV_A |
| mLight1.1 [synthetic construct] | 97% | gi \| 1398286575 \| AWS21706.1 |
| ssrA-tagged green fluorescent protein [synthetic construct] | 93% | gi \| 339905308 \| AEK24781.1 |
| G-GECO1.1 [synthetic construct] | 96% | gi \| 345787100 \| AEO16869.1 |
| Chain A, Crystal Structure Of Circular-permutated Egfp | 96% | gi \| 217035443 \| 3EVP_A |
| nLight2.1 [synthetic construct] | 97% | gi \| 1398286569 \| AWS21703.1 |
| nLight1.1 [synthetic construct] | 97% | gi \| 1398286567 \| AWS21702.1 |
| G-CaMP6 protein [synthetic construct] | 96% | gi \| 815006828 \| AKE44624.1 |
| G-CaMP7 protein [synthetic construct] | 96% | gi \| 815006830 \| AKE44625.1 |
| GCaMP7a [synthetic construct] | 96% | gi \| 446512552 \| BAM78547.1 |
| GEM-GECO1 [synthetic construct] | 96% | gi \| 345786945 \| AEO16864.1 |
| G-CaMP-HS protein [synthetic construct] | 96% | gi \| 815006836 \| AKE44628.1 |
| calcium-sensing GFP protein [synthetic construct] | 96% | gi \| 335060646 \| AEH27627.1 |
| Crystal structure of Calcium bound monomeric GCAMP2 | 96% | gi \| 217035444 \| 3EVR_A |
| G-CaMP4.1 protein [synthetic construct] | 96% | gi \| 810222674 \| AKE14367.1 |
| G-CaMP8 protein [synthetic construct] | 95% | gi \| 815006832 \| AKE44626.1 |
| G-GECO1.2 [synthetic construct] | 95% | gi \| 345787127 \| AEO16870.1 |
| Crystal structure of Calcium bound dimeric GCAMP2 | 96% | gi \| 217035445 \| 3EVU_A |
| Myosin light chain kinase, GFP, Calmodulin-1 chimera | 96% | gi \| 392311568 \| 3SG6_A |
| Calcium-free GCaMP2 (calcium binding deficient mutant) | 96% | gi \| 218681839 \| 3EKJ_A |
| Chain A, High Resolution Structure Of Delta-rest-gcamp3 | 96% | gi \| 576865036 \| 4IK5_A |
| GCaMP6s-P2A-mKate2 | 97% | gi \| 1442830714 \| AXK50364.1 |
| GAP43-GCaMP6s-P2A-mKate2 | 97% | gi \| 1442830705 \| AXK50358.1 |
| GCaMP6s-P2A-mRuby3 | 97% | gi \| 1442830717 \| AXK50366.1 |
| Chain A, High Resolution Structure Of Gcampj At Ph 8.5 | 96% | gi \| 582045214 \| 4IK1_A |

In one embodiment, the fusion protein comprises the genus X1-B1-X2-B2-X3-B3-X4, wherein: one of X2 and X4 comprises an amino acid sequence at least 90%, 91%, 92%, 93%, 94% 95%, 96%, 97%, 98%, 99%, or 100% identical to the amino acid sequence of SEQ ID NO:6 or 7; and the other of X2 and X4 comprises an amino acid sequence at least 90%, 91%, 92%, 93%, 94% 95%, 96%, 97%, 98%, 99%, or 100% identical to the amino acid sequence of SEQ ID NO:3, 4, or 5. In another embodiment, one of X2 and X4 comprises an amino acid sequence at least 90%, 91%, 92%, 93%, 94% 95%, 96%, 97%, 98%, 99%, or 100% identical to the amino acid sequence of SEQ ID NO:6; and the other of X2 and X4 comprises an amino acid sequence at least 90%, 91%, 92%, 93%, 94% 95%, 96%, 97%, 98%, 99%, or 100% identical to the amino acid sequence of SEQ ID NO:3. In a further embodiment, X2 comprises an amino acid sequence at least 90%, 91%, 92%, 93%, 94% 95%, 96%, 97%, 98%, 99%, or 100% identical to the amino acid sequence of SEQ ID NO:6; and X4 comprises an amino acid sequence at least 90%, 91%, 92%, 93%, 94% 95%, 96%, 97%, 98%, 99%, or 100% identical to the amino acid sequence of SEQ ID NO:3.

B1, B2, and B3 are independently absent or comprise an amino acid linker. When any of B1, B2, and/or B3 are present, the linker may comprise any suitable amino acid linker. In one embodiment B1 is absent, or comprises G, SG, SHG, SAHG (SEQ ID NO: 177), SAGHG (SEQ ID NO: 178), SAAGHG (SEQ ID NO: 179), or SAAGGHG (SEQ IS NO: 180);

B2 is T or is absent; and

B3 is S, GS or is absent.

The various domains may comprise additional amino acid residues. In one non-limiting embodiment, X1 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:8 or 9 (RexA), wherein residues in parentheses are optional and may be present or absent (SEQ ID NO: 8)
(M)KVPEAAISRLITYLRILEELEAQGVHRTASEQLGELAQVTAFQVDK

DLSYFGSYGTDGVGYTVPVLKRELRHILGLNRKWGLCIVGMGRLGSALA

DWPGFGESFELRGFFDVDPGMVGRPVRGGVIEHVDLLPQRVPGRIEIAL

LTVPREAAQKAADLLVAAGIKGILNFAPVVLEVPKEVAVENVDILAGLT

RLSFAILNPT;
or (SEQ ID NO: 9)
(M)KVPEAAISRLITYLRILEELEAQGVHRTASEQLGELAQVTAFQVDK

DLSYFGSYGTDGVGYTVPVLKRELRHILGLNRKWGLCIVGMGRLGSALA

-continued
DWPGFGESFELRGFFDVDPGMVGRPVRGGVIEHVDLLPQRVPGRIEIAL

LTVPREAAQKAADLLVAAGIKGILNFAPVVLEVPKEVAVENVDILAGLT

RLSFAILNPTW

In another embodiment, X1 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:8, and B1 is absent.

In one embodiment, X2 comprises the formula Z1—Z2—Z3, wherein
 (a) Z2 comprises an amino acid sequence at least 90%, 91%, 92%, 93%, 94% 95%, 96%, 97%, 98%, 99%, or 100% identical to the amino acid sequence of SEQ ID NO:6;
 (b) Z1 is absent or is selected from the group consisting of E, EE, GEE, KGEE (SEQ ID NO: 181), SKGEE (SEQ ID NO: 182), VSKGEE (SEQ ID NO: 183), and MVSKGEE (SEQ ID NO: 184); and
 (c) Z3 is absent or is selected from the group consisting of G, GM, GMD, GMDE (SEQ ID NO: 185), GMDEL (SEQ ID NO: 186), GMDELY (SEQ ID NO: 187), and GMDELYK (SEQ ID NO: 188).

In one embodiment, X2 comprises an amino acid sequence at least 90%, 91%, 92%, 93%, 94% 95%, 96%, 97%, 98%, 99%, or 100% identical to the amino acid sequence of SEQ ID NO:10.

(SEQ ID NO: 10)
(MVSKGEE)LFTGVVPILVELDGDVNGHKFSVSGEGEGDATYGKLTLKF

ICTTGKLPVPWPTLVTTLTYGVOCESRYPDHMKQHDFFKSAMPEGYVQE

RTIFFKDDGNYKTRAEVKFEGDTLVNRIELKGIDFKEDGNILGHKLEYN

YNSHNVYIMADKQKNGIKVNFKIRHNIEDGSVQLADHYQQNTPIGDGPV

LLPDNHYLSTQSKLSKDPNEKRDHMVLLEFVTAAGITL(GMDELYK)

In another embodiment, X3 comprises the formula Z5—Z6—Z7, wherein
 Z6 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:2;
 Z5 is absent or is selected from the group consisting of E, PE, VPE, and KVPE; and
 Z7 is absent or is selected from the group consisting of E, EM, EMM, and EMMG (SEQ ID NO: 189).

In one embodiment, X3 comprises an amino acid sequence at least 75%, 80%, 85%, 90%, 91%, 92%, 93%, 94% 95%, 96%, 97%, 98%, 99%, or 100% identical to the amino acid sequence of SEQ ID NO:11.

(SEQ ID NO: 11)
KVPEAAISRLITYLRILEELEAQGVHRTASEQLGELAQVTAFQVDEDLS

YFGSYGTDGVGYTVPVLKRELRHILGLNRKWGLCIVGMGRLGSALADWP

GFGESFELRGFFDVDPGMVGRPVRGGVIEHVDLLPQRVPGRIEIALLTV

PREAAQKAADLLVAAGIKGILNFAPVVLEVPKEVAVENVDFLAGLTRLS

FAILNPKWREEMMG

In another embodiment, X4 comprises the formula Z9—Z10, wherein
 Z9 is absent or is selected from the group consisting of V, SV, VSV, and MVSV (SEQ ID NO: 190); and
 Z10 comprises the amino acid sequence of SEQ ID NO:3.

In one embodiment, X4 comprises an amino acid sequence at least 90%, 91%, 92%, 93%, 94% 95%, 96%, 97%, 98%, 99%, or 100% identical to the amino acid sequence of SEQ ID NO:12.

(SEQ ID NO: 12)
MVSVIKPEMKMRYYMDGSVNGHEFTIEGEGTGRPYEGHQEMTLRVTMAE

GGPMPFAFDLVSHVFCYGHRVFTKYPEEIPDYFKQAFPEGLSWERSLEF

EDGGSASVSAHISLRGNTFYHKSKFTGVNFPADGPIMQNQSVDWEPSTE

KITASDGVLKGDVTMYLKLEGGGNHKCQFKTTYKAAKEILEMPGDHYIG

HRLVRKTEGNITEQVEDAVAHS EASMDELYK

The fusion proteins may be produced by any suitable means, including but not limited to chemical synthesis and production by recombinant cells. When produced by recombinant cells, the fusion proteins may include additional residues at the N- and/or C-terminus. For example, expression in mammalian or bacterial cells may utilize vectors that add different C-terminal tails to the fusion proteins. In one embodiment, the fusion proteins comprise the genus X1-B1-X2-B2-X3-B3-X4-X5, wherein X5 comprises the amino acid sequence EASMDELYK (SEQ ID NO: 157), MDELYK (SEQ ID NO: 156), or EASTSAWSHPQFEKGGGSGGGSGGSAWSHPQFEK (SEQ ID NO: 158).

In specific embodiments, the fusion protein comprises the amino acid sequence selected from the group consisting of SEQ ID NO: 13-93, 95-154, and 191-193; the sequences are provided in Table 2 and the examples. The table also provides signal window as demonstrated in bacterial lysates and detailed in the examples that follow.

TABLE 2

| Full clone name | SEQ ID NO | Signal window (ex mode), measured in lysates | Full protein sequence |
|---|---|---|---|
| 1-F8 | 13 | 0.55 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEVPEAAISRLITYLRILEELEAQGVHRTASEQLGELAQVTAFQVDEDLSYFGSYGTDGVGYTVPVLKRELR HILGLNRKWGLCIVGMGRLGSALADWPGFGESFELRGFFDVDPGMVGRPVRGGVIEHVDLLPQRVPGRIEIALL |

TABLE 2-continued

| Full clone name | SEQ ID NO | Signal window (ex mode), measured in lysates | Full protein sequence |
|---|---|---|---|
| | | | TVPREAAQKAADLLVAAGIKGILNFAPVVLEVPKEVAVENVDFLAGLTRLSFAILNPKWREIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 3-C8 | 14 | 0.4 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWGMVSKGEELFTGVVPIL VELDGDVNGHKFSVSGEGEGDATYGKLTLKFICTTGKLPVPWPTLVTTLTYGVQCFSRYPDHMKQHDFFKSAMP EGYVQERTIFFKDDGNYKTRAEVKFEGDTLVNRIELKGIDFKEDGNILGHKLEYNYNSHNVYIMADKQKNGIKV NFKIRHNIEDGSVQLADHYQQNTPIGDGPVLLPDNHYLSTQSKLSKDPNEKRDHMVLLEFVTAAGITLGMDEPE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREVIKPEMKMRYYMDGSVNGHE FTIEGEGTGRPYEGHQEMTLRVTMAEGGPMPFAFDLVSHVFCYGHRVFTKYPEEIPDYFKQAFPEGLSWERSLE FEDGGSASVSAHISLRGNTFYHKSKFTGVNFPADGPIMQNQSVDWEPSTEKITASDGVLKGDVTMYLKLEGGGN HKCQFKTTYKAAKEILEMPGDHYIGHRLVRKTEGNITEQVEDAVAHSEASMDELYK |
| 2-F3 | 15 | 0.34 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKOHDFFKSA MPEGYVQERTIFFKDDGNYKTRAEVKFEGDTLVNRIELKGIDFKEDGNILGHKLEYNYNSHNVYIMADKOKNGI KVNFKIRHNIEDGSVQLADHYQQNTPIGDGPVLLPDNHYLSTQSKLSKDPNEKRDHMVLLEFVTAAGITLGMDE PEAAISRLITYLRILEELEAQGVHRTASEQLGELAQVTAFQVDEDLSYFGSYGTDGVGYTVPVLKRELRHILGL NRKWGLCIVGMGRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREVIKPEMKMRYYMDGSVNG HEFTIEGEGTGRPYEGHQEMTLRVTMAEGGPMPFAFDLVSHVFCYGHRVFTKYPEEIPDYFKQAFPEGLSWERS LEFEDGGSASVSAHISLRGNTFYHKSKFTGVNFPADGPIMQNQSVDWEPSTEKITASDGVLKGDVTMYLKLEGG GNHKCQFKTTYKAAKEILEMPGDHYIGHRLVRKTEGNITEQVEDAVAHSEASMDELYK |
| 1-G8 | 16 | 0.34 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKOHDFFKSA MPEGYVQERTIFFKDDGNYKTRAEVKFEGDTLVNRIELKGIDFKEDGNILGHKLEYNYNSHNVYIMADKOKNGI KVNFKIRHNIEDGSVQLADHYQQNTPIGDGPVLLPDNHYLSTQSKLSKDPNEKRDHMVLLEFVTAAGITLGMDP EAAISRLITYLRILEELEAQGVHRTASEQLGELAQVTAFQVDEDLSYFGSYGTDGVGYTVPVLKRELRHILGLN RKWGLCIVGMGRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNQSVDWEPSTEKITASDGVLKGDVTMYLKLEGGG NHKCQFKTTYKAAKEILEMPGDHYIGHRLVRKTEGNITEQVEDAVAHSEASMDELYK |
| 4-D10 | 17 | 0.34 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKLEYNYNSHNVYIMADKOKNGIKVNFKI RHNIEDGSVQLADHYQQNTPIGDGPVLLPDNHYLSTQSKLSKDPNEKRDHMVLLEFVTAAGITLGMPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREVIKPEMKMRYYMDGSVNGHEFTIEGE GTGRPYEGHQEMTLRVTMAEGGPMPFAFDLVSHVFCYGHRVFTKYPEEIPDYFKQAFPEGLSWERSLEFEDGGS ASVSAHISLRGNTFYHKSKFTGVNFPADGPIMQNQSVDWEPSTEKITASDGVLKGDVTMYLKLEGGGNHKCQFK TTYKAAKEILEMPGDHYIGHRLVRKTEGNITEQVEDAVAHSEASMDELYK |
| 4-F1 | 18 | 0.33 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREESVIKPEMKMRYYMDGSVNGHEFTIE GEGTGRPYEGHQEMTLRVTMAEGGPMPFAFDLVSHVFCYGHRVFTKYPEEIPDYFKQAFPEGLSWERSLEFEDG GSASVSAHISLRGNTFYHKSKFTGVNFPADGPIMQNQSVDWEPSTEKITASDGVLKGDVTMYLKLEGGGNHKCQ FKTTYKAAKEILEMPGDHYIGHRLVRKTEGNITEQVEDAVAHSEASMDELYK |
| 4-A2 | 19 | 0.32 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV |

TABLE 2-continued

| Full clone name | SEQ ID NO | Signal window (ex mode), measured in lysates | Full protein sequence |
|---|---|---|---|
| | | | PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREEMMGMVSVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNQSVDWEPSTEKITASDGVLKGDVTMYLKLEGGG NHKCQFKTTYKAAKEILEMPGDHYIGHRLVRKTEGNITEQVEDAVAHSEASMDELYK |
| 1-A7 | 20 | 0.31 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DEPEAAISRLITYLRILEELEAQGVHRTASEQLGELAQVTAFQVDEDLSYFGSYGTDGVGYTVPVLKRELRHIL GLNRKWGLCIVGMGRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 2-A11 | 21 | 0.30 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEVPEAAISRLITYLRILEELEAQGVHRTASEQLGELAQVTAFQVDEDLSYFGSYGTDGVGYTVPVLKRELR HILGLNRKWGLCIVGMGRLGSALADWPGFGESFELRGFFDVDPGMVGRPVRGGVIEHVDLLPQRVPGRIEIALL TVPREAAQKAADLLVAAGIKGILNFAPVVLEVPKEVAVENVDFLAGLTRLSFAILNPKWREVIKPEMKMRYYMD GSVNGHEFTIEGEGTGRPYEGHQEMTLRVTMAEGGPMPFAFDLVSHVFCYGHRVFTKYPEEIPDYFKQAFPEGL SWERSLEFEDGGSASVSAHISLRGNTFYHKSKFTGVNFPADGPIMQNQSVDWEPSTEKITASDGVLKGDVTMYL KLEGGGNHKCQFKTTYKAAKEILEMPGDHYIGHRLVRKTEGNITEQVEDAVAHSEASMDELYK |
| 2-A9 | 22 | 0.29 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DEVPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNQSVDWEPSTEKITASDGVLKGDVTMYLKL EGGGNHKCQFKTTYKAAKEILEMPGDHYIGHRLVRKTEGNITEQVEDAVAHSEASMDELYK |
| 4-H7 | 23 | 0.28 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREVIKPEMKMRYYMDGSVNGHEFTIEG EGTGRPYEGHQEMTLRVTMAEGGPMPFAFDLVSHVFCYGHRVFTKYPEEIPDYFKQAFPEGLSWERSLEFEDGG SASVSAHISLRGNTFYHKSKFTGVNFPADGPIMQNQSVDWEPSTEKITASDGVLKGDVTMYLKLEGGGNHKCQF KTTYKAAKEILEMPGDHYIGHRLVRKTEGNITEQVEDAVAHSEASMDELYK |
| 2-C12 | 24 | 0.28 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTGEELFTGVVPILVELDGD VNGHKFSVSGEGEGDATYGKLTLKFICTTGKLPVPWPTLVTTLTYGVQCFSRYPDHMKQHDFFKSAMPEGYVQE RTIFFKDDGNYKTRAEVKFEGDTLVNRIELKGIDFKEDGNILGHKLEYNYNSHNVYIMADKQKNGIKVNFKIRH NIEDGSVQLADHYQQNTPIGDGPVLLPDNHYLSTQSKLSKDPNEKRDHMVLLEFVTAAGITLGMPEAAISRLIT YLRILEELEAQGVHRTASEQLGELAQVTAFQVDEDLSYFGSYGTDGVGYTVPVLKRELRHILGLNRKWGLCIVG MGRLGSALADWPGFGESFELRGFFDVDPGMVGRPVRGGVIEHVDLLPQRVPGRIEIALLTVPREAAQKAADLLV AAGIKGILNFAPVVLEVPKEVAVENVDFLAGLTRLSFAILNPKWREVIKPEMKMRYYMDGSVNGHEFTIEGEGT |

TABLE 2-continued

| Full clone name | SEQ ID NO | Signal window (ex mode), measured in lysates | Full protein sequence |
|---|---|---|---|
| | | | GRPYEGHQEMTLRVTMAEGGPMPFAFDLVSHVFCYGHRVFTKYPEEIPDYFKQAFPEGLSWERSLEFEDGGSAS VSAHISLRGNTFYHKSKFTGVNFPADGPIMQNSVDWEPSTEKITASDGVLKGDVTMYLKLEGGGNHKCQFKTT YKAAKEILEMPGDHYIGHRLVRKTEGNITEQVEDAVAHSEASMDELYK |
| 1-B10 | 25 | 0.26 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNSVDWEPSTEKITASDGVLKGDVTMYLK LEGGGNHKCQFKTTYKAAKEILEMPGDHYIGHRLVRKTEGNITEQVEDAVAHSEASMDELYK |
| 1-F7 | 26 | 0.26 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWMVSKGEELFTGVVPILV ELDGDVNGHKFSVSGEGEGDATYGKLTLKFICTTGKLPVPWPTLVTTLTYGVQCFSRYPDHMKQHDFFKSAMPE GYVQERTIFFKDDGNYKTRAEVKFEGDTLVNRIELKGIDFKEDGNILGHKLEYNYNSHNVYIMADKQKNGIKVN FKIRHNIEDGSVQLADHYQQNTPIGDGPVLLPDNHYLSTQSKLSKDPNEKRDHMVLLEFVTAAGITLEAAISRL ITYLRILEELEAQGVHRTASEQLGELAQVTAFQVDEDLSYFGSYGTDGVGYTVPVLKRELRHILGLNRKWGLCI VGMRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREEMSVIKPEMKMRYYMDGSVNGHEFTI EGEGTGRPYEGHQEMTLRVTMAEGGPMPFAFDLVSHVFCYGHRVFTKYPEEIPDYFKQAFPEGLSWERSLEFED GGSASVSAHISLRGNTFYHKSKFTGVNFPADGPIMQNSVDWEPSTEKITASDGVLKGDVTMYLKLEGGGNHKC QFKTTYKAAKEILEMPGDHYIGHRLVRKTEGNITEQVEDAVAHSEASMDELYK |
| 1-B7 | 27 | 0.25 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNSVDWEPSTEKITASDGVLKGDVTMYLK LEGGGNHKCQFKTTYKAAKEILEMPGDHYIGHRLVRKTEGNITEQVEDAVAHSEASMDELYK |
| 2-H5 | 28 | 0.24 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKOHDFFKSAMPEG YVQERTIFFKDDGNYKTRAEVKFEGDTLVNRIELKGIDFKEDGNILGHKLEYNYNSHNVYIMADKQKNGIKVNF KIRHNIEDGSVQLADHYQQNTPIGDGPVLLPDNHYLSTQSKLSKDPNEKRDHMVLLEFVTAAGITLGMDEVPEA AISRLITYLRILEELEAQGVHRTASEQLGELAQVTAFQVDEDLSYFGSYGTDGVGYTVPVLKRELRHILGLNRK WGLCIVGMRLGSALADWPGFGESFELRGFFDVDPGMVGRPVRGGVIEHVDLLPQRVPGRIEIALLTVPREAAQ KAADLLVAAGIKGILNFAPVVLEVPKEVAVENVDFLAGLTRLSFAILNPKWREEVIKPEMKMRYYMDGSVNGHE FTIEGEGTGRPYEGHQEMTLRVTMAEGGPMPFAFDLVSHVFCYGHRVFTKYPEEIPDYFKQAFPEGLSWERSLE FEDGGSASVSAHISLRGNTFYHKSKFTGVNFPADGPIMQNSVDWEPSTEKITASDGVLKGDVTMYLKLEGGGN HKCQFKTTYKAAKEILEMPGDHYIGHRLVRKTEGNITEQVEDAVAHSEASMDELYK |
| 3-E6 | 29 | 0.24 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMPEAAISRL ITYLRILEELEAQGVHRTASEQLGELAQVTAFQVDEDLSYFGSYGTDGVGYTVPVLKRELRHILGLNRKWGLCI VGMRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREEMGMVSVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNSVDWEPSTEKITASDGVLKGDVTMYLKLEGGG NHKCQFKTTYKAAKEILEMPGDHYIGHRLVRKTEGNITEQVEDAVAHSEASMDELYK |
| 4-G1 | 30 | 0.24 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWMVSKGEELFTGVVPILV |

TABLE 2-continued

| Full clone name | SEQ ID NO | Signal window (ex mode), measured in lysates | Full protein sequence |
|---|---|---|---|
| | | | ELDGDVNGHKFSVSGEGEGDATYGKLTLKFICTTGKLPVPWPTLVTTLTYGVQCFSRYPDHMKQHDFFKSAMPE GYVQERTIFFKDDGNYKTRAEVKFEGDTLVNRIELKGIDFKEDGNILGHKLEYNYNSHNVYIMADKQKNGIKVN FKIRHNIEDGSVQLADHYQQNTPIGDGPVLLPDNHYLSTQSKLSKDPNEKRDHMVLLEFVTAAGITLGMPEAAI SRLITYLRILEELEAQGVHRTASEQLGELAQVTAFQVDEDLSYFGSYGTDGVGYTVPVLKRELRHILGLNRKWG LCIVGMGRLGSALADWPGFGESFELRGFFDVDPGMVGRPVRGGVIEHVDLLPQRVPGRIEIALLTVPREAAQKA ADLLVAAGIKGILNFAPVVLEVPKEVAVENVDFLAGLTRLSFAILNPKWREEMMGMVSVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 2-F6 | 31 | 0.23 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDELVPEAAISRLITYLRILEELEAQGVHRTASEQLGELAQVTAFQVDEDLSYFGSYGTDGVGYTVPVLKREL RHILGLNRKWGLCIVGMGRLGSALADWPGFGESFELRGFFDVDPGMVGRPVRGGVIEHVDLLPQRVPGRIEIAL LTVPREAAQKAADLLVAAGIKGILNFAPVVLEVPKEVAVENVDFLAGLTRLSFAILNPKWREVIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 2-C6 | 32 | 0.23 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDELVPEAAISRLITYLRILEELEAQGVHRTASEQLGELAQVTAFQVDEDLSYFGSYGTDGVGYTVPVLKREL RHILGLNRKWGLCIVGMGRLGSALADWPGFGESFELRGFFDVDPGMVGRPVRGGVIEHVDLLPQRVPGRIEIAL LTVPREAAQKAADLLVAAGIKGILNFAPVVLEVPKEVAVENVDFLAGLTRLSFAILNPKWREEMSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 4-F5 | 33 | 0.23 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTSKGEELFTGVVPILVELD GDVNGHKFSVSGEGEGDATYGKLTLKFICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMDEPEAAIS RLITYLRILEELEAQGVHRTASEQLGELAQVTAFQVDEDLSYFGSYGTDGVGYTVPVLKRELRHILGLNRKWGL CIVGMGRLGSALADWPGFGESFELRGFFDVDPGMVGRPVRGGVIEHVDLLPQRVPGRIEIALLTVPREAAQKAA DLLVAAGIKGILNFAPVVLEVPKEVAVENVDFLAGLTRLSFAILNPKWREVIKPEMKMRYYMDGSVNGHEFTIE GEGTGRPYEGHQEMTLRVTMAEGGPMPFAFDLVSHVFCYGHRVFTKYPEEIPDYFKQAFPEGLSWERSLEFEDG GSASVSAHISLRGNTFYHKSKFTGVNFPADGPIMQNQSVDWEPSTEKITASDGVLKGDVTMYLKLEGGGNHKCQ FKTTYKAAKEILEMPGDHYIGHRLVRKTEGNITEQVEDAVAHSEASMDELYK |
| 3-D8 | 34 | 0.23 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFTG VVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKQK NGIKVNFKIRHNIEDGSVQLADHYQQNTPIGDGPVLLPDNHYLSTQSKLSKDPNEKRDHMVLLEFVTAAGITLG MDEPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNQSVDWEPSTEKITASDGVLKGDVTMYLKL EGGGNHKCQFKTTYKAAKEILEMPGDHYIGHRLVRKTEGNITEQVEDAVAHSEASMDELYK |
| 2-G2 | 35 | 0.23 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL EAAISRLITYLRILEELEAQGVHRTASEQLGELAQVTAFQVDEDLSYFGSYGTDGVGYTVPVLKRELRHILGLN RKWGLCIVGMGRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL |

TABLE 2-continued

| Full clone name | SEQ ID NO | Signal window (ex mode), measured in lysates | Full protein sequence |
|---|---|---|---|
| | | | EFEDGGSASVSAHISLRGNTFYHKSKFTGVNFPADGPIMQNQSVDWEPSTEKITASDGVLKGDVTMYLKLEGGG NHKCQFKTTYKAAKEILEMPGDHYIGHRLVRKTEGNITEQVEDAVAHSEASMDELYK |
| 2-D12 | 36 | 0.22 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGHGMVSKGEELFTG VVVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REEAAQKAADLLVAAGIKGILNFAPVVLEVPKEVAVENVDFLAGLTRLSFAILNPKWREIKPEMKMRYYMDGSVN GHEFTIEGEGTGRPYEGHQEMTLRVTMAEGGPMPFAFDLVSHVFCYGHRVFTKYPEEIPDYFKQAFPEGLSWER SLEFEDGGSASVSAHISLRGNTFYHKSKFTGVNFPADGPIMQNQSVDWEPSTEKITASDGVLKGDVTMYLKLEG GGNHKCQFKTTYKAAKEILEMPGDHYIGHRLVRKTEGNITEQVEDAVAHSEASMDELYK |
| 3-B2 | 37 | 0.22 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGHGMVSKGEELFTG VVVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDELYKVPEAAISRLITYLRILEELEAQGVHRTASEQLGELAQVTAFQVDEDLSYFGSYGTDGVGYTVPVLKRE LRHILGLNRKWGLCIVGMRLGSALADWPGFGESFELRGFFDVDPGMVGRPVRGGVIEHVDLLPQRVPGRIEIA LLTVPREEAAQKAADLLVAAGIKGILNFAPVVLEVPKEVAVENVDFLAGLTRLSFAILNPKWREIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 1-F10 | 38 | 0.22 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKQHDFFKSAMPEG YVQERTIFFKDDGNYKTRAEVKFEGDTLVNRIELKGIDFKEDGNILGHKLEYNYNSHNVYIMADKOKNGIKVNF KIRHNIEDGSVQLADHYQQNTPIGDGPVLLPDNHYLSTQSKLSKDPNEKRDHMVLLEFVTAAGITLGMDELVPE AAISRLITYLRILEELEAQGVHRTASEQLGELAQVTAFQVDEDLSYFGSYGTDGVGYTVPVLKRELRHILGLNR KWGLCIVGMRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREEMMSVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 2-B12 | 39 | 0.22 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWGMVSKGEELFTGVVPIL VELDGDVNGHKFSVSGEGEGDATYGKLTLKFICTTGKLPVPWPTLVTTLTYGVQCFSRYPDHMKOHDFFKSAMP EGYVQERTIFFKDDGNYKTRAEVKFEGDTLVNRIELKGIDFKEDGNILGHKLEYNYNSHNVYIMADKOKNGIKV NFKIRHNIEDGSVQLADHYQQNTPIGDGPVLLPDNHYLSTQSKLSKDPNEKRDHMVLLEFVTAAGITLGMDEVP EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMGMVSVIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 2-B5 | 40 | 0.20 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEVPEAAISRLITYLRILEELEAQGVHRTASEQLGELAQVTAFQVDEDLSYFGSYGTDGVGYTVPVLKRELR HILGLNRKWGLCIVGMRLGSALADWPGFGESFELRGFFDVDPGMVGRPVRGGVIEHVDLLPQRVPGRIEIALL TVPREEAAQKAADLLVAAGIKGILNFAPVVLEVPKEVAVENVDFLAGLTRLSFAILNPKWREVIKPEMKMRYMD GSVNGHEFTIEGEGTGRPYEGHQEMTLRVTMAEGGPMPFAFDLVSHVFCYGHRVFTKYPEEIPDYFKQAFPEGL SWERSLEFEDGGSASVSAHISLRGNTFYHKSKFTGVNFPADGPIMQNQSVDWEPSTEKITASDGVLKGDVTMYL KLEGGGNHKCQFKTTYKAAKEILEMPGDHYIGHRLVRKTEGNITEQVEDAVAHSEASMDELYK |
| 2-F1 | 41 | 0.20 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWGMVSKGEELFTGVVPIL VELDGDVNGHKFSVSGEGEGDATYGKLTLKFICTTGKLPVPWPTLVTTLTYGVQCFSRYPDHMKQHDFFKSAMP |

TABLE 2-continued

| Full clone name | SEQ ID NO | Signal window (ex mode), measured in lysates | Full protein sequence |
|---|---|---|---|
| | | | EGYVQERTIFFKDDNYKTRAEVKFEGDTLVNRIELKGIDFKEDGNILGHKLEYNYNSHNVYIMADKQKNGIKV NFKIRHNIEDGSVQLADHYQQNTPIGDGPVLLPDNHYLSTQSKLSKDPNEKRDHMVLLEFVTAAGITLGMDEVP EAAISRLITYLRILEELEAQGVHRTASEQLGELAQVTAFQVDEDLSYFGSYGTDGVGYTVPVLKRELRHILGLN RKWGLCIVGMGRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMVSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 2-B4 | 42 | 0.20 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKOHDFFKSAMPEG YVQERTIFFKDDNYKTRAEVKFEGDTLVNRIELKGIDFKEDGNILGHKLEYNYNSHNVYIMADKOKNGIKVNF KIRHNIEDGSVQLADHYQQNTPIGDGPVLLPDNHYLSTQSKLSKDPNEKRDHMVLLEFVTAAGITLGMDEVPEA AISRLITYLRILEELEAQGVHRTASEQLGELAQVTAFQVDEDLSYFGSYGTDGVGYTVPVLKRELRHILGLNRK WGLCIVGMGRLGSALADWPGFGESFELRGFFDVDPGMVGRPVRGGVIEHVDLLPQRVPGRIEIALLTVPREAAQ KAADLLVAAGIKGILNFAPVVLEVPKEVAVENVDFLAGLTRLSFAILNPKWREEMMGMVSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 2-c7 | 43 | 0.20 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTGEELFTGVVPILVELDGD VNGHKFSVSGEGEGDATYGKLTLKFICTTGKLPVPWPTLVTTLTYGVQCFSRYPDHMKQHDFFKSAMPEGYVQE RTIFFKDDNYKTRAEVKFEGDTLVNRIELKGIDFKEDGNILGHKLEYNYNSHNVYIMADKOKNGIKVNFKIRH NIEDGSVQLADHYQQNTPIGDGPVLLPDNHYLSTQSKLSKDPNEKRDHMVLLEFVTAAGITLGMDEPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREESVIKPEMKMRYYMDGSVNGHEFTIE GEGTGRPYEGHQEMTLRVTMAEGGPMPFAFDLVSHVFCYGHRVFTKYPEEIPDYFKQAFPEGLSWERSLEFEDG GSASVSAHISLRGNTFYHSKFTGVNFPADGPIMQNQSVDWEPSTEKITASDGVLKGDVTMYLKLEGGGNHKCQ FKTTYKAAKEILEMPGDHYIGHRLVRKTEGNITEQVEDAVAHSEASMDELYK |
| 2-E4 | 44 | 0.19 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAHGMVSKGEELFTGVV PILVELDGDVNGHKFSVSGEGEGDATYGKLTLKFICTTGKLPVPWPTLVTTLTYGVQCFSRYPDHMKOHDFFKS AMPEGYVQERTIFFKDDNYKTRAEVKFEGDTLVNRIELKGIDFKEDGNILGHKLEYNYNSHNVYIMADKOKNG IKVNFKIRHNIEDGSVQLADHYQQNTPIGDGPVLLPDNHYLSTQSKLSKDPNEKRDHMVLLEFVTAAGITLEAA ISRLITYLRILEELEAQGVHRTASEQLGELAQVTAFQVDEDLSYFGSYGTDGVGYTVPVLKRELRHILGLNRKW GLCIVGMGRLGSALADWPGFGESFELRGFFDVDPGMVGRPVRGGVIEHVDLLPQRVPGRIEIALLTVPREAAQK AADLLVAAGIKGILNFAPVVLEVPKEVAVENVDFLAGLTRLSFAILNPKWREESVIKPEMKMRYYMDGSVNGHE FTIEGEGTGRPYEGHQEMTLRVTMAEGGPMPFAFDLVSHVFCYGHRVFTKYPEEIPDYFKQAFPEGLSWERSLE FEDGGSASVSAHISLRGNTFYHSKFTGVNFPADGPIMQNQSVDWEPSTEKITASDGVLKGDVTMYLKLEGGGN HKCQFKTTYKAAKEILEMPGDHYIGHRLVRKTEGNITEQVEDAVAHSEASMDELYK |
| 2-G12 | 45 | 0.19 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWMVSKGEELFTGVVPILV ELDGDVNGHKFSVSGEGEGDATYGKLTLKFICTTGKLPVPWPTLVTTLTYGVQCFSRYPDHMKOHDFFKSAMPE GYVQERTIFFKDDNYKTRAEVKFEGDTLVNRIELKGIDFKEDGNILGHKLEYNYNSHNVYIMADKQKNGIKVN FKIRHNIEDGSVQLADHYQQNTPIGDGPVLLPDNHYLSTQSKLSKDPNEKRDHMVLLEFVTAAGITLGMDEVPE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREESVIKPEMKMRYYMDGSVNG HEFTIEGEGTGRPYEGHQEMTLRVTMAEGGPMPFAFDLVSHVFCYGHRVFTKYPEEIPDYFKQAFPEGLSWERS LEFEDGGSASVSAHISLRGNTFYHSKFTGVNFPADGPIMQNQSVDWEPSTEKITASDGVLKGDVTMYLKLEGG GNHKCQFKTTYKAAKEILEMPGDHYIGHRLVRKTEGNITEQVEDAVAHSEASMDELYK |
| 3-H8 | 46 | 0.18 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGHGMVSKGEELFTG VVPILVELDGDVNGHKFSVSGEGEGDATYGKLTLKFICTTGKLPVPWPTLVTTLTYGVQCFSRYPDHMKOHDFF KSAMPEGYVQERTIFFKDDNYKTRAEVKFEGDTLVNRIELKGIDFKEDGNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDELYKVPEAAISRLITYLRILEELEAQGVHRTASEQLGELAQVTAFQVDEDLSYFGSYGTDGVGYTVPVLKRE LRHILGLNRKWGLCIVGMGRLGSALADWPGFGESFELRGFFDVDPGMVGRPVRGGVIEHVDLLPQRVPGRIEIA |

TABLE 2-continued

| Full clone name | SEQ ID NO | Signal window (ex mode), measured in lysates | Full protein sequence |
|---|---|---|---|
| | | | LLTVPREAAQKAADLLVAAGIKGILNFAPVVLEVPKEVAVENVDFLAGLTRLSFAILNPKWREIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 1-D6 | 47 | 0.18 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWMVSKGEELFTGVVPILV ELDGDVNGHKFSVSGEGEGDATYGKLTLKFICTTGKLPVPWPTLVTTLTYGVQCFSRYPDHMKOHDFFKSAMPE GYVQERTIFFKDDGNYKTRAEVKFEGDTLVNRIELKGIDFKEDGNILGHKLEYNYNSHNVYIMADKQKNGIKVN FKIRHNIEDGSVQLADHYQQNTPIGDGPVLLPDNHYLSTQSKLSKDPNEKRDHMVLLEFVTAAGITLGMDELYV PEAAISRLITYLRILEELEAQGVHRTASEQLGELAQVTAFQVDEDLSYFGSYGTDGVGYTVPVLKRELRHILGL NRKWGLCIVGMGRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREEMMVSVIKPEMKMRYYMD GSVNGHEFTIEGEGTGRPYEGHQEMTLRVTMAEGGPMPFAFDLVSHVFCYGHRVFTKYPEEIPDYFKQAFPEGL SWERSLEFEDGGSASVSAHISLRGNTFYHKSKFTGVNFPADGPIMQNQSVDWEPSTEKITASDGVLKGDVTMYL KLEGGGNHKCQFKTTYKAAKEILEMPGDHYIGHRLVRKTEGNITEQVEDAVAHSEASMDELYK |
| 1-E6 | 48 | 0.18 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTGEELFTGVVPILVELDGD VNGHKFSVSGEGEGDATYGKLTLKFICTTGKLPVPWPTLVTTLTYGVQCFSRYPDHMKQHDFFKSAMPEGYVQE RTIFFKDDGNYKTRAEVKFEGDTLVNRIELKGIDFKEDGNILGHKLEYNYNSHNVYIMADKQKNGIKVNFKIRH NIEDGSVQLADHYQQNTPIGDGPVLLPDNHYLSTQSKLSKDPNEKRDHMVLLEFVTAAGITLGMDEPEAAISRL ITYLRILEELEAQGVHRTASEQLGELAQVTAFQVDEDLSYFGSYGTDGVGYTVPVLKRELRHILGLNRKWGLCI VGMGRLGSALADWPGFGESFELRGFFDVDPGMVGRPVRGGVIEHVDLLPQRVPGRIEIALLTVPREAAQKAADL LVAAGIKGILNFAPVVLEVPKEVAVENVDFLAGLTRLSFAILNPKWREESVIKPEMKMRYYMDGSVNGHEFTIE GEGTGRPYEGHQEMTLRVTMAEGGPMPFAFDLVSHVFCYGHRVFTKYPEEIPDYFKQAFPEGLSWERSLEFEDG GSASVSAHISLRGNTFYHKSKFTGVNFPADGPIMQNQSVDWEPSTEKITASDGVLKGDVTMYLKLEGGGNHKCQ FKTTYKAAKEILEMPGDHYIGHRLVRKTEGNITEQVEDAVAHSEASMDELYK |
| 1-E7 | 49 | 0.18 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDFLAGLTRLSFAILNPKWREEVIKPEMKMRYYMDG SVNGHEFTIEGEGTGRPYEGHQEMTLRVTMAEGGPMPFAFDLVSHVFCYGHRVFTKYPEEIPDYFKOAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 1-D8 | 50 | 0.17 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDELYVPEAAISRLITYLRILEELEAQGVHRTASEQLGELAQVTAFQVDEDLSYFGSYGTDGVGYTVPVLKRE LRHILGLNRKWGLCIVGMGRLGSALADWPGFGESFELRGFFDVDPGMVGRPVRGGVIEHVDLLPQRVPGRIEIA LLTVPREAAQKAADLLVAAGIKGILNFAPVVLEVPKEVAVENVDFLAGLTRLSFAILNPKWREVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 2-A10 | 51 | 0.16 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMDELYKVPE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREEMGGSMVSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 2-D5 | 52 | 0.15 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV |

TABLE 2-continued

| Full clone name | SEQ ID NO | Signal window (ex mode), measured in lysates | Full protein sequence |
|---|---|---|---|
| | | | PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMDELYKVPE AAISRLITYLRILEELEAQGVHRTASEQLGELAQVTAFQVDEDLSYFGSYGTDGVGYTVPVLKRELRHILGLNR KWGLCIVGMRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREVIKPEMKMRYYMDGSVNGHE FTIEGEGTGRPYEGHQEMTLRVTMAEGGPMPFAFDLVSHVFCYGHRVFTKYPEEIPDYFKQAFPEGLSWERSLE FEDGGSASVSAHISLRGNTFYHKSKFTGVNFPADGPIMQNQSVDWEPSTEKITASDGVLKGDVTMYLKLEGGGN HKCQFKTTYKAAKEILEMPGDHYIGHRLVRKTEGNITEQVEDAVAHSEASMDELYK |
| 2-C11 | 53 | 0.15 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGHGMVSKGEELFTG VVPILVELDGDVNGHKFSVSGEGEGDATYGKLTLKFICTTGKLPVPWPTLVTTLTYGVQCFSRYPDHMKOHDFF KSAMPEGYVQERTIFFKDDGNYKTRAEVKFEGDTLVNRIELKGIDFKEDGNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREESVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 1-H7 | 54 | 0.14 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWMVSKGEELFTGVVPILV ELDGDVNGHKFSVSGEGEGDATYGKLTLKFICTTGKLPVPWPTLVTTLTYGVQCFSRYPDHMKOHDFFKSAMPE GYVQERTIFFKDDGNYKTRAEVKFEGDTLVNRIELKGIDFKEDGNILGHKLEYNYNSHNVYIMADKOKNGIKVN FKIRHNIEDGSVQLADHYQQNTPIGDGPVLLPDNHYLSTQSKLSKDPNEKRDHMVLLEFVTAAGITLGMDELYK VPEAAISRLITYLRILEELEAQGVHRTASEQLGELAQVTAFQVDEDLSYFGSYGTDGVGYTVPVLKRELRHILG LNRKWGLCIVGMRLGSALADWPGFGESFELRGFFDVDPGMVGRPVRGGVIEHVDLLPQRVPGRIEIALLTVPR EAAQKAADLLVAAGIKGILNFAPVVLEVPKEVAVENVDFLAGLTRLSFAILNPKWREEVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 2-F11 | 55 | 0.13 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLGMDELYKVPE AAISRLITYLRILEELEAQGVHRTASEQLGELAQVTAFQVDEDLSYFGSYGTDGVGYTVPVLKRELRHILGLNR KWGLCIVGMRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREEMMSVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 1-H11 | 56 | 0.13 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKOHDFFKSAMPEG YVQERTIFFKDDGNYKTRAEVKFEGDTLVNRIELKGIDFKEDGNILGHKLEYNYNSHNVYIMADKOKNGIKVNF KIRHNIEDGSVQLADHYQQNTPIGDGPVLLPDNHYLSTQSKLSKDPNEKRDHMVLLEFVTAAGITLGMDELVPE AAISRLITYLRILEELEAQGVHRTASEQLGELAQVTAFQVDEDLSYFGSYGTDGVGYTVPVLKRELRHILGLNR KWGLCIVGMRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREESVIKPEMKMRYYMDGSVNG HEFTIEGEGTGRPYEGHQEMTLRVTMAEGGPMPFAFDLVSHVFCYGHRVFTKYPEEIPDYFKQAFPEGLSWERS LEFEDGGSASVSAHISLRGNTFYHKSKFTGVNFPADGPIMQNQSVDWEPSTEKITASDGVLKGDVTMYLKLEGG GNHKCQFKTTYKAAKEILEMPGDHYIGHRLVRKTEGNITEQVEDAVAHSEASMDELYK |
| 1-D9 | 57 | 0.13 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKOKNGIKVNFKI RHNIEDGSVQLADHYQQNTPIGDGPVLLPDNHYLSTQSKLSKDPNEKRDHMVLLEFVTAAGITLGMEAAISRLI TYLRILEELEAQGVHRTASEQLGELAQVTAFQVDEDLSYFGSYGTDGVGYTVPVLKRELRHILGLNRKWGLCIV GMRLGSALADWPGFGESFELRGFFDVDPGMVGRPVRGGVIEHVDLLPQRVPGRIEIALLTVPREAAQKAADLL VAAGIKGILNFAPVVLEVPKEVAVENVDFLAGLTRLSFAILNPKWREEMMGSMVSVIKPEMKMRYYMDGSVNGH |

TABLE 2-continued

| Full clone name | SEQ ID NO | Signal window (ex mode), measured in lysates | Full protein sequence |
|---|---|---|---|
| | | | EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNQSVDWEPSTEKITASDGVLKGDVTMYLKLEGGG NHKCQFKTTYKAAKEILEMPGDHYIGHRLVRKTEGNITEQVEDAVAHSEASMDELYK |
| 1-G2 | 58 | 0.12 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGHGMVSKGEELFTG VVPILVELDGDVNGHKFSVSGEGEGDATYGKLTLKFICTTGKLPVPWPTLVTTLTYGVQCFSRYPDHMKOHDFF KSAMPEGYVQERTIFFKDDGNYKTRAEVKFEGDTLVNRIELKGIDFKEGDNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDELYKKVPEAAISRLITYLRILEELEAQGVHRTASEQLGELAQVTAFQVDEDLSYFGSYGTDGVGYTVPVLKR ELRHILGLNRKWGLCIVGMRLGSALADWPGFGESFELRGFFDVDPGMVGRPVRGGVIEHVDLLPQRVPGRIEI ALLTVPREEAAQKAADLLVAAGIKGILNFAPVVLEVPKEVAVENVDFLAGLTRLSFAILNPKWREESVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 1-A6 | 59 | 0.12 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDELYKVPEAAISRLITYLRILEELEAQGVHRTASEQLGELAQVTAFQVDEDLSYFGSYGTDGVGYTVPVLKR ELRHILGLNRKWGLCIVGMRLGSALADWPGFGESFELRGFFDVDPGMVGRPVRGGVIEHVDLLPQRVPGRIEI ALLTVPREEAAQKAADLLVAAGIKGILNFAPVVLEVPKEVAVENVDFLAGLTRLSFAILNPKWREIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 2-B10 | 60 | 0.12 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTGEELFTGVVPILVELDGD VNGHKFSVSGEGEGDATYGKLTLKFICTTGKLPVPWPTLVTTLTYGVQCFSRYPDHMKQHDFFKSAMPEGYVQE RTIFFKDDGNYKTRAEVKFEGDTLVNRIELKGIDFKEDGNILGHKLEYNYNSHNVYIMADKQKNGIKVNFKIRH NIEDGSVQLADHYQQNTPIGDGPVLLPDNHYLSTQSKLSKDPNEKRDHMVLLEFVTAAGITLGMDEPEAAISRL ITYLRILEELEAQGVHRTASEQLGELAQVTAFQVDEDLSYFGSYGTDGVGYTVPVLKRELRHILGLNRKWGLCI VGMRLGSALADWPGFGESFELRGFFDVDPGMVGRPVRGGVIEHVDLLPQRVPGRIEIALLTVPREEAAQKAADL LVAAGIKGILNFAPVVLEVPKEVAVENVDFLAGLTRLSFAILNPKWREEMMGSMVSVIKPEMKMRYYMDGSVNG HEFTIEGEGTGRPYEGHQEMTLRVTMAEGGPMPFAFDLVSHVFCYGHRVFTKYPEEIPDYFKQAFPEGLSWERS LEFEDGGSASVSAHISLRGNTFYHKSKFTGVNFPADGPIMQNQSVDWEPSTEKITASDGVLKGDVTMYLKLEGG GNHKCQFKTTYKAAKEILEMPGDHYIGHRLVRKTEGNITEQVEDAVAHSEASMDELYK |
| 1-F1 | 61 | 0.12 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKOHDFFKSAMPEG YVQERTIFFKDDGNYKTRAEVKFEGDTLVNRIELKGIDFKEDGNILGHKLEYNYNSHNVYIMADKQKNGIKVNF KIRHNIEDGSVQLADHYQQNTPIGDGPVLLPDNHYLSTQSKLSKDPNEKRDHMVLLEFVTAAGITLGMDELYKV PEAAISRLITYLRILEELEAQGVHRTASEQLGELAQVTAFQVDEDLSYFGSYGTDGVGYTVPVLKRELRHILGL NRKWGLCIVGMRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREEMSVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNQSVDWEPSTEKITASDGVLKGDVTMYLKL EGGGNHKCQFKTTYKAAKEILEMPGDHYIGHRLVRKTEGNITEQVEDAVAHSEASMDELYK |
| 2-B2 | 62 | 0.12 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAHGMVSKGEELFTGVV PILVELDGDVNGHKFSVSGEGEGDATYGKLTLKFICTTGKLPVPWPTLVTTLTYGVQCFSRYPDHMKOHDFFKS AMPEGYVQERTIFFKDDGNYKTRAEVKFEGDTLVNRIELKGIDFKEDGNILGHKLEYNYNSHNVYIMADKOKNG IKVNFKIRHNIEDGSVQLADHYQQNTPIGDGPVLLPDNHYLSTQSKLSKDPNEKRDHMVLLEFVTAAGITLGMD ELVPEAAISRLITYLRILEELEAQGVHRTASEQLGELAQVTAFQVDEDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDFLAGLTRLSFAILNPKWREEMMGMVSVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 1-F9 | 63 | 0.11 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT |

TABLE 2-continued

| Full clone name | SEQ ID NO | Signal window (ex mode), measured in lysates | Full protein sequence |
|---|---|---|---|
| | | | GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMEAAISRLITYLRILEELEAQGVHRTASEQLGELAQVTAFQVDEDLSYFGSYGTDGVGYTVPVLKRELRHILG LNRKWGLCIVGMGRLGSALADWPGFGESFELRGFFDVDPGMVGRPVRGGVIEHVDLLPQRVPGRIEIALLTVPR EAAQKAADLLVAAGIKGILNFAPVVLEVPKEVAVENVDFLAGLTRLSFAILNPKWREESVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNSVDWEPSTEKITASDGVLKGDVTMYLKL EGGGNHKCQFKTTYKAAKEILEMPGDHYIGHRLVRKTEGNITEQVEDAVAHSEASMDELYK |
| 1-G4 | 64 | 0.11 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREEVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNSVDWEPSTEKITASDGVLKGDVTMYLKLEGGG NHKCQFKTTYKAAKEILEMPGDHYIGHRLVRKTEGNITEQVEDAVAHSEASMDELYK |
| 1-H3 | 65 | 0.11 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAHGMVSKGEELFTGVV PILVELDGDVNGHKFSVSGEGEGDATYGKLTLKFICTTGKLPVPWPTLVTTLTYGVQCFSRYPDHMKQHDFFKS AMPEGYVQERTIFFKDDGNYKTRAEVKFEGDTLVNRIELKGIDFKEDGNILGHKLEYNYNSHNVYIMADKQKNG IKVNFKIRHNIEDGSVQLADHYQQNTPIGDGPVLLPDNHYLSTQSKLSKDPNEKRDHMVLLEFVTAAGITLGMD EVPEAAISRLITYLRILEELEAQGVHRTASEQLGELAQVTAFQVDEDLSYFGSYGTDGVGYTVPVLKRELRHIL GLNRKWGLCIVGMGRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMVSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNSVDWEPSTEKITASDGVLKGDVTM YLKLEGGGNHKCQFKTTYKAAKEILEMPGDHYIGHRLVRKTEGNITEQVEDAVAHSEASMDELYK |
| 1-H1 | 66 | 0.11 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREESVIKPEMKMRYYMDGSVNG HEFTIEGEGTGRPYEGHQEMTLRVTMAEGGPMPFAFDLVSHVFCYGHRVFTKYPEEIPDYFKQAFPEGLSWERS LEFEDGGSASVSAHISLRGNTFYHKSKFTGVNFPADGPIMQNSVDWEPSTEKITASDGVLKGDVTMYLKLEGG GNHKCQFKTTYKAAKEILEMPGDHYIGHRLVRKTEGNITEQVEDAVAHSEASMDELYK |
| 1-D1 | 67 | 0.11 | LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKQHDFFKSA MPEGYVQERTIFFKDDGNYKTRAEVKFEGDTLVNRIELKGIDFKEDGNILGHKLEYNYNSHNVYIMADKQKNGI KVNFKIRHNIEDGSVQLADHYQQNTPIGDGPVLLPDNHYLSTQSKLSKDPNEKRDHMVLLEFVTAAGITLGMDE LYVPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMMGSMVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNSVDWEPSTEKITASDGVLKG DVTMYLKLEGGGNHKCQFKTTYKAAKEILEMPGDHYIGHRLVRKTEGNITEQVEDAVAHSEASMDELYK |
| 1-G12 | 68 | 0.11 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DPEAAISRLITYLRILEELEAQGVHRTASEQLGELAQVTAFQVDEDLSYFGSYGTDGVGYTVPVLKRELRHILG LNRKWGLCIVGMGRLGSALADWPGFGESFELRGFFDVDPGMVGRPVRGGVIEHVDLLPQRVPGRIEIALLTVPR |

TABLE 2-continued

| Full clone name | SEQ ID NO | Signal window (ex mode), measured in lysates | Full protein sequence |
|---|---|---|---|
| | | | EAAQKAADLLVAAGIKGILNFAPVVLEVPKEVAVENVDFLAGLTRLSFAILNPKWREEMSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 2-E11 | 69 | 0.11 | MKVPEAAISRLITYLRILEELEAQGVHRTASEQLGELAQVTAFQVDKDLSYFSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DEPEAAISRLITYLRILEELEAQGVHRTASEQLGELAQVTAFQVDEDLSYFGSYGTDGVGYTVPVLKRELRHIL GLNRKWGLCIVGMGRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREESVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 2-C8 | 70 | 0.11 | MKVPEAAISRLITYLRILEELEAQGVHRTASEQLGELAQVTAFQVDKDLSYFSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKQHDFFKSA MPEGYVQERTIFFKDDGNYKTRAEVKFEGDTLVNRIELKGIDFKEDGNILGHKLEYNYNSHNVYIMADKOKNGI KVNFKIRHNIEDGSVQLADHYQQNTPIGDGPVLLPDNHYLSTQSKLSKDPNEKRDHMVLLEFVTAAGITLGMDE LYVPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMMGMVSVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 1-D11 | 71 | 0.10 | MKVPEAAISRLITYLRILEELEAQGVHRTASEQLGELAQVTAFQVDKDLSYFSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWVSKGEELFTGVVPILVE LDGDVNGHKFSVSGEGEGDATYGKLTLKFICTTGKLPVPWPTLVTTLTYGVQCFSRYPDHMKOHDFFKSAMPEG YVQERTIFFKDDGNYKTRAEVKFEGDTLVNRIELKGIDFKEDGNILGHKLEYNYNSHNVYIMADKQKNGIKVNF KIRHNIEDGSVQLADHYQQNTPIGDGPVLLPDNHYLSTQSKLSKDPNEKRDHMVLLEFVTAAGITLGMDELYVP EAAISRLITYLRILEELEAQGVHRTASEQLGELAQVTAFQVDEDLSYFGSYGTDGVGYTVPVLKRELRHILGLN RKWGLCIVGMGRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMVSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 1-H8 | 72 | 0.10 | MKVPEAAISRLITYLRILEELEAQGVHRTASEQLGELAQVTAFQVDKDLSYFSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSGMVSKGEELFTGVVPI LVELDGDVNGHKFSVSGEGEGDATYGKLTLKFICTTGKLPVPWPTLVTTLTYGVQCFSRYPDHMKQHDFFKSAM PEGYVQERTIFFKDDGNYKTRAEVKFEGDTLVNRIELKGIDFKEDGNILGHKLEYNYNSHNVYIMADKQKNGIK VNFKIRHNIEDGSVQLADHYQQNTPIGDGPVLLPDNHYLSTQSKLSKDPNEKRDHMVLLEFVTAAGITLGMDEL YVPEAAISRLITYLRILEELEAQGVHRTASEQLGELAQVTAFQVDEDLSYFGSYGTDGVGYTVPVLKRELRHIL GLNRKWGLCIVGMGRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGSMVSVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 1-E4 | 73 | 0.10 | MKVPEAAISRLITYLRILEELEAQGVHRTASEQLGELAQVTAFQVDKDLSYFSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWGMVSKGEELFTGVVPIL VELDGDVNGHKFSVSGEGEGDATYGKLTLKFICTTGKLPVPWPTLVTTLTYGVQCFSRYPDHMKQHDFFKSAMP EGYVQERTIFFKDDGNYKTRAEVKFEGDTLVNRIELKGIDFKEDGNILGHKLEYNYNSHNVYIMADKOKNGIKV NFKIRHNIEDGSVQLADHYQQNTPIGDGPVLLPDNHYLSTQSKLSKDPNEKRDHMVLLEFVTAAGITLGMDELY KVPEAAISRLITYLRILEELEAQGVHRTASEQLGELAQVTAFQVDEDLSYFGSYGTDGVGYTVPVLKRELRHIL GLNRKWGLCIVGMGRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGVSVIKPEMKMRY YMDGSVNGHEFTIEGEGTGRPYEGHQEMTLRVTMAEGGPMPFAFDLVSHVFCYGHRVFTKYPEEIPDYFKQAFP EGLSWERSLEFEDGGSASVSAHISLRGNTFYHKSKFTGVNFPADGPIMQNQSVDWEPSTEKITASDGVLKGDVT MYLKLEGGGNHKCQFKTTYKAAKEILEMPGDHYIGHRLVRKTEGNITEQVEDAVAHSEASMDELYK |
| 1-A10 | 74 | 0.10 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV |

TABLE 2-continued

| Full clone name | SEQ ID NO | Signal window (ex mode), measured in lysates | Full protein sequence |
|---|---|---|---|
| | | | PREAAQKAADLLVAAGIKGILNFAPVVLEVPKEVAVENVDILAGLTRLSFAILNPTWSAAGGHGMVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMDPEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-D4 | 75 | 0.10 | MKVPEAAISRLITYLRILEELEAQGVHRTASEQLGELAQVTAFQVDKDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDILAGLTRLSFAILNPTSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMVSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-H5 | 76 | 0.10 | MKVPEAAISRLITYLRILEELEAQGVHRTASEQLGELAQVTAFQVDKDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDILAGLTRLSFAILNPTSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREESVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 2-E6 | 77 | 0.10 | MKVPEAAISRLITYLRILEELEAQGVHRTASEQLGELAQVTAFQVDKDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDILAGLTRLSFAILNPTGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMDPEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMGVSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-G3 | 78 | 0.10 | MKVPEAAISRLITYLRILEELEAQGVHRTASEQLGELAQVTAFQVDKDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDILAGLTRLSFAILNPTGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-G9 | 79 | 0.09 | MKVPEAAISRLITYLRILEELEAQGVHRTASEQLGELAQVTAFQVDKDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDILAGLTRLSFAILNPTGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMDEVPEAAISRLITYLRILEELEAQGVHRTASEQLGELAQVTAFQVDEDLSYFGSYGTDGVGYTVPVLKRELRHILGLNRKWGLCIVGMRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMSVIKPEMKMRYYMDGSVNGHEF |

TABLE 2-continued

| Full clone name | SEQ ID NO | Signal window (ex mode), measured in lysates | Full protein sequence |
|---|---|---|---|
| | | | TIEGEGTGRPYEGHQEMTLRVTMAEGGPMPFAFDLVSHVFCYGHRVFTKYPEEIPDYFKQAFPEGLSWERSLEF EDGGSASVSAHISLRGNTFYHKSKFTGVNFPADGPIMQNQSVDWEPSTEKITASDGVLKGDVTMYLKLEGGGNH KCQFKTTYKAAKEILEMPGDHYIGHRLVRKTEGNITEQVEDAVAHSEASMDELYK |
| 1-c4 | 80 | 0.09 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSGMVSKGEELFTGVVPI LVELDGDVNGHKFSVSGEGEGDATYGKLTLKFICTTGKLPVPWPTLVTTLTYGVQCFSRYPDHMKQHDFFKSAM PEGYVQERTIFFKDDGNYKTRAEVKFEGDTLVNRIELKGIDFKEDGNILGHKLEYNYNSHNVYIMADKQKNGIK VNFKIRHNIEDGSVQLADHYQQNTPIGDGPVLLPDNHYLSTQSKLSKDPNEKRDHMVLLEFVTAAGITLGMDEP EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMGVSVIKPEMKMRYYMD GSVNGHEFTIEGEGTGRPYEGHQEMTLRVTMAEGGPMPFAFDLVSHVFCYGHRVFTKYPEEIPDYFKQAFPEGL SWERSLEFEDGGSASVSAHISLRGNTFYHKSKFTGVNFPADGPIMQNQSVDWEPSTEKITASDGVLKGDVTMYL KLEGGGNHKCQFKTTYKAAKEILEMPGDHYIGHRLVRKTEGNITEQVEDAVAHSEASMDELYK |
| 1-B2 | 81 | 0.09 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKOHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLAA ISRLITYLRILEELEAQGVHRTASEQLGELAQVTAFQVDEDLSYFGSYGTDGVGYTVPVLKRELRHILGLNRKW GLCIVGMRLGSALADWPGFGESFELRGFFDVDPGMVGRPVRGGVIEHVDLLPQRVPGRIEIALLTVPREAAQK AADLLVAAGIKGILNFAPVVLEVPKEVAVENVDFLAGLTRLSFAILNPKWREVIKPEMKMRYYMDGSVNGHEFT IEGEGTGRPYEGHQEMTLRVTMAEGGPMPFAFDLVSHVFCYGHRVFTKYPEEIPDYFKQAFPEGLSWERSLEFE DGGSASVSAHISLRGNTFYHKSKFTGVNFPADGPIMQNQSVDWEPSTEKITASDGVLKGDVTMYLKLEGGGNHK CQFKTTYKAAKEILEMPGDHYIGHRLVRKTEGNITEQVEDAVAHSEASMDELYK |
| 2-B1 | 82 | 0.09 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREEMMGVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSEASMDELYK |
| 2-E3 | 83 | 0.08 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKOHDFFKSA MPEGYVQERTIFFKDDGNYKTRAEVKFEGDTLVNRIELKGIDFKEDGNILGHKLEYNYNSHNVYIMADKOKNGI KVNFKIRHNIEDGSVQLADHYQQNTPIGDGPVLLPDNHYLSTQSKLSKDPNEKRDHMVLLEFVTAAGITLGMDP EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMGVSVIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 2-F5 | 84 | 0.08 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREEMMGVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSEASMDELYK |
| 1-F12 | 85 | 0.08 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT |

TABLE 2-continued

| Full clone name | SEQ ID NO | Signal window (ex mode), measured in lysates | Full protein sequence |
|---|---|---|---|
| | | | GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMGRLGSALADWPGFGESFELRGFFDVDPGMVGRPVRGGVIEHVDLLPQRVPGRIEIALLT VPREEAAQKAADLLVAAGIKGILNFAPVVLEVPKEVAVENVDFLAGLTRLSFAILNPKWREEMSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 1-C2 | 86 | 0.08 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSHGMVSKGEELFTGVVP ILVELDGDVNGHKFSVSGEGEGDATYGKLTLKFICTTGKLPVPWPTLVTTLTYGVQCFSRYPDHMKQHDFFKSA MPEGYVQERTIFFKDDGNYKTRAEVKFEGDTLVNRIELKGIDFKEDGNILGHKLEYNYNSHNVYIMADKQKNGI KVNFKIRHNIEDGSVQLADHYQQNTPIGDGPVLLPDNHYLSTQSKLSKDPNEKRDHMVLLEFVTAAGITLGMDE PEAAISRLITYLRILEELEAQGVHRTASEQLGELAQVTAFQVDEDLSYFGSYGTDGVGYTVPVLKRELRHILGL NRKWGLCIVGMGRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREEMMGGSMVSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 2-A3 | 87 | 0.08 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEVPEAAISRLITYLRILEELEAQGVHRTASEQLGELAQVTAFQVDEDLSYFGSYGTDGVGYTVPVLKRELR HILGLNRKWGLCIVGMGRLGSALADWPGFGESFELRGFFDVDPGMVGRPVRGGVIEHVDLLPQRVPGRIEIALL TVPREAAQKAADLLVAAGIKGILNFAPVVLEVPKEVAVENVDFLAGLTRLSFAILNPKWREEMMGMVSVIKPEM KMRYYMDGSVNGHEFTIEGEGTGRPYEGHQEMTLRVTMAEGGPMPFAFDLVSHVFCYGHRVFTKYPEEIPDYFK QAFPEGLSWERSLEFEDGGSASVSAHISLRGNTFYHKSKFTGVNFPADGPIMQNQSVDWEPSTEKITASDGVLK GDVTMYLKLEGGGNHKCQFKTTYKAAKEILEMPGDHYIGHRLVRKTEGNITEQVEDAVAHSEASMDELYK |
| 1-H9 | 88 | 0.08 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGHGMVSKGEELFTG VVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKQK NGIKVNFKIRHNIEDGSVQLADHYQQNTPIGDGPVLLPDNHYLSTQSKLSKDPNEKRDHMVLLEFVTAAGITLG MDELVPEAAISRLITYLRILEELEAQGVHRTASEQLGELAQVTAFQVDEDLSYFGSYGTDGVGYTVPVLKRELR HILGLNRKWGLCIVGMGRLGSALADWPGFGESFELRGFFDVDPGMVGRPVRGGVIEHVDLLPQRVPGRIEIALL TVPREAAQKAADLLVAAGIKGILNFAPVVLEVPKEVAVENVDFLAGLTRLSFAILNPKWREEMMVSVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 2-C2 | 89 | 0.08 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAHGMVSKGEELFTGVV PILVELDGDVNGHKFSVSGEGEGDATYGKLTLKFICTTGKLPVPWPTLVTTLTYGVQCFSRYPDHMKQHDFFKS AMPEGYVQERTIFFKDDGNYKTRAEVKFEGDTLVNRIELKGIDFKEDGNILGHKLEYNYNSHNVYIMADKQKNG IKVNFKIRHNIEDGSVQLADHYQQNTPIGDGPVLLPDNHYLSTQSKLSKDPNEKRDHMVLLEFVTAAGITLGMD ELYVPEAAISRLITYLRILEELEAQGVHRTASEQLGELAQVTAFQVDEDLSYFGSYGTDGVGYTVPVLKRELRH ILGLNRKWGLCIVGMGRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREEMMGMVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSEASMDELYK |
| 1-A11 | 90 | 0.07 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGHGMVSKGEELFTG VVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKQK NGIKVNFKIRHNIEDGSVQLADHYQQNTPIGDGPVLLPDNHYLSTQSKLSKDPNEKRDHMVLLEFVTAAGITLG MDEPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMMVSVIKPEMKMRY YMDGSVNGHEFTIEGEGTGRPYEGHQEMTLRVTMAEGGPMPFAFDLVSHVFCYGHRVFTKYPEEIPDYFKQAFP |

TABLE 2-continued

| Full clone name | SEQ ID NO | Signal window (ex mode), measured in lysates | Full protein sequence |
|---|---|---|---|
| | | | EGLSWERSLEFEDGGSASVSAHISLRGNTFYHKSKFTGVNFPADGPIMQNQSVDWEPSTEKITASDGVLKGDVT<br>MYLKLEGGGNHKCQFKTTYKAAKEILEMPGDHYIGHRLVRKTEGNITEQVEDAVAHSEASMDELYK |
| 1-D3 | 91 | 0.07 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWGMVSKGEELFTGVVPIL<br>VELDGDVNGHKFSVSGEGEGDATYGKLTLKFICTTGKLPVPWPTLVTTLTYGVQCFSRYPDHMKQHDFFKSAMP<br>EGYVQERTIFFKDDGNYKTRAEVKFEGDTLVNRIELKGIDFKEDGNILGHKLEYNYNSHNVYIMADKOKNGIKV<br>NFKIRHNIEDGSVQLADHYQQNTPIGDGPVLLPDNHYLSTQSKLSKDPNEKRDHMVLLEFVTAAGITLGEAAIS<br>RLITYLRILEELEAQGVHRTASEQLGELAQVTAFQVDEDLSYFGSYGTDGVGYTVPVLKRELRHILGLNRKWGL<br>CIVGMGRLGSALADWPGFGESFELRGFFDVDPGMVGRPVRGGVIEHVDLLPQRVPGRIEIALLTVPREAAQKAA<br>DLLVAAGIKGILNFAPVVLEVPKEVAVENVDFLAGLTRLSFAILNPKWREESVIKPEMKMRYYMDGSVNGHEFT<br>IEGEGTGRPYEGHQEMTLRVTMAEGGPMPFAFDLVSHVFCYGHRVFTKYPEEIPDYFKQAFPEGLSWERSLEFE<br>DGGSASVSAHISLRGNTFYHKSKFTGVNFPADGPIMQNQSVDWEPSTEKITASDGVLKGDVTMYLKLEGGGNHK<br>CQFKTTYKAAKEILEMPGDHYIGHRLVRKTEGNITEQVEDAVAHSEASMDELYK |
| 2-F10 | 92 | 0.06 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTGEELFTGVVPILVELDGD<br>VNGHKFSVSGEGEGDATYGKLTLKFICTTGKLPVPWPTLVTTLTYGVQCFSRYPDHMKQHDFFKSAMPEGYVQE<br>RTIFFKDDGNYKTRAEVKFEGDTLVNRIELKGIDFKEDGNILGHKLEYNYNSHNVYIMADKQKNGIKVNFKIRH<br>NIEDGSVQLADHYQQNTPIGDGPVLLPDNHYLSTQSKLSKDPNEKRDHMVLLEFVTAAGITLGMDELYKVPEAA<br>ISRLITYLRILEELEAQGVHRTASEQLGELAQVTAFQVDEDLSYFGSYGTDGVGYTVPVLKRELRHILGLNRKW<br>GLCIVGMGRLGSALADWPGFGESFELRGFFDVDPGMVGRPVRGGVIEHVDLLPQRVPGRIEIALLTVPREAAQK<br>AADLLVAAGIKGILNFAPVVLEVPKEVAVENVDFLAGLTRLSFAILNPKWREEMMSVIKPEMKMRYYMDGSVNG<br>HEFTIEGEGTGRPYEGHQEMTLRVTMAEGGPMPFAFDLVSHVFCYGHRVFTKYPEEIPDYFKQAFPEGLSWERS<br>LEFEDGGSASVSAHISLRGNTFYHKSKFTGVNFPADGPIMQNQSVDWEPSTEKITASDGVLKGDVTMYLKLEGG<br>GNHKCQFKTTYKAAKEILEMPGDHYIGHRLVRKTEGNITEQVEDAVAHSEASMDELYK |
| 2-G6 | 93 | 0.06 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTSKGEELFTGVVPILVELD<br>GDVNGHKFSVSGEGEGDATYGKLTLKFICTTGKLPVPWPTLVTTLTYGVQCFSRYPDHMKQHDFFKSAMPEGYV<br>QERTIFFKDDGNYKTRAEVKFEGDTLVNRIELKGIDFKEDGNILGHKLEYNYNSHNVYIMADKQKNGIKVNFKI<br>RHNIEDGSVQLADHYQQNTPIGDGPVLLPDNHYLSTOSKLSKDPNEKRDHMVLLEFVTAAGITLGEAAISRLIT<br>YLRILEELEAQGVHRTASEQLGELAQVTAFQVDEDLSYFGSYGTDGVGYTVPVLKRELRHILGLNRKWGLCIVG<br>MGRLGSALADWPGFGESFELRGFFDVDPGMVGRPVRGGVIEHVDLLPQRVPGRIEIALLTVPREAAQKAADLLV<br>AAGIKGILNFAPVVLEVPKEVAVENVDFLAGLTRLSFAILNPKWREEMMSVIKPEMKMRYYMDGSVNGHEFTIE<br>GEGTGRPYEGHQEMTLRVTMAEGGPMPFAFDLVSHVFCYGHRVFTKYPEEIPDYFKQAFPEGLSWERSLEFEDG<br>GSASVSAHISLRGNTFYHKSKFTGVNFPADGPIMQNQSVDWEPSTEKITASDGVLKGDVTMYLKLEGGGNHKCQ<br>FKTTYKAAKEILEMPGDHYIGHRLVRKTEGNITEQVEDAVAHSEASMDELYK |
| 1-c5 | 95 | 0.06 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSAAGGHGMVSKGEELFT<br>GVVPILVELDGDVNGHKFSVSGEGEGDATYGKLTLKFICTTGKLPVPWPTLVTTLTYGVQCFSRYPDHMKQHDF<br>FKSAMPEGYVQERTIFFKDDGNYKTRAEVKFEGDTLVNRIELKGIDFKEDGNILGHKLEYNYNSHNVYIMADKQ<br>KNGIKVNFKIRHNIEDGSVQLADHYQQNTPIGDGPVLLPDNHYLSTQSKLSKDPNEKRDHMVLLEFVTAAGITL<br>GMEAAISRLITYLRILEELEAQGVHRTASEQLGELAQVTAFQVDEDLSYFGSYGTDGVGYTVPVLKRELRHILG<br>LNRKWGLCIVGMGRLGSALADWPGFGESFELRGFFDVDPGMVGRPVRGGVIEHVDLLPQRVPGRIEIALLTVPR<br>EAAQKAADLLVAAGIKGILNFAPVVLEVPKEVAVENVDFLAGLTRLSFAILNPKWREEMMGMVSVIKPEMKMRY<br>YMDGSVNGHEFTIEGEGTGRPYEGHQEMTLRVTMAEGGPMPFAFDLVSHVFCYGHRVFTKYPEEIPDYFKQAFP<br>EGLSWERSLEFEDGGSASVSAHISLRGNTFYHKSKFTGVNFPADGPIMQNQSVDWEPSTEKITASDGVLKGDVT<br>MYLKLEGGGNHKCQFKTTYKAAKEILEMPGDHYIGHRLVRKTEGNITEQVEDAVAHSEASMDELYK |
| 2-A7 | 96 | 0.06 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTSKGEELFTGVVPILVELD<br>GDVNGHKFSVSGEGEGDATYGKLTLKFICTTGKLPVPWPTLVTTLTYGVQCFSRYPDHMKQHDFFKSAMPEGYV<br>QERTIFFKDDGNYKTRAEVKFEGDTLVNRIELKGIDFKEDGNILGHKLEYNYNSHNVYIMADKOKNGIKVNFKI<br>RHNIEDGSVQLADHYQQNTPIGDGPVLLPDNHYLSTQSKLSKDPNEKRDHMVLLEFVTAAGITLGMDPEAAISR<br>LITYLRILEELEAQGVHRTASEQLGELAQVTAFQVDEDLSYFGSYGTDGVGYTVPVLKRELRHILGLNRKWGLC<br>IVGMGRLGSALADWPGFGESFELRGFFDVDPGMVGRPVRGGVIEHVDLLPQRVPGRIEIALLTVPREAAQKAAD<br>LLVAAGIKGILNFAPVVLEVPKEVAVENVDFLAGLTRLSFAILNPKWREEMMSVIKPEMKMRYYMDGSVNGHEF<br>TIEGEGTGRPYEGHQEMTLRVTMAEGGPMPFAFDLVSHVFCYGHRVFTKYPEEIPDYFKQAFPEGLSWERSLEF<br>EDGGSASVSAHISLRGNTFYHKSKFTGVNFPADGPIMQNQSVDWEPSTEKITASDGVLKGDVTMYLKLEGGGNH<br>KCQFKTTYKAAKEILEMPGDHYIGHRLVRKTEGNITEQVEDAVAHSEASMDELYK |
| 1-C12 | 97 | 0.06 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSAAGGHGMVSKGEELFT<br>GVVPILVELDGDVNGHKFSVSGEGEGDATYGKLTLKFICTTGKLPVPWPTLVTTLTYGVQCFSRYPDHMKQHDF |

TABLE 2-continued

| Full clone name | SEQ ID NO | Signal window (ex mode), measured in lysates | Full protein sequence |
|---|---|---|---|
| | | | FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEVPEAAISRLITYLRILEELEAQGVHRTASEQLGELAQVTAFQVDEDLSYFGSYGTDGVGYTVPVLKRELR HILGLNRKWGLCIVGMGRLGSALADWPGFGESFELRGFFDVDPGMVGRPVRGGVIEHVDLLPQRVPGRIEIALL TVPREAAQKAADLLVAAGIKILNFAPVVLEVPKEVAVENVDFLAGLTRLSFAILNPKWREEMMGVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSEASMDELYK |
| 2-H7 | 98 | 0.06 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAHGMVSKGEELFTGVV PILVELDGDVNGHKFSVSGEGEGDATYGKLTLKFICTTGKLPVPWPTLVTTLTYGVQCFSRYPDHMKOHDFFKS AMPEGYVQERTIFFKDDGNYKTRAEVKFEGDTLVNRIELKGIDFKEDGNILGHKLEYNYNSHNVYIMADKOKNG IKVNFKIRHNIEDGSVQLADHYQQNTPIGDGPVLLPDNHYLSTQSKLSKDPNEKRDHMVLLEFVTAAGITLGMD ELYVPEAAISRLITYLRILEELEAQGVHRTASEQLGELAQVTAFQVDEDLSYFGSYGTDGVGYTVPVLKRELRH ILGLNRKWGLCIVGMGRLGSALADWPGFGESFELRGFFDVDPGMVGRPVRGGVIEHVDLLPQRVPGRIEIALLT VPREAAQKAADLLVAAGIKILNFAPVVLEVPKEVAVENVDFLAGLTRLSFAILNPKWREEMMGSMVSVIKPEM KMRYYMDGSVNGHEFTIEGEGTGRPYEGHQEMTLRVTMAEGGPMPFAFDLVSHVFCYGHRVFTKYPEEIPDYFK QAFPEGLSWERSLEFEDGGSASVSAHISLRGNTFYHKSKFTGVNFPADGPIMQNQSVDWEPSTEKITASDGVLK GDVTMYLKLEGGGNHKCQFKTTYKAAKEILEMPGDHYIGHRLVRKTEGNITEQVEDAVAHSEASMDELYK |
| 1-B8 | 99 | 0.05 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKILNFAPVVLEVPKEVAVENVDFLAGLTRLSFAILNPKWREEMSVIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 2-F9 | 100 | 0.05 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSGMVSKGEELFTGVVPI LVELDGDVNGHKFSVSGEGEGDATYGKLTLKFICTTGKLPVPWPTLVTTLTYGVQCFSRYPDHMKOHDFFKSAM PEGYVQERTIFFKDDGNYKTRAEVKFEGDTLVNRIELKGIDFKEDGNILGHKLEYNYNSHNVYIMADKQKNGIK VNFKIRHNIEDGSVQLADHYQQNTPIGDGPVLLPDNHYLSTQSKLSKDPNEKRDHMVLLEFVTAAGITLGMDEL YKVPEAAISRLITYLRILEELEAQGVHRTASEQLGELAQVTAFQVDEDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKILNFAPVVLEVPKEVAVENVDFLAGLTRLSFAILNPKWREEMMVSVIKPEMKMRY YMDGSVNGHEFTIEGEGTGRPYEGHQEMTLRVTMAEGGPMPFAFDLVSHVFCYGHRVFTKYPEEIPDYFKQAFP EGLSWERSLEFEDGGSASVSAHISLRGNTFYHKSKFTGVNFPADGPIMQNQSVDWEPSTEKITASDGVLKGDVT MYLKLEGGGNHKCQFKTTYKAAKEILEMPGDHYIGHRLVRKTEGNITEQVEDAVAHSEASMDELYK |
| 2-E8 | 101 | 0.05 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKOHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMGRLGSALADWPGFGESFELRGFFDVDPGMVGRPVRGGVIEHVDLLPQRVPGRIEIALLT VPREAAQKAADLLVAAGIKILNFAPVVLEVPKEVAVENVDFLAGLTRLSFAILNPKWREEMMVSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 2-B11 | 102 | 0.05 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTSKGEELFTGVVPILVELD GDVNGHKFSVSGEGEGDATYGKLTLKFICTTGKLPVPWPTLVTTLTYGVQCFSRYPDHMKOHDFFKSAMPEGYV QERTIFFKDDGNYKTRAEVKFEGDTLVNRIELKGIDFKEDGNILGHKLEYNYNSHNVYIMADKQKNGIKVNFKI RHNIEDGSVQLADHYQQNTPIGDGPVLLPDNHYLSTQSKLSKDPNEKRDHMVLLEFVTAAGITLAAISRLITYL RILEELEAQGVHRTASEQLGELAQVTAFQVDEDLSYFGSYGTDGVGYTVPVLKRELRHILGLNRKWGLCIVGMG RLGSALADWPGFGESFELRGFFDVDPGMVGRPVRGGVIEHVDLLPQRVPGRIEIALLTVPREAAQKAADLLVAA |

TABLE 2-continued

| Full clone name | SEQ ID NO | Signal window (ex mode), measured in lysates | Full protein sequence |
|---|---|---|---|
| | | | GIKGILNFAPVVLEVPKEVAVENVDFLAGLTRLSFAILNPKWREEVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-B1 | 103 | 0.05 | MKVPEAAISRLITYLRILEELEAQGVHRTASEQLGELAQVTAFQVDKDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREEAAQKAADLLVAAGIKGILNFAPVVLEVPKEVAVENVDILAGLTRLSFAILNPTWSAHGMVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNLGHKLEYNYNSHNVYIMADKOKNGIKVNFKIRHNIEDGSVQLADHYQQNTPIGDGPVLLPDNHYLSTQSKLSKDPNEKRDHMVLLEFVTAAGITLGMDELYKVPEAAISRLITYLRILEELEAQGVHRTASEQLGELAQVTAFQVDEDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-c7 | 104 | 0.05 | MKVPEAAISRLITYLRILEELEAQGVHRTASEQLGELAQVTAFQVDKDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREEAAQKAADLLVAAGIKGILNFAPVVLEVPKEVAVENVDILAGLTRLSFAILNPTWSAAGGHGMVSKGEELFTGVVPILVELDGDVNGHKFSVSGEGEGDATYGKLTLKFICTTGKLPVPWPTLVTTLTYGVQCFSRYPDHMKOHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMPEAAISRLITYLRILEELEAQGVHRTASEQLGELAQVTAFQVDEDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-c1 | 105 | 0.05 | MKVPEAAISRLITYLRILEELEAQGVHRTASEQLGELAQVTAFQVDKDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREEAAQKAADLLVAAGIKGILNFAPVVLEVPKEVAVENVDILAGLTRLSFAILNPTWGMVSKGEELFTGVVPILVELDGDVNGHKFSVSGEGEGDATYGKLTLKFICTTGKLPVPWPTLVTTLTYGVQCFSRYPDHMKOHDFFKSAMPEGYVQERTIFFKDDGNYKTRAEVKFEGDTLVNRIELKGIDFKEDGNILGHKLEYNYNSHNVYIMADKOKNGIKVNFKIRHNIEDGSVQLADHYQQNTPIGDGPVLLPDNHYLSTQSKLSKDPNEKRDHMVLLEFVTAAGITLGEAAISRLITYLRILEELEAQGVHRTASEQLGELAQVTAFQVDEDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-H12 | 106 | 0.04 | MKVPEAAISRLITYLRILEELEAQGVHRTASEQLGELAQVTAFQVDKDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREEAAQKAADLLVAAGIKGILNFAPVVLEVPKEVAVENVDILAGLTRLSFAILNPTWSAAGGHGMVSKGEELFTGVVPILVELDGDVNGHKFSVSGEGEGDATYGKLTLKFICTTGKLPVPWPTLVTTLTYGVQCFSRYPDHMKOHDEFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSKLSKDPNEKRDHMVLLEFVTAAGITLGMDELYKTKVPEAAISRLITYLRILEELEAQGVHRTASEQLGELAQVTAFQVDEDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMGMVSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |
| 1-H4 | 107 | 0.04 | MKVPEAAISRLITYLRILEELEAQGVHRTASEQLGELAQVTAFQVDKDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREEAAQKAADLLVAAGIKGILNFAPVVLEVPKEVAVENVDILAGLTRLSFAILNPTWSAAGGHGMVSKGEELFTGVVPILVELDGDVNGHKFSVSGEGEGDATYGKLTLKFICTTGKLPVPWPTLVTTLTYGVQCFSRYPDHMKOHDEFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTOSKLSKDPNEKRDHMVLLEFVTAAGITLGMDEPEAAISRLITYLRILEELEAQGVHRTASEQLGELAQVTAFQVDEDLSYFGSYGTDGVGYTVPVLKRELRHILGLNRKWGLCIVGMGRLGSALADWPGFGESFELRGFFDVDPGMVGRPVRGGVIEHVDLLPQRVPGRIEIALLTVPREAAQKAADLLVAAGIKGILNFAPVVLEVPKEVAVENVDFLAGLTRLSFAILNPKWREEMMGVSVIKPEMKMRYYMDGSVNGHEFTIEGEGTGRPYEGHQEMTLRVTMAEGGPMPFAFDLVSHVFCYGHRVFTKYPEEIPDYFKQAFPEGLSWERSLEFEDGGSASVSAHISLRGNTFYHKSKFTGVNFPADGPIMQNQSVDWEPSTEKITASDGVLKGDVTMYLKLEGGGNHKCQFKTTYKAAKEILEMPGDHYIGHRLVRKTEGNITEQVEDAVAHSEASMDELYK |

TABLE 2-continued

| Full clone name | SEQ ID NO | Signal window (ex mode), measured in lysates | Full protein sequence |
|---|---|---|---|
| 2-D9 | 108 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGMVSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 1-F5 | 109 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGHGMVSKGEELFTG VVPILVELDGDVNGHKFSVSGEGEGDATYGKLTLKFICTTGKLPVPWPTLVTTLTYGVQCFSRYPDHMKQHDFF KSAMPEGYVQERTIFFKDDGNYKTRAEVKFEGDTLVNRIELKGIDFKEDGNILGHKLEYNYNSHNVYIMADKOK NGIKVNFKIRHNIEDGSVQLADHYQQNTPIGDGPVLLPDNHYLSTQSKLSKDPNEKRDHMVLLEFVTAAGITLG MDPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGMVSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 1-B4 | 110 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKOKNGIKVNFKIRHNIED GSVQLADHYQQNTPIGDGPVLLPDNHYLSTQSKLSKDPNEKRDHMVLLEFVTAAGITLGMEAAISRLITYLRIL EELEAQGVHRTASEQLGELAQVTAFQVDEDLSYFGSYGTDGVGYTVPVLKRELRHILGLNRKWGLCIVGMRLG SALADWPGFGESFELRGFFDVDPGMVGRPVRGGVIEHVDLLPQRVPGRIEIALLTVPREAAQKAADLLVAAGIK GILNFAPVVLEVPKEVAVENVDFLAGLTRLSFAILNPKWREESVIKPEMKMRYYMDGSVNGHEFTIEGEGTGRP YEGHQEMTLRVTMAEGGPMPFAFDLVSHVFCYGHRVFTKYPEEIPDYFKQAFPEGLSWERSLEFEDGGSASVSA HISLRGNTFYHKSKFTGVNFPADGPIMQNQSVDWEPSTEKITASDGVLKGDVTMYLKLEGGGNHKCQFKTTYKA AKEILEMPGDHYIGHRLVRKTEGNITEQVEDAVAHSEASMDELYK |
| 1-B6 | 111 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DEPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGMVSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 1-C3 | 112 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMEAAISRLITYLRILEELEAQGVHRTASEQLGELAQVTAFQVDEDLSYFGSYGTDGVGYTVPVLKRELRHILG LNRKWGLCIVGMRLGSALADWPGFGESFELRGFFDVDPGMVGRPVRGGVIEHVDLLPQRVPGRIEIALLTVPR EAAQKAADLLVAAGIKGILNFAPVVLEVPKEVAVENVDFLAGLTRLSFAILNPKWREEMMGMVSVIKPEMKMRY YMDGSVNGHEFTIEGEGTGRPYEGHQEMTLRVTMAEGGPMPFAFDLVSHVFCYGHRVFTKYPEEIPDYFKQAFP EGLSWERSLEFEDGGSASVSAHISLRGNTFYHKSKFTGVNFPADGPIMQNQSVDWEPSTEKITASDGVLKGDVT MYLKLEGGGNHKCQFKTTYKAAKEILEMPGDHYIGHRLVRKTEGNITEQVEDAVAHSEASMDELYK |
| 1-F11 | 113 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL |

TABLE 2-continued

| Full clone name | SEQ ID NO | Signal window (ex mode), measured in lysates | Full protein sequence |
|---|---|---|---|
| | | | GMDPEAAISRLITYLRILEELEAQGVHRTASEQLGELAQVTAFQVDEDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMMGVSVIKPEMKMR YYMDGSVNGHEFTIEGEGTGRPYEGHQEMTLRVTMAEGGPMPFAFDLVSHVFCYGHRVFTKYPEEIPDYFKQAF PEGLSWERSLEFEDGGSASVSAHISLRGNTFYHKSKFTGVNFPADGPIMQNQSVDWEPSTEKITASDGVLKGDV TMYLKLEGGGNHKCQFKTTYKAAKEILEMPGDHYIGHRLVRKTEGNITEQVEDAVAHSEASMDELYK |
| 1-D2 | 114 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTGEELFTGVVPILVELDGD VNGHKFSVSGEGEGDATYGKLTLKFICTTGKLPVPWPTLVTTLTYGVQCFSRYPDHMKQHDFFKSAMPEGYVQE RTIFFKDDGNYKTRAEVKFEGDTLVNRIELKGIDFKEDGNILGHKLEYNYNSHNVYIMADKOKNGIKVNFKIRH NIEDGSVQLADHYQQNTPIGDGPVLLPDNHYLSTOSKLSKDPNEKRDHMVLLEFVTAAGITLGMDELVPEAAIS RLITYLRILEELEAQGVHRTASEQLGELAQVTAFQVDEDLSYFGSYGTDGVGYTVPVLKRELRHILGLNRKWGL CIVGMGRLGSALADWPGFGESFELRGFFDVDPGMVGRPVRGGVIEHVDLLPQRVPGRIEIALLTVPREAAQKAA DLLVAAGIKGILNFAPVVLEVPKEVAVENVDFLAGLTRLSFAILNPKWREEMMGGSMVSVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNQSVDWEPSTEKITASDGVLKGDVTMYLKL EGGGNHKCQFKTTYKAAKEILEMPGDHYIGHRLVRKTEGNITEQVEDAVAHSEASMDELYK |
| 1-H2 | 115 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAHGMVSKGEELFTGVV PILVELDGDVNGHKFSVSGEGEGDATYGKLTLKFICTTGKLPVPWPTLVTTLTYGVQCFSRYPDHMKOHDFFKS AMPEGYVQERTIFFKDDGNYKTRAEVKFEGDTLVNRIELKGIDFKEDGNILGHKLEYNYNSHNVYIMADKOKNG IKVNFKIRHNIEDGSVQLADHYQQNTPIGDGPVLLPDNHYLSTQSKLSKDPNEKRDHMVLLEFVTAAGITLGEA AISRLITYLRILEELEAQGVHRTASEQLGELAQVTAFQVDEDLSYFGSYGTDGVGYTVPVLKRELRHILGLNRK WGLCIVGMRLGSALADWPGFGESFELRGFFDVDPGMVGRPVRGGVIEHVDLLPQRVPGRIEIALLTVPREAAQ KAADLLVAAGIKGILNFAPVVLEVPKEVAVENVDFLAGLTRLSFAILNPKWREEMMGSMVSVIKPEMKMRYYMD GSVNGHEFTIEGEGTGRPYEGHQEMTLRVTMAEGGPMPFAFDLVSHVFCYGHRVFTKYPEEIPDYFKQAFPEGL SWERSLEFEDGGSASVSAHISLRGNTFYHKSKFTGVNFPADGPIMQNQSVDWEPSTEKITASDGVLKGDVTMYL KLEGGGNHKCQFKTTYKAAKEILEMPGDHYIGHRLVRKTEGNITEQVEDAVAHSEASMDELYK |
| 2-H4 | 116 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKOHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTOSKLSKDPNEKRDHMVLLEFVTAAGITL GMDPEAAISRLITYLRILEELEAQGVHRTASEQLGELAQVTAFQVDEDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMSVIKPEMKMRYYM DGSVNGHEFTIEGEGTGRPYEGHQEMTLRVTMAEGGPMPFAFDLVSHVFCYGHRVFTKYPEEIPDYFKQAFPEG LSWERSLEFEDGGSASVSAHISLRGNTFYHKSKFTGVNFPADGPIMQNQSVDWEPSTEKITASDGVLKGDVTMY LKLEGGGNHKCQFKTTYKAAKEILEMPGDHYIGHRLVRKTEGNITEQVEDAVAHSEASMDELYK |
| 2-B8 | 117 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDPEAAISRLITYLRILEELEAQGVHRTASEQLGELAQVTAFQVDEDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDFLAGLTRLSFAILNPKWREEMMGMVSVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |
| 1-E3 | 118 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKOKN GIKVNFKIRHNIEDGSVQLADHYQQNTPIGDGPVLLPDNHYLSTQSKLSKDPNEKRDHMVLLEFVTAAGITLGM PEAAISRLITYLRILEELEAQGVHRTASEQLGELAQVTAFQVDEDLSYFGSYGTDGVGYTVPVLKRELRHILGL NRKWGLCIVGMGRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREEMMGMVSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |

TABLE 2-continued

| Full clone name | SEQ ID NO | Signal window (ex mode), measured in lysates | Full protein sequence |
|---|---|---|---|
| 1-E5 | 119 | 0.04 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM DEPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMGGSMVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSEASMDELYK |
| 1-B12 | 120 | 0.03 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMSVIKPEMKMRYYMDGS VNGHEFTIEGEGTGRPYEGHQEMTLRVTMAEGGPMPFAFDLVSHVFCYGHRVFTKYPEEIPDYFKQAFPEGLSW ERSLEFEDGGSASVSAHISLRGNTFYHKSKFTGVNFPADGPIMQNQSVDWEPSTEKITASDGVLKGDVTMYLKL EGGGNHKCQFKTTYKAAKEILEMPGDHYIGHRLVRKTEGNITEQVEDAVAHSEASMDELYK |
| 2-E7 | 121 | 0.03 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREESVIKPEMKMRYYMDGSVN GHEFTIEGEGTGRPYEGHQEMTLRVTMAEGGPMPFAFDLVSHVFCYGHRVFTKYPEEIPDYFKQAFPEGLSWER SLEFEDGGSASVSAHISLRGNTFYHKSKFTGVNFPADGPIMQNQSVDWEPSTEKITASDGVLKGDVTMYLKLEG GGNHKCQFKTTYKAAKEILEMPGDHYIGHRLVRKTEGNITEQVEDAVAHSEASMDELYK |
| 1-A9 | 122 | 0.03 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDELYKVPEAAISRLITYLRILEELEAQGVHRTASEQLGELAQVTAFQVDEDLSYFGSYGTDGVGYTVPVLKR ELRHILGLNRKWGLCIVGMRLGSALADWPGFGESFELRGFFDVDPGMVGRPVRGGVIEHVDLLPQRVPGRIEI ALLTVPREAAQKAADLLVAAGIKGILNFAPVVLEVPKEVAVENVDFLAGLTRLSFAILNPKWREEMMGSMVSVI KPEMKMRYYMDGSVNGHEFTIEGEGTGRPYEGHQEMTLRVTMAEGGPMPFAFDLVSHVFCYGHRVFTKYPEEIP DYFKQAFPEGLSWERSLEFEDGGSASVSAHISLRGNTFYHKSKFTGVNFPADGPIMQNQSVDWEPSTEKITASD GVLKGDVTMYLKLEGGGNHKCQFKTTYKAAKEILEMPGDHYIGHRLVRKTEGNITEQVEDAVAHSEASMDELYK |
| 2-D4 | 123 | 0.03 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGEAAISRLITYLRILE ELEAQGVHRTASEQLGELAQVTAFQVDEDLSYFGSYGTDGVGYTVPVLKRELRHILGLNRKWGLCIVGMRLGS ALADWPGFGESFELRGFFDVDPGMVGRPVRGGVIEHVDLLPQRVPGRIEIALLTVPREAAQKAADLLVAAGIKG ILNFAPVVLEVPKEVAVENVDFLAGLTRLSFAILNPKWREVIKPEMKMRYYMDGSVNGHEFTIEGEGTGRPYEG HQEMTLRVTMAEGGPMPFAFDLVSHVFCYGHRVFTKYPEEIPDYFKQAFPEGLSWERSLEFEDGGSASVSAHIS LRGNTFYHKSKFTGVNFPADGPIMQNQSVDWEPSTEKITASDGVLKGDVTMYLKLEGGGNHKCQFKTTYKAAKE ILEMPGDHYIGHRLVRKTEGNITEQVEDAVAHSEASMDELYK |
| 1-D5 | 124 | 0.03 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAGHGMVSKGEELFTGV VPILVELDGDVNGHKFSVSGEGEGDATYGKLTLKFICTTGKLPVPWPTLVTTLTYGVQCFSRYPDHMKQHDFFK SAMPEGYVQERTIFFKDDGNYKTRAEVKFEGDTLVNRIELKGIDFKEDGNILGHKLEYNYNSHNVYIMADKQKN GIKVNFKIRHNIEDGSVQLADHYQQNTPIGDGPVLLPDNHYLSTQSKLSKDPNEKRDHMVLLEFVTAAGITLGM EAAISRLITYLRILEELEAQGVHRTASEQLGELAQVTAFQVDEDLSYFGSYGTDGVGYTVPVLKRELRHILGLN |

TABLE 2-continued

| Full clone name | SEQ ID NO | Signal window (ex mode), measured in lysates | Full protein sequence |
|---|---|---|---|
| | | | RKWGLCIVGMGRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMVSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| 1-G7 | 125 | 0.03 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMDELYKTKVPEAAIS RLITYLRILEELEAQGVHRTASEQLGELAQVTAFQVDEDLSYFGSYGTDGVGYTVPVLKRELRHILGLNRKWGL CIVGMGRLGSALADWPGFGESFELRGFFDVDPGMVGRPVRGGVIEHVDLLPQRVPGRIEIALLTVPREAAQKAA DLLVAAGIKGILNFAPVVLEVPKEVAVENVDFLAGLTRLSFAILNPKWREEVIKPEMKMRYYMDGSVNGHEFTI EGEGTGRPYEGHQEMTLRVTMAEGGPMPFAFDLVSHVFCYGHRVFTKYPEEIPDYFKQAFPEGLSWERSLEFED GGSASVSAHISLRGNTFYHKSKFTGVNFPADGPIMQNQSVDWEPSTEKITASDGVLKGDVTMYLKLEGGGNHKC QFKTTYKAAKEILEMPGDHYIGHRLVRKTEGNITEQVEDAVAHSEASMDELYK |
| 1-D10 | 126 | 0.03 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMEAAISRLITYLRIL EELEAQGVHRTASEQLGELAQVTAFQVDEDLSYFGSYGTDGVGYTVPVLKRELRHILGLNRKWGLCIVGMGRLG SALADWPGFGESFELRGFFDVDPGMVGRPVRGGVIEHVDLLPQRVPGRIEIALLTVPREAAQKAADLLVAAGIK GILNFAPVVLEVPKEVAVENVDFLAGLTRLSFAILNPKWREESVIKPEMKMRYYMDGSVNGHEFTIEGEGTGRP YEGHQEMTLRVTMAEGGPMPFAFDLVSHVFCYGHRVFTKYPEEIPDYFKQAFPEGLSWERSLEFEDGGSASVSA HISLRGNTFYHKSKFTGVNFPADGPIMQNQSVDWEPSTEKITASDGVLKGDVTMYLKLEGGGNHKCQFKTTYKA AKEILEMPGDHYIGHRLVRKTEGNITEQVEDAVAHSEASMDELYK |
| 2-D8 | 127 | 0.03 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSHGMVSKGEELFTGVVP ILVELDGDVNGHKFSVSGEGEGDATYGKLTLKFICTTGKLPVPWPTLVTTLTYGVQCFSRYPDHMKQHDFFKSA MPEGYVQERTIFFKDDGNYKTRAEVKFEGDTLVNRIELKGIDFKEDGNILGHKLEYNYNSHNVYIMADKQKNGI KVNFKIRHNIEDGSVQLADHYQQNTPIGDGPVLLPDNHYLSTQSKLSKDPNEKRDHMVLLEFVTAAGITLGMPE AAISRLITYLRILEELEAQGVHRTASEQLGELAQVTAFQVDEDLSYFGSYGTDGVGYTVPVLKRELRHILGLNR KWGLCIVGMGRLGSALADWPGFGESFELRGFFDVDPGMVGRPVRGGVIEHVDLLPQRVPGRIEIALLTVPREAA QKAADLLVAAGIKGILNFAPVVLEVPKEVAVENVDFLAGLTRLSFAILNPKWREEMMSVIKPEMKMRYYMDGSV NGHEFTIEGEGTGRPYEGHQEMTLRVTMAEGGPMPFAFDLVSHVFCYGHRVFTKYPEEIPDYFKQAFPEGLSWE RSLEFEDGGSASVSAHISLRGNTFYHKSKFTGVNFPADGPIMQNQSVDWEPSTEKITASDGVLKGDVTMYLKLE GGGNHKCQFKTTYKAAKEILEMPGDHYIGHRLVRKTEGNITEQVEDAVAHSEASMDELYK |
| 2-E5 | 128 | 0.02 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGEAAISRLITYLRILE ELEAQGVHRTASEQLGELAQVTAFQVDEDLSYFGSYGTDGVGYTVPVLKRELRHILGLNRKWGLCIVGMGRLGS ALADWPGFGESFELRGFFDVDPGMVGRPVRGGVIEHVDLLPQRVPGRIEIALLTVPREAAQKAADLLVAAGIKG ILNFAPVVLEVPKEVAVENVDFLAGLTRLSFAILNPKWREVIKPEMKMRYYMDGSVNGHEFTIEGEGTGRPYEG HQEMTLRVTMAEGGPMPFAFDLVSHVFCYGHRVFTKYPEEIPDYFKQAFPEGLSWERSLEFEDGGSASVSAHIS LRGNTFYHKSKFTGVNFPADGPIMQNQSVDWEPSTEKITASDGVLKGDVTMYLKLEGGGNHKCQFKTTYKAAKE ILEMPGDHYIGHRLVRKTEGNITEQVEDAVAHSEASMDELYK |
| 2-H8 | 129 | 0.02 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMDEPEAAISRLITYLRILEELEAQGVHRTASEQLGELAQVTAFQVDEDLSYFGSYGTDGVGYTVPVLKRELRH ILGLNRKWGLCIVGMGRLGSALADWPGFGESFELRGFFDVDPGMVGRPVRGGVIEHVDLLPQRVPGRIEIALLT VPREAAQKAADLLVAAGIKGILNFAPVVLEVPKEVAVENVDFLAGLTRLSFAILNPKWREEMMGVSIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHSEASMDELYK |

TABLE 2-continued

| Full clone name | SEQ ID NO | Signal window (ex mode), measured in lysates | Full protein sequence |
|---|---|---|---|
| 2-H11 | 130 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWVSKGEELFTGVVPILVE<br>LDGDVNGHKFSVSGEGEGDATYGKLTLKFICTTGKLPVPWPTLVTTLTYGVQCFSRYPDHMKOHDFFKSAMPEG<br>YVQERTIFFKDDGNYKTRAEVKFEGDTLVNRIELKGIDFKEDGNILGHKLEYNYNSHNVYIMADKOKNGIKVNF<br>KIRHNIEDGSVQLADHYQQNTPIGDGPVLLPDNHYLSTQSKLSKDPNEKRDHMVLLEFVTAAGITLAAISRLIT<br>YLRILEELEAQGVHRTASEQLGELAQVTAFQVDEDLSYFGSYGTDGVGYTVPVLKRELRHILGLNRKWGLCIVG<br>MGRLGSALADWPGFGESFELRGFFDVDPGMVGRPVRGGVIEHVDLLPQRVPGRIEIALLTVPREAAQKAADLLV<br>AAGIKGILNFAPVVLEVPKEVAVENVDFLAGLTRLSFAILNPKWREEMSVIKPEMKMRYYMDGSVNGHEFTIEG<br>EGTGRPYEGHQEMTLRVTMAEGGPMPFAFDLVSHVFCYGHRVFTKYPEEIPDYFKQAFPEGLSWERSLEFEDGG<br>SASVSAHISLRGNTFYHKSKFTGVNFPADGPIMQNQSVDWEPSTEKITASDGVLKGDVTMYLKLEGGGNHKCQF<br>KTTYKAAKEILEMPGDHYIGHRLVRKTEGNITEQVEDAVAHSEASMDELYK |
| 1-B5 | 131 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSAAGGHGMVSKGEELFT<br>GVVPILVELDGDVNGHKFSVSGEGEGDATYGKLTLKFICTTGKLPVPWPTLVTTLTYGVQCFSRYPDHMKQHDF<br>FKSAMPEGYVQERTIFFKDDGNYKTRAEVKFEGDTLVNRIELKGIDFKEDGNILGHKLEYNYNSHNVYIMADKQ<br>KNGIKVNFKIRHNIEDGSVQLADHYQQNTPIGDGPVLLPDNHYLSTQSKLSKDPNEKRDHMVLLEFVTAAGITL<br>GMDPEAAISRLITYLRILEELEAQGVHRTASEQLGELAQVTAFQVDEDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDFLAGLTRLSFAILNPKWREEMMGVSVIKPEMKMR<br>YYMDGSVNGHEFTIEGEGTGRPYEGHQEMTLRVTMAEGGPMPFAFDLVSHVFCYGHRVFTKYPEEIPDYFKQAF<br>PEGLSWERSLEFEDGGSASVSAHISLRGNTFYHKSKFTGVNFPADGPIMQNQSVDWEPSTEKITASDGVLKGDV<br>TMYLKLEGGGNHKCQFKTTYKAAKEILEMPGDHYIGHRLVRKTEGNITEQVEDAVAHSEASMDELYK |
| 2-G4 | 132 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSAHGMVSKGEELFTGVV<br>PILVELDGDVNGHKFSVSGEGEGDATYGKLTLKFICTTGKLPVPWPTLVTTLTYGVQCFSRYPDHMKOHDFFKS<br>AMPEGYVQERTIFFKDDGNYKTRAEVKFEGDTLVNRIELKGIDFKEDGNILGHKLEYNYNSHNVYIMADKOKNG<br>IKVNFKIRHNIEDGSVQLADHYQQNTPIGDGPVLLPDNHYLSTQSKLSKDPNEKRDHMVLLEFVTAAGITLGEA<br>AISRLITYLRILEELEAQGVHRTASEQLGELAQVTAFQVDEDLSYFGSYGTDGVGYTVPVLKRELRHILGLNRK<br>WGLCIVGMGRLGSALADWPGFGESFELRGFFDVDPGMVGRPVRGGVIEHVDLLPQRVPGRIEIALLTVPREAAQ<br>KAADLLVAAGIKGILNFAPVVLEVPKEVAVENVDFLAGLTRLSFAILNPKWREEMGSMVSVIKPEMKMRYYMD<br>GSVNGHEFTIEGEGTGRPYEGHQEMTLRVTMAEGGPMPFAFDLVSHVFCYGHRVFTKYPEEIPDYFKQAFPEGL<br>SWERSLEFEDGGSASVSAHISLRGNTFYHKSKFTGVNFPADGPIMQNQSVDWEPSTEKITASDGVLKGDVTMYL<br>KLEGGGNHKCQFKTTYKAAKEILEMPGDHYIGHRLVRKTEGNITEQVEDAVAHSEASMDELYK |
| 2-F8 | 133 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSGMVSKGEELFTGVVPI<br>LVELDGDVNGHKFSVSGEGEGDATYGKLTLKFICTTGKLPVPWPTLVTTLTYGVQCFSRYPDHMKQHDFFKSAM<br>PEGYVQERTIFFKDDGNYKTRAEVKFEGDTLVNRIELKGIDFKEDGNILGHKLEYNYNSHNVYIMADKQKNGIK<br>VNFKIRHNIEDGSVQLADHYQQNTPIGDGPVLLPDNHYLSTQSKLSKDPNEKRDHMVLLEFVTAAGITLAAISR<br>LITYLRILEELEAQGVHRTASEQLGELAQVTAFQVDEDLSYFGSYGTDGVGYTVPVLKRELRHILGLNRKWGLC<br>IVGMGRLGSALADWPGFGESFELRGFFDVDPGMVGRPVRGGVIEHVDLLPQRVPGRIEIALLTVPREAAQKAAD<br>LLVAAGIKGILNFAPVVLEVPKEVAVENVDFLAGLTRLSFAILNPKWREVIKPEMKMRYYMDGSVNGHEFTIEG<br>EGTGRPYEGHQEMTLRVTMAEGGPMPFAFDLVSHVFCYGHRVFTKYPEEIPDYFKQAFPEGLSWERSLEFEDGG<br>SASVSAHISLRGNTFYHKSKFTGVNFPADGPIMQNQSVDWEPSTEKITASDGVLKGDVTMYLKLEGGGNHKCOF<br>KTTYKAAKEILEMPGDHYIGHRLVRKTEGNITEQVEDAVAHSEASMDELYK |
| 2-F2 | 134 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPTWSAGHGMVSKGEELFTGV<br>VPILVELDGDVNGHKFSVSGEGEGDATYGKLTLKFICTTGKLPVPWPTLVTTLTYGVOCFSRYPDHMKQHDFFK<br>SAMPEGYVQERTIFFKDDGNYKTRAEVKFEGDTLVNRIELKGIDFKEDGNILGHKLEYNYNSHNVYIMADKOKN<br>GIKVNFKIRHNIEDGSVQLADHYQQNTPIGDGPVLLPDNHYLSTQSKLSKDPNEKRDHMVLLEFVTAAGITLGM<br>DEPEAAISRLITYLRILEELEAQGVHRTASEQLGELAQVTAFQVDEDLSYFGSYGTDGVGYTVPVLKRELRHIL<br>GLNRKWGLCIVGMGRLGSALADWPGFGESFELRGFFDVDPGMVGRPVRGGVIEHVDLLPQRVPGRIEIALLTVP<br>REAAQKAADLLVAAGIKGILNFAPVVLEVPKEVAVENVDFLAGLTRLSFAILNPKWREEMMGVSVIKPEMKMRY<br>YMDGSVNGHEFTIEGEGTGRPYEGHQEMTLRVTMAEGGPMPFAFDLVSHVFCYGHRVFTKYPEEIPDYFKQAFP<br>EGLSWERSLEFEDGGSASVSAHISLRGNTFYHKSKFTGVNFPADGPIMQNQSVDWEPSTEKITASDGVLKGDVT<br>MYLKLEGGGNHKCQFKTTYKAAKEILEMPGDHYIGHRLVRKTEGNITEQVEDAVAHSEASMDELYK |
| 2-H9 | 135 | 0.02 | MKVPEAAISRLITYLRILEELEAQGVHRTASEQLGELAQVTAFQVDKDLSYFGSYGTDGVGYTVPVLKRELRHI<br>LGLNRKWGLCIVGMGRLGSALADWPGFGESFELRGFFDVDPGMVGRPVRGGVIEHVDLLPQRVPGRIEIALLTV<br>PREAAQKAADLLVAAGIKGILNFAPVVLEVPKEVAVENVDILAGLTRLSFAILNPLFTGVVPILVELDGDVNGH<br>KFSVSGEGEGDATYGKLTLKFICTTGKLPVPWPTLVTTLTYGVQCFSRYPDHMKQHDFFKSAMPEGYVQERTIF<br>FKDDGNYKTRAEVKFEGDTLVNRIELKGIDFKEDGNILGHKLEYNYNSHNVYIMADKOKNGIKVNFKIRHNIED<br>GSVQLADHYQQNTPIGDGPVLLPDNHYLSTQSKLSKDPNEKRDHMVLLEFVTAAGITLGEAAISRLITYLRILE |

TABLE 2-continued

| Full clone name | SEQ ID NO | Signal window (ex mode), measured in lysates | Full protein sequence |
|---|---|---|---|
| | | | ELEAQGVHRTASEQLGELAQVTAFQVDEDLSYFGSYGTDGVGYTVPVLKRELRHILGLNRKWGLCIVGMRLGS ALADWPGFGESFELRGFFDVDPGMVGRPVRGGVIEHVDLLPQRVPGRIEIALLTVPREAAQKAADLLVAAGIKG ILNFAPVVLEVPKEVAVENVDFLAGLTRLSFAILNPKWREEMMGSMVSVIKPEMKMRYYMDGSVNGHEFTIEGE GTGRPYEGHQEMTLRVTMAEGGPMPFAFDLVSHVFCYGHRVFTKYPEEIPDYFKQAFPEGLSWERSLEFEDGGS ASVSAHISLRGNTFYHKSKFTGVNFPADGPIMQNQSVDWEPSTEKITASDGVLKGDVTMYLKLEGGGNHKCQFK TTYKAAKEILEMPGDHYIGHRLVRKTEGNITEQVEDAVAHSEASMDELYK |
| 1-B9 | 136 | 0.02 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILLNPTWSAAGGHGMVSKGEELFT GVVPILVELDGDVNGHKFSVSGEGEGDATYGKLTLKFICTTGKLPVPWPTLVTTLTYGVQCESRYPDHMKQHDE FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GMPEAAISRLITYLRILEELEAQGVHRTASEQLGELAQVTAFQVDEDLSYFGSYGTDGVGYTVPVLKRELRHIL GLNRKWGLCIVGMRLGSALADWPGFGESFELRGFFDVDPGMVGRPVRGGVIEHVDLLPQRVPGRIEIALLTVP REAAQKAADLLVAAGIKGILNFAPVVLEVPKEVAVENVDFLAGLTRLSFAILNPKWREEMMVSVIKPEMKMRYY MDGSVNGHEFTIEGEGTGRPYEGHQEMTLRVTMAEGGPMPFAFDLVSHVFCYGHRVFTKYPEEIPDYFKQAFPE GLSWERSLEFEDGGSASVSAHISLRGNTFYHKSKFTGVNFPADGPIMQNQSVDWEPSTEKITASDGVLKGDVTM YLKLEGGGNHKCQFKTTYKAAKEILEMPGDHYIGHRLVRKTEGNITEQVEDAVAHSEASMDELYK |
| 1-C8 | 137 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLAAISRLIAAISRLITY LRILEELEAQGVHRTASEQLGELAQVTAFQVDEDLSYFGSYGTDGVGYTVPVLKRELRHILGLNRKWGLCIVGM GRLGSALADWPGFGESFELRGFFDVDPGMVGRPVRGGVIEHVDLLPQRVPGRIEIALLTVPREAAQKAADLLVA AGIKGILNFAPVVLEVPKEVAVENVDFLAGLTRLSFAILNPKWREEVIKPEMKMRYYMDGSVNGHEFTIEGEGT GRPYEGHQEMTLRVTMAEGGPMPFAFDLVSHVFCYGHRVFTKYPEEIPDYFKQAFPEGLSWERSLEFEDGGSAS VSAHISLRGNTFYHKSKFTGVNFPADGPIMQNQSVDWEPSTEKITASDGVLKGDVTMYLKLEGGGNHKCQFKTT YKAAKEILEMPGDHYIGHRLVRKTEGNITEQVEDAVAHSEASMDELYK |
| 2-E12 | 138 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSGMVSKGEELFTGVVPI LVELDGDVNGHKFSVSGEGEGDATYGKLTLKFICTTGKLPVPWPTLVTTLTYGVQCFSRYPDHMKQHDFFKSAM PEGYVQERTIFFKDDGNYKTRAEVKFEGDTLVNRIELKGIDFKEDGNILGHKLEYNYNSHNVYIMADKQKNGIK VNFKIRHNIEDGSVQLADHYQQNTPIGDGPVLLPDNHYLSTQSKLSKDPNEKRDHMVLLEFVTAAGITLGMPEA AISRLITYLRILEELEAQGVHRTASEQLGELAQVTAFQVDEDLSYFGSYGTDGVGYTVPVLKRELRHILGLNRK WGLCIVGMRLGSALADWPGFGESFELRGFFDVDPGMVGRPVRGGVIEHVDLLPQRVPGRIEIALLTVPREAAQ KAADLLVAAGIKGILNFAPVVLEVPKEVAVENVDFLAGLTRLSFAILNPKWREESVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNQSVDWEPSTEKITASDGVLKGDVTMYLKLEGGG NHKCQFKTTYKAAKEILEMPGDHYIGHRLVRKTEGNITEQVEDAVAHSEASMDELYK |
| 2-H1 | 139 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMEAAISRLITYLRIL EELEAQGVHRTASEQLGELAQVTAFQVDEDLSYFGSYGTDGVGYTVPVLKRELRHILGLNRKWGLCIVGMRLG SALADWPGFGESFELRGFFDVDPGMVGRPVRGGVIEHVDLLPQRVPGRIEIALLTVPREAAQKAADLLVAAGIK GILNFAPVVLEVPKEVAVENVDFLAGLTRLSFAILNPKWREEMMSVIKPEMKMRYYMDGSVNGHEFTIEGEGTG RPYEGHQEMTLRVTMAEGGPMPFAFDLVSHVFCYGHRVFTKYPEEIPDYFKQAFPEGLSWERSLEFEDGGSASV SAHISLRGNTFYHKSKFTGVNFPADGPIMQNQSVDWEPSTEKITASDGVLKGDVTMYLKLEGGGNHKCQFKTTY KAAKEILEMPGDHYIGHRLVRKTEGNITEQVEDAVAHSEASMDELYK |
| 2-B6 | 140 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMEAAISRLITYLRIL EELEAQGVHRTASEQLGELAQVTAFQVDEDLSYFGSYGTDGVGYTVPVLKRELRHILGLNRKWGLCIVGMRLG SALADWPGFGESFELRGFFDVDPGMVGRPVRGGVIEHVDLLPQRVPGRIEIALLTVPREAAQKAADLLVAAGIK GILNFAPVVLEVPKEVAVENVDFLAGLTRLSFAILNPKWREEMMGSMVSVIKPEMKMRYYMDGSVNGHEFTIEG EGTGRPYEGHQEMTLRVTMAEGGPMPFAFDLVSHVFCYGHRVFTKYPEEIPDYFKQAFPEGLSWERSLEFEDGG SASVSAHISLRGNTFYHKSKFTGVNFPADGPIMQNQSVDWEPSTEKITASDGVLKGDVTMYLKLEGGGNHKCQF KTTYKAAKEILEMPGDHYIGHRLVRKTEGNITEQVEDAVAHSEASMDELYK |

TABLE 2-continued

| Full clone name | SEQ ID NO | Signal window (ex mode), measured in lysates | Full protein sequence |
|---|---|---|---|
| 2-G1 | 141 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV KFSVSGEGEGDATYGKLTLKFICTTGKLPVPWPTLVTTLTYGVQCFSRYPDHMKQHDFFKSAMPEGYVQERTIF PREEAAQKAADLLVAAGIKGILNFAPVVLEVPKEVAVENVDILAGLTRLSFAILNPLFTGVVPILVELDGDVNGH FKDDGNYKTRAEVKFEGDTLVNRIELKGIDFKEDGNILGHKLEYNYNSHNVYIMADKOKNGIKVNFKIRHNIED GSVQLADHYQQNTPIGDGPVLLPDNHYLSTQSKLSKDPNEKRDHMVLLEFVTAAGITLGMEAAISRLITYLRIL EELEAQGVHRTASEQLGELAQVTAFQVDEDLSYFGSYGTDGVGYTVPVLKRELRHILGLNRKWGLCIVGMRLG SALADWPGFGESFELRGFFDVDPGMVGRPVRGGVIEHVDLLPQRVPGRIEIALLTVPREAAQKAADLLVAAGIK GILNFAPVVLEVPKEVAVENVDFLAGLTRLSFAILNPKWREEMSVIKPEMKMRYYMDGSVNGHEFTIEGEGTGR PYEGHQEMTLRVTMAEGGPMPFAFDLVSHVFCYGHRVFTKYPEEIPDYFKQAFPEGLSWERSLEFEDGGSASVS AHISLRGNTFYHKSKFTGVNFPADGPIMQNSVDWEPSTEKITASDGVLKGDVTMYLKLEGGGNHKCQFKTTYK AAKEILEMPGDHYIGHRLVRKTEGNITEQVEDAVAHSEASMDELYK |
| 2-B9 | 142 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKOKNGIKVNFKIRHNIED GSVQLADHYQQNTPIGDGPVLLPDNHYLSTQSKLSKDPNEKRDHMVLLEFVTAAGITLEAAISRLITYLRILEE LEAQGVHRTASEQLGELAQVTAFQVDEDLSYFGSYGTDGVGYTVPVLKRELRHILGLNRKWGLCIVGMRLGSA LADWPGFGESFELRGFFDVDPGMVGRPVRGGVIEHVDLLPQRVPGRIEIALLTVPREAAQKAADLLVAAGIKGI LNFAPVVLEVPKEVAVENVDFLAGLTRLSFAILNPKWREEMMSVIKPEMKMRYYMDGSVNGHEFTIEGEGTGRP YEGHQEMTLRVTMAEGGPMPFAFDLVSHVFCYGHRVFTKYPEEIPDYFKQAFPEGLSWERSLEFEDGGSASVSA HISLRGNTFYHKSKFTGVNFPADGPIMQNSVDWEPSTEKITASDGVLKGDVTMYLKLEGGGNHKCQFKTTYKA AKEILEMPGDHYIGHRLVRKTEGNITEQVEDAVAHSEASMDELYK |
| 1-E11 | 143 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWGMVSKGEELFTGVVPIL VELDGDVNGHKFSVSGEGEGDATYGKLTLKFICTTGKLPVPWPTLVTTLTYGVQCFSRYPDHMKQHDFFKSAMP EGYVQERTIFFKDDGNYKTRAEVKFEGDTLVNRIELKGIDFKEDGNILGHKLEYNYNSHNVYIMADKOKNGIKV NFKIRHNIEDGSVQLADHYQQNTPIGDGPVLLPDNHYLSTQSKLSKDPNEKRDHMVLLEFVTAAGITLGMDEVP EAAISRLITYLRILEELEAQGVHRTASEQLGELAQVTAFQVDEDLSYFGSYGTDGVGYTVPVLKRELRHILGLN RKWGLCIVGMRLGSALADWPGFGESFELRGFFDVDPGMVGRPVRGGVIEHVDLLPQRVPGRIEIALLTVPREA AQKAADLLVAAGIKGILNFAPVVLEVPKEVAVENVDFLAGLTRLSFAILNPKWREEMMVSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNSVDWEPSTEKITASDGVLKGDVTMYLK LEGGGNHKCQFKTTYKAAKEILEMPGDHYIGHRLVRKTEGNITEQVEDAVAHSEASMDELYK |
| 1-G5 | 144 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKOKNGIKVNFKIRHNIED GSVQLADHYQQNTPIGDGPVLLPDNHYLSTQSKLSKDPNEKRDHMVLLEFVTAAGITLEAAISRLITYLRILEE LEAQGVHRTASEQLGELAQVTAFQVDEDLSYFGSYGTDGVGYTVPVLKRELRHILGLNRKWGLCIVGMRLGSA LADWPGFGESFELRGFFDVDPGMVGRPVRGGVIEHVDLLPQRVPGRIEIALLTVPREAAQKAADLLVAAGIKGI LNFAPVVLEVPKEVAVENVDFLAGLTRLSFAILNPKWREEMSVIKPEMKMRYYMDGSVNGHEFTIEGEGTGRPY EGHQEMTLRVTMAEGGPMPFAFDLVSHVFCYGHRVFTKYPEEIPDYFKQAFPEGLSWERSLEFEDGGSASVSAH ISLRGNTFYHKSKFTGVNFPADGPIMQNSVDWEPSTEKITASDGVLKGDVTMYLKLEGGGNHKCQFKTTYKAA KEILEMPGDHYIGHRLVRKTEGNITEQVEDAVAHSEASMDELYK |
| 2-A8 | 145 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMDELVPEAAISRLIT YLRILEELEAQGVHRTASEQLGELAQVTAFQVDEDLSYFGSYGTDGVGYTVPVLKRELRHILGLNRKWGLCIVG MGRLGSALADWPGFGESFELRGFFDVDPGMVGRPVRGGVIEHVDLLPQRVPGRIEIALLTVPREAAQKAADLLV AAGIKGILNFAPVVLEVPKEVAVENVDFLAGLTRLSFAILNPKWREEMMGGSMVSVIKPEMKMRYYMDGSVNGH EFTIEGEGTGRPYEGHQEMTLRVTMAEGGPMPFAFDLVSHVFCYGHRVFTKYPEEIPDYFKQAFPEGLSWERSL EFEDGGSASVSAHISLRGNTFYHKSKFTGVNFPADGPIMQNSVDWEPSTEKITASDGVLKGDVTMYLKLEGGG NHKCQFKTTYKAAKEILEMPGDHYIGHRLVRKTEGNITEQVEDAVAHSEASMDELYK |
| 2-H3 | 146 | 0.01 | MKVPEAAISRLITYLRILEELEAQGVHRTASEQLGELAQVTAFQVDKDLSYFGSYGTDGVGYTVPVLKRELRHI LGLNRKWGLCIVGMRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKOKNGIKVNFKIRHNIED GSVQLADHYQQNTPIGDGPVLLPDNHYLSTQSKLSKDPNEKRDHMVLLEFVTAAGITLGEAAISRLITYLRILE ELEAQGVHRTASEQLGELAQVTAFQVDEDLSYFGSYGTDGVGYTVPVLKRELRHILGLNRKWGLCIVGMRLGS |

TABLE 2-continued

| Full clone name | SEQ ID NO | Signal window (ex mode), measured in lysates | Full protein sequence |
|---|---|---|---|
| | | | ALADWPGFGESFELRGFFDVDPGMVGRPVRGGVIEHVDLLPQRVPGRIEIALLTVPREAAQKAADLLVAAGIKG ILNFAPVVLEVPKEVAVENVDFLAGLTRLSFAILNPKWREEMMGMVSVIKPEMKMRYYMDGSVNGHEFTIEGEG TGRPYEGHQEMTLRVTMAEGGPMPFAFDLVSHVFCYGHRVFTKYPEEIPDYFKQAFPEGLSWERSLEFEDGGSA SVSAHISLRGNTFYHKSKFTGVNFPADGPIMQNQSVDWEPSTEKITASDGVLKGDVTMYLKLEGGGNHKCQFKT TYKAAKEILEMPGDHYIGHRLVRKTEGNITEQVEDAVAHSEASMDELYK |
| 1-A2 | 147 | 0.01 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLEAAISRLITYLRILEE LEAQGVHRTASEQLGELAQVTAFQVDEDLSYFGSYGTDGVGYTVPVLKRELRHILGLNRKWGLCIVGMGRLGSA LADWPGFGESFELRGFFDVDPGMVGRPVRGGVIEHVDLLPQRVPGRIEIALLTVPREAAQKAADLLVAAGIKGI LNFAPVVLEVPKEVAVENVDFLAGLTRLSFAILNPKWREEMMGGSMVSVIKPEMKMRYYMDGSVNGHEFTIEGE GTGRPYEGHQEMTLRVTMAEGGPMPFAFDLVSHVFCYGHRVFTKYPEEIPDYFKQAFPEGLSWERSLEFEDGGS ASVSAHISLRGNTFYHKSKFTGVNFPADGPIMQNQSVDWEPSTEKITASDGVLKGDVTMYLKLEGGGNHKCQFK TTYKAAKEILEMPGDHYIGHRLVRKTEGNITEQVEDAVAHSEASMDELYK |
| 2-A5 | 148 | 0.01 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPLFTGVVPILVELDGDVNGH KFSVSGEGEGDATYGKLTLKFICTTGKLPVPWPTLVTTLTYGVQCFSRYPDHMKQHDFFKSAMPEGYVQERTIF FKDDGNYKTRAEVKFEGDTLVNRIELKGIDFKEDGNILGHKLEYNYNSHNVYIMADKQKNGIKVNFKIRHNIED GSVQLADHYQQNTPIGDGPVLLPDNHYLSTQSKLSKDPNEKRDHMVLLEFVTAAGITLGMDEPEAAISRLITYL RILEELEAQGVHRTASEQLGELAQVTAFQVDEDLSYFGSYGTDGVGYTVPVLKRELRHILGLNRKWGLCIVGMG RLGSALADWPGFGESFELRGFFDVDPGMVGRPVRGGVIEHVDLLPQRVPGRIEIALLTVPREAAQKAADLLVAA GIKGILNFAPVVLEVPKEVAVENVDFLAGLTRLSFAILNPKWREEVIKPEMKMRYYMDGSVNGHEFTIEGEGTG RPYEGHQEMTLRVTMAEGGPMPFAFDLVSHVFCYGHRVFTKYPEEIPDYFKQAFPEGLSWERSLEFEDGGSASV SAHISLRGNTFYHKSKFTGVNFPADGPIMQNQSVDWEPSTEKITASDGVLKGDVTMYLKLEGGGNHKCQFKTTY KAAKEILEMPGDHYIGHRLVRKTEGNITEQVEDAVAHSEASMDELYK |
| 2-E1 | 149 | 0.01 | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGMVSKGEELFT GVVPILVELDGDVNGHKFSVSGEGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYNSHNVYIMADKQ KNGIKVNFKIRHNIEDGSVQLADHYQQNTPIGDGPVLLPDNHYLSTQSKLSKDPNEKRDHMVLLEFVTAAGITL GEAAISRLITYLRILEELEAQGVHRTASEQLGELAQVTAFQVDEDLSYFGSYGTDGVGYTVPVLKRELRHILGL NRKWGLCIVGMGRLGSALADWPGFGESFELRGFFDVDPGMVGRPVRGGVIEHVDLLPQRVPGRIEIALLTVPRE AAQKAADLLVAAGIKGILNFAPVVLEVPKEVAVENVDFLAGLTRLSFAILNPKWREEMMSVIKPEMKMRYYMDG SVNGHEFTIEGEGTGRPYEGHQEMTLRVTMAEGGPMPFAFDLVSHVFCYGHRVFTKYPEEIPDYFKQAFPEGLS WERSLEFEDGGSASVSAHISLRGNTFYHKSKFTGVNFPADGPIMQNQSVDWEPSTEKITASDGVLKGDVTMYLK LEGGGNHKCQFKTTYKAAKEILEMPGDHYIGHRLVRKTEGNITEQVEDAVAHSEASMDELYK |
| Initial construct #10 | 150 | ND | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGYNSHNVYIMA DKQKNGIKVNFKIRHNIEDGSVQLADHYQQNTPIGDGPVLLPDNHYLSTQSKLSKDPNEKRDHMVLLEFVTAAG ITLGMDELYKGGSGGMVSKGEELFTGVVPILVELDGDVNGHKFSVSGEGEGDATYGKLTLKFICTTGKLPVPWP TLVTTLTYGVQCFSRYPDHMKQHDFFKSAMPEGYVQERTIFFKDDGNYKTRAEVKFEGDTLVNRIELKGIDFKE DGNILGHKLEYNTKVPEAAISRLITYLRILEELEAQGVHRTASEQLGELAQVTAFQVDEDLSYFGSYGTDGVGY TVPVLKRELRHILGLNRKWGLCIVGMGRLGSALADWPGFGESFELRGFFDVDPGMVGRPVRGGVIEHVDLLPQR VPGRIEIALLTVPREAAQKAADLLVAAGIKGILNFAPVVLEVPKEVAVENVDFLAGLTRLSFAILNPKWREEMM GMVSVIKPEMKMRYYMDGSVNGHEFTIEGEGTGRPYEGHQEMTLRVTMAEGGPMPFAFDLVSHVFCYGHRVFTK YPEEIPDYFKQAFPEGLSWERSLEFEDGGSASVSAHISLRGNTFYHKSKFTGVNFPADGPIMQNQSVDWEPSTE KITASDGVLKGDVTMYLKLEGGGNHKCQFKTTYKAAKEILEMPGDHYIGHRLVRKTEGNITEQVEDAVAHS |
| Initial construct #12 | 151 | ND | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREAAQKAADLLVAAGIKGILNFAPVVLEVPKEVAVENVDILAGLTRLSFAILNPTWSAAGGHGDGSVQLADHY QQNTPIGDGPVLLPDNHYLSTQSKLSKDPNEKRDHMVLLEFVTAAGITLGMDELYKGGSGGMVSKGEELFTGVV PILVELDGDVNGHKFSVSGEGEGDATYGKLTLKFICTTGKLPVPWPTLVTTLTYGVQCFSRYPDHMKQHDFFKS AMPEGYVQERTIFFKDDGNYKTRAEVKFEGDTLVNRIELKGIDFKEDGNILGHKLEYNYNSHNVYIMADKQKNG IKVNFKIRHNIETKVPEAAISRLITYLRILEELEAQGVHRTASEQLGELAQVTAFQVDEDLSYFGSYGTDGVGY TVPVLKRELRHILGLNRKWGLCIVGMGRLGSALADWPGFGESFELRGFFDVDPGMVGRPVRGGVIEHVDLLPQR VPGRIEIALLTVPREAAQKAADLLVAAGIKGILNFAPVVLEVPKEVAVENVDFLAGLTRLSFAILNPKWREEMM GMVSVIKPEMKMRYYMDGSVNGHEFTIEGEGTGRPYEGHQEMTLRVTMAEGGPMPFAFDLVSHVFCYGHRVFTK YPEEIPDYFKQAFPEGLSWERSLEFEDGGSASVSAHISLRGNTFYHKSKFTGVNFPADGPIMQNQSVDWEPSTE KITASDGVLKGDVTMYLKLEGGGNHKCQFKTTYKAAKEILEMPGDHYIGHRLVRKTEGNITEQVEDAVAHS |

TABLE 2-continued

| Full clone name | SEQ ID NO | Signal window (ex mode), measured in lysates | Full protein sequence |
|---|---|---|---|
| Initial construct #16 | 152 | ND | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSAAGGHGMVSVIKPEMK MRYYMDGSVNGHEFTIEGEGTGRPYEGHQEMTLRVTMAEGGPMPFAFDLVSHVFCYGHRVFTKYPEEIPDYFKQ AFPEGLSWERSLEFEDGGSASVSAHISLRGNTFYHKSKFTGVNFPADGPIMQNQSVDWEPSTEKITASDGVLKG DVTMYLKLEGGGNHKCQFKTTYKAAKEILEMPGDHYIGHRLVRKTEGNITEQVEDAVAHSTKVPEAAISRLITY LRILEELEAQGVHRTASEQLGELAQVTAFQVDEDLSYFGSYGTDGVGYTVPVLKRELRHILGLNRKWGLCIVGM GRLGSALADWPGFGESFELRGFFDVDPGMVGRPVRGGVIEHVDLLPQRVPGRIEIALLTVPREAAQKAADLLVA AGIKGILNFAPVVLEVPKEVAVENVDFLAGLTRLSFAILNPKWREEMMGMVSKGEELFTGVVPILVELDGDVNG HKFSVSGEGEGDATYGKLTLKFICTTGKLPVPWPTLVTTLTYGVQCFSRYPDHMKQHDFFKSAMPEGYVQERTI FFKDDGNYKTRAEVKFEGDTLVNRIELKGIDFKEDGNILGHKLEYNYNSHNVYIMADKQKNGIKVNFKIRHNIE DGSVQLADHYQQNTPIGDGPVLLPDNHYLSTQSKLSKDPNEKRDHMVLLEFVTAAGITLGMDELYK |
| 10-11-F7 | 153 | ND | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWYNSHNVYIMADKQKNGI KVNFKIRHNIEDGSVQLADHYQQNTPIGDGPVLLPDNHYLSTQSKLSKDPNEKRDHMVLLEFVTAAGITLGMDE LYKGGSGGMVSKGEELFTGVVPILVELDGDVNGHKFSVSGEGEGDATYGKLTLKFICTTGKLPVPWPTLVTTLT YGVQCFSRYPDHMKQHDFFKSAMPEGYVQERTIFFKDDGNYKTRAEVKFEGDTLVNRIELKGIDFKEDGNILGH KLEYNTKVPEAAISRLITYLRILEELEAQGVHRTASEQLGELAQVTAFQVDEDLSYFGSYGTDGVGYTVPVLKR ELRHILGLNRKWGLCIVGMGRLGSALADWPGFGESFELRGFFDVDPGMVGRPVRGGVIEHVDLLPQRVPGRIEI ALLTVPREAAQKAADLLVAAGIKGILNFAPVVLEVPKEVAVENVDFLAGLTRLSFAILNPKWREVIKPEMKMRY YMDGSVNGHEFTIEGEGTGRPYEGHQEMTLRVTMAEGGPMPFAFDLVSHVFCYGHRVFTKYPEEIPDYFKQAFP EGLSWERSLEFEDGGSASVSAHISLRGNTFYHKSKFTGVNFPADGPIMQNQSVDWEPSTEKITASDGVLKGDVT MYLKLEGGGNHKCQFKTTYKAAKEILEMPGDHYIGHRLVRKTEGNITEQVEDAVAHS |
| 10-14-F6 | 154 | ND | MKVPEAAISRLITYLRILEELEAQGVHRTASEQLGELAQVTAFQVDKDLSYFGSYGTDGVGYTVPVLKRELRHI LGLNRKWGLCIVGMGRLGSALADWPGFGESFELRGFFDVDPGMVGRPVRGGVIEHVDLLPQRVPGRIEIALLTV PREEAAQKAADLLVAAGIKGILNFAPVVLEVPKEVAVENVDILAGLTRLSFAILNPTWSGYNSHNVYIMADKQKN GIKVNFKIRHNIEDGSVQLADHYQQNTPIGDGPVLLPDNHYLSTQSKLSKDPNEKRDHMVLLEFVTAAGITLGM DELYKGGSGGMVSKGEELFTGVVPILVELDGDVNGHKFSVSGEGEGDATYGKLTLKFICTTGKLPVPWPTLVTT LTYGVQCFSRYPDHMKQHDFFKSAMPEGYVQERTIFFKDDGNYKTRAEVKFEGDTLVNRIELKGIDFKEDGNIL GHKLEYNTKVPEAAISRLITYLRILEELEAQGVHRTASEQLGELAQVTAFQVDEDLSYFGSYGTDGVGYTVPVL KRELRHILGLNRKWGLCIVGMGRLGSALADWPGFGESFELRGFFDVDPGMVGRPVRGGVIEHVDLLPQRVPGRI EIALLTVPREAAQKAADLLVAAGIKGILNFAPVVLEVPKEVAVENVDFLAGLTRLSFAILNPKWREVIKPEMKM RYYMDGSVNGHEFTIEGEGTGRPYEGHQEMTLRVTMAEGGPMPFAFDLVSHVFCYGHRVFTKYPEEIPDYFKQA FPEGLSWERSLEFEDGGSASVSAHISLRGNTFYHKSKFTGVNFPADGPIMQNQSVDWEPSTEKITASDGVLKGD VTMYLKLEGGGNHKCQFKTTYKAAKEILEMPGDHYIGHRLVRKTEGNITEQVEDAVAHS |

In one embodiment, the fusion protein comprises an amino acid sequence at least 90%, 91%, 92%, 93%, 94% 95%, 96%, 97%, 98%, 99%, or 100% identical to the amino acid sequence selected from the group consisting of SEQ ID NO:13-43 and 191-193. In another embodiment, the fusion protein comprises an amino acid sequence at least 90%, 91%, 92%, 93%, 94% 95%, 96%, 97%, 98%, 99%, or 100% identical to the amino acid sequence selected from the group consisting of SEQ ID NO:13-28 and 191-193. In a further embodiment, the fusion protein comprises an amino acid sequence at least 90%, 91%, 92%, 93%, 94% 95%, 96%, 97%, 98%, 99%, or 100% identical to the amino acid sequence selected from the group consisting of SEQ ID NO:13-22 and 191-193. In a still further embodiment, the fusion protein comprises an amino acid sequence at least 90%, 91%, 92%, 93%, 94% 95%, 96%, 97%, 98%, 99%, or 100% identical to the amino acid sequence selected from the group consisting of SEQ ID NO:13-14 and 191-193.

In one aspect, the disclosure provides fusion proteins comprising the amino acid sequence selected from the group consisting of SEQ ID NO: 13-93, 95-154, and 191-193, SEQ ID NO:13-43 and 191-193, SEQ ID NO:13-28 and 191-193, SEQ ID NO:13-22 and 191-193, or SEQ ID NO:13-14 and 191-193.

In another aspect, the disclosure provides control fusion proteins comprising the fusion protein of any embodiment or combination of embodiments disclosed above, with the proviso that X1 and X3 comprises a mutation to confer non-responsiveness to NAD+/NADH ratio change. The control fusion proteins do not bind to NAD(H) and thus the control biosensor reports on non-NAD(H) related changes of the biosensor activity (e.g., fluorescent protein brightness change due to variation of intracellular pH). Any suitable mutation to confer such non-responsiveness may be employed. In one embodiment, the mutation comprises:

(a) a G89A mutation in X1 relative to SEQ ID NO:1 residue numbering, and (b) a G84A mutation in X3 relative to SEQ ID NO:2 residue numbering.

Those of skill in the art will be able to determine, based on the teachings herein, the position of the G89A mutation in variations of the RexA sequence (G89A in SEQ ID NOS:8 and 9) and the G84A mutation in variations of the RexB sequence (G88A in SEQ ID NO:11). By way of non-limiting example, the position of G84 is highlighted and underlined in SEQ ID NO:2 below, and SEQ ID NO:11 includes 4 additional residues at the N-terminus, so that the mutation is G88A in the control fusion protein based on X3 comprising SEQ ID NO:11.

(SEQ ID NO: 2)
AAISRLITYLRILEELEAQGVHRTASEQLGELAQVTAFQVDEDLSYFGS

YGTDGVGYTVPVLKRELRHILGLNRKWGLCIVGM<u>G</u>RLGSALADWPGFGE

SFELRGFFDVDPGMVGRPVRGGVIEHVDLLPQRVPGRIEIALLTVPREA

AQKAADLLVAAGIKGILNFAPVVLEVPKEVAVENVDFLAGLTRLSFAIL

NPKWRE.

(SEQ ID NO: 11)
KVPEAAISRLITYLRILEELEAQGVHRTASEQLGELAQVTAFQVDEDLS

YFGSYGTDGVGYTVPVLKRELRHILGLNRKWGLCIVGM<u>G</u>RLGSALADWP

GFGESFELRGFFDVDPGMVGRPVRGGVIEHVDLLPQRVPGRIEIALLTV

PREAAQKAADLLVAAGIKGILNFAPVVLEVPKEVAVENVDFLAGLTRLS

FAILNPKWREEMMG

Thus, in specific embodiments, the control fusion proteins comprise the amino acid sequence selected from the group consisting of SEQ ID NO: 13-93, 95-154, and 191-193; the sequences are provided in Table 2 and the examples, with the proviso that each include a G89A mutation. One specific example of a control is provided in SEQ ID NO:194. By way of example, SEQ ID NO:13 is provided below, and the position of G89 is bolded and underlined—mutating this residue to alanine renders SEQ ID NO:13 a control fusion protein. Similarly, each of SEQ ID NO: 13-93, 95-154, and 191-193 include a G89 that becomes a control fusion protein when G89 is mutated to G89A.

SEQ ID NO: 13:
MKVPEAAISRLITYLRILEELEAQGVHRTASEQLGELAQVTAFQVDKDL

SYFGSYGTDGVGYTVPVLKRELRHILGLNRKWGLCIVGM<u>G</u>RLGSALAD

WPGFGESFELRGFFDVDPGMVGRPVRGGVIEHVDLLPQRVPGRIEIALL

TVPREAAQKAADLLVAAGIKGILNFAPVVLEVPKEVAVENVDILAGLT

RLSFAILNPTWSAAGGHGMVSKGEELFTGVVPILVELDGDVNGHKFSVS

GEGEGDATYGKLTLKFICTTGKLPVPWPTLVTTLTYGVQCFSRYPDHM

KQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGS

VQLADHYQQNTPIGDGPVLLPDNHYLSTQSKLSKDPNEKRDHMVLLEFV

TAAGITLGMDEVPEAAISRLITYLRILEELEAQGVHRTASEQLGELAQ

VTAFQVDEDLSYFGSYGTDGVGYTVPVLKRELRHILGLNRKWGLCIVGM

GRLGSALADWPGFGESFELRGFFDVDPGMVGRPVRGGVIEHVDLLPQR

VPGRIEIALLTVPREAAQKAADLLVAAGIKGILNFAPVVLEVPKEVAVE

NVDFLAGLTRLSFAILNPKWREIKPEMKMRYYMDGSVNGHEFTIEGEG

TGRPYEGHQEMTLRVTMAEGGPMPFAFDLVSHVFCYGHRVFTKYPEEIP

DYFKQAFPEGLSWERSLEFEDGGSASVSAHISLRGNTFYHKSKFTGVN

FPADGPIMQNQSVDWEPSTEKITASDGVLKGDVTMYLKLEGGGNHKCQF

KTTYKAAKEILEMPGDHYIGHRLVRKTEGNITEQVEDAVAHSEASMDE

LYK

As will be understood by those of skill in the art, the fusion proteins of the disclosure may include additional residues at the N-terminus, C-terminus, or both that are not present in the described fusion proteins; these additional residues are not included in determining the percent identity of the polypeptides of the disclosure relative to the reference polypeptide. Such residues may be any residues suitable for an intended use, including but not limited to ligands suitable for purposes of purification (His tags, etc.), and additional peptide domains that add functionality to the polypeptides.

In one embodiment, changes relative to the reference fusion proteins comprises conservative amino acid substitution. As used herein, "conservative amino acid substitution" means amino acid or nucleic acid substitutions that do not alter or substantially alter fusion protein or domain function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in the assays described herein to confirm that a desired activity is retained.

In another aspect, the disclosure provides polynucleotides encoding the fusion protein or control fusion protein ("control polynucleotides") of any embodiment or combination of embodiments of the disclosure. The polynucleotides may comprise RNA or DNA. Such polynucleotides may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what polynucleotides will encode the fusion proteins of the disclosure.

In specific embodiments, the nucleic acids may comprise the following nucleotide sequence, or an RNA transcript thereof:

1-F8 1-2

(SEQ ID NO: 159)
ATGaaaGTTCCTGAGGCAGCCATTTCCAGACTGATTACTTATCTCCGCATTCTGGAAGAGTTGGAGGCAC

AAGGTGTACACCGCACCGCCTCCGAACAACTCGGAGAGCTGGCCCAGGTCACCGCCTTTCAGGTTGATAA

GGACCTGTCCTACTTTGGCAGTTACGGAACTGACGGCGTGGGATACACTGTACCAGTCCTCAAGAGAGAA

CTCAGACATATCCTCGGTCTCAACAGAAAATGGGGCCTGTGTATCGTGGGGATGGGACGCCTGGGATCCG

CTCTTGCTGATTGGCCTGGTTTCGGCGAGAGCTTTGAGCTGAGGGGTTTCTTTGATGTGGACCCAGGTAT

GGTCGGTCGGCCGGTTCGCGGTGGTGTGATCGAACACGTGGATCTGTTGCCCCAACGCGTACCTGGTAGA

-continued

```
ATCGAAATCGCTCTGCTTACGGTCCCAAGAGAGGCAGCACAGAAAGCTGCCGACCTGCTGGTTGCAGCTG
GCATCAAAGGAATCCTCAATTTCGCTCCAGTTGTACTCGAGGTTCCCAAAGAGGTGGCAGTTGAGAATGT
GGACATCCTTGCCGGTCTTACGCGTCTGAGCTTTGCCATTCTGAACCCCACGTGGagcgcagcaggtggg
catggtATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCGTGACCACCCTGACCTACGGC
GTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACGGCAACATCCTG
GGGCACAAGCTGGAGTACAACTACAACAGCCACAACGTCTATATCATGGCCGACAAGCAGAAGAACGGCA
TCAAGGTGAACTTCAAGATCCGCCACAACATCGAGGACGGCAGCGTGCAGCTCGCCGACCACTACCAGCA
GAACACCCCCATCGGCGACGGCCCCGTGCTGCTGCCCGACAACCACTACCTGAGCACCCAGTCCAAGCTG
AGCAAAGACCCCAACGAGAAGCGCGATCACATGGTCCTGCTGGAGTTCGTGACCGCCGCGGGATCACTC
TCGGCATGGACGAGGTACCAGAAGCCGCTATCAGCCGCTTGATCACATACTTGAGAATCTTGGAGGAACT
CGAAGCTCAGGGAGTTCATAGAACTGCAAGCGAGCAGTTGGGCGAACTCGCACAAGTTACAGCATTCCAA
GTGGACGAAGATCTCAGTTATTTCGGTTCCTATGGCACCGATGGTGTTGGCTATACAGTCCCTGTTTTGA
AACGCGAGTTGCGCCACATTTTGGGCCTGAATCGCAAGTGGGGATTATGCATTGTTGGCATGGGCAGGTT
AGGTAGTGCACTGGCAGACTGGCCGGGCTTTGGTGAATCTTTCGAACTCAGAGGCTTTTTCGACGTTGAT
CCTGGCATGGTTGGGAGACCTGTCAGAGGAGGCGTTATTGAGCATGTTGACCTCCTGCCACAGAGAGTCC
CGGGACGCATTGAGATTGCCCTCCTGACCGTTCCTCGCGAAGCTGCCCAAAAGGCAGCTGATTTACTAGT
CGCCGCAGGTATTAAGGGCATTTTGAACTTTGCCCCTGTGGTTCTGGAAGTGCCTAAGGAAGTTGCTGTC
GAAAACGTTGATTTCCTGGCTGGCTTGACCCGCCTTTCCTTCGCAATCCTCAATCCTAAGTGGcgcgaag
tgATTAAACCAGAGATGAAGATGAGGTACTACATGGACGGCTCCGTCAATGGGCATGAGTTCACAATTGA
AGGTGAAGGCACAGGCAGACCTTACGAGGGACATCAAGAGATGACACTACGCGTCACAATGGCCGAGGGC
GGGCCAATGCCTTTCGCGTTTGACTTAGTGTCACACGTGTTCTGTTACGGCCACAGAGTATTTACTAAAT
ATCCAGAAGAGATACCAGACTATTTCAAACAAGCATTTCCTGAAGGCCTGTCATGGGAAAGGTCGTTGGA
GTTCGAAGATGGTGGGTCCGCTTCAGTCAGTGCGCATATAAGCCTTAGAGGAAACACCTTCTACCACAAA
TCCAAATTTACTGGGGTTAACTTTCCTGCCGATGGTCCTATCATGCAAAACCAAAGTGTTGATTGGGAGC
CATCAACCGAGAAAATTACTGCCAGCGACGGAGTTCTGAAGGGTGATGTTACGATGTACCTAAAACTTGA
AGGAGGCGGCAATCACAAATGCCAATTCAAGACTACTTACAAGGCGGCAAAAGAGATTCTTGAAATGCCA
GGAGACCATTACATCGGCCATCGCCTCGTCAGGAAAACCGAAGGCAACATTACTGAGCAggtagaagatg
cagtagctcattccGAAGCTAGCATGGACGAGCTCTACAAG
```

1-F8 1-2 control (SEQ ID NO: 160)

```
ATGaaaGTTCCTGAGGCAGCCATTTCCAGACTGATTACTTATCTCCGCATTCTGGAAGAGTTGGAGGCAC
AAGGTGTACACCGCACCGCCTCCGAACAACTCGGAGAGCTGGCCCAGGTCACCGCCTTTCAGGTTGATAA
GGACCTGTCCTACTTTGGCAGTTACGGAACTGACGGCGTGGGATACACTGTACCAGTCCTCAAGAGAGAA
CTCAGACATATCCTCGGTCTCAACAGAAAATGGGGCCTGTGTATCGTGGGGATGGCTCGCCTGGGATCCG
CTCTTGCTGATTGGCCTGGTTTCGGCGAGAGCTTTGAGCTGAGGGGTTTCTTTGATGTGGACCCAGGTAT
GGTCGGTCGGCCGGTTCGCGGTGGTGTGATCGAACACGTGGATCTGTTGCCCCAACGCGTACCTGGTAGA
ATCGAAATCGCTCTGCTTACGGTCCCAAGAGAGGCAGCACAGAAAGCTGCCGACCTGCTGGTTGCAGCTG
GCATCAAAGGAATCCTCAATTTCGCTCCAGTTGTACTCGAGGTTCCCAAAGAGGTGGCAGTTGAGAATGT
```

-continued

```
GGACATCCTTGCCGGTCTTACGCGTCTGAGCTTTGCCATTCTGAACCCCACGTGGagcgcagcaggtggg
catggtATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCGTGACCACCCTGACCTACGGC
GTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACGGCAACATCCTG
GGGCACAAGCTGGAGTACAACTACAACAGCCACAACGTCTATATCATGGCCGACAAGCAGAAGAACGGCA
TCAAGGTGAACTTCAAGATCCGCCACAACATCGAGGACGGCAGCGTGCAGCTCGCCGACCACTACCAGCA
GAACACCCCCATCGGCGACGGCCCCGTGCTGCTGCCCGACAACCACTACCTGAGCACCCAGTCCAAGCTG
AGCAAAGACCCCAACGAGAAGCGCGATCACATGGTCCTGCTGGAGTTCGTGACCGCCGCCGGGATCACTC
TCGGCATGGACGAGGTACCAGAAGCCGCTATCAGCCGCTTGATCACATACTTGAGAATCTTGGAGGAACT
CGAAGCTCAGGGAGTTCATAGAACTGCAAGCGAGCAGTTGGGCGAACTCGCACAAGTTACAGCATTCCAA
GTGGACGAAGATCTCAGTTATTTCGGTTCCTATGGCACCGATGGTGTTGGCTATACAGTCCCTGTTTTGA
AACGCGAGTTGCGCCACATTTTGGGCCTGAATCGCAAGTGGGGATTATGCATTGTTGGCATGGCCAGGTT
AGGTAGTGCACTGGCAGACTGGCCGGGCTTTGGTGAATCTTTCGAACTCAGAGGCTTTTTCGACGTTGAT
CCTGGCATGGTTGGGAGACCTGTCAGAGGAGGCGTTATTGAGCATGTTGACCTCCTGCCACAGAGAGTCC
CGGGACGCATTGAGATTGCCCTCCTGACCGTTCCTCGCGAAGCTGCCCAAAAGGCAGCTGATTTACTAGT
CGCCGCAGGTATTAAGGGCATTTTGAACTTTGCCCCTGTGGTTCTGGAAGTGCCTAAGGAAGTTGCTGTC
GAAAACGTTGATTTCCTGGCTGGCTTGACCCGCCTTTCCTTCGCAATCCTCAATCCTAAGTGGcgcgaag
tgATTAAACCAGAGATGAAGATGAGGTACTACATGGACGGCTCCGTCAATGGGCATGAGTTCACAATTGA
AGGTGAAGGCACAGGCAGACCTTACGAGGGACATCAAGAGATGACACTACGCGTCACAATGGCCGAGGGC
GGGCCAATGCCTTTCGCGTTTGACTTAGTGTCACACGTGTTCTGTTACGGCCACAGAGTATTTACTAAAT
ATCCAGAAGAGATACCAGACTATTTCAAACAAGCATTTCCTGAAGGCCTGTCATGGGAAAGGTCGTTGGA
GTTCGAAGATGGTGGGTCCGCTTCAGTCAGTGCGCATATAAGCCTTAGAGGAAACACCTTCTACCACAAA
TCCAAATTTACTGGGGTTAACTTTCCTGCCGATGGTCCTATCATGCAAAACCAAAGTGTTGATTGGGAGC
CATCAACCGAGAAAATTACTGCCAGCGACGGAGTTCTGAAGGGTGATGTTACGATGTACCTAAAACTTGA
AGGAGGCGGCAATCACAAATGCCAATTCAAGACTACTTACAAGGCGGCAAAAGAGATTCTTGAAATGCCA
GGAGACCATTACATCGGCCATCGCCTCGTCAGGAAAACCGAAGGCAACATTACTGAGCAggtagaagatg
cagtagctcattccGAAGCTAGCATGGACGAGCTCTACAAG
```

In another aspect, the disclosure provides recombinant expression vectors comprising the polynucleotides or control polynucleotides ("control expression vectors") of any embodiment or combination of embodiments of the disclosure operatively linked to a promoter sequence capable of directing expression of the polynucleotide. "Recombinant expression vector" includes vectors that operatively link the polynucleotides to any promoter sequence capable of effecting expression of the fusion proteins. "Promoter sequences" operatively linked to the nucleic acid sequences of the disclosure are nucleic acid sequences capable of effecting the expression of the polynucleotides. The promoter need not be contiguous with the polynucleotide, so long as it functions to direct polynucleotide expression. Thus, for example, intervening untranslated yet transcribed sequences can be present between a promoter sequence and the polynucleotide and the promoter sequence can still be considered "operably linked" to the coding sequence. Such expression vectors can be of any type known in the art, including but not limited plasmid and viral-based expression vectors. The promoter may be constitutive (driven by any of a variety of promoters, including but not limited to, CMV, SV40, RSV, actin, EF-1α) or inducible (driven by any of a number of inducible promoters including, but not limited to, tetracycline, ecdysone, steroid-responsive). In various embodiments, the expression vector may comprise a plasmid, viral-based vector, or any other suitable expression vector.

In a further aspect, the present disclosure provides recombinant host cells that comprise the recombinant expression vectors or control expression vectors ("control recombinant host cells") disclosed herein, wherein the host cells can be either prokaryotic or eukaryotic. The cells can be transiently or stably engineered to incorporate the expression vector of the disclosure. A method of producing a fusion protein according to the disclosure is an additional part of the disclosure. The method comprises the steps of (a) culturing a host according to this aspect of the disclosure under conditions conducive to the expression of the fusion protein, and (b) optionally, recovering the expressed fusion protein. The expressed fusion protein can be recovered from the cell free extract or the cell culture medium.

The disclosure further provides kits, comprising
  (a) the fusion protein of any embodiment of the disclosure, and the control fusion protein of any embodiment of the disclosure;
  (b) the polynucleotide of any embodiment of the disclosure and the control polynucleotide of any embodiment of the disclosure;
  (c) the expression vector of any embodiment of the disclosure and the control expression vector of any embodiment of the disclosure; and/or
  (d) the recombinant host cell of any embodiment of the disclosure and the control recombinant host cell of any embodiment of the disclosure.

The kits can be used, for example, to carry out the methods of the disclosure.

In another aspect, the disclosure provides methods for determining an NAD+/NADH ratio change in a cell of interest, comprising of expressing a FRET biosensor in a cell that undergoes a detectable change upon binding of the FRET biosensor to NAD(H) in the cell, and performing live-cell imaging to determine the ratio of NAD+/NADH inside living cells. Any suitable FRET biosensor can be used, so long as it undergoes a detectable change upon binding of the FRET biosensor to NAD(H) in the cell. Any cell imaging system may be used, including but not limited to a live cell imaging microscope and incubator system. In one non-limiting embodiment, the live cell imaging microscope and incubator system IncuCyte® SX5 (Sartorius). The IncuCyte® SX5 hardware may be used for any method of the disclosure, and is composed of 2 components: 1) gantry and 2) controller. The gantry houses the microscope, camera, and consumable trays that enable automated image acquisition of live-cell cultures and is installed inside a standard tissue culture incubator. In the NAD+/NADH ratio change application the microscope system contains a filter module that is tailored to collecting fluorescent images in the desired spectrum (or spectra). The controller contains processors, memory and data storage drives that enable image storage, data handling, database storage, file systems, automated image processing, graphing and over-the-network interaction from the client computer through a graphical user interface (GUI). The software on the controller serves two purposes: 1) server interaction, and 2) instrument control.

The gantry is installed in an incubator and houses the microscope and camera. The controller controls the microscope system and functions as a server. The controller plugs into a communications port, such as, but not limited to, an ethernet port. A graphical user interface (GUI) is loaded on to a computer and interacts with the controller (i.e., server) to control the microscope system and interact with the data. All automated image processing is completed on the controller according to aspects of the present disclosure.

The Incucyte ° SX5 microscope moves to user defined locations of cell culture vessels, such as, but not limited to, 96-well plates, turns on the appropriate LED and captures images at a desired exposure time using a desired microscope objective, such as, 700 ms using the 10× objective.

Data may be calculated for each object, each well, or each set of wells, stored in a database, and displayed to the user shortly following data acquisition in the client computer through the graphical user interface. Wells may be scanned as deemed appropriate, such as every 2 hours. Following each scan, metrics are calculated and stored, for instance in the database, at those time points. For example, over the course of a 3-day experiment, 36 time points may be collected for each metric, are concatenated into a time series and can be graphed over the course of the full experimental time frame, i.e. minutes, hours, days, weeks, months.

In one embodiment, the disclosure provides a method of measuring an NAD+/NADH ratio change in a cell of interest, comprising:
  (a) expressing the fusion protein of any embodiment of the disclosure in one or more first cells, and generating one or more images selected from the group consisting of:
    (i) a first fluorescence image generated by detecting fluorescent signals produced by light having the FRET acceptor polypeptide emission wavelength emitted from the one or more first cells upon exposing the one or more first cells to light having the FRET donor polypeptide excitation wavelength; and/or
    (ii) a second fluorescence image generated by detecting fluorescent signals produced by light having the FRET acceptor polypeptide emission wavelength emitted from the one or more first cells upon exposing the one or more first cells to light having the FRET acceptor polypeptide excitation wavelength; and/or
    (iii) a third fluorescence image generated by detecting fluorescent signals produced by light having the FRET donor polypeptide emission wavelength emitted from the one or more first cells upon exposing the one or more first cells to light having the FRET donor polypeptide excitation wavelength; and
  (b) determining a FRET ratio in the one or more first cells by comparing the output of fluorescent signals in the first fluorescent image, the second fluorescent image, and/or the third fluorescent image;
  wherein an NAD+/NADH ratio in the one or more first cells is proportional to the determined FRET ratio.

In this embodiment, "comparing" the output of fluorescent signals means dividing the output of fluorescent signals in one image by the output of fluorescent signals in a different image. For example:
  the output of fluorescent signals in the first fluorescent image can be divided by the output of fluorescent signals in the second fluorescent image;
  the output of fluorescent signals in the first fluorescent image can be divided by the output of fluorescent signals in the third fluorescent image;
  the output of fluorescent signals in the second fluorescent image can be divided by the output of fluorescent signals in the first fluorescent image;
  the output of fluorescent signals in the second fluorescent image can be divided by the output of fluorescent signals in the third fluorescent image;
  the output of fluorescent signals in the third fluorescent image can be divided by the output of fluorescent signals in the first fluorescent image; or
  the output of fluorescent signals in the third fluorescent image can be divided by the output of fluorescent signals in the second fluorescent image.

The "outputs" of fluorescent signals can be determined on any suitable basis, including but not limited to on a whole image basis, per cell basis, on a per pixel basis, or using any alternative intensity measurements.

In another embodiment, the methods further comprise expressing the control fusion protein of any embodiment or combination of embodiments of the disclosure in one or more first cells, and detecting a control signal produced by light having the acceptor emission wavelength emitted from the one or more first cells. Any suitable method for using the control signal to correct the determined FRET ratio may be used. In one embodiment, detecting the control signal comprises (c) expressing the control fusion protein of any embodiment of the disclosure in one or more control cells (such as the first cells, or second cells), and generating one or more images selected from the group consisting of:
  (i) a fourth fluorescence image generated by detecting fluorescent signals produced by light having the FRET acceptor polypeptide emission wavelength emitted from the one or more control cells upon exposing the one or more control cells to light having the FRET donor polypeptide excitation wavelength; and/or
  (ii) a fifth fluorescence image generated by detecting fluorescent signals produced by light having the FRET acceptor polypeptide emission wavelength emitted from the one or more control cells upon exposing the one or more control cells to light having the FRET acceptor polypeptide excitation wavelength; and/or
  (iii) a sixth fluorescence image generated by detecting fluorescent signals produced by light having the FRET donor polypeptide emission wavelength emitted from the one or more control cells upon exposing the one or more control cells to light having the FRET donor polypeptide excitation wavelength; and
(d) determining a control fusion FRET ratio in the one or more control cells by comparing the output of fluorescent signals in the fourth fluorescent image, the fifth fluorescent image, and/or the sixth fluorescent image;
wherein alterations in the control fusion FRET ratio are determined to be the result of experimental conditions unrelated to NAD+/NADH ratio, and wherein the determined FRET ratio is corrected based on the alterations in the control fusion FRET ratio.

The one or more cells may be any cell or cell population in which determining NAD+/NADH ratio is of interest. In one embodiment, the one or more first cells are in culture in an incubator. In another embodiment, all imaging steps are performed without removing the one or more first cells from the incubator. In this embodiment, the cells are cultured in a suitable cell culture medium in an incubator, and the incubator is configured such that the cells to be assayed do not have to be removed from the incubator during observation and/or recording of assays for detecting changes in NAD+/NADH ratio.

The assays can be used, for example, to test the effect of one or more test compounds on NAD+/NADH ratio in cells of interest. Thus, in one embodiment, the methods further comprise contacting the one or more first cells with one or more test substance and determining an effect of the test substance on NAD+/NADH ratio in the one or more first cells. The effect of the one or more test substance on the NAD+/NADH ratio in the one or more first cells may be determined over any time period of interest, including but not limited to continuously or intermittently over a time period in the range of 1 minute to three months.

Embodiments of the compositions and methods of the disclosure are illustrated in the following examples. These examples are provided for illustrative purposes and are not considered limitations on the scope of the claimed compositions and methods.

Examples 16 initial FRET constructs (See Table 3) were constructed using expression vector pET28c with a T7 promoter and lac operator and expressed in *E. coli*. Cells were collected and lysed using a commercially-available lysis buffer. Proteins of interest were isolated from the lysates using Ni-NTA magnetic beads. Eluted proteins were subjected to buffer exchange and final protein concentrating. To test performance of the initial FRET constructs, their emission spectra was recorded on a plate reader in absence or presence of 40 uM NADH. Resulting emission spectra with or without the ligand were normalized and overlaid for each construct. Constructs with very clear and robust spectra separation were labeled as having "good response", those with noticeable but small spectra separation were labeled as having "poor response", and finally those having no spectra separation were labeled as having "no response".

TABLE 3

| | Initial constructs | |
|---|---|---|
| 1 | mKOk-Rex(78-189)-cpmEGFP(145/146)-Rex(190-211)-Rex(78-211) | No response |
| 2 | Rex(78-189)-cpmEGFP(145/146)-Rex(190-211)-Rex(78-211)-mKOk | Poor response |
| 3 | mKOk-Rex(78-211)-Rex(78-189)-cpmEGFP(145/146)-Rex(190-211) | No response |
| 4 | Rex(78-211)-Rex(78-189)-cpmEGFP(145/146)-Rex(190-211)-mKOk | No response |
| 5 | mKOk-Rex(78-189)-cpmEGFP(173/174)-Rex(190-211)-Rex(78-211) | No response |
| 6 | Rex(78-189)-cpmEGFP(173/174)-Rex(190-211)-Rex(78-211)-mKOk | No response |
| 7 | mKOk-Rex(78-211)-Rex(78-189)-cpmEGFP(173/174)-Rex(190-211) | No response |
| 8 | Rex(78-211)-Rex(78-189)-cpmEGFP(173/174)-Rex(190-211)-mKOk | No response |
| 9 | mKOk-Rex(A)-cpmEGFP(145/146)-Rex(B) | No response |
| 10 | Rex(A)-cpmEGFP(145/146)-Rex(B)-mKOk | Good response |
| 11 | mKOk-Rex(A)-cpmEGFP(173/174)-Rex(B) | Poor response |
| 12 | Rex(A)-cpmEGFP(173/174)-Rex(B)-mKOk | Good response |
| 13 | mKOk-Rex(A)-mEGFP-Rex(B) | Poor response |
| 14 | Rex(A)-mEGFP-Rex(B)-mKOk | Good response |

TABLE 3-continued

| Initial constructs | |
|---|---|
| 15 mEGFP-Rex(A)-mKOk-Rex(B) | No response |
| 16 Rex(A)-mKOk-Rex(B)-mEGFP | Good response |

Rex(78-189) - WT T-Rex from aa 78 to aa 189
Rex(190-211) - WT T-Rex from aa 190 to aa 211
Rex(78-211) - WT T-Rex from aa 78 to aa 211
Rex(A) - T-Rex from aa 1 to aa 205, mutations compared to WT: S30A, R46D, K58D, Y98W, E116G, K117M, F189I, K204T
Rex(B) - T-Rex from aa 2 to aa 211, mutations compared to WT: S30A, R46D, K47E, K58D, Y98W, E116G, K117M
cpmEGFP(145/146) - mEGFP permuted between amino acids N145 and Y146
cpmEGFP(173/174) - mEGFP permuted between amino acids E173 and D174

Full sequences of the initial constructs are shown below.

```
Initial construct #1
                                                       (SEQ ID NO: 161)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSNRKWGLCIVGMGRLGSALADYPGFGESFELRGFFDVDPEKVGRPVRGGVIEHVDLLPQRVPG

RIEIALLTVPREAAQKAADLLVAAGIKGILNFAPVVLEVPKEVAVENVDFSAYNSHNVYIMADKQKNGIK

VNFKIRHNIEDGSVQLADHYQQNTPIGDGPVLLPDNHYLSTQSKLSKDPNEKRDHMVLLEFVTAAGITLG

MDELYKGGSGGMVSKGEELFTGVVPILVELDGDVNGHKFSVSGEGEGDATYGKLTLKFICTTGKLPVPWP

TLVTTLTYGVQCFSRYPDHMKQHDFFKSAMPEGYVQERTIFFKDDGNYKTRAEVKFEGDTLVNRIELKGI

DFKEDGNILGHKLEYNGLAGLTRLSFAILNPKWREEMMGNRKWGLCIVGMGRLGSALADYPGFGESFELR

GFFDVDPEKVGRPVRGGVIEHVDLLPQRVPGRIEIALLTVPREAAQKAADLLVAAGIKGILNFAPVVLEV

PKEVAVENVDFLAGLTRLSFAILNPKWREEMMG

Initial construct #2
                                                       (SEQ ID NO: 162)
MNRKWGLCIVGMGRLGSALADYPGFGESFELRGFFDVDPEKVGRPVRGGVIEHVDLLPQRVPGRIEIALL

TVPREAAQKAADLLVAAGIKGILNFAPVVLEVPKEVAVENVDESAYNSHNVYIMADKQKNGIKVNEKIRH

NIEDGSVQLADHYQQNTPIGDGPVLLPDNHYLSTQSKLSKDPNEKRDHMVLLEFVTAAGITLGMDELYKG

GSGGMVSKGEELFTGVVPILVELDGDVNGHKFSVSGEGEGDATYGKLTLKFICTTGKLPVPWPTLVTTLT

YGVQCFSRYPDHMKQHDFFKSAMPEGYVQERTIFFKDDGNYKTRAEVKFEGDTLVNRIELKGIDFKEDGN

ILGHKLEYNGLAGLTRLSFAILNPKWREEMMGNRKWGLCIVGMGRLGSALADYPGFGESFELRGFFDVDP

EKVGRPVRGGVIEHVDLLPQRVPGRIEIALLTVPREAAQKAADLLVAAGIKGILNFAPVVLEVPKEVAVE

NVDFLAGLTRLSFAILNPKWREEMMGMVSVIKPEMKMRYYMDGSVNGHEFTIEGEGTGRPYEGHQEMTLR

VTMAEGGPMPFAFDLVSHVFCYGHRVFTKYPEEIPDYFKQAFPEGLSWERSLEFEDGGSASVSAHISLRG

NTFYHKSKFTGVNFPADGPIMQNQSVDWEPSTEKITASDGVLKGDVTMYLKLEGGGNHKCQFKTTYKAAK

EILEMPGDHYIGHRLVRKTEGNITEQVEDAVAHS

Initial construct #3
                                                       (SEQ ID NO: 163)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSNRKWGLCIVGMGRLGSALADYPGFGESFELRGFFDVDPEKVGRPVRGGVIEHVDLLPQRVPG

RIEIALLTVPREAAQKAADLLVAAGIKGILNFAPVVLEVPKEVAVENVDFLAGLTRLSFAILNPKWREEM

MGNRKWGLCIVGMGRLGSALADYPGFGESFELRGFFDVDPEKVGRPVRGGVIEHVDLLPQRVPGRIEIAL
```

```
LTVPREAAQKAADLLVAAGIKGILNFAPVVLEVPKEVAVENVDFSAYNSHNVYIMADKQKNGIKVNFKIR

HNIEDGSVQLADHYQQNTPIGDGPVLLPDNHYLSTQSKLSKDPNEKRDHMVLLEFVTAAGITLGMDELYK

GGSGGMVSKGEELFTGVVPILVELDGDVNGHKESVSGEGEGDATYGKLTLKFICTTGKLPVPWPTLVTTL

TYGVQCFSRYPDHMKQHDFFKSAMPEGYVQERTIFFKDDGNYKTRAEVKFEGDTLVNRIELKGIDFKEDG

NILGHKLEYNGLAGLTRLSFAILNPKWREEMMG

Initial construct #4
                                                          (SEQ ID NO: 164)
MNRKWGLCIVGMGRLGSALADYPGFGESFELRGFFDVDPEKVGRPVRGGVIEHVDLLPQRVPGRIEIALL

TVPREAAQKAADLLVAAGIKGILNFAPVVLEVPKEVAVENVDFLAGLTRLSFAILNPKWREEMMGNRKWG

LCIVGMGRLGSALADYPGFGESFELRGFFDVDPEKVGRPVRGGVIEHVDLLPQRVPGRIEIALLTVPREA

AQKAADLLVAAGIKGILNFAPVVLEVPKEVAVENVDESAYNSHNVYIMADKQKNGIKVNFKIRHNIEDGS

VQLADHYQQNTPIGDGPVLLPDNHYLSTQSKLSKDPNEKRDHMVLLEFVTAAGITLGMDELYKGGSGGMV

SKGEELFTGVVPILVELDGDVNGHKFSVSGEGEGDATYGKLTLKFICTTGKLPVPWPTLVTTLTYGVQCE

SRYPDHMKQHDFFKSAMPEGYVQERTIFFKDDGNYKTRAEVKFEGDTLVNRIELKGIDFKEDGNILGHKL

EYNGLAGLTRLSFAILNPKWREEMMGMVSVIKPEMKMRYYMDGSVNGHEFTIEGEGTGRPYEGHQEMTLR

VTMAEGGPMPFAFDLVSHVFCYGHRVFTKYPEEIPDYFKQAFPEGLSWERSLEFEDGGSASVSAHISLRG

NTFYHKSKFTGVNFPADGPIMQNQSVDWEPSTEKITASDGVLKGDVTMYLKLEGGGNHKCQFKTTYKAAK

EILEMPGDHYIGHRLVRKTEGNITEQVEDAVAHS

Initial construct #5
                                                          (SEQ ID NO: 165)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSNRKWGLCIVGMGRLGSALADYPGFGESFELRGFFDVDPEKVGRPVRGGVIEHVDLLPQRVPG

RIEIALLTVPREAAQKAADLLVAAGIKGILNFAPVVLEVPKEVAVENVDFSADGSVQLADHYQQNTPIGD

GPVLLPDNHYLSTQSKLSKDPNEKRDHMVLLEFVTAAGITLGMDELYKGGSGGMVSKGEELFTGVVPILV

ELDGDVNGHKFSVSGEGEGDATYGKLTLKFICTTGKLPVPWPTLVTTLTYGVQCESRYPDHMKQHDEFKS

AMPEGYVQERTIFFKDDGNYKTRAEVKFEGDTLVNRIELKGIDFKEDGNILGHKLEYNYNSHNVYIMADK

QKNGIKVNFKIRHNIEGLAGLTRLSFAILNPKWREEMMGNRKWGLCIVGMGRLGSALADYPGFGESFELR

GFFDVDPEKVGRPVRGGVIEHVDLLPQRVPGRIEIALLTVPREAAQKAADLLVAAGIKGILNFAPVVLEV

PKEVAVENVDFLAGLTRLSFAILNPKWREEMMG

Initial construct #6
                                                          (SEQ ID NO: 166)
MNRKWGLCIVGMGRLGSALADYPGFGESFELRGFFDVDPEKVGRPVRGGVIEHVDLLPQRVPGRIEIALL

TVPREAAQKAADLLVAAGIKGILNFAPVVLEVPKEVAVENVDESADGSVQLADHYQQNTPIGDGPVLLPD

NHYLSTQSKLSKDPNEKRDHMVLLEFVTAAGITLGMDELYKGGSGGMVSKGEELFTGVVPILVELDGDVN

GHKFSVSGEGEGDATYGKLTLKFICTTGKLPVPWPTLVTTLTYGVQCFSRYPDHMKQHDFFKSAMPEGYV

QERTIFFKDDGNYKTRAEVKFEGDTLVNRIELKGIDFKEDGNILGHKLEYNYNSHNVYIMADKQKNGIKV

NEKIRHNIEGLAGLTRLSFAILNPKWREEMMGNRKWGLCIVGMGRLGSALADYPGFGESFELRGFFDVDP

EKVGRPVRGGVIEHVDLLPQRVPGRIEIALLTVPREAAQKAADLLVAAGIKGILNFAPVVLEVPKEVAVE

NVDFLAGLTRLSFAILNPKWREEMMGMVSVIKPEMKMRYYMDGSVNGHEFTIEGEGTGRPYEGHQEMTLR

VTMAEGGPMPFAFDLVSHVFCYGHRVFTKYPEEIPDYFKQAFPEGLSWERSLEFEDGGSASVSAHISLRG

NTFYHKSKFTGVNFPADGPIMQNQSVDWEPSTEKITASDGVLKGDVTMYLKLEGGGNHKCQFKTTYKAAK

EILEMPGDHYIGHRLVRKTEGNITEQVEDAVAHS
```

-continued

Initial construct #7
(SEQ ID NO: 167)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSNRKWGLCIVGMGRLGSALADYPGFGESFELRGFFDVDPEKVGRPVRGGVIEHVDLLPQRVPG

RIEIALLTVPREAAQKAADLLVAAGIKGILNFAPVVLEVPKEVAVENVDFLAGLTRLSFAILNPKWREEM

MGNRKWGLCIVGMGRLGSALADYPGFGESFELRGFFDVDPEKVGRPVRGGVIEHVDLLPQRVPGRIEIAL

LTVPREAAQKAADLLVAAGIKGILNFAPVVLEVPKEVAVENVDFSADGSVQLADHYQQNTPIGDGPVLLP

DNHYLSTQSKLSKDPNEKRDHMVLLEFVTAAGITLGMDELYKGGSGGMVSKGEELFTGVVPILVELDGDV

NGHKFSVSGEGEGDATYGKLTLKFICTTGKLPVPWPTLVTTLTYGVQCESRYPDHMKQHDFFKSAMPEGY

VQERTIFFKDDGNYKTRAEVKFEGDTLVNRIELKGIDFKEDGNILGHKLEYNYNSHNVYIMADKQKNGIK

VNFKIRHNIEGLAGLTRLSFAILNPKWREEMMG

Initial construct #8
(SEQ ID NO: 168)
MNRKWGLCIVGMGRLGSALADYPGFGESFELRGFFDVDPEKVGRPVRGGVIEHVDLLPQRVPGRIEIALL

TVPREAAQKAADLLVAAGIKGILNFAPVVLEVPKEVAVENVDFLAGLTRLSFAILNPKWREEMMGNRKWG

LCIVGMGRLGSALADYPGFGESFELRGFFDVDPEKVGRPVRGGVIEHVDLLPQRVPGRIEIALLTVPREA

AQKAADLLVAAGIKGILNFAPVVLEVPKEVAVENVDESADGSVQLADHYQQNTPIGDGPVLLPDNHYLST

QSKLSKDPNEKRDHMVLLEFVTAAGITLGMDELYKGGSGGMVSKGEELFTGVVPILVELDGDVNGHKESV

SGEGEGDATYGKLTLKFICTTGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHNVYIMADKQKNGIKVNEKIRH

NIEGLAGLTRLSFAILNPKWREEMMGMVSVIKPEMKMRYYMDGSVNGHEFTIEGEGTGRPYEGHQEMTLR

VTMAEGGPMPFAFDLVSHVFCYGHRVFTKYPEEIPDYFKQAFPEGLSWERSLEFEDGGSASVSAHISLRG

NTFYHKSKFTGVNFPADGPIMQNQSVDWEPSTEKITASDGVLKGDVTMYLKLEGGGNHKCQFKTTYKAAK

EILEMPGDHYIGHRLVRKTEGNITEQVEDAVAHS

Initial construct #9
(SEQ ID NO: 169)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNEPADGPIMQNQSV

DWEPSTEKITASDGVLKGDVTMYLKLEGGGNHKCQFKTTYKAAKEILEMPGDHYIGHRLVRKTEGNITEQ

VEDAVAHSKVPEAAISRLITYLRILEELEAQGVHRTASEQLGELAQVTAFQVDKDLSYFGSYGTDGVGYT

VPVLKRELRHILGLNRKWGLCIVGMGRLGSALADWPGFGESFELRGFFDVDPGMVGRPVRGGVIEHVDLL

PQRVPGRIEIALLTVPREAAQKAADLLVAAGIKGILNFAPVVLEVPKEVAVENVDILAGLTRLSFAILNP

TWSAAGGHGYNSHNVYIMADKQKNGIKVNFKIRHNIEDGSVQLADHYQQNTPIGDGPVLLPDNHYLSTQS

KLSKDPNEKRDHMVLLEFVTAAGITLGMDELYKGGSGGMVSKGEELFTGVVPILVELDGDVNGHKFSVSG

EGEGDATYGKLTLKFICTTGKLPVPWPTLVTTLTYGVQCFSRYPDHMKQHDFFKSAMPEGYVQERTIFFK

DDGNYKTRAEVKFEGDTLVNRIELKGIDFKEDGNILGHKLEYNTKVPEAAISRLITYLRILEELEAQGVH

RTASEQLGELAQVTAFQVDEDLSYFGSYGTDGVGYTVPVLKRELRHILGLNRKWGLCIVGMGRLGSALAD

WPGFGESFELRGFFDVDPGMVGRPVRGGVIEHVDLLPQRVPGRIEIALLTVPREAAQKAADLLVAAGIKG

ILNFAPVVLEVPKEVAVENVDFLAGLTRLSFAILNPKWREEMMG

Initial construct #10

(SEQ ID NO: 170)
MKVPEAAISRLITYLRILEELEAQGVHRTASEQLGELAQVTAFQVDKDLSYFGSYGTDGVGYTVPVLKRE

LRHILGLNRKWGLCIVGMGRLGSALADWPGFGESFELRGFFDVDPGMVGRPVRGGVIEHVDLLPQRVPGR

IEIALLTVPREAAQKAADLLVAAGIKGILNFAPVVLEVPKEVAVENVDILAGLTRLSFAILNPTWSAAGG

HGYNSHNVYIMADKQKNGIKVNFKIRHNIEDGSVQLADHYQQNTPIGDGPVLLPDNHYLSTQSKLSKDPN

EKRDHMVLLEFVTAAGITLGMDELYKGGSGGMVSKGEELFTGVVPILVELDGDVNGHKESVSGEGEGDAT

YGKLTLKFICTTGKLPVPWPTLVTTLTYGVQCFSRYPDHMKQHDFFKSAMPEGYVQERTIFFKDDGNYKT

RAEVKFEGDTLVNRIELKGIDFKEDGNILGHKLEYNTKVPEAAISRLITYLRILEELEAQGVHRTASEQL

GELAQVTAFQVDEDLSYFGSYGTDGVGYTVPVLKRELRHILGLNRKWGLCIVGMGRLGSALADWPGFGES

FELRGFFDVDPGMVGRPVRGGVIEHVDLLPQRVPGRIEIALLTVPREAAQKAADLLVAAGIKGILNFAPV

VLEVPKEVAVENVDFLAGLTRLSFAILNPKWREEMMGMVSVIKPEMKMRYYMDGSVNGHEFTIEGEGTGR

PYEGHQEMTLRVTMAEGGPMPFAFDLVSHVFCYGHRVFTKYPEEIPDYFKQAFPEGLSWERSLEFEDGGS

ASVSAHISLRGNTFYHKSKFTGVNFPADGPIMQNQSVDWEPSTEKITASDGVLKGDVTMYLKLEGGGNHK

CQFKTTYKAAKEILEMPGDHYIGHRLVRKTEGNITEQVEDAVAHS

Initial construct #11

(SEQ ID NO: 171)
MVSVIKPEMKMRYYMDGSVNGHEFTIEGEGTGRPYEGHQEMTLRVTMAEGGPMPFAFDLVSHVECYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSKVPEAAISRLITYLRILEELEAQGVHRTASEQLGELAQVTAFQVDKDLSYFGSYGTDGVGYT

VPVLKRELRHILGLNRKWGLCIVGMGRLGSALADWPGFGESFELRGFFDVDPGMVGRPVRGGVIEHVDLL

PQRVPGRIEIALLTVPREAAQKAADLLVAAGIKGILNFAPVVLEVPKEVAVENVDILAGLTRLSFAILNP

TWSAAGGHGDGSVQLADHYQQNTPIGDGPVLLPDNHYLSTQSKLSKDPNEKRDHMVLLEFVTAAGITLGM

DELYKGGSGGMVSKGEELFTGVVPILVELDGDVNGHKESVSGEGEGDATYGKLTLKFICTTGKLPVPWPT

LVTTLTYGVQCFSRYPDHMKQHDFFKSAMPEGYVQERTIFFKDDGNYKTRAEVKFEGDTLVNRIELKGID

FKEDGNILGHKLEYNYNSHNVYIMADKQKNGIKVNFKIRHNIETKVPEAAISRLITYLRILEELEAQGVH

RTASEQLGELAQVTAFQVDEDLSYFGSYGTDGVGYTVPVLKRELRHILGLNRKWGLCIVGMGRLGSALAD

WPGFGESFELRGFFDVDPGMVGRPVRGGVIEHVDLLPQRVPGRIEIALLTVPREAAQKAADLLVAAGIKG

ILNFAPVVLEVPKEVAVENVDFLAGLTRLSFAILNPKWREEMMG

Initial construct #12

(SEQ ID NO: 172)
MKVPEAAISRLITYLRILEELEAQGVHRTASEQLGELAQVTAFQVDKDLSYFGSYGTDGVGYTVPVLKRE

LRHILGLNRKWGLCIVGMGRLGSALADWPGFGESFELRGFFDVDPGMVGRPVRGGVIEHVDLLPQRVPGR

IEIALLTVPREAAQKAADLLVAAGIKGILNFAPVVLEVPKEVAVENVDILAGLTRLSFAILNPTWSAAGG

HGDGSVQLADHYQQNTPIGDGPVLLPDNHYLSTQSKLSKDPNEKRDHMVLLEFVTAAGITLGMDELYKGG

SGGMVSKGEELFTGVVPILVELDGDVNGHKFSVSGEGEGDATYGKLTLKFICTTGKLPVPWPTLVTTLTY

GVQCFSRYPDHMKQHDFFKSAMPEGYVQERTIFFKDDGNYKTRAEVKFEGDTLVNRIELKGIDFKEDGNI

LGHKLEYNYNSHNVYIMADKQKNGIKVNFKIRHNIETKVPEAAISRLITYLRILEELEAQGVHRTASEQL

GELAQVTAFQVDEDLSYFGSYGTDGVGYTVPVLKRELRHILGLNRKWGLCIVGMGRLGSALADWPGFGES

FELRGFFDVDPGMVGRPVRGGVIEHVDLLPQRVPGRIEIALLTVPREAAQKAADLLVAAGIKGILNFAPV

VLEVPKEVAVENVDFLAGLTRLSFAILNPKWREEMMGMVSVIKPEMKMRYYMDGSVNGHEFTIEGEGTGR

PYEGHQEMTLRVTMAEGGPMPFAFDLVSHVFCYGHRVFTKYPEEIPDYFKQAFPEGLSWERSLEFEDGGS

-continued

ASVSAHISLRGNTFYHKSKFTGVNFPADGPIMQNQSVDWEPSTEKITASDGVLKGDVTMYLKLEGGGNHK

CQFKTTYKAAKEILEMPGDHYIGHRLVRKTEGNITEQVEDAVAHS

Initial construct #13
(SEQ ID NO: 173)
MVSVIKPEMKMRYYMDGSVNGHEFTIEGEGTGRPYEGHQEMTLRVTMAEGGPMPFAFDLVSHVFCYGHRV

FTKYPEEIPDYFKQAFPEGLSWERSLEFEDGGSASVSAHISLRGNTFYHKSKFTGVNFPADGPIMQNQSV

DWEPSTEKITASDGVLKGDVTMYLKLEGGGNHKCQFKTTYKAAKEILEMPGDHYIGHRLVRKTEGNITEQ

VEDAVAHSKVPEAAISRLITYLRILEELEAQGVHRTASEQLGELAQVTAFQVDKDLSYFGSYGTDGVGYT

VPVLKRELRHILGLNRKWGLCIVGMGRLGSALADWPGFGESFELRGFFDVDPGMVGRPVRGGVIEHVDLL

PQRVPGRIEIALLTVPREAAQKAADLLVAAGIKGILNFAPVVLEVPKEVAVENVDILAGLTRLSFAILNP

TWSAAGGHGMVSKGEELFTGVVPILVELDGDVNGHKESVSGEGEGDATYGKLTLKFICTTGKLPVPWPTL

VTTLTYGVQCFSRYPDHMKQHDFFKSAMPEGYVQERTIFFKDDGNYKTRAEVKFEGDTLVNRIELKGIDE

KEDGNILGHKLEYNYNSHNVYIMADKQKNGIKVNFKIRHNIEDGSVQLADHYQQNTPIGDGPVLLPDNHY

LSTQSKLSKDPNEKRDHMVLLEFVTAAGITLGMDELYKTKVPEAAISRLITYLRILEELEAQGVHRTASE

QLGELAQVTAFQVDEDLSYFGSYGTDGVGYTVPVLKRELRHILGLNRKWGLCIVGMGRLGSALADWPGFG

ESFELRGFFDVDPGMVGRPVRGGVIEHVDLLPQRVPGRIEIALLTVPREAAQKAADLLVAAGIKGILNFA

PVVLEVPKEVAVENVDFLAGLTRLSFAILNPKWREEMMG

Initial construct #14
(SEQ ID NO: 174)
MKVPEAAISRLITYLRILEELEAQGVHRTASEQLGELAQVTAFQVDKDLSYFGSYGTDGVGYTVPVLKRE

LRHILGLNRKWGLCIVGMGRLGSALADWPGFGESFELRGFFDVDPGMVGRPVRGGVIEHVDLLPQRVPGR

IEIALLTVPREAAQKAADLLVAAGIKGILNFAPVVLEVPKEVAVENVDILAGLTRLSFAILNPTWSAAGG

HGMVSKGEELFTGVVPILVELDGDVNGHKFSVSGEGEGDATYGKLTLKFICTTGKLPVPWPTLVTTLTYG

VQCFSRYPDHMKQHDFFKSAMPEGYVQERTIFFKDDGNYKTRAEVKFEGDTLVNRIELKGIDFKEDGNIL

GHKLEYNYNSHNVYIMADKQKNGIKVNFKIRHNIEDGSVQLADHYQQNTPIGDGPVLLPDNHYLSTQSKL

SKDPNEKRDHMVLLEFVTAAGITLGMDELYKTKVPEAAISRLITYLRILEELEAQGVHRTASEQLGELAQ

VTAFQVDEDLSYFGSYGTDGVGYTVPVLKRELRHILGLNRKWGLCIVGMGRLGSALADWPGFGESFELRG

FFDVDPGMVGRPVRGGVIEHVDLLPQRVPGRIEIALLTVPREAAQKAADLLVAAGIKGILNFAPVVLEVP

KEVAVENVDFLAGLTRLSFAILNPKWREEMMGMVSVIKPEMKMRYYMDGSVNGHEFTIEGEGTGRPYEGH

QEMTLRVTMAEGGPMPFAFDLVSHVFCYGHRVFTKYPEEIPDYFKQAFPEGLSWERSLEFEDGGSASVSA

HISLRGNTFYHKSKFTGVNFPADGPIMQNQSVDWEPSTEKITASDGVLKGDVTMYLKLEGGGNHKCQFKT

TYKAAKEILEMPGDHYIGHRLVRKTEGNITEQVEDAVAHS

Initial construct #15
(SEQ ID NO: 175)
MVSKGEELFTGVVPILVELDGDVNGHKFSVSGEGEGDATYGKLTLKFICTTGKLPVPWPTLVTTLTYGVQ

CFSRYPDHMKQHDFFKSAMPEGYVQERTIFFKDDGNYKTRAEVKFEGDTLVNRIELKGIDFKEDGNILGH

KLEYNYNSHNVYIMADKQKNGIKVNFKIRHNIEDGSVQLADHYQQNTPIGDGPVLLPDNHYLSTQSLSK

DPNEKRDHMVLLEFVTAAGITLGMDELYKKVPEAAISRLITYLRILEELEAQGVHRTASEQLGELAQVTA

FQVDKDLSYFGSYGTDGVGYTVPVLKRELRHILGLNRKWGLCIVGMGRLGSALADWPGFGESFELRGFFD

VDPGMVGRPVRGGVIEHVDLLPQRVPGRIEIALLTVPREAAQKAADLLVAAGIKGILNFAPVVLEVPKEV

AVENVDILAGLTRLSFAILNPTWSAAGGHGMVSVIKPEMKMRYYMDGSVNGHEFTIEGEGTGRPYEGHQE

MTLRVTMAEGGPMPFAFDLVSHVFCYGHRVFTKYPEEIPDYFKQAFPEGLSWERSLEFEDGGSASVSAHI

SLRGNTFYHKSKFTGVNFPADGPIMQNQSVDWEPSTEKITASDGVLKGDVTMYLKLEGGGNHKCQFKTTY

KAAKEILEMPGDHYIGHRLVRKTEGNITEQVEDAVAHSTKVPEAAISRLITYLRILEELEAQGVHRTASE

-continued

QLGELAQVTAFQVDEDLSYFGSYGTDGVGYTVPVLKRELRHILGLNRKWGLCIVGMGRLGSALADWPGFG

ESFELRGFFDVDPGMVGRPVRGGVIEHVDLLPQRVPGRIEIALLTVPREAAQKAADLLVAAGIKGILNFA

PVVLEVPKEVAVENVDFLAGLTRLSFAILNPKWREEMMG

Initial construct #16
(SEQ ID NO: 176)
MKVPEAAISRLITYLRILEELEAQGVHRTASEQLGELAQVTAFQVDKDLSYFGSYGTDGVGYTVPVLKRE

LRHILGLNRKWGLCIVGMGRLGSALADWPGFGESFELRGFFDVDPGMVGRPVRGGVIEHVDLLPQRVPGR

IEIALLTVPREAAQKAADLLVAAGIKGILNFAPVVLEVPKEVAVENVDILAGLTRLSFAILNPTWSAAGG

HGMVSVIKPEMKMRYYMDGSVNGHEFTIEGEGTGRPYEGHQEMTLRVTMAEGGPMPFAFDLVSHVECYGH

RVFTKYPEEIPDYFKQAFPEGLSWERSLEFEDGGSASVSAHISLRGNTFYHKSKFTGVNFPADGPIMQNQ

SVDWEPSTEKITASDGVLKGDVTMYLKLEGGGNHKCQFKTTYKAAKEILEMPGDHYIGHRLVRKTEGNIT

EQVEDAVAHSTKVPEAAISRLITYLRILEELEAQGVHRTASEQLGELAQVTAFQVDEDLSYFGSYGTDGV

GYTVPVLKRELRHILGLNRKWGLCIVGMGRLGSALADWPGFGESFELRGFFDVDPGMVGRPVRGGVIEHV

DLLPQRVPGRIEIALLTVPREAAQKAADLLVAAGIKGILNFAPVVLEVPKEVAVENVDFLAGLTRLSFAI

LNPKWREEMMGMVSKGEELFTGVVPILVELDGDVNGHKESVSGEGEGDATYGKLTLKFICTTGKLPVPWP

TLVTTLTYGVQCFSRYPDHMKQHDFFKSAMPEGYVQERTIFFKDDGNYKTRAEVKFEGDTLVNRIELKGI

DFKEDGNILGHKLEYNYNSHNVYIMADKQKNGIKVNFKIRHNIEDGSVQLADHYQQNTPIGDGPVLLPDN

HYLSTQSKLSKDPNEKRDHMVLLEFVTAAGITLGMDELYK

Constructs #10 and #14 in Table 3 were used to generate protein libraries. Protein #12 was not used because it showed poor performance under dual-excitation FRET signal collection mode. Protein #16 had very similar properties to protein #14 and thus also was not used. Mutagenesis of both constructs resulted in clones with substantially improved signal windows. In vitro data also shows that signal window values identified during the screening in bacterial lysates have reliable prediction power. This is evidenced by the fact that all clones chosen from the libraries to proceed with have in vitro a substantial increase in signal window, compared to the original template protein (constructs #10 or #14). These increases are also roughly similar fold-wise between the numbers obtained in bacterial lysate screening and in the process of in vitro characterization.

Library 14-1 produced the most promising clones both in terms of signal window and sensitivity, compared to library 10-1.

Protein library DNA was generated following cloning that assembled pieces of DNA that were generated using PCRs with mixtures of primers. DNA was transformed into E. coli, and the first round of protein library expression was done in bacterial colonies on agar plates. The colonies, each expressing different library members, were imaged, and then classified into groups based on their FRET ratio signal. Colonies from different groups were inoculated into 96-deep-well plates for further protein expression in liquid culture. The original construct that was used to generate the library (e.g., construct #14 in Table 2) was also inoculated on the same plates, along with non-expressing bacteria. The latter served as a negative control.

Upon completion of expression, bacteria cells were lysed, lysates were cleared by centrifugation, and protein variants were tested for their response to NADH. For that, the lysates were excited with 488 nm or 550 nm light and emission was collected at 590 nm at a plate reader. The fluorescence signal upon excitation with 488 light was divided by the signal upon excitation with 550 nm light to generate FRET ratio, which was measured for all the selected protein variants in presence or absence of 200 uM NADH. The difference between FRET ratios with and without the ligand was the signal window—the final metric used to identify the most promising mutants.

Figure 1A:
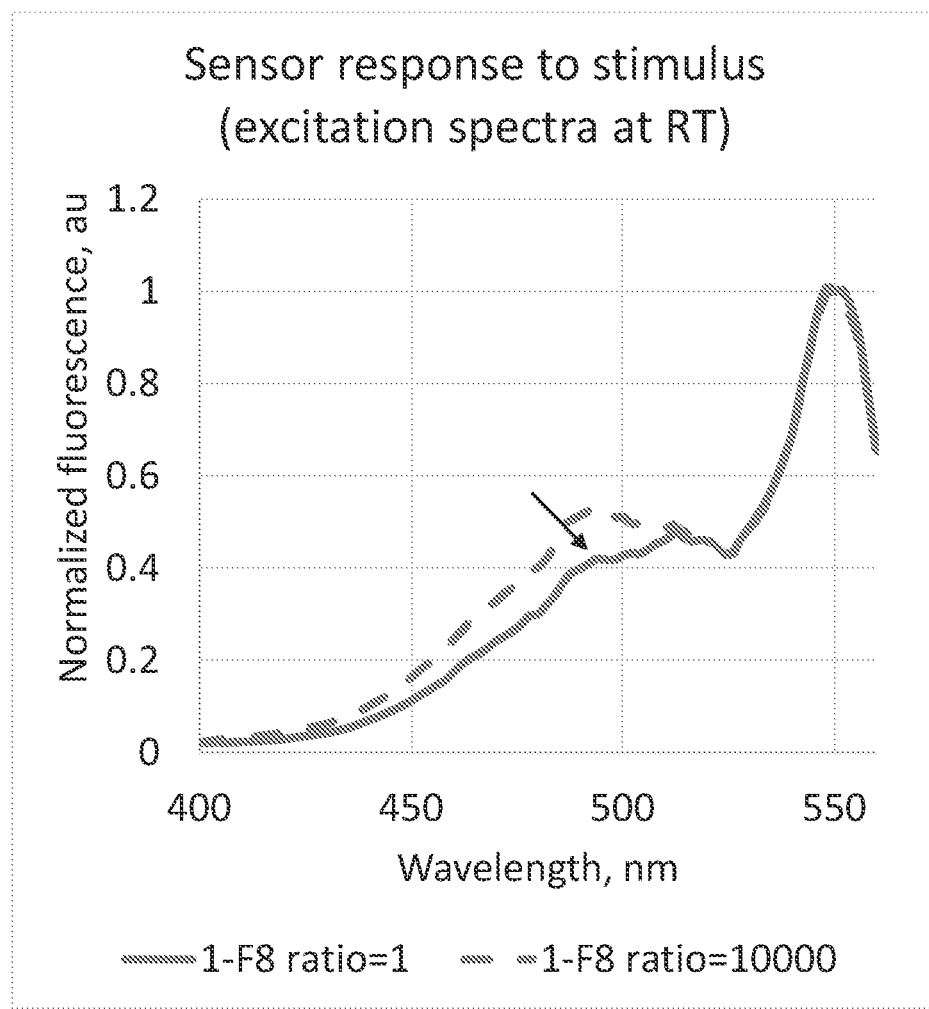
FIG. 1A Directed evolution of construct 14 produced a variant (1-F8) with substantially improved signal window. Purified protein 1-F8 was mixed with NAD+ and NADH so in one case NAD+/NADH ratio was 1 and in another 10,000. Total concentration of NAD+ was kept constant at 80 uM in both cases. Excitation spectra of 1-F8 with low and high NAD+/NADH ratio were recorded on a plate reader and then normalized and overlaid. The substantial difference between the spectra (indicated with the arrow) signifies the large signal window of the resulting biosensor.
Figure 1B:
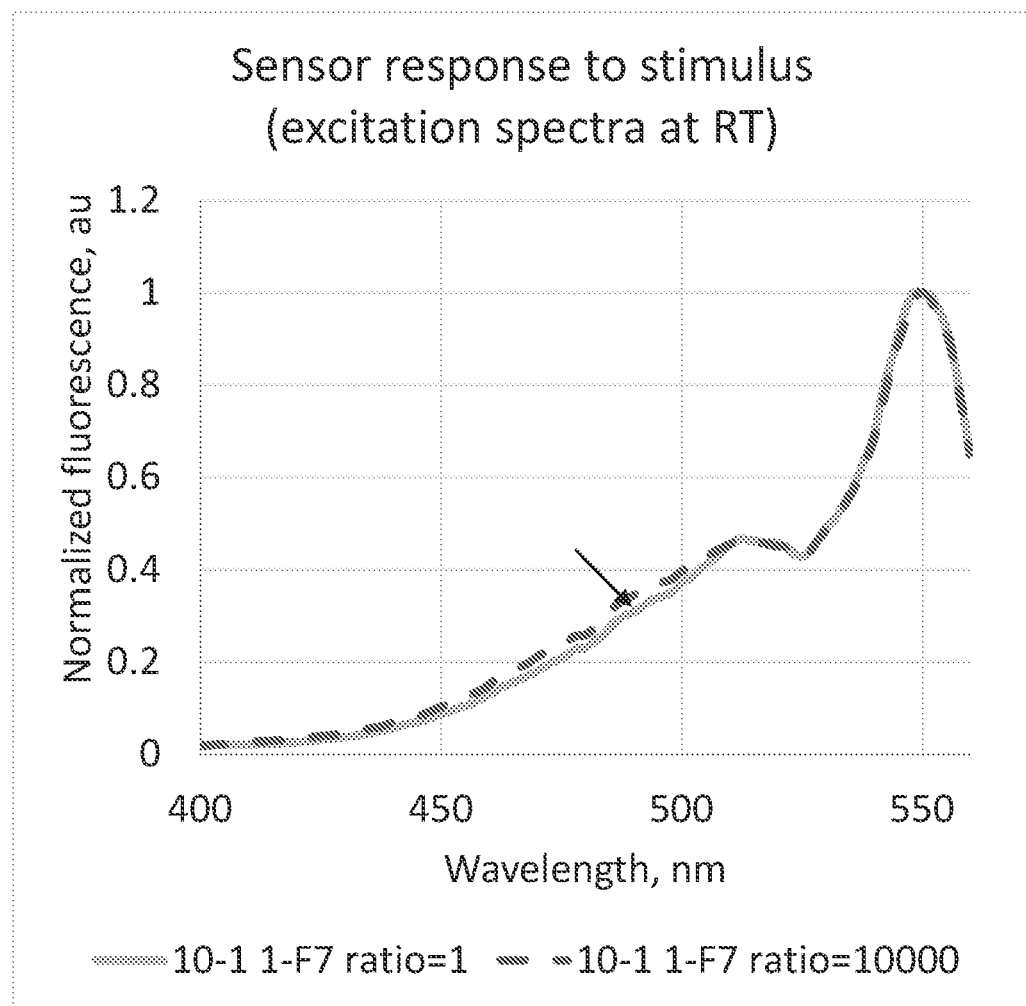
FIG. 1B. Directed evolution of construct 10 produced a variant (10-1 1-F7) with improved signal window. Purified protein 10-11-F7 was mixed with NAD+ and NADH so in one case NAD+/NADH ratio was 1 and in another 10,000. Total concentration of NAD+ was kept constant at 80 uM in both cases. Excitation spectra of 10-1 1-F7 with low and high NAD+/NADH ratio were recorded on a plate reader, and then normalized and overlaid. The noticeable difference between the spectra (indicated with the arrow) signifies now detectable signal window of the resulting biosensor.

To provide more accurate data on biosensor response to NAD+/NADH ratio changes, the most promising protein variants, identified during screening in bacterial lysates, were purified. For that, the proteins were expressed in E. coli, bacteria were harvested, lysed, and proteins were isolated using two sequential rounds of affinity chromatography on a FPLC instrument. Upon buffer exchange and protein concentrating, 50 nM of protein was mixed with NAD+ and NADH so the ratio NAD+/NADH was either 1 or 10,000. The final NAD+ concentration was kept at 80 uM (close to reported physiological concentration) and final NADH concentration was either 80 uM or 8 nM. Protein excitation spectra in presence of high or low NAD+/NADH was recorded at 590 nm emission wavelength on a plate reader, and then for each protein variant two spectra were normalized to the maximal value, plotted and overlaid. In Figure TA, purified protein 1-F8 was mixed with NAD+ and NADH so in one case NAD+/NADH ratio was 1 and in another 10,000. The substantial difference between the spectra (indicated with the arrow) signifies the large signal window of the resulting biosensor. Similar data is shown in FIG. 1B for construct 10-1 1-7.

Figure 2:
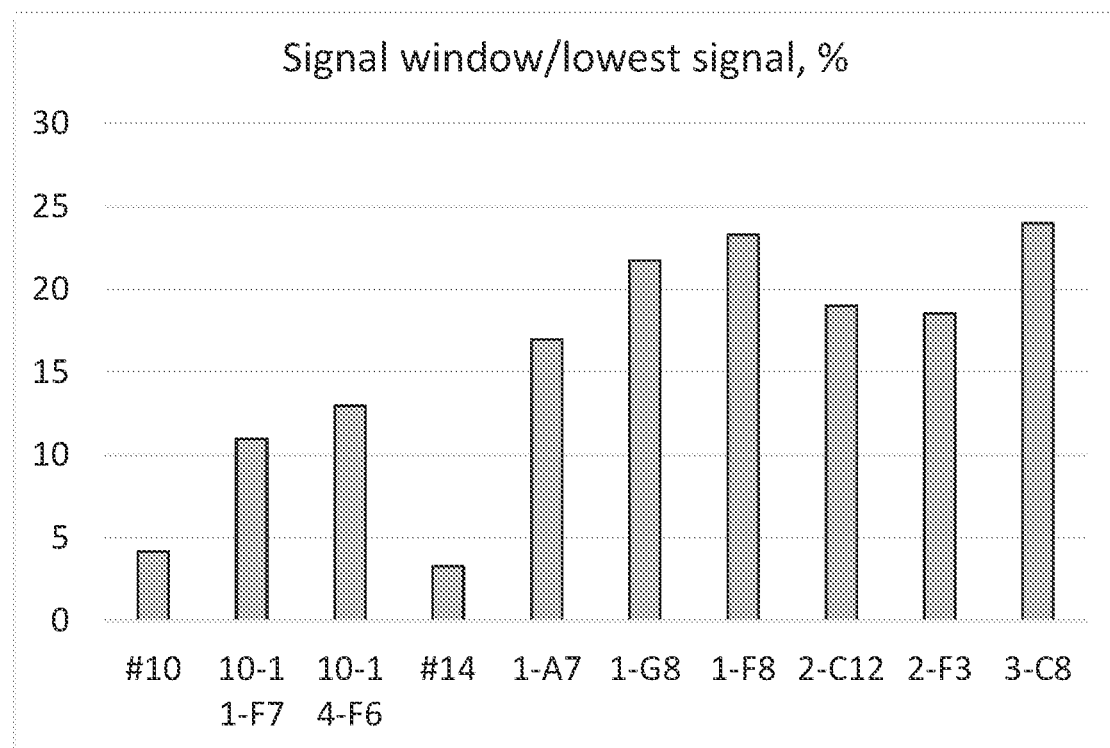
FIG. 2. Signal window of selected clones from libraries measured in vitro (purified proteins). Proteins were expressed, purified and treated as described in FIG. 1 legends, and their excitation spectra was recorded the same way as well. To calculate the signal window, the areas under the high NAD+/NADH ratio and low NAD+/NADH ratio curves were calculated for the 400-526 nm wavelength interval, which is where the FRET signal change is observed. The difference between two calculated areas, normalized to the smallest area of these two, is presented in FIG. 2 on the bar graph as signal window/lowest signal. Proteins with higher signal window values were selected for further characterization in mammalian cells.

We next calculated signal window for the constructs. To calculate the signal window, the areas under the high NAD+/NADH ratio and low NAD+/NADH ratio excitation spectra curves were calculated for the 400-526 nm wavelength interval, which is where the FRET signal change is observed. The difference between two calculated areas, normalized to the lowest area of these two, is presented in FIG. 2 on the bar graph as signal window/lowest signal.

Proteins with higher signal window values were selected for further characterization in mammalian cells.

To plot the sensitivity curves, purified proteins were mixed with NAD+ and NADH so the resulting NAD+/NADH ratios varied, and then excited at 460 nm and emissions at 510 nm and 560 nm were collected. The FRET ratio was calculated as emission at 560 nm divided by emission at 510 nm, and the values were normalized to the FRET ratio value at the highest NAD+/NADH ratio. Normalized FRET ratio was measured for each protein at different NAD+/NADH ratios, ranging from 1 to 10,000. For each NAD+/NADH ratio, the final NAD+ concentration was kept constant at 80 uM and NADH concentration was varied.

Figure 3:
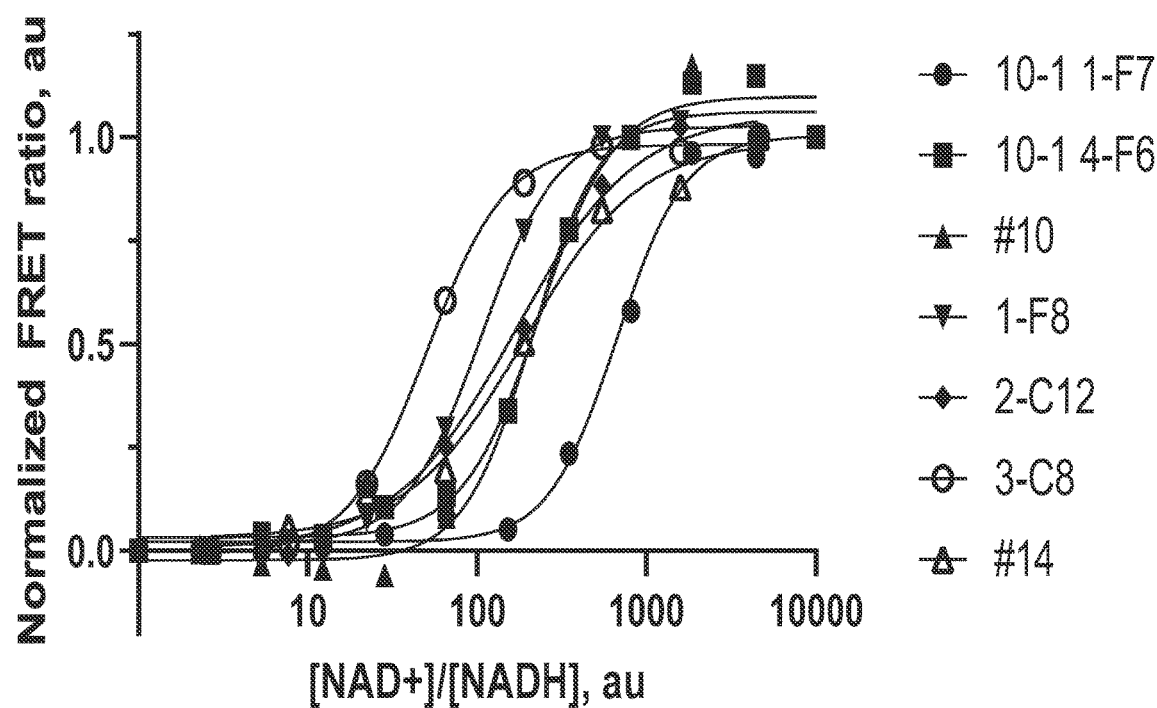
FIG. 3. EC50 (sensitivity) curves of selected clones from libraries based on constructs #10 and #14.

TABLE 4 summarizes data for selected protein. EC50 values are approximate and calculated by FIG. 3 curve fitting in GraphPad ™ Prism ($R^2$ values ~0.99).

| Protein | Signal window/ lowest signal, % (in vitro) | ~EC50, [NAD+]/[NADH], au |
|---|---|---|
| 10-1 1-F7 | 11 | 670 |
| 10-1 4-F6 | 13 | 232 |
| #10 (template) | 4 | 211 |
| 2-C12 | 19 | 164 |
| #14 (template) | 3 | 152 |
| 1-G8 | 22 | 146 |
| 1-F8 | 23 | 105 |
| 2-F3 | 19 | 92 |
| 1-A7 | 17 | 65 |
| 3-C8 | 24 | 51 |

Signal window data presented in the table clearly shows that directed evolution substantially increased biosensor performance, with the best clones achieving 3 to 8 fold improvement compared to parental constructs #10 or #14.

Additionally, directed evolution resulted in clones with more than 10-fold variation in the value of EC50. The latter determines the sensitivity of the sensor, i.e., what range of NAD+/NADH ratio change the sensor is best applicable for. Large EC50 variation provides greater biosensor choice flexibility since some cell types/lines may have different, compared to the average, NAD+/NADH ratio change ranges. See FIG. 3.

In a further study, proteins were expressed in HEK 293 mammalian cells following transient transfection with the plasmids encoding those proteins. Transfected cells were imaged using Incucyte ° SX5 equipped with a Metabolism Optical Module (Sartorius) and the data was processed using the built-in ATP analysis software module that allows quantification of average FRET ratio in all cells in the image. To measure signal window, cells were treated with either 10 mM lactate or 20 mM pyruvate. The former drives the NAD+/NADH ratio, and thus FRET signal down, and the latter drives the NAD+/NADH ratio, and thus FRET signal up. The difference between highest and lowest FRET ratios is the signal window in mammalian cells. Data is shown in FIG. 4. Mammalian cell data demonstrates that most of generated biosensor clones have large signal windows. Signal window values above 0.2 generally allow the most robust FRET ratio change measurements. Also, most clones identified in bacterial lysates and then in vitro as promising showed large signal windows in mammalian cells as well. This indicates that biosensor screening in bacterial lysates has reliable predictive power.

Clone 1-F8 showed the largest signal window in mammalian cells and also had sensitivity suitable for reporting physiological changes of NAD+/NADH ratio. However, imaging in mammalian cells revealed that clone 1-F8 had lower, compared to other promising clones, brightness of mKOk protein. Sequence analysis of clone 1-F8 showed that Z9 was completely absent, which could affect the brightness of mKOk which is immediately adjacent to it. To attempt restoring the brightness of 1-F8 we reintroduced V into Z9 while (1) keeping the rest of 1-F8 the same (generating variant 1), (2) removing E from the N terminus of Z6 (SEQ ID NO:2) (generating variant 2), and (3) removing RE from the N terminus of Z6 (SEQ ID NO:2) (generating variant 3).

Cloning these constructs generated 1-F8 1-2 (variant 1, clone 2) (sEQ ID No: 191), 1-F8 2-3 (variant 2, clone 3) (sEQ ID No: 192) and 1-F8 3-3 (variant 3, clone 3) (sEQ ID No: 193). These constructs were tested in mammalian cells by comparing their brightness with the brightness of the original 1-F8 construct in the mKOk imaging channel. We also assessed signal window of the resulting constructs in comparison with the signal window of 1-F8 to confirm that the signal window was not affected substantially by the mutagenesis.

Construct 1-F8 1-2 (sEQ ID No: 191) showed the most restoration of the brightness of mKOk, compared to 1-F8, while retaining nearly identical to 1-F8 signal window (FIG. 5 and FIG. 6). Thus, construct 1-F 1-2 (SEQ ID NO:191) and its control protein (SEQ ID NO: 194) were selected to be used as the main biosensor protein sequences for imaging NAD+/NADH changes in living cells.

1-F8 1-2

(SEQ ID NO: 191)

MKVPEAAISRLITYLRILEELEAQGVHRTASEQLGELAQVTAFQVDKDLSYFGSYGTDGVGYTVPVLKRELRHILGL

NRKWGLCIVGMGRLGSALADWPGFGESFELRGFFDVDPGMVGRPVRGGVIEHVDLLPQRVPGRIEIALLTVPREAAQ

KAADLLVAAGIKGILNFAPVVLEVPKEVAVENVDILAGLTRLSFAILNPTWSAAGGHGMVSKGEELFTGVVPILVEL

DGDVNGHKFSVSGEGEGDATYGKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYIMADKQKNGIKVNFKIRHNIE

DGSVQLADHYQQNTPIGDGPVLLPDNHYLSTQSKLSKDPNEKRDHMVLLEFVTAAGITLGMDEVPEAAISRLITYLR

ILEELEAQGVHRTASEQLGELAQVTAFQVDEDLSYFGSYGTDGVGYTVPVLKRELRHILGLNRKWGLCIVGMGRLGS

ALADWPGFGESFELRGFFDVDPGMVGRPVRGGVIEHVDLLPQRVPGRIEIALLTVPREAAQKAADLLVAAGIKGILN

FAPVVLEVPKEVAVENVDFLAGLTRLSFAILNPKWREVIKPEMKMRYYMDGSVNGHEFTIEGEGTGRPYEGHQEMTL

RVTMAEGGPMPFAFDLVSHVFCYGHRVFTKYPEEIPDYFKQAFPEGLSWERSLEFEDGGSASVSAHISLRGNTFYHK

SKFTGVNFPADGPIMQNQSVDWEPSTEKITASDGVLKGDVTMYLKLEGGGNHKCQFKTTYKAAKEILEMPGDHYIGH

RLVRKTEGNITEQVEDAVAHSEASMDELYK

1-F8 2-3

(SEQ ID NO: 192)

MKVPEAAISRLITYLRILEELEAQGVHRTASEQLGELAQVTAFQVDKDLSYFGSYGTDGVGYTVPVLKRELRHILGL

NRKWGLCIVGMGRLGSALADWPGFGESFELRGFFDVDPGMVGRPVRGGVIEHVDLLPQRVPGRIEIALLTVPREAAQ

KAADLLVAAGIKGILNFAPVVLEVPKEVAVENVDILAGLTRLSFAILNPTWSAAGGHGMVSKGEELFTGVVPILVEL

DGDVNGHKFSVSGEGEGDATYGKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYIMADKQKNGIKVNFKIRHNIE

DGSVQLADHYQQNTPIGDGPVLLPDNHYLSTQSKLSKDPNEKRDHMVLLEFVTAAGITLGMDEVPEAAISRLITYLR

ILEELEAQGVHRTASEQLGELAQVTAFQVDEDLSYFGSYGTDGVGYTVPVLKRELRHILGLNRKWGLCIVGMGRLGS

ALADWPGFGESFELRGFFDVDPGMVGRPVRGGVIEHVDLLPQRVPGRIEIALLTVPREAAQKAADLLVAAGIKGILN

FAPVVLEVPKEVAVENVDFLAGLTRLSFAILNPKWRVIKPEMKMRYYMDGSVNGHEFTIEGEGTGRPYEGHQEMTLR

VTMAEGGPMPFAFDLVSHVFCYGHRVFTKYPEEIPDYFKQAFPEGLSWERSLEFEDGGSASVSAHISLRGNTFYHKS

KFTGVNFPADGPIMQNQSVDWEPSTEKITASDGVLKGDVTMYLKLEGGGNHKCQFKTTYKAAKEILEMPGDHYIGHR

LVRKTEGNITEQVEDAVAHSEASMDELYK

1-F8 3-3

(SEQ ID NO: 193)

MKVPEAAISRLITYLRILEELEAQGVHRTASEQLGELAQVTAFQVDKDLSYFGSYGTDGVGYTVPVLKRELRHILGL

NRKWGLCIVGMGRLGSALADWPGFGESFELRGFFDVDPGMVGRPVRGGVIEHVDLLPQRVPGRIEIALLTVPREAAQ

KAADLLVAAGIKGILNFAPVVLEVPKEVAVENVDILAGLTRLSFAILNPTWSAAGGHGMVSKGEELFTGVVPILVEL

DGDVNGHKFSVSGEGEGDATYGKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYIMADKQKNGIKVNFKIRHNIE

DGSVQLADHYQQNTPIGDGPVLLPDNHYLSTQSKLSKDPNEKRDHMVLLEFVTAAGITLGMDEVPEAAISRLITYLR

ILEELEAQGVHRTASEQLGELAQVTAFQVDEDLSYFGSYGTDGVGYTVPVLKRELRHILGLNRKWGLCIVGMGRLGS

ALADWPGFGESFELRGFFDVDPGMVGRPVRGGVIEHVDLLPQRVPGRIEIALLTVPREAAQKAADLLVAAGIKGILN

FAPVVLEVPKEVAVENVDFLAGLTRLSFAILNPKWVIKPEMKMRYYMDGSVNGHEFTIEGEGTGRPYEGHQEMTLRV

TMAEGGPMPFAFDLVSHVFCYGHRVFTKYPEEIPDYFKQAFPEGLSWERSLEFEDGGSASVSAHISLRGNTFYHKSK

FTGVNFPADGPIMQNQSVDWEPSTEKITASDGVLKGDVTMYLKLEGGGNHKCQFKTTYKAAKEILEMPGDHYIGHRL

VRKTEGNITEQVEDAVAHSEASMDELYK

1-F8 1-2 control (SEQ ID NO: 194)

MKVPEAAISRLITYLRILEELEAQGVHRTASEQLGELAQVTAFQVDKDLSYFGSYGTDGVGYTVPVLKRELRHILGL

NRKWGLCIVGMARLGSALADWPGFGESFELRGFFDVDPGMVGRPVRGGVIEHVDLLPQRVPGRIEIALLTVPREAAQ

KAADLLVAAGIKGILNFAPVVLEVPKEVAVENVDILAGLTRLSFAILNPTWSAAGGHGMVSKGEELFTGVVPILVEL

DGDVNGHKFSVSGEGEGDATYGKLTLKFICTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEYNYNSHNVYIMADKQKNGIKVNFKIRHNIE

DGSVQLADHYQQNTPIGDGPVLLPDNHYLSTQSKLSKDPNEKRDHMVLLEFVTAAGITLGMDEVPEAAISRLITYLR

ILEELEAQGVHRTASEQLGELAQVTAFQVDEDLSYFGSYGTDGVGYTVPVLKRELRHILGLNRKWGLCIVGMARLGS

ALADWPGFGESFELRGFFDVDPGMVGRPVRGGVIEHVDLLPQRVPGRIEIALLTVPREAAQKAADLLVAAGIKGILN

FAPVVLEVPKEVAVENVDFLAGLTRLSFAILNPKWREVIKPEMKMRYYMDGSVNGHEFTIEGEGTGRPYEGHQEMTL

RVTMAEGGPMPFAFDLVSHVFCYGHRVFTKYPEEIPDYFKQAFPEGLSWERSLEFEDGGSASVSAHISLRGNTFYHK

SKFTGVNFPADGPIMQNQSVDWEPSTEKITASDGVLKGDVTMYLKLEGGGNHKCQFKTTYKAAKEILEMPGDHYIGH

RLVRKTEGNITEQVEDAVAHSEASMDELYK

---

```
                              SEQUENCE LISTING

Sequence total quantity: 195
SEQ ID NO: 1            moltype = AA   length = 203
FEATURE                 Location/Qualifiers
REGION                  1
                        note = MISC_FEATURE - optionally absent
source                  1..203
                        mol_type = protein
                        organism = synthetic construct
SEQUENCE: 1
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNP                                          203

SEQ ID NO: 2            moltype = AA   length = 202
FEATURE                 Location/Qualifiers
REGION                  1..202
                        note = Synthetic
source                  1..202
                        mol_type = protein
                        organism = synthetic construct
SEQUENCE: 2
AAISRLITYL RILEELEAQG VHRTASEQLG ELAQVTAFQV DEDLSYFGSY GTDGVGYTVP    60
VLKRELRHIL GLNRKWGLCI VGMGRLGSAL ADWPGFGESF ELRGFFDVDP GMVGRPVRGG   120
VIEHVDLLPQ RVPGRIEIAL LTVPREAAQK AADLLVAAGI KGILNFAPVV LEVPKEVAVE   180
NVDFLAGLTR LSFAILNPKW RE                                           202

SEQ ID NO: 3            moltype = AA   length = 214
FEATURE                 Location/Qualifiers
source                  1..214
                        mol_type = protein
                        organism = synthetic construct
SEQUENCE: 3
IKPEMKMRYY MDGSVNGHEF TIEGEGTGRP YEGHQEMTLR VTMAEGGPMP FAFDLVSHVF    60
CYGHRVFTKY PEEIPDYFKQ APFEGLSWER SLEFEDGGSA SVSAHISLRG NTFYHKSKFT   120
GVNFPADGPI MQNQSVDWEP STEKITASDG VLKGDVTMYL KLEGGGNHKC QFKTTYKAAK   180
EILEMPGDHY IGHRLVRKTE GNITEQVEDA VAHS                              214

SEQ ID NO: 4            moltype = AA   length = 217
FEATURE                 Location/Qualifiers
REGION                  1..5
                        note = MISC_FEATURE - optionally absent
REGION                  216..217
                        note = MISC_FEATURE - optionally absent
source                  1..217
                        mol_type = protein
                        organism = synthetic construct
SEQUENCE: 4
MSVIKPEMKM RYYMDGSVNG HEFTIEGEGT GRPYEGHQEM TLRVTMAKGG PMPFAFDLVS    60
HVFCYGHRPF TKYPEEIPDY FKQAFPEGLS WERSLEFEDG GSASVSAHIS LRGNTFYHKS   120
KFTGVNFPAD GPIMQNQSVD WEPSTEKITA SDGVLKGDVT MYLKLEGGGN HKCQFKTTYK   180
AAKKILKMPG SHYISHRLVR KTEGNITELV EDAVAHS                           217

SEQ ID NO: 5            moltype = AA   length = 218
FEATURE                 Location/Qualifiers
REGION                  1..5
                        note = MISC_FEATURE - optionally absent
REGION                  217..218
                        note = MISC_FEATURE - optionally absent
source                  1..218
                        mol_type = protein
                        organism = synthetic construct
SEQUENCE: 5
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNQSV DWEPSTEKIT ASDGVLKGDV TMYLKLEGGG NHKCQMKTTY   180
KAAKEILEMP GDHYIGHRLV RKTEGNITEQ VEDAVAHS                          218

SEQ ID NO: 6            moltype = AA   length = 225
```

| FEATURE | Location/Qualifiers |
|---|---|
| REGION | 1..225 |
| | note = Synthetic |
| source | 1..225 |
| | mol_type = protein |
| | organism = synthetic construct |

SEQUENCE: 6
```
LFTGVVPILV ELDGDVNGHK FSVSGEGEGD ATYGKLTLKF ICTTGKLPVP WPTLVTTLTY   60
GVQCFSRYPD HMKQHDFFKS AMPEGYVQER TIFFKDDGNY KTRAEVKFEG DTLVNRIELK  120
GIDFKEDGNI LGHKLEYNYN SHNVYIMADK QKNGIKVNFK IRHNIEDGSV QLADHYQQNT  180
PIGDGPVLLP DNHYLSTQSK LSKDPNEKRD HMVLLEFVTA AGITL                 225
```

| SEQ ID NO: 7 | moltype = AA  length = 246 |
|---|---|
| FEATURE | Location/Qualifiers |
| REGION | 1..246 |
| | note = Synthetic |
| REGION | 1..2 |
| | note = MISC_FEATURE - optionally absent |
| SITE | 34 |
| | note = MISC_FEATURE - X is A or K |
| REGION | 245..246 |
| | note = MISC_FEATURE - optionally absent |
| source | 1..246 |
| | mol_type = protein |
| | organism = synthetic construct |

SEQUENCE: 7
```
DGSVQLADHY QQNTPIGDGP VLLPDNHYLS TQSXLSKDPN EKRDHMVLLE FVTAAGITLG   60
MDELYKGGSG GMVSKGEELF TGVVPILVEL DGDVNGHKFS VSGEGEGDAT YGKLTLKFIC  120
TTGKLPVPWP TLVTTLTYGV QCFSRYPDHM KQHDFFKSAM PEGYVQERTI FFKDDGNYKT  180
RAEVKFEGDT LVNRIELKGI DFKEDGNILG HKLEYNYNSH NVYIMADKQK NGIKVNFKIR  240
HNIEEA                                                            246
```

| SEQ ID NO: 8 | moltype = AA  length = 204 |
|---|---|
| FEATURE | Location/Qualifiers |
| REGION | 1..204 |
| | note = Synthetic |
| SITE | 1 |
| | note = MISC_FEATURE - optionally absent |
| source | 1..204 |
| | mol_type = protein |
| | organism = synthetic construct |

SEQUENCE: 8
```
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPT                                        204
```

| SEQ ID NO: 9 | moltype = AA  length = 205 |
|---|---|
| FEATURE | Location/Qualifiers |
| REGION | 1..205 |
| | note = Synthetic |
| SITE | 1 |
| | note = MISC_FEATURE - optionally absent |
| source | 1..205 |
| | mol_type = protein |
| | organism = synthetic construct |

SEQUENCE: 9
```
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTW                                       205
```

| SEQ ID NO: 10 | moltype = AA  length = 239 |
|---|---|
| FEATURE | Location/Qualifiers |
| REGION | 1..239 |
| | note = Synthetic |
| REGION | 1..7 |
| | note = MISC_FEATURE - optionally absent |
| REGION | 233..239 |
| | note = MISC_FEATURE - optionally absent |
| source | 1..239 |
| | mol_type = protein |
| | organism = synthetic construct |

SEQUENCE: 10
```
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF KDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSKLSK DPNEKRDHMV LLEFVTAAGI TLGMDELYK   239
```

```
SEQ ID NO: 11              moltype = AA   length = 210
FEATURE                    Location/Qualifiers
REGION                     1..210
                           note = Synthetic
source                     1..210
                           mol_type = protein
                           organism = synthetic construct
SEQUENCE: 11
KVPEAAISRL ITYLRILEEL EAQGVHRTAS EQLGELAQVT AFQVDEDLSY FGSYGTDGVG    60
YTVPVLKREL RHILGLNRKW GLCIVGMGRL GSALADWPGF GESFELRGFF DVDPGMVGRP   120
VRGGVIEHVD LLPQRVPGRI EIALLTVPRE AAQKAADLLV AAGIKGILNF APVVLEVPKE   180
VAVENVDFLA GLTRLSFAIL NPKWREEMMG                                    210

SEQ ID NO: 12              moltype = AA   length = 227
FEATURE                    Location/Qualifiers
REGION                     1..227
                           note = Synthetic
source                     1..227
                           mol_type = protein
                           organism = synthetic construct
SEQUENCE: 12
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNQSV DWEPSTEKIT ASDGVLKGDV TMYLKLEGGG NHKCQFKTTY   180
KAAKEILEMP GDHYIGHRLV RKTEGNITEQ VEDAVAHSEA SMDELYK                 227

SEQ ID NO: 13              moltype = AA   length = 876
FEATURE                    Location/Qualifiers
REGION                     1..876
                           note = Synthetic
source                     1..876
                           mol_type = protein
                           organism = synthetic construct
SEQUENCE: 13
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEKV PEAAISRLIT YLRILEELEA QGVHRTASEQL 480
GELAQVTAFQ VDEDLSYFGS YGTDGVGYTV PVLKRELRHI LGLNRKWGLC IVGMGRLGSA   540
LADWPGFGES FELRGFFDVD PGMVGRPVRG GVIEHVDLLP QRVPGRIEIA LLTVPREAAQ   600
KAADLLVAAG IKGILNFAPV VLEVPKEVAV ENVDFLAGLT RLSFAILNPK WREIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876

SEQ ID NO: 14              moltype = AA   length = 870
FEATURE                    Location/Qualifiers
REGION                     1..870
                           note = Synthetic
source                     1..870
                           mol_type = protein
                           organism = synthetic construct
SEQUENCE: 14
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWGMVSK GEELFTGVVP ILVELDGDVN GHKFSVSGEG   240
EGDATYGKLT LKFICTTGKL PVPWPTLVTT LTYGVQCFSR YPDHMKQHDF FKSAMPEGYV   300
QERTIFFKDD GNYKTRAEVK FEGDTLVNRI ELKGIDFKED GNILGHKLEY NYNSHNVYIM   360
ADKQKNGIKV NFKIRHNIED GSVQLADHYQ QNTPIGDGPV LLPDNHYLST QSKLSKDPNE   420
KRDHMVLLEF VTAAGITLGM DEPEAAISRL ITYLRILEEL EAQGVHRTAS EQLGELAQVT   480
AFQVDEDLSY FGSYGTDGVG YTVPVLKREL RHILGLNRKW GLCIVGMGRL GSALADWPGF   540
GESFELRGFF DVDPGMVGRP VRGGVIEHVD LLPQRVPGRI EIALLTVPRE AAQKAADLLV   600
AAGIKGILNF APVVLEVPKE VAVENVDFLA GLTRLSFAIL NPKWREVIKP EMKMRYYMDG   660
SVNGHEFTIE GEGTGRPYEG HQEMTLRVTM AEGGPMPFAF DLVSHVFCYG HRVFTKYPEE   720
IPDYFKQAFP EGLSWERSLE FEDGGSASVS AHISLRGNTF YHKSKFTGVN FPADGPIMQN   780
QSVDWEPSTE KITASDGVLK GDVTMYLKLE GGGNHKCQFK TTYKAAKEIL EMPGDHYIGH   840
RLVRKTEGNI TEQVEDAVAH SEASMDELYK                                    870

SEQ ID NO: 15              moltype = AA   length = 872
FEATURE                    Location/Qualifiers
REGION                     1..872
                           note = Synthetic
source                     1..872
```

```
                        mol_type = protein
                        organism = synthetic construct
SEQUENCE: 15
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSHGMV SKGEELFTGV VPILVELDGD VNGHKFSVSG   240
EGEGDATYGK LTLKFICTTG KLPVPWPTLV TTLTYGVQCF SRYPDHMKQH DFFKSAMPEG   300
YVQERTIFFK DDGNYKTRAE VKFEGDTLVN RIELKGIDFK EDGNILGHKL EYNYNSHNVY   360
IMADKQKNGI KVNFKIRHNI EDGSVQLADH YQQNTPIGDG PVLLPDNHYL STQSKLSKDP   420
NEKRDHMVLL EFVTAAGITL GMDEPEAAIS RLITYLRILE LEAQGVHRT ASEQLGELAQ    480
VTAFQVDEDL SYFGSYGTDG VGYTVPVLKR ELRHILGLNR KWGLCIVGMG RLGSALADWP   540
GFGESFELRG FFDVDPGMVG RPVRGGVIEH VDLLPQRVPG RIEIALLTVP REAAQKAADL   600
LVAAGIKGIL NFAPVVLEVP KEVAVENVDF LAGLTRLSFA ILNPKWREVI KPEMKMRYYM   660
DGSVNGHEFT IEGEGTGRPY EGHQEMTLRV TMAEGGPMPF AFDLVSHVFC YGHRVFTKYP   720
EEIPDYFKQA FPEGLSWERS LEFEDGGSAS VSAHISLRGN TFYHKSKFTG VNFPADGPIM   780
QNQSVDWEPS TEKITASDGV LKGDVTMYLK LEGGGNHKCQ FKTTYKAAKE ILEMPGDHYI   840
GHRLVRKTEG NITEQVEDAV AHSEASMDEL YK                                872

SEQ ID NO: 16           moltype = AA  length = 871
FEATURE                 Location/Qualifiers
REGION                  1..871
                        note = Synthetic
source                  1..871
                        mol_type = protein
                        organism = synthetic construct
SEQUENCE: 16
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSHGMV SKGEELFTGV VPILVELDGD VNGHKFSVSG   240
EGEGDATYGK LTLKFICTTG KLPVPWPTLV TTLTYGVQCF SRYPDHMKQH DFFKSAMPEG   300
YVQERTIFFK DDGNYKTRAE VKFEGDTLVN RIELKGIDFK EDGNILGHKL EYNYNSHNVY   360
IMADKQKNGI KVNFKIRHNI EDGSVQLADH YQQNTPIGDG PVLLPDNHYL STQSKLSKDP   420
NEKRDHMVLL EFVTAAGITL GMDEPEAAIS LITYLRILEE LEAQGVHRTA SEQLGELAQV   480
TAFQVDEDLS YFGSYGTDGV GYTVPVLKRE LRHILGLNRK WGLCIVGMGR LGSALADWPG   540
FGESFELRGF FDVDPGMVGR PVRGGVIEHV DLLPQRVPGR IEIALLTVPR EAAQKAADLL   600
VAAGIKGILN FAPVVLEVPK EVAVENVDFL AGLTRLSFAI LNPKWREVIK PEMKMRYYMD   660
GSVNGHEFTI EGEGTGRPYE GHQEMTLRVT MAEGGPMPFA FDLVSHVFCY GHRVFTKYPE   720
EIPDYFKQAF PEGLSWERSL EFEDGGSASV SAHISLRGNT FYHKSKFTGV NFPADGPIMQ   780
NQSVDWEPST EKITASDGVL KGDVTMYLKL EGGGNHKCQF KTTYKAAKEI LEMPGDHYIG   840
HRLVRKTEGN ITEQVEDAVA HSEASMDELY K                                 871

SEQ ID NO: 17           moltype = AA  length = 864
FEATURE                 Location/Qualifiers
REGION                  1..864
                        note = Synthetic
source                  1..864
                        mol_type = protein
                        organism = synthetic construct
SEQUENCE: 17
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTSKGEEL FTGVVPILVE LDGDVNGHKF SVSGEGEGDA   240
TYGKLTLKFI CTTGKLPVPW PTLVTTLTYG VQCFSRYPDH MKQHDFFKSA MPEGYVQERT   300
IFFKDDGNYK TRAEVKFEGD TLVNRIELKG IDFKEDGNIL GHKLEYNYNS HNVYIMADKQ   360
KNGIKVNFKI RHNIEDGSVQ LADHYQQNTP IGDGPVLLPD NHYLSTQSKL SKDPNEKRDH   420
MVLLEFVTAA GITLGMPEAA ISRLITYLRI LEELEAQGVH RTASEQLGEL AQVTAFQVDE   480
DLSYFGSYGT DGVGYTVPVL KRELRHILGL NRKWGLCIVG MGRLGSALAD WPGFGESFEL   540
RGFFDVDPGM VGRPVRGGVI EHVDLLPQRV PGRIEIALLT VPREAAQKAA DLLVAAGIKG   600
ILNFAPVVLE VPKEVAVENV DFLAGLTRLS FAILNPKWRE VIKPEMKMRY YMDGSVNGHE   660
FTIEGEGTGR PYEGHQEMTL RVTMAEGGPM PFAFDLVSHV FCYGHRVFTK YPEEIPDYFK   720
QAFPEGLSWE RSLEFEDGGS ASVSAHISLR GNTFYHKSKF TGVNFPADGP IMQNQSVDWE   780
PSTEKITASD GVLKGDVTMY LKLEGGGNHK CQFKTTYKAA KEILEMPGDH YIGHRLVRKT   840
EGNITEQVED AVAHSEASMD ELYK                                         864

SEQ ID NO: 18           moltype = AA  length = 866
FEATURE                 Location/Qualifiers
REGION                  1..866
                        note = Synthetic
source                  1..866
                        mol_type = protein
                        organism = synthetic construct
SEQUENCE: 18
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTSKGEEL FTGVVPILVE LDGDVNGHKF SVSGEGEGDA   240
```

```
TYGKLTLKFI  CTTGKLPVPW  PTLVTTLTYG  VQCFSRYPDH  MKQHDFFKSA  MPEGYVQERT   300
IFFKDDGNYK  TRAEVKFEGD  TLVNRIELKG  IDFKEDGNIL  GHKLEYNYNS  HNVYIMADKQ   360
KNGIKVNFKI  RHNIEDGSVQ  LADHYQQNTP  IGDGPVLLPD  NHYLSTQSKL  SKDPNEKRDH   420
MVLLEFVTAA  GITLGMPEAA  ISRLITYLRI  LEELEAQGVH  RTASEQLGEL  AQVTAFQVDE   480
DLSYFGSYGT  DGVGYTVPVL  KRELRHILGL  NRKWGLCIVG  MGRLGSALAD  WPGFGESFEL   540
RGFFDVDPGM  VGRPVRGGVI  EHVDLLPQRV  PGRIEIALLT  VPREAAQKAA  DLLVAAGIKG   600
ILNFAPVVLE  VPKEVAVENV  DFLAGLTRLS  FAILNPKWRE  ESVIKPEMKM  RYYMDGSVNG   660
HEFTIEGEGT  GRPYEGHQEM  TLRVTMAEGG  PMPFAFDLVS  HVFCYGHRVF  TKYPEEIPDY   720
FKQAFPEGLS  WERSLEFEDG  GSASVSAHIS  LRGNTFYHKS  KFTGVNFPAD  GPIMQNQSVD   780
WEPSTEKITA  SDGVLKGDVT  MYLKLEGGGN  HKCQFKTTYK  AAKEILEMPG  DHYIGHRLVR   840
KTEGNITEQV  EDAVAHSEAS  MDELYK                                          866

SEQ ID NO: 19              moltype = AA  length = 871
FEATURE                    Location/Qualifiers
REGION                     1..871
                           note = Synthetic
source                     1..871
                           mol_type = protein
                           organism = synthetic construct
SEQUENCE: 19
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTSKGEEL  FTGVVPILVE  LDGDVNGHKF  SVSGEGEGDA   240
TYGKLTLKFI  CTTGKLPVPW  PTLVTTLTYG  VQCFSRYPDH  MKQHDFFKSA  MPEGYVQERT   300
IFFKDDGNYK  TRAEVKFEGD  TLVNRIELKG  IDFKEDGNIL  GHKLEYNYNS  HNVYIMADKQ   360
KNGIKVNFKI  RHNIEDGSVQ  LADHYQQNTP  IGDGPVLLPD  NHYLSTQSKL  SKDPNEKRDH   420
MVLLEFVTAA  GITLGMPEAA  ISRLITYLRI  LEELEAQGVH  RTASEQLGEL  AQVTAFQVDE   480
DLSYFGSYGT  DGVGYTVPVL  KRELRHILGL  NRKWGLCIVG  MGRLGSALAD  WPGFGESFEL   540
RGFFDVDPGM  VGRPVRGGVI  EHVDLLPQRV  PGRIEIALLT  VPREAAQKAA  DLLVAAGIKG   600
ILNFAPVVLE  VPKEVAVENV  DFLAGLTRLS  FAILNPKWRE  EMMGMVSVIK  PEMKMRYYMD   660
GSVNGHEFTI  EGEGTGRPYE  GHQEMTLRVT  MAEGGPMPFA  FDLVSHVFCY  GHRVFTKYPE   720
EIPDYFKQAF  PEGLSWERSL  EFEDGGSASV  SAHISLRGNT  FYHKSKFTGV  NFPADGPIMQ   780
NQSVDWEPST  EKITASDGVL  KGDVTMYLKL  EGGGNHKCQF  KTTYKAAKEI  LEMPGDHYIG   840
HRLVRKTEGN  ITEQVEDAVA  HSEASMDELY  K                                   871

SEQ ID NO: 20              moltype = AA  length = 874
FEATURE                    Location/Qualifiers
REGION                     1..874
                           note = Synthetic
source                     1..874
                           mol_type = protein
                           organism = synthetic construct
SEQUENCE: 20
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTWSAGHG  MVSKGEELFT  GVVPILVELD  GDVNGHKFSV   240
SGEGEGDATY  GKLTLKFICT  TGKLPVPWPT  LVTTLTYGVQ  CFSRYPDHMK  QHDFFKSAMP   300
EGYVQERTIF  FKDDGNYKTR  AEVKFEGDTL  VNRIELKGID  FKEDGNILGH  KLEYNYNSHN   360
VYIMADKQKN  GIKVNFKIRH  NIEDGSVQLA  DHYQQNTPIG  DGPVLLPDNH  YLSTQSKLSK   420
DPNEKRDHMV  LLEFVTAAGI  TLGMDEPEAA  ISRLITYLRI  LEELEAQGVH  RTASEQLGEL   480
AQVTAFQVDE  DLSYFGSYGT  DGVGYTVPVL  KRELRHILGL  NRKWGLCIVG  MGRLGSALAD   540
WPGFGESFEL  RGFFDVDPGM  VGRPVRGGVI  EHVDLLPQRV  PGRIEIALLT  VPREAAQKAA   600
DLLVAAGIKG  ILNFAPVVLE  VPKEVAVENV  DFLAGLTRLS  FAILNPKWRE  VIKPEMKMRY   660
YMDGSVNGHE  FTIEGEGTGR  PYEGHQEMTL  RVTMAEGGPM  PFAFDLVSHV  FCYGHRVFTK   720
YPEEIPDYFK  QAFPEGLSWE  RSLEFEDGGS  ASVSAHISLR  GNTFYHKSKF  TGVNFPADGP   780
IMQNQSVDWE  PSTEKITASD  GVLKGDVTMY  LKLEGGGNHK  CQFKTTYKAA  KEILEMPGDH   840
YIGHRLVRKT  EGNITEQVED  AVAHSEASMD  ELYK                                874

SEQ ID NO: 21              moltype = AA  length = 877
FEATURE                    Location/Qualifiers
REGION                     1..877
                           note = Synthetic
source                     1..877
                           mol_type = protein
                           organism = synthetic construct
SEQUENCE: 21
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTWSAAGG  HGMVSKGEEL  FTGVVPILVE  LDGDVNGHKF   240
SVSGEGEGDA  TYGKLTLKFI  CTTGKLPVPW  PTLVTTLTYG  VQCFSRYPDH  MKQHDFFKSA   300
MPEGYVQERT  IFFKDDGNYK  TRAEVKFEGD  TLVNRIELKG  IDFKEDGNIL  GHKLEYNYNS   360
HNVYIMADKQ  KNGIKVNFKI  RHNIEDGSVQ  LADHYQQNTP  IGDGPVLLPD  NHYLSTQSKL   420
SKDPNEKRDH  MVLLEFVTAA  GITLGMDEVP  EAAISRLITY  LRILEELEAQ  GVHRTASEQL   480
GELAQVTAFQ  VDEDLSYFGS  YGTDGVGYTV  PVLKRELRHI  LGLNRKWGLC  IVGMGRLGSA   540
LADWPGFGES  FELRGFFDVD  PGMVGRPVRG  GVIEHVDLLP  QRVPGRIEIA  LLTVPREAAQ   600
KAADLLVAAG  IKGILNFAPV  VLEVPKEVAV  ENVDFLAGLT  RLSFAILNPK  WREVIKPEMK   660
```

-continued

```
MRYYMDGSVN GHEFTIEGEG TGRPYEGHQE MTLRVTMAEG GPMPFAFDLV SHVFCYGHRV    720
FTKYPEEIPD YFKQAFPEGL SWERSLEFED GGSASVSAHI SLRGNTFYHK SKFTGVNFPA    780
DGPIMQNQSV DWEPSTEKIT ASDGVLKGDV TMYLKLEGGG NHKCQFKTTY KAAKEILEMP    840
GDHYIGHRLV RKTEGNITEQ VEDAVAHSEA SMDELYK                            877

SEQ ID NO: 22           moltype = AA   length = 875
FEATURE                 Location/Qualifiers
REGION                  1..875
                        note = Synthetic
source                  1..875
                        mol_type = protein
                        organism = synthetic construct
SEQUENCE: 22
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAGHG MVSKGEELFT GVVPILVELD GDVNGHKFSV    240
SGEGEGDATY GKLTLKFICT TGKLPVPWPT LVTTLTYGVQ CFSRYPDHMK QHDFFKSAMP    300
EGYVQERTIF FKDDGNYKTR AEVKFEGDTL VNRIELKGID FKEDGNILGH KLEYNYNSHN    360
VYIMADKQKN GIKVNFKIRH NIEDGSVQLA DHYQQNTPIG DGPVLLPDNH YLSTQSKLSK    420
DPNEKRDHMV LLEFVTAAGI TLGMDEVPEA AISRLITYLR ILEELEAQGV HRTASEQLGE    480
LAQVTAFQVD EDLSYFGSYG TDGVGYTVPV LKRELRHILG LNRKWGLCIV GMGRLGSALA    540
DWPGFGESFE LRGFFDVDPG MVGRPVRGGV IEHVDLLPQR VPGRIEIALL TVPREAAQKA    600
ADLLVAAGIK GILNFAPVVL EVPKEVAVEN VDFLAGLTRL SFAILNPKWR EVIKPEMKMR    660
YYMDGSVNGH EFTIEGEGTG RPYEGHQEMT LRVTMAEGGP MPFAFDLVSH VFCYGHRVFT    720
KYPEEIPDYF KQAFPEGLSW ERSLEFEDGG SASVSAHISL RGNTFYHKSK FTGVNFPADG    780
PIMQNQSVDW EPSTEKITAS DGVLKGDVTM YLKLEGGGNH KCQFKTTYKA AKEILEMPGD    840
HYIGHRLVRK TEGNITEQVE DAVAHSEASM DELYK                              875

SEQ ID NO: 23           moltype = AA   length = 865
FEATURE                 Location/Qualifiers
REGION                  1..865
                        note = Synthetic
source                  1..865
                        mol_type = protein
                        organism = synthetic construct
SEQUENCE: 23
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGMPEAA ISRLITYLRI LEELEAQGVH RTASEQLGEL AQVTAFQVDE    480
DLSYFGSYGT DGVGYTVPVL KRELRHILGL NRKWGLCIVG MGRLGSALAD WPGFGESFEL    540
RGFFDVDPGM VGRPVRGGVI EHVDLLPQRV PGRIEIALLT VPREAAQKAA DLLVAAGIKG    600
ILNFAPVVLE VPKEVAVENV DFLAGLTRLS FAILNPKWRE VIKPEMKMRY YMDGSVNGH     660
EFTIEGEGTG RPYEGHQEMT LRVTMAEGGP MPFAFDLVSH VFCYGHRVFT KYPEEIPDYF    720
KQAFPEGLSW ERSLEFEDGG SASVSAHISL RGNTFYHKSK FTGVNFPADG PIMQNQSVDW    780
EPSTEKITAS DGVLKGDVTM YLKLEGGGNH KCQFKTTYKA AKEILEMPGD HYIGHRLVRK    840
TEGNITEQVE DAVAHSEASM DELYK                                         865

SEQ ID NO: 24           moltype = AA   length = 862
FEATURE                 Location/Qualifiers
REGION                  1..862
                        note = Synthetic
source                  1..862
                        mol_type = protein
                        organism = synthetic construct
SEQUENCE: 24
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTGEELFT GVVPILVELD GDVNGHKFSV SGEGEGDATY    240
GKLTLKFICT TGKLPVPWPT LVTTLTYGVQ CFSRYPDHMK QHDFFKSAMP EGYVQERTIF    300
FKDDGNYKTR AEVKFEGDTL VNRIELKGID FKEDGNILGH KLEYNYNSHN VYIMADKQKN    360
GIKVNFKIRH NIEDGSVQLA DHYQQNTPIG DGPVLLPDNH YLSTQSKLSK DPNEKRDHMV    420
LLEFVTAAGI TLGMPEAAIS RLITYLRILE ELEAQGVHRT ASEQLGELAQ VTAFQVDEDL    480
SYFGSYGTDG VGYTVPVLKR ELRHILGLNR KWGLCIVGMG RLGSALADWP GFGESFELRG    540
FFDVDPGMVG RPVRGGVIEH VDLLPQRVPG RIEIALLTVP REAAQKAADL LVAAGIKGIL    600
NFAPVVLEVP KEVAVENVDF LAGLTRLSFA ILNPKWREVI KPEMKMRYYM DGSVNGHEFT    660
IEGEGTGRPY EGHQEMTLRV TMAEGGPMPF AFDLVSHVFC YGHRVFTKYP EEIPDYFKQA    720
FPEGLSWERS LEFEDGGSAS VSAHISLRGN TFYHKSKFTG VNFPADGPIM QNQSVDWEPS    780
TEKITASDGV LKGDVTMYLK LEGGGNHKCQ FKTTYKAAKE ILEMPGDHYI GHRLVRKTEG    840
NITEQVEDAV AHSEASMDEL YK                                            862

SEQ ID NO: 25           moltype = AA   length = 876
FEATURE                 Location/Qualifiers
```

| REGION | 1..876 |
| --- | --- |
| | note = Synthetic |
| source | 1..876 |
| | mol_type = protein |
| | organism = synthetic construct |

SEQUENCE: 25

```
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEPE AAISRLITYL RILEELEAQG VHRTASEQLG   480
ELAQVTAFQV DEDLSYFGSY GTDGVGYTVP VLKRELRHIL GLNRKWGLCI VGMGRLGSAL   540
ADWPGFGESF ELRGFFDVDP GMVGRPVRGG VIEHVDLLPQ RVPGRIEIAL LTVPREAAQK   600
AADLLVAAGI KGILNFAPVV LEVPKEVAVE NVDFLAGLTR LSFAILNPKW REVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876
```

| SEQ ID NO: 26 | moltype = AA   length = 867 |
| --- | --- |
| FEATURE | Location/Qualifiers |
| REGION | 1..867 |
| | note = Synthetic |
| source | 1..867 |
| | mol_type = protein |
| | organism = synthetic construct |

SEQUENCE: 26

```
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWMVSKG EELFTGVVPI LVELDGDVNG HKFSVSGEGE   240
GDATYGKLTL KFICTTGKLP VPWPTLVTTL TYGVQCFSRY PDHMKQHDFF KSAMPEGYVQ   300
ERTIFFKDDG NYKTRAEVKF EGDTLVNRIE LKGIDFKEDG NILGHKLEYN YNSHNVYIMA   360
DKQKNGIKVN FKIRHNIEDG SVQLADHYQQ NTPIGDGPVL LPDNHYLSTQ SKLSKDPNEK   420
RDHMVLLEFV TAAGITLEAA ISRLITYLRI LEELEAQGVH RTASEQLGEL AQVTAFQVDE   480
DLSYFGSYGT DGVGYTVPVL KRELRHILGL NRKWGLCIVG MGRLGSALAD WPGFGESFEL   540
RGFFDVDPGM VGRPVRGGVI EHVDLLPQRV PGRIEIALLT VPREAAQKAA DLLVAAGIKG   600
ILNFAPVVLE VPKEVAVENV DFLAGLTRLS FAILNPKWRE EMSVIKPEMK MRYYMDGSVN   660
GHEFTIEGEG TGRPYEGHQE MTLRVTMAEG GPMPFAFDLV SHVFCYGHRV FTKYPEEIPD   720
YFKQAFPEGL SWERSLEFED GGSASVSAHI SLRGNTFYHK SKFTGVNFPA DGPIMQNQSV   780
DWEPSTEKIT ASDGVLKGDV TMYLKLEGGG NHKCQFKTTY KAAKEILEMP GDHYIGHRLV   840
RKTEGNITEQ VEDAVAHSEA SMDELYK                                       867
```

| SEQ ID NO: 27 | moltype = AA   length = 876 |
| --- | --- |
| FEATURE | Location/Qualifiers |
| REGION | 1..876 |
| | note = Synthetic |
| source | 1..876 |
| | mol_type = protein |
| | organism = synthetic construct |

SEQUENCE: 27

```
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEPE AAISRLITYL RILEELEAQG VHRTASEQLG   480
ELAQVTAFQV DEDLSYFGSY GTDGVGYTVP VLKRELRHIL GLNRKWGLCI VGMGRLGSAL   540
ADWPGFGESF ELRGFFDVDP GMVGRPVRGG VIEHVDLLPQ RVPGRIEIAL LTVPREAAQK   600
AADLLVAAGI KGILNFAPVV LEVPKEVAVE NVDFLAGLTR LSFAILNPKW REVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876
```

| SEQ ID NO: 28 | moltype = AA   length = 870 |
| --- | --- |
| FEATURE | Location/Qualifiers |
| REGION | 1..870 |
| | note = Synthetic |
| source | 1..870 |
| | mol_type = protein |
| | organism = synthetic construct |

SEQUENCE: 28

```
MKVPEAAISR LITYLRILEE LEAQGVHRTA SEQLGELAQV TAFQVDKDLS YFGSYGTDGV    60
```

```
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWVSKGE ELFTGVVPIL VELDGDVNGH KFSVSGEGEG    240
DATYGKLTLK FICTTGKLPV PWPTLVTTLT YGVQCFSRYP DHMKQHDFFK SAMPEGYVQE    300
RTIFFKDDGN YKTRAEVKFE GDTLVNRIEL KGIDFKEDGN ILGHKLEYNY NSHNVYIMAD    360
KQKNGIKVNF KIRHNIEDGS VQLADHYQQN TPIGDGPVLL PDNHYLSTQS KLSKDPNEKR    420
DHMVLLEFVT AAGITLGMDE VPEAAISRLI TYLRILEELE AQGVHRTASE QLGELAQVTA    480
FQVDEDLSYF GSYGTDGVGY TVPVLKRELR HILGLNRKWG LCIVGMGRLG SALADWPGFG    540
ESFELRGFFD VDPGMVGRPV RGGVIEHVDL LPQRVPGRIE IALLTVPREA AQKAADLLVA    600
AGIKGILNFA PVVLEVPKEV AVENVDFLAG LTRLSFAILN PKWREEVIKP EMKRYYMDG    660
SVNGHEFTIE GEGTGRPYEG HQEMTLRVTM AEGGPMPFAF DLVSHVFCYG HRVFTKYPEE    720
IPDYFKQAFP EGLSWERSLE FEDGGSASVS AHISLRGNTF YHKSKFTGVN FPADGPIMQN    780
QSVDWEPSTE KITASDGVLK GDVTMYLKLE GGGNHKCQFK TTYKAAKEIL EMPGDHYIGH    840
RLVRKTEGNI TEQVEDAVAH SEASMDELYK                                     870

SEQ ID NO: 29           moltype = AA  length = 871
FEATURE                 Location/Qualifiers
REGION                  1..871
                        note = Synthetic
source                  1..871
                        mol_type = protein
                        organism = synthetic construct
SEQUENCE: 29
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGMPEAA ISRLITYLRI LEELEAQGVH RTASEQLGEL AQVTAFQVDE    480
DLSYFGSYGT DGVGYTVPVL KRELRHILGL NRKWGLCIVG MGRLGSALAD WPGFGESFEL    540
RGFFDVDPGM VGRPVRGGVI EHVDLLPQRV PGRIEIALLT VPREAAQKAA DLLVAAGIKG    600
ILNFAPVVLE VPKEVAVENV DFLAGLTRLS FAILNPKWRE EMMGMVSVIK PEMKMRYYMD    660
GSVNGHEFTI EGEGTGRPYE GHQEMTLRVT MAEGGPMPFA FDLVSHVFCY GHRVFTKYPE    720
EIPDYFKQAF PEGLSWERSL EFEDGGSASV SAHISLRGNT FYHKSKFTGV NFPADGPIMQ    780
NQSVDWEPST EKITASDGVL KGDVTMYLKL EGGGNHKCQF KTTYKAAKEI LEMPGDHYIG    840
HRLVRKTEGN ITEQVEDAVA HSEASMDELY K                                   871

SEQ ID NO: 30           moltype = AA  length = 874
FEATURE                 Location/Qualifiers
REGION                  1..874
                        note = Synthetic
source                  1..874
                        mol_type = protein
                        organism = synthetic construct
SEQUENCE: 30
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWMVSKG EELFTGVVPI LVELDGDVNG HKFSVSGEGE    240
GDATYGKLTL KFICTTGKLP VPWPTLVTTL TYGVQCFSRY PDHMKQHDFF KSAMPEGYVQ    300
ERTIFFKDDG NYKTRAEVKF EGDTLVNRIE LKGIDFKEDG NILGHKLEYN YNSHNVYIMA    360
DKQKNGIKVN FKIRHNIEDG SVQLADHYQQ NTPIGDGPVL LPDNHYLSTQ SKLSKDPNEK    420
RDHMVLLEFV TAAGITLGMP EEAAISRLIT YLRILEELEA QGVHRTASEQL GELAQVTAFQ    480
VDEDLSYFGS YGTDGVGYTV PVLKRELRHI LGLNRKWGLC IVGMGRLGSA LADWPGFGES    540
FELRGFFDVD PGMVGRPVRG GVIEHVDLLP QRVPGRIEIA LLTVPREAAQ KAADLLVAAG    600
IKGILNFAPV VLEVPKEVAV ENVDFLAGLT RLSFAILNPK WREEMMGMVS VIKPEMKMRY    660
YMDGSVNGHE FTIEGEGTGR PYEGHQEMTL RVTMAEGGPM PFAFDLVSHV FCYGHRVFTK    720
YPEEIPDYFK QAFPEGLSWE RSLEFEDGGS ASVSAHISLR GNTFYHKSKF TGVNFPADGP    780
IMQNQSVDWE PSTEKITASD GVLKGDVTMY LKLEGGGNHK CQFKTTYKAA KEILEMPGDH    840
YIGHRLVRKT EGNITEQVED AVAHSEASMD ELYK                                874

SEQ ID NO: 31           moltype = AA  length = 878
FEATURE                 Location/Qualifiers
REGION                  1..878
                        note = Synthetic
source                  1..878
                        mol_type = protein
                        organism = synthetic construct
SEQUENCE: 31
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDELV PEAAISRLIT YLRILEELEA QGVHRTASEQ    480
```

```
LGELAQVTAF QVDEDLSYFG SYGTDGVGYT VPVLKRELRH ILGLNRKWGL CIVGMGRLGS    540
ALADWPGFGE SFELRGFFDV DPGMVGRPVR GGVIEHVDLL PQRVPGRIEI ALLTVPREAA    600
QKAADLLVAA GIKGILNFAP VVLEVPKEVA VENVDFLAGL TRLSFAILNP KWREVIKPEM    660
KMRYYMDGSV NGHEFTIEGE GTGRPYEGHQ EMTLRVTMAE GGPMPFAFDL VSHVFCYGHR    720
VFTKYPEEIP DYFKQAFPEG LSWERSLEFE DGGSASVSAH ISLRGNTFYH KSKFTGVNFP    780
ADGPIMQNQS VDWEPSTEKI TASDGVLKGD VTMYLKLEGG GNHKCQFKTT YKAAKEILEM    840
PGDHYIGHRL VRKTEGNITE QVEDAVAHSE ASMDELYK                           878

SEQ ID NO: 32              moltype = AA  length = 881
FEATURE                    Location/Qualifiers
REGION                     1..881
                           note = Synthetic
source                     1..881
                           mol_type = protein
                           organism = synthetic construct
SEQUENCE: 32
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDELV PEEAAISRLIT YLRILEELEA QGVHRTASEQ   480
LGELAQVTAF QVDEDLSYFG SYGTDGVGYT VPVLKRELRH ILGLNRKWGL CIVGMGRLGS    540
ALADWPGFGE SFELRGFFDV DPGMVGRPVR GGVIEHVDLL PQRVPGRIEI ALLTVPREAA    600
QKAADLLVAA GIKGILNFAP VVLEVPKEVA VENVDFLAGL TRLSFAILNP KWREEMSVIK    660
PEMKMRYYMD GSVNGHEFTI EGEGTGRPYE GHQEMTLRVT MAEGGPMPFA FDLVSHVFCY    720
GHRVFTKYPE EIPDYFKQAF PEGLSWERSL EFEDGGSASV SAHISLRGNT FYHKSKFTGV    780
NFPADGPIMQ NQSVDWEPST EKITASDGVL KGDVTMYLKL EGGGNHKCQF KTTYKAAKEI    840
LEMPGDHYIG HRLVRKTEGN ITEQVEDAVA HSEASMDELY K                       881

SEQ ID NO: 33              moltype = AA  length = 866
FEATURE                    Location/Qualifiers
REGION                     1..866
                           note = Synthetic
source                     1..866
                           mol_type = protein
                           organism = synthetic construct
SEQUENCE: 33
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGMDEPE AAISRLITYL RILEELEAQG VHRTASEQLG ELAQVTAFQV    480
DEDLSYFGSY GTDGVGYTVP VLKRELRHIL GLNRKWGLCI VGMGRLGSAL ADWPGFGESF    540
ELRGFFDVDP GMVGRPVRGG VIEHVDLLPQ RVPGRIEIAL LTVPREAAQK AADLLVAAGI    600
KGILNFAPVV LEVPKEVAVE NVDFLAGLTR LSFAILNPKW REVIKPEMKM RYYMDGSVNG    660
HEFTIEGEGT GRPYEGHQEM TLRVTMAEGG PMPFAFDLVS HVFCYGHRVF TKYPEEIPDY    720
FKQAFPEGLS WERSLEFEDG GSASVSAHIS LRGNTFYHKS KFTGVNFPAD GPIMQNQSVD    780
WEPSTEKITA SDGVLKGDVT MYLKLEGGGN HKCQFKTTYK AAKEILEMPG DHYIGHRLVR    840
KTEGNITEQV EDAVAHSEAS MDELYK                                        866

SEQ ID NO: 34              moltype = AA  length = 875
FEATURE                    Location/Qualifiers
REGION                     1..875
                           note = Synthetic
source                     1..875
                           mol_type = protein
                           organism = synthetic construct
SEQUENCE: 34
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGH GMVSKGEELF TGVVPILVEL DGDVNGHKFS    240
VSGEGEGDAT YGKLTLKFIC TTGKLPVPWP TLVTTLTYGV QCFSRYPDHM KQHDFFKSAM    300
PEGYVQERTI FFKDDGNYKT RAEVKFEGDT LVNRIELKGI DFKEDGNILG HKLEYNYNSH    360
NVYIMADKQK NGIKVNFKIR HNIEDGSVQL ADHYQQNTPI GDGPVLLPDN HYLSTQSKLS    420
KDPNEKRDHM VLLEFVTAAG ITLGMDEPEA AISRLITYLR ILEELEAQGV HRTASEQLGE    480
LAQVTAFQVD EDLSYFGSYG TDGVGYTVPV LKRELRHILG LNRKWGLCIV GMGRLGSALA    540
DWPGFGESFE LRGFFDVDPG MVGRPVRGGV IEHVDLLPQR VPGRIEIALL TVPREAAQKA    600
ADLLVAAGIK GILNFAPVVL EVPKEVAVEN VDFLAGLTRL SFAILNPKWR EVIKPEMKMR    660
YYMDGSVNGH EFTIEGEGTG RPYEGHQEMT LRVTMAEGGP MPFAFDLVSH VFCYGHRVFT    720
KYPEEIPDYF KQAFPEGLSW ERSLEFEDGG SASVSAHISL RGNTFYHKSK FTGVNFPADG    780
PIMQNQSVDW EPSTEKITAS DGVLKGDVTM YLKLEGGGNH KCQFKTTYKA AKEILEMPGD    840
HYIGHRLVRK TEGNITEQVE DAVAHSEASM DELYK                              875
```

```
SEQ ID NO: 35           moltype = AA  length = 871
FEATURE                 Location/Qualifiers
REGION                  1..871
                        note = Synthetic
source                  1..871
                        mol_type = protein
                        organism = synthetic construct
SEQUENCE: 35
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLEAAISR LITYLRILEE LEAQGVHRTA SEQLGELAQV  480
TAFQVDEDLS YFGSYGTDGV GYTVPVLKRE LRHILGLNRK WGLCIVGMGR LGSALADWPG  540
FGESFELRGF FDVDPGMVGR PVRGGVIEHV DLLPQRVPGR IEIALLTVPR EAAQKAADLL  600
VAAGIKGILN FAPVVLEVPK EVAVENVDFL AGLTRLSFAI LNPKWREVIK PEMKMRYYMD  660
GSVNGHEFTI EGEGTGRPYE GHQEMTLRVT MAEGGPMPFA FDLVSHVFCY GHRVFTKYPE  720
EIPDYFKQAF PEGLSWERSL EFEDGGSASV SAHISLSRGNT FYHKSKFTGV NFPADGPIMQ  780
NQSVDWEPST EKITASDGVL KGDVTMYLKL EGGGNHKCQF KTTYKAAKEI LEMPGDHYIG  840
HRLVRKTEGN ITEQVEDAVA HSEASMDELY K                                871

SEQ ID NO: 36           moltype = AA  length = 873
FEATURE                 Location/Qualifiers
REGION                  1..873
                        note = Synthetic
source                  1..873
                        mol_type = protein
                        organism = synthetic construct
SEQUENCE: 36
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGH GMVSKGEELF TGVVPILVEL DGDVNGHKFS  240
VSGEGEGDAT YGKLTLKFIC TTGKLPVPWP TLVTTLTYGV QCFSRYPDHM KQHDFFKSAM  300
PEGYVQERTI FFKDDGNYKT RAEVKFEGDT LVNRIELKGI DFKEDGNILG HKLEYNYNSH  360
NVYIMADKQK NGIKVNFKIR HNIEDGSVQL ADHYQQNTPI GDGPVLLPDN HYLSTQSKLS  420
KDPNEKRDHM VLLEFVTAAG ITLGMDPEAA ISRLITYLRI LEELEAQGVH RTASEQLGEL  480
AQVTAFQVDE DLSYFGSYGT DGVGYTVPVL KRELRHILGL NRKWGLCIVG MGRLGSALAD  540
WPGFGESFEL RGFFDVDPGM VGRPVRGGVI EHVDLLPQRV PGRIEIALLT VPREAAQKAA  600
DLLVAAGIKG ILNFAPVVLE VPKEVAVENV DFLAGLTRLS FAILNPKWRE IKPEMKMRYY  660
MDGSVNGHEF TIEGEGTGRP YEGHQEMTLR VTMAEGGPMP FAFDLVSHVF CYGHRVFTKY  720
PEEIPDYFKQ AFPEGLSWER SLEFEDGGSA SVSAHISLRG NTFYHKSKFT GVNFPADGPI  780
MQNQSVDWEP STEKITASDG VLKGDVTMYL KLEGGGNHKC QFKTTYKAAK EILEMPGDHY  840
IGHRLVRKTE GNITEQVEDA VAHSEASMDE LYK                              873

SEQ ID NO: 37           moltype = AA  length = 878
FEATURE                 Location/Qualifiers
REGION                  1..878
                        note = Synthetic
source                  1..878
                        mol_type = protein
                        organism = synthetic construct
SEQUENCE: 37
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGH GMVSKGEELF TGVVPILVEL DGDVNGHKFS  240
VSGEGEGDAT YGKLTLKFIC TTGKLPVPWP TLVTTLTYGV QCFSRYPDHM KQHDFFKSAM  300
PEGYVQERTI FFKDDGNYKT RAEVKFEGDT LVNRIELKGI DFKEDGNILG HKLEYNYNSH  360
NVYIMADKQK NGIKVNFKIR HNIEDGSVQL ADHYQQNTPI GDGPVLLPDN HYLSTQSKLS  420
KDPNEKRDHM VLLEFVTAAG ITLGMDELYK VPEAAISRLI TYLRILEELE AQGVHRTASE  480
QLGELAQVTA FQVDEDLSYF GSYGTDGVGY TVPVLKRELR HILGLNRKWG LCIVGMGRLG  540
SALADWPGFG ESFELRGFFD VDPGMVGRPV RGGVIEHVDL LPQRVPGRIE IALLTVPREA  600
AQKAADLLVA AGIKGILNFA PVVLEVPKEV AVENVDFLAG LTRLSFAILN PKWREIKPEM  660
KMRYYMDGSV NGHEFTIEGE GTGRPYEGHQ EMTLRVTMAE GGPMPFAFDL VSHVFCYGHR  720
VFTKYPEEIP DYFKQAFPEG LSWERSLEFE DGGSASVSAH ISLRGNTFYH KSKFTGVNFP  780
ADGPIMQNQS VDWEPSTEKI TASDGVLKGD VTMYLKLEGG GNHKCQFKTT YKAAKEILEM  840
PGDHYIGHRL VRKTEGNITE QVEDAVAHSE ASMDELYK                         878

SEQ ID NO: 38           moltype = AA  length = 874
FEATURE                 Location/Qualifiers
REGION                  1..874
                        note = Synthetic
source                  1..874
                        mol_type = protein
```

```
                        organism = synthetic construct
SEQUENCE: 38
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWVSKGE ELFTGVVPIL VELDGDVNGH KFSVSGEGEG   240
DATYGKLTLK FICTTGKLPV PWPTLVTTLT YGVQCFSRYP DHMKQHDFFK SAMPEGYVQE   300
RTIFFKDDGN YKTRAEVKFE GDTLVNRIEL KGIDFKEDGN ILGHKLEYNY NSHNVYIMAD   360
KQKNGIKVNF KIRHNIEDGS VQLADHYQQN TPIGDGPVLL PDNHYLSTQS KLSKDPNEKR   420
DHMVLLEFVT AAGITLGMDE LVPEAAISRL ITYLRILEEL EAQGVHRTAS EQLGELAQVT   480
AFQVDEDLSY FGSYGTDGVG YTVPVLKREL RHILGLNRKW GLCIVGMGRL GSALADWPGF   540
GESFELRGFF DVDPGMVGRP VRGGVIEHVD LLPQRVPGRI EIALLTVPRE AAQKAADLLV   600
AAGIKGILNF APVVLEVPKE VAVENVDFLA GLTRLSFAIL NPKWREEMMS VIKPEMKMRY   660
YMDGSVNGHE FTIEGEGTGR PYEGHQEMTL RVTMAEGGPM PFAFDLVSHV FCYGHRVFTK   720
YPEEIPDYFK QAFPEGLSWE RSLEFEDGGS ASVSAHISLR GNTFYHKSKF TGVNFPADGP   780
IMQNQSVDWE PSTEKITASD GVLKGDVTMY LKLEGGGNHK CQFKTTYKAA KEILEMPGDH   840
YIGHRLVRKT EGNITEQVED AVAHSEASMD ELYK                              874

SEQ ID NO: 39            moltype = AA  length = 878
FEATURE                  Location/Qualifiers
REGION                   1..878
                         note = Synthetic
source                   1..878
                         mol_type = protein
                         organism = synthetic construct
SEQUENCE: 39
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWGMVSK GEELFTGVVP ILVELDGDVN GHKFSVSGEG   240
EGDATYGKLT LKFICTTGKL PVPWPTLVTT LTYGVQCFSR YPDHMKQHDF FKSAMPEGYV   300
QERTIFFKDD GNYKTRAEVK FEGDTLVNRI ELKGIDFKED GNILGHKLEY NYNSHNVYIM   360
ADKQKNGIKV NFKIRHNIED GSVQLADHYQ QNTPIGDGPV LLPDNHYLST QSKLSKDPNE   420
KRDHMVLLEF VTAAGITLGM DEVPEAAISR LITYLRILEE LEAQGVHRTA SEQLGELAQV   480
TAFQVDEDLS YFGSYGTDGV GYTVPVLKRE LRHILGLNRK WGLCIVGMGR LGSALADWPG   540
FGESFELRGF FDVDPGMVGR PVRGGVIEHV DLLPQRVPGR IEIALLTVPR EAAQKAADLL   600
VAAGIKGILN FAPVVLEVPK EVAVENVDFL AGLTRLSFAI LNPKWREEMM GMVSVIKPEM   660
KMRYYMDGSV NGHEFTIEGE GTGRPYEGHQ EMTLRVTMAE GGPMPFAFDL VSHVFCYGHR   720
VFTKYPEEIP DYFKQAFPEG LSWERSLEFE DGGSASVSAH ISLRGNTFYH KSKFTGVNFP   780
ADGPIMQNQS VDWEPSTEKI TASDGVLKGD VTMYLKLEGG GNHKCQFKTT YKAAKEILEM   840
PGDHYIGHRL VRKTEGNITE QVEDAVAHSE ASMDELYK                          878

SEQ ID NO: 40            moltype = AA  length = 877
FEATURE                  Location/Qualifiers
REGION                   1..877
                         note = Synthetic
source                   1..877
                         mol_type = protein
                         organism = synthetic construct
SEQUENCE: 40
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEVP EAAISRLITY LRILEELEAQ GVHRTASEQL   480
GELAQVTAFQ VDEDLSYFGS YGTDGVGYTV PVLKRELRHI LGLNRKWGLC IVGMGRLGSA   540
LADWPGFGES FELRGFFDVD PGMVGRPVRG GVIEHVDLLP QRVPGRIEIA LLTVPREAAQ   600
KAADLLVAAG IKGILNFAPV VLEVPKEVAV ENVDFLAGLT RLSFAILNPK WREVIKPEMK   660
MRYYMDGSVN GHEFTIEGEG TGRPYEGHQE MTLRVTMAEG GPMPFAFDLV SHVFCYGHRV   720
FTKYPEEIPD YFKQAFPEGL SWERSLEFED GGSASVSAHI SLRGNTFYHK SKFTGVNFPA   780
DGPIMQNQSV DWEPSTEKIT ASDGVLKGDV TMYLKLEGGG NHKCQFKTTY KAAKEILEMP   840
GDHYIGHRLV RKTEGNITEQ VEDAVAHSEA SMDELYK                           877

SEQ ID NO: 41            moltype = AA  length = 876
FEATURE                  Location/Qualifiers
REGION                   1..876
                         note = Synthetic
source                   1..876
                         mol_type = protein
                         organism = synthetic construct
SEQUENCE: 41
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWGMVSK GEELFTGVVP ILVELDGDVN GHKFSVSGEG   240
EGDATYGKLT LKFICTTGKL PVPWPTLVTT LTYGVQCFSR YPDHMKQHDF FKSAMPEGYV   300
```

```
QERTIFFKDD GNYKTRAEVK FEGDTLVNRI ELKGIDFKED GNILGHKLEY NYNSHNVYIM    360
ADKQKNGIKV NFKIRHNIED GSVQLADHYQ QNTPIGDGPV LLPDNHYLST QSKLSKDPNE    420
KRDHMVLLEF VTAAGITLGM DEVPEAAISR LITYLRILEE LEAQGVHRTA SEQLGELAQV    480
TAFQVDEDLS YFGSYGTDGV GYTVPVLKRE LRHILGLNRK WGLCIVGMGR LGSALADWPG    540
FGESFELRGF FDVDPGMVGR PVRGGVIEHV DLLPQRVPGR IEIALLTVPR EAAQKAADLL    600
VAAGIKGILN FAPVVLEVPK EVAVENVDFL AGLTRLSFAI LNPKWREEMM VSVIKPEMKM    660
RYYMDGSVNG HEFTIEGEGT GRPYEGHQEM TLRVTMAEGG PMPFAFDLVS HVFCYGHRVF    720
TKYPEEIPDY FKQAFPEGLS WERSLEFEDG GSASVSAHIS LRGNTFYHKS KFTGVNFPAD    780
GPIMQNQSVD WEPSTEKITA SDGVLKGDVT MYLKLEGGGN HKCQFKTTYK AAKEILEMPG    840
DHYIGHRLVR KTEGNITEQV EDAVAHSEAS MDELYK                              876

SEQ ID NO: 42           moltype = AA  length = 876
FEATURE                 Location/Qualifiers
REGION                  1..876
                        note = Synthetic
source                  1..876
                        mol_type = protein
                        organism = synthetic construct
SEQUENCE: 42
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWVSKGE ELFTGVVPIL VELDGDVNGH KFSVSGEGEG    240
DATYGKLTLK FICTTGKLPV PWPTLVTTLT YGVQCFSRYP DHMKQHDFFK SAMPEGYVQE    300
RTIFFKDDGN YKTRAEVKFE GDTLVNRIEL KGIDFKEDGN ILGHKLEYNY NSHNVYIMAD    360
KQKNGIKVNF KIRHNIEDGS VQLADHYQQN TPIGDGPVLL PDNHYLSTQS KLSKDPNEKR    420
DHMVLLEFVT AAGITLGMDE VPEAAISRLI TYLRILEELE AQGVHRTASE QLGELAQVTA    480
FQVDEDLSYF GSYGTDGVGY TVPVLKRELR HILGLNRKWG LCIVGMGRLG SALADWPGFG    540
ESFELRGFFD VDPGMVGRPV RGGVIEHVDL LPQRVPGRIE IALLTVPREA AQKAADLLVA    600
AGIKGILNFA PVVLEVPKEV AVENVDFLAG LTRLSFAILN PKWREEMMGM VSVIKPEMKM    660
RYYMDGSVNG HEFTIEGEGT GRPYEGHQEM TLRVTMAEGG PMPFAFDLVS HVFCYGHRVF    720
TKYPEEIPDY FKQAFPEGLS WERSLEFEDG GSASVSAHIS LRGNTFYHKS KFTGVNFPAD    780
GPIMQNQSVD WEPSTEKITA SDGVLKGDVT MYLKLEGGGN HKCQFKTTYK AAKEILEMPG    840
DHYIGHRLVR KTEGNITEQV EDAVAHSEAS MDELYK                              876

SEQ ID NO: 43           moltype = AA  length = 866
FEATURE                 Location/Qualifiers
REGION                  1..866
                        note = Synthetic
source                  1..866
                        mol_type = protein
                        organism = synthetic construct
SEQUENCE: 43
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTGEELFT GVVPILVELD GDVNGHKFSV SGEGEGDATY    240
GKLTLKFICT TGKLPVPWPT LVTTLTYGVQ CFSRYPDHMK QHDFFKSAMP EGYVQERTIF    300
FKDDGNYKTR AEVKFEGDTL VNRIELKGID FKEDGNILGH KLEYNYNSHN VYIMADKQKN    360
GIKVNFKIRH NIEDGSVQLA DHYQQNTPIG DGPVLLPDNH YLSTQSKLSK DPNEKRDHMV    420
LLEFVTAAGI TLGMDEPEAA ISRLITYLRI LEELEAQGVH RTASEQLGEL AQVTAFQVDE    480
DLSYFGSYGT DGVGYTVPVL KRELRHILGL NRKWGLCIVG MGRLGSALAD WPGFGESFEL    540
RGFFDVDPGM VGRPVGGVI EHVDLLPQRV PGRIEIALLT VPREAAQKAA DLLVAAGIKG     600
ILNFAPVVLE VPKEVAVENV DFLAGLTRLS FAILNPKWRE ESVIKPEMKM RYYMDGSVNG    660
HEFTIEGEGT GRPYEGHQEM TLRVTMAEGG PMPFAFDLVS HVFCYGHRVF TKYPEEIPDY    720
FKQAFPEGLS WERSLEFEDG GSASVSAHIS LRGNTFYHKS KFTGVNFPAD GPIMQNQSVD    780
WEPSTEKITA SDGVLKGDVT MYLKLEGGGN HKCQFKTTYK AAKEILEMPG DHYIGHRLVR    840
KTEGNITEQV EDAVAHSEAS MDELYK                                         866

SEQ ID NO: 44           moltype = AA  length = 870
FEATURE                 Location/Qualifiers
REGION                  1..870
                        note = Synthetic
source                  1..870
                        mol_type = protein
                        organism = synthetic construct
SEQUENCE: 44
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAHGM VSKGEELFTG VVPILVELDG DVNGHKFSVS    240
GEGEGDATYG KLTLKFICTT GKLPVPWPTL VTTLTYGVQC FSRYPDHMKQ HDFFKSAMPE    300
GYVQERTIFF KDDGNYKTRA EVKFEGDTLV NRIELKGIDF KEDGNILGHK LEYNYNSHNV    360
YIMADKQKNG IKVNFKIRHN IEDGSVQLAD HYQQNTPIGD GPVLLPDNHY LSTQSKLSKD    420
PNEKRDHMVL LEFVTAAGIT LEAAISRLIT YLRILEELEA QGVHRTASEQ LGELAQVTAF    480
QVDEDLSYFG SYGTDGVGYT VPVLKRELRH ILGLNRKWGL CIVGMGRLGS ALADWPGFGE    540
SFELRGFFDV DPGMVGRPVR GGVIEHVDLL PQRVPGRIEI ALLTVPREAA QKAADLLVAA    600
GIKGILNFAP VVLEVPKEVA VENVDFLAGL TRLSFAILNP KWREESVIKP EMKMRYYMDG    660
SVNGHEFTIE GEGTGRPYEG HQEMTLRVTM AEGGPMPFAF DLVSHVFCYG HRVFTKYPEE    720
```

```
IPDYFKQAFP EGLSWERSLE FEDGGSASVS AHISLRGNTF YHKSKFTGVN PPADGPIMQN    780
QSVDWEPSTE KITASDGVLK GDVTMYLKLE GGGNHKCQFK TTYKAAKEIL EMPGDHYIGH    840
RLVRKTEGNI TEQVEDAVAH SEASMDELYK                                    870

SEQ ID NO: 45             moltype = AA  length = 872
FEATURE                   Location/Qualifiers
REGION                    1..872
                          note = Synthetic
source                    1..872
                          mol_type = protein
                          organism = synthetic construct
SEQUENCE: 45
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWMVSKG EELFTGVVPI LVELDGDVNG HKFSVSGEGE    240
GDATYGKLTL KFICTTGKLP VPWPTLVTTL TYGVQCFSRY PDHMKQHDFF KSAMPEGYVQ    300
ERTIFFKDDG NYKTRAEVKF EGDTLVNRIE LKGIDFKEDG NILGHKLEYN YNSHNVYIMA    360
DKQKNGIKVN FKIRHNIEDG SVQLADHYQQ NTPIGDGPVL LPDNHYLSTQ SKLSKDPNEK    420
RDHMVLLEFV TAAGITLGMD EVPEAAISRL ITYLRILEEL EAQGVHRTAS EQLGELAQVT    480
AFQVDEDLSY FGSYGTDGVG YTVPVLKREL RHILGLNRKW GLCIVGMGRL GSALADWPGF    540
GESFELRGFF DVDPGMVGRP VRGGVIEHVD LLPQRVPGRI EIALLTVPRE AAQKAADLLV    600
AAGIKGILNF APVVLEVPKE VAVENVDFLA GLTRLSFAIL NPKWREESVI KPEMKMRYYM    660
DGSVNGHEFT IEGEGTGRPY EGHQEMTLRV TMAEGGPMPF AFDLVSHVFC YGHRVFTKYP    720
EEIPDYFKQA FPEGLSWERS LEFEDGGSAS VSAHISLRGN TFYHKSKFTG VNFPADGPIM    780
QNQSVDWEPS TEKITASDGV LKGDVTMYLK LEGGGNHKCQ FKTTYKAAKE ILEMPGDHYI    840
GHRLVRKTEG NITEQVEDAV AHSEASMDEL YK                                 872

SEQ ID NO: 46             moltype = AA  length = 878
FEATURE                   Location/Qualifiers
REGION                    1..878
                          note = Synthetic
source                    1..878
                          mol_type = protein
                          organism = synthetic construct
SEQUENCE: 46
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGH GMVSKGEELF TGVVPILVEL DGDVNGHKFS    240
VSGEGEGDAT YGKLTLKFIC TTGKLPVPWP TLVTTLTYGV QCFSRYPDHM KQHDFFKSAM    300
PEGYVQERTI FFKDDGNYKT RAEVKFEGDT LVNRIELKGI DFKEDGNILG HKLEYNYNSH    360
NVYIMADKQK NGIKVNFKIR HNIEDGSVQL ADHYQQNTPI GDGPVLLPDN HYLSTQSKLS    420
KDPNEKRDHM VLLEFVTAAG ITLGMDELYK VPEAAISRLI TYLRILEELE AQGVHRTASE    480
QLGELAQVTA FQVDEDLSYF GSYGTDGVGY TVPVLKRELR HILGLNRKWG LCIVGMGRLG    540
SALADWPGFG ESFELRGFFD VDPGMVGRPV RGGVIEHVDL LPQRVPGRIE IALLTVPREA    600
AQKAADLLVA AGIKGILNFA PVVLEVPKEV AVENVDFLAG LTRLSFAILN PKWREIKPEM    660
KMRYYMDGSV NGHEFTIEGE GTGRPYEGHQ EMTLRVTMAE GGPMPFAFDL VSHVFCYGHR    720
VFTKYPEEIP DYFKQAFPEG LSWERSLEFE DGGSASVSAH ISLRGNTFYH KSKFTGVNFP    780
ADGPIMQNQS VDWEPSTEKI TASDGVLKGD VTMYLKLEGG GNHKCQFKTT YKAAKEILEM    840
PGDHYIGHRL VRKTEGNITE QVEDAVAHSE ASMDELYK                           878

SEQ ID NO: 47             moltype = AA  length = 877
FEATURE                   Location/Qualifiers
REGION                    1..877
                          note = Synthetic
source                    1..877
                          mol_type = protein
                          organism = synthetic construct
SEQUENCE: 47
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWMVSKG EELFTGVVPI LVELDGDVNG HKFSVSGEGE    240
GDATYGKLTL KFICTTGKLP VPWPTLVTTL TYGVQCFSRY PDHMKQHDFF KSAMPEGYVQ    300
ERTIFFKDDG NYKTRAEVKF EGDTLVNRIE LKGIDFKEDG NILGHKLEYN YNSHNVYIMA    360
DKQKNGIKVN FKIRHNIEDG SVQLADHYQQ NTPIGDGPVL LPDNHYLSTQ SKLSKDPNEK    420
RDHMVLLEFV TAAGITLGMD ELYVPEAAIS RLITYLRILE ELEAQGVHRT ASEQLGELAQ    480
VTAFQVDEDL SYFGSYGTDG VGYTVPVLKR ELRHILGLNR KWGLCIVGMG RLGSALADWP    540
GFGESFELRG FFDVDPGMVG RPVRGGVIEH VDLLPQRVPG RIEIALLTVP REAAQKAADL    600
LVAAGIKGIL NFAPVVLEVP KEVAVENVDF LAGLTRLSFA ILNPKWREEM MVSVIKPEMK    660
MRYYMDGSVN GHEFTIEGEG TGRPYEGHQE MTLRVTMAEG GPMPFAFDLV SHVFCYGHRV    720
FTKYPEEIPD YFKQAFPEGL SWERSLEFED GGSASVSAHI SLRGNTFYHK SKFTGVNFPA    780
DGPIMQNQSV DWEPSTEKIT ASDGVLKGDV TMYLKLEGGG NHKCQFKTTY KAAKEILEMP    840
GDHYIGHRLV RKTEGNITEQ VEDAVAHSEA SMDELYK                            877

SEQ ID NO: 48             moltype = AA  length = 866
FEATURE                   Location/Qualifiers
REGION                    1..866
```

```
                           note = Synthetic
source                     1..866
                           mol_type = protein
                           organism = synthetic construct
SEQUENCE: 48
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTGEELFT GVVPILVELD GDVNGHKFSV SGEGEGDATY   240
GKLTLKFICT TGKLPVPWPT LVTTLTYGVQ CFSRYPDHMK QHDFFKSAMP EGYVQERTIF   300
FKDDGNYKTR AEVKFEGDTL VNRIELKGID FKEDGNILGH KLEYNYNSHN VYIMADKQKN   360
GIKVNFKIRH NIEDGSVQLA DHYQQNTPIG DGPVLLPDNH YLSTQSKLSK DPNEKRDHMV   420
LLEFVTAAGI TLGMDEPEAA ISRLITYLRI LEELEAQGVH RTASEQLGEL AQVTAFQVDE   480
DLSYFGSYGT DGVGYTVPVL KRELRHILGL NRKWGLCIVG MGRLGSALAD WPGFGESFEL   540
RGFFDVDPGM VGRPVRGGVI EHVDLLPQRV PGRIEIALLT VPREAAQKAA DLLVAAGIKG   600
ILNFAPVVLE VPKEVAVENV DFLAGLTRLS FAILNPKWRE ESVIKPEMKM RYYMDGSVNG   660
HEFTIEGEGT GRPYEGHQEM TLRVTMAEGG PMPFAFDLVS HVFCYGHRVF TKYPEEIPDY   720
FKQAFPEGLS WERSLEFEDG GSASVSAHIS LRGNTFYHKS KFTGVNFPAD GPIMQNQSVD   780
WEPSTEKITA SDGVLKGDVT MYLKLEGGGN HKCQFKTTYK AAKEILEMPG DHYIGHRLVR   840
KTEGNITEQV EDAVAHSEAS MDELYK                                        866

SEQ ID NO: 49              moltype = AA  length = 876
FEATURE                    Location/Qualifiers
REGION                     1..876
                           note = Synthetic
source                     1..876
                           mol_type = protein
                           organism = synthetic construct
SEQUENCE: 49
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDPEA AISRLITYLR ILEELEAQGV HRTASEQLGE   480
LAQVTAFQVD EDLSYFGSYG TDGVGYTVPV LKRELRHILG LNRKWGLCIV GMGRLGSALA   540
DWPGFGESFE LRGFFDVDPG MVGRPVRGGV IEHVDLLPQR VPGRIEIALL TVPREAAQKA   600
ADLLVAAGIK GILNFAPVVL EVPKEVAVEN VDFLAGLTRL SFAILNPKWR EEVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876

SEQ ID NO: 50              moltype = AA  length = 879
FEATURE                    Location/Qualifiers
REGION                     1..879
                           note = Synthetic
source                     1..879
                           mol_type = protein
                           organism = synthetic construct
SEQUENCE: 50
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDELY VPEAAISRLI TYLRILEELE AQGVHRTASE   480
QLGELAQVTA FQVDEDLSYF GSYGTDGVGY TVPVLKRELR HILGLNRKWG LCIVGMGRLG   540
SALADWPGFG ESFELRGFFD VDPGMVGRPV RGGVIEHVDL LPQRVPGRIE IALLTVPREA   600
AQKAADLLVA AGIKGILNFA PVVLEVPKEV AVENVDFLAG LTRLSFAILN PKWREVIKPE   660
MKMRYYMDGS VNGHEFTIEG EGTGRPYEGH QEMTLRVTMA EGGPMPFAFD LVSHVFCYGH   720
RVFTKYPEEI PDYFKQAFPE GLSWERSLEF EDGGSASVSA HISLRGNTFY HKSKFTGVNF   780
PADGPIMQNQ SVDWEPSTEK ITASDGVLKG DVTMYLKLEG GGNHKCQFKT TYKAAKEILE   840
MPGDHYIGHR LVRKTEGNIT EQVEDAVAHS EASMDELYK                          879

SEQ ID NO: 51              moltype = AA  length = 879
FEATURE                    Location/Qualifiers
REGION                     1..879
                           note = Synthetic
source                     1..879
                           mol_type = protein
                           organism = synthetic construct
SEQUENCE: 51
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
```

```
PVRGGVIEHV DLLPQRVPGR IEIALLTVPR EAAQKAADLL VAAGIKGILN FAPVVLEVPK      180
EVAVENVDIL AGLTRLSFAI LNPTSKGEEL FTGVVPILVE LDGDVNGHKF SVSGEGEGDA      240
TYGKLTLKFI CTTGKLPVPW PTLVTTLTYG VQCFSRYPDH MKQHDFFKSA MPEGYVQERT      300
IFFKDDGNYK TRAEVKFEGD TLVNRIELKG IDFKEDGNIL GHKLEYNYNS HNVYIMADKQ      360
KNGIKVNFKI RHNIEDGSVQ LADHYQQNTP IGDGPVLLPD NHYLSTQSKL SKDPNEKRDH      420
MVLLEFVTAA GITLGMDELY KVPEAAISRL ITYLRILEEL EAQGVHRTAS EQLGELAQVT      480
AFQVDEDLSY FGSYGTDGVG YTVPVLKREL RHILGLNRKW GLCIVGMGRL GSALADWPGF      540
GESFELRGFF DVDPGMVGRP VRGGVIEHVD LLPQRVPGRI EIALLTVPRE AAQKAADLLV      600
AAGIKGILNF APVVLEVPKE VAVENVDFLA GLTRLSFAIL NPKWREEMMG GSMVSVIKPE      660
MKMRYYMDGS VNGHEFTIEG EGTGRPYEGH QEMTLRVTMA EGGPMPFAFD LVSHVFCYGH      720
RVFTKYPEEI PDYFKQAFPE GLSWERSLEF EDGGSASVSA HISLRGNTFY HKSKFTGVNF      780
PADGPIMQNQ SVDWEPSTEK ITASDGVLKG DVTMYLKLEG GGNHKCQFKT TYKAAKEILE      840
MPGDHYIGHR LVRKTEGNIT EQVEDAVAHS EASMDELYK                             879

SEQ ID NO: 52          moltype = AA  length = 870
FEATURE                Location/Qualifiers
REGION                 1..870
                       note = Synthetic
source                 1..870
                       mol_type = protein
                       organism = synthetic construct
SEQUENCE: 52
MKVPEAAISR LITYLRILEE LEAQGVHRTA SEQLGELAQV TAFQVDKDLS YFGSYGTDGV       60
GYTVPVLKRE LRHILGLNRK WGLCIVGMGR LGSALADWPG FGESFELRGF FDVDPGMVGR      120
PVRGGVIEHV DLLPQRVPGR IEIALLTVPR EAAQKAADLL VAAGIKGILN FAPVVLEVPK      180
EVAVENVDIL AGLTRLSFAI LNPTSKGEEL FTGVVPILVE LDGDVNGHKF SVSGEGEGDA      240
TYGKLTLKFI CTTGKLPVPW PTLVTTLTYG VQCFSRYPDH MKQHDFFKSA MPEGYVQERT      300
IFFKDDGNYK TRAEVKFEGD TLVNRIELKG IDFKEDGNIL GHKLEYNYNS HNVYIMADKQ      360
KNGIKVNFKI RHNIEDGSVQ LADHYQQNTP IGDGPVLLPD NHYLSTQSKL SKDPNEKRDH      420
MVLLEFVTAA GITLGMDELY KVPEAAISRL ITYLRILEEL EAQGVHRTAS EQLGELAQVT      480
AFQVDEDLSY FGSYGTDGVG YTVPVLKREL RHILGLNRKW GLCIVGMGRL GSALADWPGF      540
GESFELRGFF DVDPGMVGRP VRGGVIEHVD LLPQRVPGRI EIALLTVPRE AAQKAADLLV      600
AAGIKGILNF APVVLEVPKE VAVENVDFLA GLTRLSFAIL NPKWREVIKP EMKMRYYMDG      660
SVNGHEFTIE GEGTGRPYEG HQEMTLRVTM AEGGPMPFAF DLVSHVFCYG HRVFTKYPEE      720
IPDYFKQAFP EGLSWERSLE FEDGGSASVS AHISLRGNTF YHKSKFTGVN FPADGPIMQN      780
QSVDWEPSTE KITASDGVLK GDVTMYLKLE GGGNHKCQFK TTYKAAKEIL EMPGDHYIGH      840
RLVRKTEGNI TEQVEDAVAH SEASMDELYK                                       870

SEQ ID NO: 53          moltype = AA  length = 876
FEATURE                Location/Qualifiers
REGION                 1..876
                       note = Synthetic
source                 1..876
                       mol_type = protein
                       organism = synthetic construct
SEQUENCE: 53
MKVPEAAISR LITYLRILEE LEAQGVHRTA SEQLGELAQV TAFQVDKDLS YFGSYGTDGV       60
GYTVPVLKRE LRHILGLNRK WGLCIVGMGR LGSALADWPG FGESFELRGF FDVDPGMVGR      120
PVRGGVIEHV DLLPQRVPGR IEIALLTVPR EAAQKAADLL VAAGIKGILN FAPVVLEVPK      180
EVAVENVDIL AGLTRLSFAI LNPTWSAAGH GMVSKGEELF TGVVPILVEL DGDVNGHKFS      240
VSGEGEGDAT YGKLTLKFIC TTGKLPVPWP TLVTTLTYGV QCFSRYPDHM KQHDFFKSAM      300
PEGYVQERTI FFKDDGNYKT RAEVKFEGDT LVNRIELKGI DFKEDGNILG HKLEYNYNSH      360
NVYIMADKQK NGIKVNFKIR HNIEDGSVQL ADHYQQNTPI GDGPVLLPDN HYLSTQSKLS      420
KDPNEKRDHM VLLEFVTAAG ITLGMDPEAA ISRLITYLRI LEELEAQGVH RTASEQLGEL      480
AQVTAFQVDE DLSYFGSYGT DGVGYTVPVL KRELRHILGL NRKWGLCIVG MGRLGSALAD      540
WPGFGESFEL RGFFDVDPGM VGRPVRGGVI EHVDLLPQRV PGRIEIALLT VPREAAQKAA      600
DLLVAAGIKG ILNFAPVVLE VPKEVAVENV DFLAGLTRLS FAILNPKWRE ESVIKPEMKM      660
RYYMDGSVNG HEFTIEGEGT GRPYEGHQEM TLRVTMAEGG PMPFAFDLVS HVFCYGHRVF      720
TKYPEEIPDY FKQAFPEGLS WERSLEFEDG GSASVSAHIS LRGNTFYHKS KFTGVNFPAD      780
GPIMQNQSVD WEPSTEKITA SDGVLKGDVT MYLKLEGGGN HKCQFKTTYK AAKEILEMPG      840
DHYIGHRLVR KTEGNITEQV EDAVAHSEAS MDELYK                                876

SEQ ID NO: 54          moltype = AA  length = 874
FEATURE                Location/Qualifiers
REGION                 1..874
                       note = Synthetic
source                 1..874
                       mol_type = protein
                       organism = synthetic construct
SEQUENCE: 54
MKVPEAAISR LITYLRILEE LEAQGVHRTA SEQLGELAQV TAFQVDKDLS YFGSYGTDGV       60
GYTVPVLKRE LRHILGLNRK WGLCIVGMGR LGSALADWPG FGESFELRGF FDVDPGMVGR      120
PVRGGVIEHV DLLPQRVPGR IEIALLTVPR EAAQKAADLL VAAGIKGILN FAPVVLEVPK      180
EVAVENVDIL AGLTRLSFAI LNPTWMVSKG EELFTGVVPI LVELDGDVNG HKFSVSGEGE      240
GDATYGKLTL KFICTTGKLP VPWPTLVTTL TYGVQCFSRY PDHMKQHDFF KSAMPEGYVQ      300
ERTIFFKDDG NYKTRAEVKF EGDTLVNRIE LKGIDFKEDG NILGHKLEYN YNSHNVYIMA      360
DKQKNGIKVN FKIRHNIEDG SVQLADHYQQ NTPIGDPVL LPDNHYLSTQ SKLSKDPNEK       420
RDHMVLLEFV TAAGITLGMD ELYKVPEAAI SRLITYLRIL EELEAQGVHR TASEQLGELA      480
QVTAFQVDED LSYFGSYGTD GVGYTVPVLK RELRHILGLN RKWGLCIVGM GRLGSALADW      540
```

```
PGFGESFELR GFFDVDPGMV GRPVRGGVIE HVDLLPQRVP GRIEIALLTV PREAAQKAAD    600
LLVAAGIKGI LNFAPVVLEV PKEVAVENVD FLAGLTRLSF AILNPKWREE VIKPEMKMRY    660
YMDGSVNGHE FTIEGEGTGR PYEGHQEMTL RVTMAEGGPM PFAFDLVSHV FCYGHRVFTK    720
YPEEIPDYFK QAFPEGLSWE RSLEFEDGGS ASVSAHISLR GNTFYHKSKF TGVNFPADGP    780
IMQNQSVDWE PSTEKITASD GVLKGDVTMY LKLEGGGNHK CQFKTTYKAA KEILEMPGDH    840
YIGHRLVRKT EGNITEQVED AVAHSEASMD ELYK                                874

SEQ ID NO: 55           moltype = AA  length = 874
FEATURE                 Location/Qualifiers
REGION                  1..874
                        note = Synthetic
source                  1..874
                        mol_type = protein
                        organism = synthetic construct
SEQUENCE: 55
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGMDELY KVPEAAISRL ITYLRILEEL EAQGVHRTAS EQLGELAQVT    480
AFQVDEDLSY FGSYGTDGVG YTVPVLKREL RHILGLNRKW GLCIVGMGRL GSALADWPGF    540
GESFELRGFF DVDPGMVGRP VRGGVIEHVD LLPQRVPGRI EIALLTVPRE AAQKAADLLV    600
AAGIKGILNF APVVLEVPKE VAVENVDFLA GLTRLSFAIL NPKWREEMMS VIKPEMKMRY    660
YMDGSVNGHE FTIEGEGTGR PYEGHQEMTL RVTMAEGGPM PFAFDLVSHV FCYGHRVFTK    720
YPEEIPDYFK QAFPEGLSWE RSLEFEDGGS ASVSAHISLR GNTFYHKSKF TGVNFPADGP    780
IMQNQSVDWE PSTEKITASD GVLKGDVTMY LKLEGGGNHK CQFKTTYKAA KEILEMPGDH    840
YIGHRLVRKT EGNITEQVED AVAHSEASMD ELYK                                874

SEQ ID NO: 56           moltype = AA  length = 872
FEATURE                 Location/Qualifiers
REGION                  1..872
                        note = Synthetic
source                  1..872
                        mol_type = protein
                        organism = synthetic construct
SEQUENCE: 56
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWVSKGE ELFTGVVPIL VELDGVNGHK FSVSGEGEG     240
DATYGKLTLK FICTTGKLPV PWPTLVTTLT YGVQCFSRYP DHMKQHDFFK SAMPEGYVQE    300
RTIFFKDDGN YKTRAEVKFE GDTLVNRIEL KGIDFKEDGN ILGHKLEYNY NSHNVYIMAD    360
KQKNGIKVNF KIRHNIEDGS VQLADHYQQN TPIGDGPVLL PDNHYLSTQS KLSKDPNEKR    420
DHMVLLEFVT AAGITLGMDE LVPEAAISRL ITYLRILEEL EAQGVHRTAS EQLGELAQVT    480
AFQVDEDLSY FGSYGTDGVG YTVPVLKREL RHILGLNRKW GLCIVGMGRL GSALADWPGF    540
GESFELRGFF DVDPGMVGRP VRGGVIEHVD LLPQRVPGRI EIALLTVPRE AAQKAADLLV    600
AAGIKGILNF APVVLEVPKE VAVENVDFLA GLTRLSFAIL NPKWREESVI KPEMKMRYYM    660
DGSVNGHEFT IEGEGTGRPY EGHQEMTLRV TMAEGGPMPF AFDLVSHVFC YGHRVFTKYP    720
EEIPDYFKQA FPEGLSWERS LEFEDGGSAS VSAHISLRGN TFYHKSKFTG VNFPADGPIM    780
QNQSVDWEPS TEKITASDGV LKGDVTMYLK LEGGGNHKCQ FKTTYKAAKE ILEMPGDHYI    840
GHRLVRKTEG NITEQVEDAV AHSEASMDEL YK                                  872

SEQ ID NO: 57           moltype = AA  length = 871
FEATURE                 Location/Qualifiers
REGION                  1..871
                        note = Synthetic
source                  1..871
                        mol_type = protein
                        organism = synthetic construct
SEQUENCE: 57
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGMEAAI SRLITYLRIL EELEAQGVHR TASEQLGELA QVTAFQVDED    480
LSYFGSYGTD GVGYTVPVLK RELRHILGLN RKWGLCIVGM GRLGSALADW PGFGESFELR    540
GFFDVDPGMV GRPVRGGVIE HVDLLPQRVP GRIEIALLTV PREAAQKAAD LLVAAGIKGI    600
LNFAPVVLEV PKEVAVENVD FLAGLTRLSF AILNPKWREE MMGSMSVIK PEMKMRYYMD     660
GSVNGHEFTI EGEGTGRPYE GHQEMTLRVT MAEGGPMPFA FDLVSHVFCY GHRVFTKYPE    720
EIPDYFKQAF PEGLSWERSL EFEDGGSASV SAHISLRGNT FYHKSKFTGV NFPADGPIMQ    780
NQSVDWEPST EKITASDGVL KGDVTMYLKL EGGGNHKCQF KTTYKAAKEI LEMPGDHYIG    840
HRLVRKTEGN ITEQVEDAVA HSEASMDELY K                                   871
```

```
SEQ ID NO: 58              moltype = AA  length = 882
FEATURE                    Location/Qualifiers
REGION                     1..882
                           note = Synthetic
source                     1..882
                           mol_type = protein
                           organism = synthetic construct
SEQUENCE: 58
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGH GMVSKGEELF TGVVPILVEL DGDVNGHKFS   240
VSGEGEGDAT YGKLTLKFIC TTGKLPVPWP TLVTTLTYGV QCFSRYPDHM KQHDFFKSAM   300
PEGYVQERTI FFKDDGNYKT RAEVKFEGDT LVNRIELKGI DFKEDGNILG HKLEYNYNSH   360
NVYIMADKQK NGIKVNFKIR HNIEDGSVQL ADHYQQNTPI GDGPVLLPDN HYLSTQSKLS   420
KDPNEKRDHM VLLEFVTAAG ITLGMDELYK KVPEAAISRL ITYLRILEEL EAQGVHRTAS   480
EQLGELAQVT AFQVDEDLSY FGSYGTDGVG YTVPVLKREL RHILGLNRKW GLCIVGMGRL   540
GSALADWPGF GESFELRGFF DVDPGMVGRP VRGGVIEHVD LLPQRVPGRI EIALLTVPRE   600
AAQKAADLLV AAGIKGILNF APVVLEVPKE VAVENVDFLA GLTRLSFAIL NPKWREESVI   660
KPEMKMRYYM DGSVNGHEFT IEGEGTGRPY EGHQEMTLRV TMAEGGPMPF AFDLVSHVFC   720
YGHRVFTKYP EEIPDYFKQA FPEGLSWERS LEFEDGGSAS VSAHISLRGN TFYHKSKFTG   780
VNFPADGPIM QNQSVDWEPS TEKITASDGV LKGDVTMYLK LEGGGNHKCQ FKTTYKAAKE   840
ILEMPGDHYI GHRLVRKTEG NITEQVEDAV AHSEASMDEL YK                     882

SEQ ID NO: 59              moltype = AA  length = 879
FEATURE                    Location/Qualifiers
REGION                     1..879
                           note = Synthetic
source                     1..879
                           mol_type = protein
                           organism = synthetic construct
SEQUENCE: 59
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDELY KKVPEAAISRL ITYLRILEEL EAQGVHRTAS   480
EQLGELAQVT AFQVDEDLSY FGSYGTDGVG YTVPVLKREL RHILGLNRKW GLCIVGMGRL   540
GSALADWPGF GESFELRGFF DVDPGMVGRP VRGGVIEHVD LLPQRVPGRI EIALLTVPRE   600
AAQKAADLLV AAGIKGILNF APVVLEVPKE VAVENVDFLA GLTRLSFAIL NPKWREIKPE   660
MKMRYYMDGS VNGHEFTIEG EGTGRPYEGH QEMTLRVTMA EGGPMPFAFD LVSHVFCYGH   720
RVFTKYPEEI PDYFKQAFPE GLSWERSLEF EDGGSASVSA HISLRGNTFY HKSKFTGVNF   780
PADGPIMQNQ SVDWEPSTEK ITASDGVLKG DVTMYLKLEG GGNHKCQFKT TYKAAKEILE   840
MPGDHYIGHR LVRKTEGNIT EQVEDAVAHS EASMDELYK                         879

SEQ ID NO: 60              moltype = AA  length = 872
FEATURE                    Location/Qualifiers
REGION                     1..872
                           note = Synthetic
source                     1..872
                           mol_type = protein
                           organism = synthetic construct
SEQUENCE: 60
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTGEELFT GVVPILVELD GDVNGHKFSV SGEGEGDATY   240
GKLTLKFICT TGKLPVPWPT LVTTLTYGVQ CFSRYPDHMK QHDFFKSAMP EGYVQERTIF   300
FKDDGNYKTR AEVKFEGDTL VNRIELKGID FKEDGNILGH KLEYNYNSHN VYIMADKQKN   360
GIKVNFKIRH NIEDGSVQLA DHYQQNTPIG DGPVLLPDNH YLSTQSKLSK DPNEKRDHMV   420
LLEFVTAAGI TLGMDEPAA ISRLITYLRI LEELEAQGVH RTASEQLGEL AQVTAFQVDE    480
DLSYFGSYGT DGVGYTVPVL KRELRHILGL NRKWGLCIVG MGRLGSALAD WPGFGESFEL   540
RGFFDVDPGM VGRPVRGGVI EHVDLLPQRV PGRIEIALLT VPREAAQKAA DLLVAAGIKG   600
ILNFAPVVLE VPKEVAVENV DFLAGLTRLS FAILNPKWRE EMMGSMVSVI KPEMKMRYYM   660
DGSVNGHEFT IEGEGTGRPY EGHQEMTLRV TMAEGGPMPF AFDLVSHVFC YGHRVFTKYP   720
EEIPDYFKQA FPEGLSWERS LEFEDGGSAS VSAHISLRGN TFYHKSKFTG VNFPADGPIM   780
QNQSVDWEPS TEKITASDGV LKGDVTMYLK LEGGGNHKCQ FKTTYKAAKE ILEMPGDHYI   840
GHRLVRKTEG NITEQVEDAV AHSEASMDEL YK                                872

SEQ ID NO: 61              moltype = AA  length = 875
FEATURE                    Location/Qualifiers
REGION                     1..875
                           note = Synthetic
source                     1..875
                           mol_type = protein
                           organism = synthetic construct
```

```
SEQUENCE: 61
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWVSKGE ELFTGVVPIL VELDGDVNGH KFSVSGEGEG  240
DATYGKLTLK FICTTGKLPV PWPTLVTTLT YGVQCFSRYP DHMKQHDFFK SAMPEGYVQE  300
RTIFFKDDGN YKTRAEVKFE GDTLVNRIEL KGIDFKEDGN ILGHKLEYNY NSHNVYIMAD  360
KQKNGIKVNF KIRHNIEDGS VQLADHYQQN TPIGDGPVLL PDNHYLSTQS KLSKDPNEKR  420
DHMVLLEFVT AAGITLGMDE LYKVPEAAIS RLITYLRILE ELEAQGVHRT ASEQLGELAQ  480
VTAFQVDEDL SYFGSYGTDG VGYTVPVLKR ELRHILGLNR KWGLCIVGMG RLGSALADWP  540
GFGESFELRG FFDVDPGMVG RPVRGGVIEH VDLLPQRVPG RIEIALLTVP REAAQKAADL  600
LVAAGIKGIL NFAPVVLEVP KEVAVENVDF LAGLTRLSFA ILNPKWREEM SVIKPEMKMR  660
YYMDGSVNGH EFTIEGEGTG RPYEGHQEMT LRVTMAEGGP MPFAFDLVSH VFCYGHRVFT  720
KYPEEIPDYF KQAFPEGLSW ERSLEFEDGG SASVSAHISL RGNTFYHKSK FTGVNFPADG  780
PIMQNQSVDW EPSTEKITAS DGVLKGDVTM YLKEGGGNH KCQFKTTYKA AKEILEMPGD  840
HYIGHRLVRK TEGNITEQVE DAVAHSEASM DELYK                           875

SEQ ID NO: 62           moltype = AA  length = 882
FEATURE                 Location/Qualifiers
REGION                  1..882
                        note = Synthetic
source                  1..882
                        mol_type = protein
                        organism = synthetic construct
SEQUENCE: 62
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAHGM VSKGEELFTG VVPILVELDG DVNGHKFSVS  240
GEGEGDATYG KLTLKFICTT GKLPVPWPTL VTTLTYGVQ FSRYPDHMKQ HDFFKSAMPE  300
GYVQERTIFF KDDGNYKTRA EVKFEGDTLV NRIELKGIDF KEDGNILGHK LEYNYNSHNV  360
YIMADKQKNG IKVNFKIRHN IEDGSVQLAD HYQQNTPIGD GPVLLPDNHY LSTQSKLSKD  420
PNEKRDHMVL LEFVTAAGIT LGMDELVPEA AISRLITYLR ILEELEAQGV HRTASEQLGE  480
LAQVTAFQVD EDLSYFGSYG TDGVGYTVPV LKRELRHILG LNRKWGLCIV GMGRLGSALA  540
DWPGFGESFE LRGFFDVDPG MVGRPVRGGV IEHVDLLPQR VPGRIEIALL TVPREAAQKA  600
ADLLVAAGIK GILNFAPVVL EVPKEVAVEN VDFLAGLTRL SFAILNPKWR EEMMGMVSVI  660
KPEMKMRYYM DGSVNGHEFT IEGEGTGRPY EGHQEMTLRV TMAEGGPMPF AFDLVSHVFC  720
YGHRVFTKYP EEIPDYFKQA FPEGLSWERS LEFEDGGSAS VSAHISLRGN TFYHKSKFTG  780
VNFPADGPIM QNQSVDWEPS TEKITASDGV LKGDVTMYLK EGGGNHKCQ FKTTYKAAKE  840
ILEMPGDHYI GHRLVRKTEG NITEQVEDAV AHSEASMDEL YK                   882

SEQ ID NO: 63           moltype = AA  length = 875
FEATURE                 Location/Qualifiers
REGION                  1..875
                        note = Synthetic
source                  1..875
                        mol_type = protein
                        organism = synthetic construct
SEQUENCE: 63
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLGMEAAI SRLITYLRIL EELEAQGVHR TASEQLGELA  480
QVTAFQVDED LSYFGSYGTD GVGYTVPVLK RELRHILGLN RKWGLCIVGM GRLGSALADW  540
PGFGESFELR GFFDVDPGMV GRPVRGGVIE HVDLLPQRVP GRIEIALLTV PREAAQKAAD  600
LLVAAGIKGI LNFAPVVLEV PKEVAVENVD FLAGLTRLSF AILNPKWREE SVIKPEMKMR  660
YYMDGSVNGH EFTIEGEGTG RPYEGHQEMT LRVTMAEGGP MPFAFDLVSH VFCYGHRVFT  720
KYPEEIPDYF KQAFPEGLSW ERSLEFEDGG SASVSAHISL RGNTFYHKSK FTGVNFPADG  780
PIMQNQSVDW EPSTEKITAS DGVLKGDVTM YLKEGGGNH KCQFKTTYKA AKEILEMPGD  840
HYIGHRLVRK TEGNITEQVE DAVAHSEASM DELYK                           875

SEQ ID NO: 64           moltype = AA  length = 871
FEATURE                 Location/Qualifiers
REGION                  1..871
                        note = Synthetic
source                  1..871
                        mol_type = protein
                        organism = synthetic construct
SEQUENCE: 64
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAHGM VSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
```

```
VYIMADKQKN GIKVNFKIRH NIEDGSVQLA DHYQQNTPIG DGPVLLPDNH YLSTQSKLSK    420
DPNEKRDHMV LLEFVTAAGI TLGEAAISRL ITYLRILEEL EAQGVHRTAS EQLGELAQVT    480
APFQVDEDLSY FGSYGTDGVG YTVPVLKREL RHILGLNRKW GLCIVGMGRL GSALADWPGF   540
GESFELRGFF DVDPGMVGRP VRGGVIEHVD LLPQRVPGRI EIALLTVPRE AAQKAADLLV    600
AAGIKGILNF APVVLEVPKE VAVENVDFLA GLTRLSFAIL NPKWREEVIK PEMKMRYYMD    660
GSVNGHEFTI EGEGTGRPYE GHQEMTLRVT MAEGGPMPFA FDLVSHVFCY GHRVFTKYPE    720
EIPDYFKQAF PEGLSWERSL EFEDGGSASV SAHISLRGNT FYHKSKFTGV NFPADGPIMQ    780
NQSVDWEPST EKITASDGVL KGDVTMYLKL EGGGNHKCQF KTTYKAAKEI LEMPGDHYIG    840
HRLVRKTEGN ITEQVEDAVA HSEASMDELY K                                   871

SEQ ID NO: 65           moltype = AA  length = 879
FEATURE                 Location/Qualifiers
REGION                  1..879
                        note = Synthetic
source                  1..879
                        mol_type = protein
                        organism = synthetic construct
SEQUENCE: 65
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAGHG MVSKGEELFT GVVPILVELDG DVNGHKFSVS    240
GEGEGDATYG KLTLKFICTT GKLPVPWPTL VTTLTYGVQC FSRYPDHMKQ HDFFKSAMPE    300
GYVQERTIFF KDDGNYKTRA EVKFEGDTLV NRIELKGIDF KEDGNILGHK LEYNYNSHNV    360
YIMADKQKNG IKVNFKIRHN IEDGSVQLAD HYQQNTPIGD GPVLLPDNHY LSTQSKLSKD    420
PNEKRDHMVL LEFVTAAGIT LGMDEVPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD    540
WPGFGESFEL RGFFDVDPGM VGRPVRGGVI EHVDLLPQRV PGRIEIALLT VPREAAQKAA    600
DLLVAAGIKG ILNFAPVVLE VPKEVAVENV DFLAGLTRLS FAILNPKWRE EMMVSVIKPE    660
MKMRYYMDGS VNGHEFTIEG EGTGRPYEGH QEMTLRVTMA EGGPMPFAFD LVSHVFCYGH    720
RVFTKYPEEI PDYFKQAFPE GLSWERSLEF EDGGSASVSA HISLRGNTFY HKSKFTGVNF    780
PADGPIMQNQ SVDWEPSTEK ITASDGVLKG DVTMYLKLEG GGNHKCQFKT TYKAAKEILE    840
MPGDHYIGHR LVRKTEGNIT EQVEDAVAHS EASMDELYK                           879

SEQ ID NO: 66           moltype = AA  length = 872
FEATURE                 Location/Qualifiers
REGION                  1..872
                        note = Synthetic
source                  1..872
                        mol_type = protein
                        organism = synthetic construct
SEQUENCE: 66
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAGHG MVSKGEELFT GVVPILVELD GDVNGHKFSV    240
SGEGEGDATY GKLTLKFICT TGKLPVPWPT LVTTLTYGVQ CFSRYPDHMK QHDFFKSAMP    300
EGYVQERTIF FKDDGNYKTR AEVKFEGDTL VNRIELKGID FKEDGNILGH KLEYNYNSHN    360
VYIMADKQKN GIKVNFKIRH NIEDGSVQLA DHYQQNTPIG DGPVLLPDNH YLSTQSKLSK    420
DPNEKRDHMV LLEFVTAAGI TLGEAAISRL ITYLRILEEL EAQGVHRTAS EQLGELAQVT    480
APFQVDEDLSY FGSYGTDGVG YTVPVLKREL RHILGLNRKW GLCIVGMGRL GSALADWPGF   540
GESFELRGFF DVDPGMVGRP VRGGVIEHVD LLPQRVPGRI EIALLTVPRE AAQKAADLLV    600
AAGIKGILNF APVVLEVPKE VAVNVDFLA GLTRLSFAIL NPKWREESVI KPEMKMRYYM     660
DGSVNGHEFT IEGEGTGRPY EGHQEMTLRV TMAEGGPMPF AFDLVSHVFC YGHRVFTKYP    720
EEIPDYFKQA FPEGLSWERS LEFEDGGSAS VSAHISLRGN TFYHKSKFTG VNFPADGPIM    780
QNQSVDWEPS TEKITASDGV LKGDVTMYLK LEGGGNHKCQ FKTTYKAAKE ILEMPGDHYI    840
GHRLVRKTEG NITEQVEDAV AHSEASMDEL YK                                  872

SEQ ID NO: 67           moltype = AA  length = 883
FEATURE                 Location/Qualifiers
REGION                  1..883
                        note = Synthetic
source                  1..883
                        mol_type = protein
                        organism = synthetic construct
SEQUENCE: 67
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSHGMV SKGEELFTGV VPILVELGD VNGHKFSVSG     240
EGEGDATYGK LTLKFICTTG KLPVPWPTLV TTLTYGVQCF SRYPDHMKQH DFFKSAMPEG    300
YVQERTIFFF DDGNYKTRAE VKFEGDTLVN RIELKGIDFK EDGNILGHKL EYNYNSHNVY    360
IMADKQKNGI KVNFKIRHNI EDGSVQLADH YQQNTPIGDP VLLPDNHYL STQSKLSKDP     420
NEKRDHMVLL EFVTAAGITL GMDEVPEA AISRLITYLR ILEELEAQGV HRTASEQLGE      480
LAQVTAFQVD EDLSYFGSYG TDGVGYTVPV LKRELRHILG LNRKWGLCIV GMGRLGSALA    540
DWPGFGESFE LRGFFDVDPG MVGRPVRGGV IEHVDLLPQR VPGRIEIALL TVPREAAQKA    600
ADLLVAAGIK GILNFAPVVL EVPKEVAVEN VDFLAGLTRL SFAILNPKWR EEMMGSMVSV    660
IKPEMKMRYY MDGSVNGHEF TIEGEGTGRP YEGHQEMTLR VTMAEGGPMP FAFDLVSHVF    720
CYGHRVFTKY PEEIPDYFKQ AFPEGLSWER SLEFEDGGSA SVSAHISLRG NTFYHKSKFT    780
```

```
GVNFPADGPI MQNQSVDWEP STEKITASDG VLKGDVTMYL KLEGGGNHKC QFKTTYKAAK    840
EILEMPGDHY IGHRLVRKTE GNITEQVEDA VAHSEASMDE LYK                     883

SEQ ID NO: 68           moltype = AA  length = 876
FEATURE                 Location/Qualifiers
REGION                  1..876
                        note = Synthetic
source                  1..876
                        mol_type = protein
                        organism = synthetic construct
SEQUENCE: 68
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAGHG MVSKGEELFT GVVPILVELD GDVNGHKFSV   240
SGEGEGDATY GKLTLKFICT TGKLPVPWPT LVTTLTYGVQ CFSRYPDHMK QHDFFKSAMP   300
EGYVQERTIF FKDDGNYKTR AEVKFEGDTL VNRIELKGID FKEDGNILGH KLEYNYNSHN   360
VYIMADKQKN GIKVNFKIRH NIEDGSVQLA DHYQQNTPIG DGPVLLPDNH YLSTQSKLSK   420
DPNEKRDHMV LLEFVTAAGI TLGMDPEAAI SRLITYLRIL EELEAQGVHR TASEQLGELA   480
QVTAFQVDED LSYFGSYGTD GVGYTVPVLK RELRHILGLN RKWGLCIVGM GRLGSALADW   540
PGFGESFELR GFFDVDPGMV GRPVRGGVIE HVDLLPQRVP GRIEIALLTV PREAAQKAAD   600
LLVAAGIKGI LNFAPVVLEV PKEVAVENVD FLAGLTRLSF AILNPKWREE MSVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876

SEQ ID NO: 69           moltype = AA  length = 876
FEATURE                 Location/Qualifiers
REGION                  1..876
                        note = Synthetic
source                  1..876
                        mol_type = protein
                        organism = synthetic construct
SEQUENCE: 69
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAGHG MVSKGEELFT GVVPILVELD GDVNGHKFSV   240
SGEGEGDATY GKLTLKFICT TGKLPVPWPT LVTTLTYGVQ CFSRYPDHMK QHDFFKSAMP   300
EGYVQERTIF FKDDGNYKTR AEVKFEGDTL VNRIELKGID FKEDGNILGH KLEYNYNSHN   360
VYIMADKQKN GIKVNFKIRH NIEDGSVQLA DHYQQNTPIG DGPVLLPDNH YLSTQSKLSK   420
DPNEKRDHMV LLEFVTAAGI TLGMDEPEAA ISRLITYLRI LEELEAQGVH RTASEQLGEL   480
AQVTAFQVDE DLSYFGSYGT DGVGYTVPVL KRELRHILGL NRKWGLCIVG MGRLGSALAD   540
WPGFGESFEL RGFFDVDPGM VGRPVRGGVI EHVDLLPQRV PGRIEIALLT VPREAAQKAA   600
DLLVAAGIKG ILNFAPVVLE VPKEVAVENV DFLAGLTRLS FAILNPKWRE ESVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876

SEQ ID NO: 70           moltype = AA  length = 882
FEATURE                 Location/Qualifiers
REGION                  1..882
                        note = Synthetic
source                  1..882
                        mol_type = protein
                        organism = synthetic construct
SEQUENCE: 70
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSHGMV SKGEELFTGV VPILVELDGD VNGHKFSVSG   240
EGEGDATYGK LTLKFICTTG KLPVPWPTLV TTLTYGVQCF SRYPDHMKQH DFFKSAMPEG   300
YVQERTIFFK DDGNYKTRAE VKFEGDTLVN RIELKGIDFK EDGNILGHKL EYNYNSHNVY   360
IMADKQKNGI KVNFKIRHNI EDGSVQLADH YQQNTPIGDG PVLLPDNHYL STQSKLSKDP   420
NEKRDHMVLL EFVTAAGITL GMDELYVPEA ISRLITYLR ILEELEAQGV HRTASEQLGE   480
LAQVTAFQVD EDLSYFGSYG TDGVGYTVPV LKRELRHILG LNRKWGLCIV GMGRLGSALA   540
DWPGFGESFE LRGFFDVDPG MVGRPVRGGV IEHVDLLPQR VPGRIEIALL TVPREAAQKA   600
ADLLVAAGIK GILNFAPVVL EVPKEVAVEN VDFLAGLTRL SFAILNPKWR EEMMGMVSVI   660
KPEMKMRYYM DGSVNGHEFT IEGEGTGRPY EGHQEMTLRV TMAEGGPMPF AFDLVSHVFC   720
YGHRVFTKYP EEIPDYFKQA FPEGLSWERS LEFEDGGSAS VSAHISLRGN TFYHKSKFTG   780
VNFPADGPIM QNQSVDWEPS TEKITASDGV LKGDVTMYLK LEGGGNHKCQ FKTTYKAAKE   840
ILEMPGDHYI GHRLVRKTEG NITEQVEDAV AHSEASMDEL YK                      882

SEQ ID NO: 71           moltype = AA  length = 876
FEATURE                 Location/Qualifiers
REGION                  1..876
                        note = Synthetic
```

-continued

```
source                  1..876
                        mol_type = protein
                        organism = synthetic construct
SEQUENCE: 71
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWVSKGE ELFTGVVPIL VELDGDVNGH KFSVSGEGEG   240
DATYGKLTLK FICTTGKLPV PWPTLVTTLT YGVQCFSRYP DHMKQHDFFK SAMPEGYVQE   300
RTIFFKDDGN YKTRAEVKFE GDTLVNRIEL KGIDFKEDGN ILGHKLEYNY NSHNVYIMAD   360
KQKNGIKVNF KIRHNIEDGS VQLADHYQQN TPIGDGPVLL PDNHYLSTQS KLSKDPNEKR   420
DHMVLLEFVT AAGITLGMDE LYVPEAAISR LITYLRILEE LEAQGVHRTA SEQLGELAQV   480
TAFQVDEDLS YFGSYGTDGV GYTVPVLKRE LRHILGLNRK WGLCIVGMGR LGSALADWPG   540
FGESFELRGF FDVDPGMVGR PVRGGVIEHV DLLPQRVPGR IEIALLTVPR EAAQKAADLL   600
VAAGIKGILN FAPVVLEVPK EVAVENVDFL AGLTRLSFAI LNPKWREEMM VSVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                            876

SEQ ID NO: 72           moltype = AA  length = 882
FEATURE                 Location/Qualifiers
REGION                  1..882
                        note = Synthetic
source                  1..882
                        mol_type = protein
                        organism = synthetic construct
SEQUENCE: 72
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSGMVS KGEELFTGVV PILVELDGDV NGHKFSVSGE   240
GEGDATYGKL TLKFICTTGK LPVPWPTLVT TLTYGVQCFS RYPDHMKQHD FFKSAMPEGY   300
VQERTIFFKD DGNYKTRAEV KFEGDTLVNR IELKGIDFKE DGNILGHKLE YNYNSHNVYI   360
MADKQKNGIK VNFKIRHNIE DGSVQLADHY QQNTPIGDGP VLLPDNHYLS TQSKLSKDPN   420
EKRDHMVLLE FVTAAGITLG MDELYVPEAA ISRLITYLRI LEELEAQGVH RTASEQLGEL   480
AQVTAFQVDE DLSYFGSYGT DGVGYTVPVL KRELRHILGL NRKWGLCIVG MGRLGSALAD   540
WPGFGESFEL RGFFDVDPGM VGRPVRGGVI EHVDLLPQRV PGRIEIALLT VPREAAQKAA   600
DLLVAAGIKG ILNFAPVVLE VPKEVAVENV DFLAGLTRLS FAILNPKWRE EMMGSMVSVI   660
KPEMKMRYYM DGSVNGHEFT IEGEGTGRPY EGHQEMTLRV TMAEGGPMPF AFDLVSHVFC   720
YGHRVFTKYP EEIPDYFKQA FPEGLSWERS LEFEDGGSAS VSAHISLRGN TFYHKSKFTG   780
VNFPADGPIM QNQSVDWEPS TEKITASDGV LKGDVTMYLK LEGGGNHKCQ FKTTYKAAKE   840
ILEMPGDHYI GHRLVRKTEG NITEQVEDAV AHSEASMDEL YK                     882

SEQ ID NO: 73           moltype = AA  length = 880
FEATURE                 Location/Qualifiers
REGION                  1..880
                        note = Synthetic
source                  1..880
                        mol_type = protein
                        organism = synthetic construct
SEQUENCE: 73
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWGMVSK GEELFTGVVP ILVELDGDVN GHKFSVSGEG   240
EGDATYGKLT LKFICTTGKL PVPWPTLVTT LTYGVQCFSR YPDHMKQHDF FKSAMPEGYV   300
QERTIFFKDD GNYKTRAEVK FEGDTLVNRI ELKGIDFKED GNILGHKLEY NYNSHNVYIM   360
ADKQKNGIKV NFKIRHNIED GSVQLADHYQ QNTPIGDGPV LLPDNHYLST QSKLSKDPNE   420
KRDHMVLLEF VTAAGITLGM DELYVPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD   540
WPGFGESFEL RGFFDVDPGM VGRPVRGGVI EHVDLLPQRV PGRIEIALLT VPREAAQKAA   600
DLLVAAGIKG ILNFAPVVLE VPKEVAVENV DFLAGLTRLS FAILNPKWRE EMMGVSVIKP   660
EMKMRYYMDG SVNGHEFTIE GEGTGRPYEG HQEMTLRVTM AEGGPMPFAF DLVSHVFCYG   720
HRVFTKYPEE IPDYFKQAFP EGLSWERSLE FEDGGSASVS AHISLRGNTF YHKSKFTGVN   780
FPADGPIMQN QSVDWEPSTE KITASDGVLK GDVTMYLKLE GGGNHKCQFK TTYKAAKEIL   840
EMPGDHYIGH RLVRKTEGNI TEQVEDAVAH SEASMDELYK                        880

SEQ ID NO: 74           moltype = AA  length = 878
FEATURE                 Location/Qualifiers
REGION                  1..878
                        note = Synthetic
source                  1..878
                        mol_type = protein
                        organism = synthetic construct
SEQUENCE: 74
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
```

```
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLGMDPEA AISRLITYLR ILEELEAQGV HRTASEQLGE  480
LAQVTAFQVD EDLSYFGSYG TDGVGYTVPV LKRELRHILG LNRKWGLCIV GMGRLGSALA  540
DWPGFGESFE LRGFFDVDPG MVGRPVRGGV IEHVDLLPQR VPGRIEIALL TVPREAAQKA  600
ADLLVAAGIK GILNFAPVVL EVPKEVAVEN VDFLAGLTRL SFAILNPKWR EEMSVIKPEM  660
KMRYYMDGSV NGHEFTIEGE GTGRPYEGHQ EMTLRVTMAE GGPMPFAFDL VSHVFCYGHR  720
VFTKYPEEIP DYFKQAFPEG LSWERSLEFE DGGSASVSAH ISLRGNTFYH KSKFTGVNFP  780
ADGPIMQNQS VDWEPSTEKI TASDGVLKGD VTMYLKLEGG GNHKCQFKTT YKAAKEILEM  840
PGDHYIGHRL VRKTEGNITE QVEDAVAHSE ASMDELYK                        878

SEQ ID NO: 75           moltype = AA  length = 868
FEATURE                 Location/Qualifiers
REGION                  1..868
                        note = Synthetic
source                  1..868
                        mol_type = protein
                        organism = synthetic construct
SEQUENCE: 75
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTSKGEEL FTGVVPILVE LDGDVNGHKF SVSGEGEGDA  240
TYGKLTLKFI CTTGKLPVPW PTLVTTLTYG VQCFSRYPDH MKQHDFFKSA MPEGYVQERT  300
IFFKDDGNYK TRAEVKFEGD TLVNRIELKG IDFKEDGNIL GHKLEYNYNS HNVYIMADKQ  360
KNGIKVNFKI RHNIEDGSVQ LADHYQQNTP IGDGPVLLPD NHYLSTQSKL SKDPNEKRDH  420
MVLLEFVTAA GITLGMEAAI SRLITYLRIL EELEAQGVHR TASEQLGELA QVTAFQVDED  480
LSYFGSYGTD GVGYTVPVLK RELRHILGLN RKWGLCIVGM GRLGSALADW PGFGESFELR  540
GFFDVDPGMV GRPVRGGVIE HVDLLPQRVP GRIEIALLTV PREAAQKAAD LLVAAGIKGI  600
LNFAPVVLEV PKEVAVENVD FLAGLTRLSF AILNPKWREE MMVSVIKPEM KMRYYMDGSV  660
NGHEFTIEGE GTGRPYEGHQ EMTLRVTMAE GGPMPFAFDL VSHVFCYGHR VFTKYPEEIP  720
DYFKQAFPEG LSWERSLEFE DGGSASVSAH ISLRGNTFYH KSKFTGVNFP ADGPIMQNQS  780
VDWEPSTEKI TASDGVLKGD VTMYLKLEGG GNHKCQFKTT YKAAKEILEM PGDHYIGHRL  840
VRKTEGNITE QVEDAVAHSE ASMDELYK                                    868

SEQ ID NO: 76           moltype = AA  length = 865
FEATURE                 Location/Qualifiers
REGION                  1..865
                        note = Synthetic
source                  1..865
                        mol_type = protein
                        organism = synthetic construct
SEQUENCE: 76
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTSKGEEL FTGVVPILVE LDGDVNGHKF SVSGEGEGDA  240
TYGKLTLKFI CTTGKLPVPW PTLVTTLTYG VQCFSRYPDH MKQHDFFKSA MPEGYVQERT  300
IFFKDDGNYK TRAEVKFEGD TLVNRIELKG IDFKEDGNIL GHKLEYNYNS HNVYIMADKQ  360
KNGIKVNFKI RHNIEDGSVQ LADHYQQNTP IGDGPVLLPD NHYLSTQSKL SKDPNEKRDH  420
MVLLEFVTAA GITLGMEAAI SRLITYLRIL EELEAQGVHR TASEQLGELA QVTAFQVDED  480
LSYFGSYGTD GVGYTVPVLK RELRHILGLN RKWGLCIVGM GRLGSALADW PGFGESFELR  540
GFFDVDPGMV GRPVRGGVIE HVDLLPQRVP GRIEIALLTV PREAAQKAAD LLVAAGIKGI  600
LNFAPVVLEV PKEVAVENVD FLAGLTRLSF AILNPKWREE SVIKPEMKMR YYMDGSVNGH  660
EFTIEGEGTG RPYEGHQEMT LRVTMAEGGP MPFAFDLVSH VFCYGHRVFT KYPEEIPDYF  720
KQAFPEGLSW ERSLEFEDGG SASVSAHISL RGNTFYHKSK FTGVNFPADG PIMQNQSVDW  780
EPSTEKITAS DGVLKGDVTM YLKLEGGGNH KCQFKTTYKA AKEILEMPGD HYIGHRLVRK  840
TEGNITEQVE DAVAHSEASM DELYK                                       865

SEQ ID NO: 77           moltype = AA  length = 869
FEATURE                 Location/Qualifiers
REGION                  1..869
                        note = Synthetic
source                  1..869
                        mol_type = protein
                        organism = synthetic construct
SEQUENCE: 77
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTGEELFT GVVPILVELD GDVNGHKFSV SGEGEGDATY  240
GKLTLKFICT TGKLPVPWPT LVTTLTYGVQ CFSRYPDHMK QHDFFKSAMP EGYVQERTIF  300
FKDDGNYKTR AEVKFEGDTL VNRIELKGID FKEDGNILGH KLEYNYNSHN VYIMADKQKN  360
GIKVNFKIRH NIEDGSVQLA DHYQQNTPIG DGPVLLPDNH YLSTQSKLSK DPNEKRDHMV  420
LLEFVTAAGI TLGMDPEAAI SRLITYLRIL EELEAQGVHR TASEQLGELA QVTAFQVDED  480
LSYFGSYGTD GVGYTVPVLK RELRHILGLN RKWGLCIVGM GRLGSALADW PGFGESFELR  540
GFFDVDPGMV GRPVRGGVIE HVDLLPQRVP GRIEIALLTV PREAAQKAAD LLVAAGIKGI  600
```

```
LNFAPVVLEV PKEVAVENVD FLAGLTRLSF AILNPKWREE MMGVSVIKPE MKMRYYMDGS    660
VNGHEFTIEG EGTGRPYEGH QEMTLRVTMA EGGPMPFAFD LVSHVFCYGH RVFTKYPEEI    720
PDYFKQAFPE GLSWERSLEF EDGGSASVSA HISLRGNTFY HKSKFTGVNF PADGPIMQNQ    780
SVDWEPSTEK ITASDGVLKG DVTMYLKLEG GGNHKCQFKT TYKAAKEILE MPGDHYIGHR    840
LVRKTEGNIT EQVEDAVAHS EASMDELYK                                     869

SEQ ID NO: 78              moltype = AA  length = 865
FEATURE                    Location/Qualifiers
REGION                     1..865
                           note = Synthetic
source                     1..865
                           mol_type = protein
                           organism = synthetic construct
SEQUENCE: 78
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTGEELFT GVVPILVELD GDVNGHKFSV SGEGEGDATY    240
GKLTLKFICT TGKLPVPWPT LVTTLTYGVQ CFSRYPDHMK QHDFFKSAMP EGYVQERTIF    300
FKDDGNYKTR AEVKFEGDTL VNRIELKGID FKEDGNILGH KLEYNYNSHN VYIMADKQKN    360
GIKVNFKIRH NIEDGSVQLA DHYQQNTPIG DGPVLLPDNH YLSTQSKLSK DPNEKRDHMV    420
LLEFVTAAGI TLGMEAAISR LITYLRILEE LEAQGVHRTA SEQLGELAQV TAFQVDEDLS    480
YFGSYGTDGV GYTVPVLKRE LRHILGLNRK WGLCIVGMGR LGSALADWPG FGESFELRGF    540
FDVDPGMVGR PVRGGVIEHV DLLPQRVPGR IEIALLTVPR EAAQKAADLL VAAGIKGILN    600
FAPVVLEVPK EVAVENVDFL AGLTRLSFAI LNPKWREEMM SVIKPEMKMR YYMDGSVNGH    660
EFTIEGEGTG RPYEGHQEMT LRVTMAEGGP MPFAFDLVSH VFCYGHRVFT KYPEEIPDYF    720
KQAFPEGLSW ERSLEFEDGG SASVSAHISL RGNTFYHKSK FTGVNFPADG PIMQNQSVDW    780
EPSTEKITAS DGVLKGDVTM YLKLEGGGNH KCQFKTTYKA AKEILEMPGD HYIGHRLVRK    840
TEGNITEQVE DAVAHSEASM DELYK                                         865

SEQ ID NO: 79              moltype = AA  length = 869
FEATURE                    Location/Qualifiers
REGION                     1..869
                           note = Synthetic
source                     1..869
                           mol_type = protein
                           organism = synthetic construct
SEQUENCE: 79
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTGEELFT GVVPILVELD GDVNGHKFSV SGEGEGDATY    240
GKLTLKFICT TGKLPVPWPT LVTTLTYGVQ CFSRYPDHMK QHDFFKSAMP EGYVQERTIF    300
FKDDGNYKTR AEVKFEGDTL VNRIELKGID FKEDGNILGH KLEYNYNSHN VYIMADKQKN    360
GIKVNFKIRH NIEDGSVQLA DHYQQNTPIG DGPVLLPDNH YLSTQSKLSK DPNEKRDHMV    420
LLEFVTAAGI TLGMDEVPEA AISRLITYLR ILEELEAQGV HRTASEQLGE LAQVTAFQVD    480
EDLSYFGSYG TDGVGYTVPV LKRELRHILG LNRKWGLCIV GMGRLGSALA DWPGFGESFE    540
LRGFFDVDPG MVGRPVRGGV IEHVDLLPQR VPGRIEIALL TVPREAAQKA ADLLVAAGIK    600
GILNFAPVVL EVPKEVAVEN VDFLAGLTRL SFAILNPKWR EEMMSVIKPE MKMRYYMDGS    660
VNGHEFTIEG EGTGRPYEGH QEMTLRVTMA EGGPMPFAFD LVSHVFCYGH RVFTKYPEEI    720
PDYFKQAFPE GLSWERSLEF EDGGSASVSA HISLRGNTFY HKSKFTGVNF PADGPIMQNQ    780
SVDWEPSTEK ITASDGVLKG DVTMYLKLEG GGNHKCQFKT TYKAAKEILE MPGDHYIGHR    840
LVRKTEGNIT EQVEDAVAHS EASMDELYK                                     869

SEQ ID NO: 80              moltype = AA  length = 877
FEATURE                    Location/Qualifiers
REGION                     1..877
                           note = Synthetic
source                     1..877
                           mol_type = protein
                           organism = synthetic construct
SEQUENCE: 80
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSGMVS KGEELFTGVV PILVELDGDV NGHKFSVSGE    240
GEGDATYGKL TLKFICTTGK LPVPWPTLVT TLTYGVQCFS RYPDHMKQHD FFKSAMPEGY    300
VQERTIFFKD DGNYKTRAEV KFEGDTLVNR IELKGIDFKE DGNILGHKLE YNYNSHNVYI    360
MADKQKNGIK VNFKIRHNIE DGSVQLADHY QQNTPIGDGP VLLPDNHYLS TQSKLSKDPN    420
EKRDHMVLLE FVTAAGITLG MDEPEAAISR LITYLRILEE LEAQGVHRTA SEQLGELAQV    480
TAFQVDEDLS YFGSYGTDGV GYTVPVLKRE LRHILGLNRK WGLCIVGMGR LGSALADWPG    540
FGESFELRGF FDVDPGMVGR PVRGGVIEHV DLLPQRVPGR IEIALLTVPR EAAQKAADLL    600
VAAGIKGILN FAPVVLEVPK EVAVENVDFL AGLTRLSFAI LNPKWREEMM GVSVIKPEMK    660
MRYYMDGSVN GHEFTIEGEG TGRPYEGHQE MTLRVTMAEG GPMPFAFDLV SHVFCYGHRV    720
FTKYPEEIPD YFKQAFPEGL SWERSLEFED GGSASVSAHI SLRGNTFYHK SKFTGVNFPA    780
DGPIMQNQSV DWEPSTEKIT ASDGVLKGDV TMYLKLEGGG NHKCQFKTTY KAAKEILEMP    840
GDHYIGHRLV RKTEGNITEQ VEDAVAHSEA SMDELYK                             877

SEQ ID NO: 81              moltype = AA  length = 868
```

```
FEATURE                   Location/Qualifiers
REGION                    1..868
                          note = Synthetic
source                    1..868
                          mol_type = protein
                          organism = synthetic construct
SEQUENCE: 81
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP   300
EGYVQERTIF FKDDGNYKTR AEVKFEGDTL VNRIELKGID FKEDGNILGH KLEYNYNSHN   360
VYIMADKQKN GIKVNFKIRH NIEDGSVQLA DHYQQNTPIG DGPVLLPDNH YLSTQSKLSK   420
DPNEKRDHMV LLEFVTAAGI TLAAISRLIT YLRILEELEA QGVHRTASEQ LGELAQVTAF   480
QVDEDLSYFG SYGTDGVGYT VPVLKRELRH ILGLNRKWGL CIVGMGRLGS ALADWPGFGE   540
SFELRGFFDV DPGMVGRPVR GGVIEHVDLL PQRVPGRIEI ALLTVPREAA QKAADLLVAA   600
GIKGILNFAP VVLEVPKEVA VENVDFLAGL TRLSFAILNP KWREVIKPEM KMRYYMDGSV   660
NGHEFTIEGE GTGRPYEGHQ EMTLRVTMAE GGPMPFAFDL VSHVFCYGHR VFTKYPEEIP   720
DYFKQAFPEG LSWERSLEFE DGGSASVSAH ISLRGNTFYH KSKFTGVNFP ADGPIMQNQS   780
VDWEPSTEKI TASDGVLKGD VTMYLKLEGG GNHKCQFKTT YKAAKEILEM PGDHYIGHRL   840
VRKTEGNITE QVEDAVAHSE ASMDELYK                                      868

SEQ ID NO: 82             moltype = AA  length = 883
FEATURE                   Location/Qualifiers
REGION                    1..883
                          note = Synthetic
source                    1..883
                          mol_type = protein
                          organism = synthetic construct
SEQUENCE: 82
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEPE AAISRLITYL RILEELEAQG VHRTASEQLG   480
ELAQVTAFQV DEDLSYFGSY GTDGVGYTVP VLKRELRHIL GLNRKWGLCI VGMGRLGSAL   540
ADWPGFGESF ELRGFFDVDP GMVGRPVRGG VIEHVDLLPQ RVPGRIEIAL LTVPREAAQK   600
AADLLVAAGI KGILNFAPVV LEVPKEVAVE NVDFLAGLTR LSFAILNPKW REEMMGMVSV   660
IKPEMKMRYY MDGSVNGHEF TIEGEGTGRP YEGHQEMTLR VTMAEGGPMP FAFDLVSHVF   720
CYGHRVFTKY PEEIPDYFKQ AFPEGLSWER SLEFEDGGSA SVSAHISLRG NTFYHKSKFT   780
GVNFPADGPI MQNQSVDWEP STEKITASDG VLKGDVTMYL KLEGGGNHKC QFKTTYKAAK   840
EILEMPGDHY IGHRLVRKTE GNITEQVEDA VAHSEASMDE LYK                     883

SEQ ID NO: 83             moltype = AA  length = 878
FEATURE                   Location/Qualifiers
REGION                    1..878
                          note = Synthetic
source                    1..878
                          mol_type = protein
                          organism = synthetic construct
SEQUENCE: 83
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSHGMV SKGEELFTGV VPILVELDGD VNGHKFSVSG   240
EGEGDATYGK LTLKFICTTG KLPVPWPTLV TTLTYGVQCF SRYPDHMKQH DFFKSAMPEG   300
YVQERTIFFK DDGNYKTRAE VKFEGDTLVN RIELKGIDFK EDGNILGHKL EYNYNSHNVY   360
IMADKQKNGI KVNFKIRHNI EDGSVQLADH YQQNTPIGDG PVLLPDNHYL STQSKLSKDP   420
NEKRDHMVLL EFVTAAGITL GMDPEAAISR LITYLRILEE LEAQGVHRTA SEQLGELAQV   480
TAFQVDEDLS YFGSYGTDGV GYTVPVLKRE LRHILGLNRK WGLCIVGMGR LGSALADWPG   540
FGESFELRGF FDVDPGMVGR PVRGGVIEHV DLLPQRVPGR IEIALLTVPR EAAQKAADLL   600
VAAGIKGILN FAPVVLEVPK EVAVENVDFL AGLTRLSFAI LNPKWREEMM GMVSVIKPEM   660
KMRYYMDGSV NGHEFTIEGE GTGRPYEGHQ EMTLRVTMAE GGPMPFAFDL VSHVFCYGHR   720
VFTKYPEEIP DYFKQAFPEG LSWERSLEFE DGGSASVSAH ISLRGNTFYH KSKFTGVNFP   780
ADGPIMQNQS VDWEPSTEKI TASDGVLKGD VTMYLKLEGG GNHKCQFKTT YKAAKEILEM   840
PGDHYIGHRL VRKTEGNITE QVEDAVAHSE ASMDELYK                           878

SEQ ID NO: 84             moltype = AA  length = 883
FEATURE                   Location/Qualifiers
REGION                    1..883
                          note = Synthetic
source                    1..883
                          mol_type = protein
                          organism = synthetic construct
SEQUENCE: 84
```

```
MKVPEAAISR LITYLRILEE LEAQGVHRTA SEQLGELAQV TAFQVDKDLS YFGSYGTDGV  60
GYTVPVLKRE LRHILGLNRK WGLCIVGMGR LGSALADWPG FGESFELRGF FDVDPGMVGR 120
PVRGGVIEHV DLLPQRVPGR IEIALLTVPR EAAQKAADLL VAAGIKGILN FAPVVLEVPK 180
EVAVENVDIL AGLTRLSFAI LNPTWSAAGG HGMVSKGEEL FTGVVPILVE LDGDVNGHKF 240
SVSGEGEGDA TYGKLTLKFI CTTGKLPVPW PTLVTTLTYG VQCFSRYPDH MKQHDFFKSA 300
MPEGYVQERT IFFKDDGNYK TRAEVKFEGD TLVNRIELKG IDFKEDGNIL GHKLEYNYNS 360
HNVYIMADKQ KNGIKVNFKI RHNIEDGSVQ LADHYQQNTP IGDGPVLLPD NHYLSTQSKL 420
SKDPNEKRDH MVLLEFVTAA GITLGMDEPE AAISRLITYL RILEELEAQG VHRTASEQLG 480
ELAQVTAFQV DEDLSYFGSY GTDGVGYTVP VLKRELRHIL GLNRKWGLCI VGMGRLGSAL 540
ADWPGFGESF ELRGFFDVDP GMVGRPVRGG VIEHVDLLPQ RVPGRIEIAL LTVPREAAQK 600
AADLLVAAGI KGILNFAPVV LEVPKEVAVE NVDFLAGLTR LSFAILNPKW REEMMGMVSV 660
IKPEMKMRYY MDGSVNGHEF TIEGEGTGRP YEGHQEMTLR VTMAEGGPMP FAFDLVSHVF 720
CYGHRVFTKY PEEIPDYFKQ AFPEGLSWER SLEFEDGGSA SVSAHISLRG NTFYHKSKFT 780
GVNFPADGPI MQNQSVDWEP STEKITASDG VLKGDVTMYL KLEGGGNHKC QFKTTYKAAK 840
EILEMPGDHY IGHRLVRKTE GNITEQVEDA VAHSEASMDE LYK                883

SEQ ID NO: 85          moltype = AA  length = 879
FEATURE                Location/Qualifiers
REGION                 1..879
                       note = Synthetic
source                 1..879
                       mol_type = protein
                       organism = synthetic construct
SEQUENCE: 85
MKVPEAAISR LITYLRILEE LEAQGVHRTA SEQLGELAQV TAFQVDKDLS YFGSYGTDGV  60
GYTVPVLKRE LRHILGLNRK WGLCIVGMGR LGSALADWPG FGESFELRGF FDVDPGMVGR 120
PVRGGVIEHV DLLPQRVPGR IEIALLTVPR EAAQKAADLL VAAGIKGILN FAPVVLEVPK 180
EVAVENVDIL AGLTRLSFAI LNPTWSAAGG HGMVSKGEEL FTGVVPILVE LDGDVNGHKF 240
SVSGEGEGDA TYGKLTLKFI CTTGKLPVPW PTLVTTLTYG VQCFSRYPDH MKQHDFFKSA 300
MPEGYVQERT IFFKDDGNYK TRAEVKFEGD TLVNRIELKG IDFKEDGNIL GHKLEYNYNS 360
HNVYIMADKQ KNGIKVNFKI RHNIEDGSVQ LADHYQQNTP IGDGPVLLPD NHYLSTQSKL 420
SKDPNEKRDH MVLLEFVTAA GITLGMDEPE AAISRLITYL RILEELEAQG VHRTASEQLG 480
ELAQVTAFQV DEDLSYFGSY GTDGVGYTVP VLKRELRHIL GLNRKWGLCI VGMGRLGSAL 540
ADWPGFGESF ELRGFFDVDP GMVGRPVRGG VIEHVDLLPQ RVPGRIEIAL LTVPREAAQK 600
AADLLVAAGI KGILNFAPVV LEVPKEVAVE NVDFLAGLTR LSFAILNPKW REEMSVIKPE 660
MKMRYYMDGS VNGHEFTIEG EGTGRPYEGH QEMTLRVTMA EGGPMPFAFD LVSHVFCYGH 720
RVFTKYPEEI PDYFKQAFPE GLSWERSLEF EDGGSASVSA HISLRGNTFY HKSKFTGVNF 780
PADGPIMQNQ SVDWEPSTEK ITASDGVLKG DVTMYLKLEG GGNHKCQFKT TYKAAKEILE 840
MPGDHYIGHR LVRKTEGNIT EQVEDAVAHS EASMDELYK                      879

SEQ ID NO: 86          moltype = AA  length = 881
FEATURE                Location/Qualifiers
REGION                 1..881
                       note = Synthetic
source                 1..881
                       mol_type = protein
                       organism = synthetic construct
SEQUENCE: 86
MKVPEAAISR LITYLRILEE LEAQGVHRTA SEQLGELAQV TAFQVDKDLS YFGSYGTDGV  60
GYTVPVLKRE LRHILGLNRK WGLCIVGMGR LGSALADWPG FGESFELRGF FDVDPGMVGR 120
PVRGGVIEHV DLLPQRVPGR IEIALLTVPR EAAQKAADLL VAAGIKGILN FAPVVLEVPK 180
EVAVENVDIL AGLTRLSFAI LNPTWSHGMV SKGEELFTGV VPILVELDGD VNGHKFSVSG 240
EGEGDATYGK LTLKFICTTG KLPVPWPTLV TTLTYGVQCF SRYPDHMKQH DFFKSAMPEG 300
YVQERTIFFK DDGNYKTRAE VKFEGDTLVN RIELKGIDFK EDGNILGHKL EYNYNSHNVY 360
IMADKQKNGI KVNFKIRHNI EDGSVQLADH YQQNTPIGDG PVLLPDNHYL STQSKLSKDP 420
NEKRDHMVLL EFVTAAGITL GMDEPEAAIS RLITYLRILE ELEAQGVHRT ASEQLGELAQ 480
VTAFQVDEDL SYFGSYGTDG VGYTVPVLKR ELRHILGLNR KWGLCIVGMG RLGSALADWP 540
GFGESFELRG FFDVDPGMVG RPVRGGVIEH VDLLPQRVPG RIEIALLTVP REAAQKAADL 600
LVAAGIKGIL NFAPVVLEVP KEVAVENVDF LAGLTRLSFA ILNPKWREEM MGGSMVSVIK 660
PEMKMRYYMD GSVNGHEFTI EGEGTGRPYE GHQEMTLRVT MAEGGPMPFA FDLVSHVFCY 720
GHRVFTKYPE EIPDYFKQAF PEGLSWERSL EFEDGGSASV SAHISLRGNT FYHKSKFTGV 780
NFPADGPIMQ NQSVDWEPST EKITASDGVL KGDVTMYLKL EGGGNHKCQF KTTYKAAKEI 840
LEMPGDHYIG HRLVRKTEGN ITEQVEDAVA HSEASMDELY K                   881

SEQ ID NO: 87          moltype = AA  length = 884
FEATURE                Location/Qualifiers
REGION                 1..884
                       note = Synthetic
source                 1..884
                       mol_type = protein
                       organism = synthetic construct
SEQUENCE: 87
MKVPEAAISR LITYLRILEE LEAQGVHRTA SEQLGELAQV TAFQVDKDLS YFGSYGTDGV  60
GYTVPVLKRE LRHILGLNRK WGLCIVGMGR LGSALADWPG FGESFELRGF FDVDPGMVGR 120
PVRGGVIEHV DLLPQRVPGR IEIALLTVPR EAAQKAADLL VAAGIKGILN FAPVVLEVPK 180
EVAVENVDIL AGLTRLSFAI LNPTWSAAGG HGMVSKGEEL FTGVVPILVE LDGDVNGHKF 240
SVSGEGEGDA TYGKLTLKFI CTTGKLPVPW PTLVTTLTYG VQCFSRYPDH MKQHDFFKSA 300
MPEGYVQERT IFFKDDGNYK TRAEVKFEGD TLVNRIELKG IDFKEDGNIL GHKLEYNYNS 360
HNVYIMADKQ KNGIKVNFKI RHNIEDGSVQ LADHYQQNTP IGDGPVLLPD NHYLSTQSKL 420
```

```
SKDPNEKRDH  MVLLEFVTAA  GITLGMDEVP  EAAISRLITY  LRILEELEAQ  GVHRTASEQL  480
GELAQVTAFQ  VDEDLSYFGS  YGTDGVGYTV  PVLKRELRHI  LGLNRKWGLC  IVGMGRLGSA  540
LADWPGFGES  FELRGFFDVD  PGMVGRPVRG  GVIEHVDLLP  QRVPGRIEIA  LLTVPREAAQ  600
KAADLLVAAG  IKGILNFAPV  VLEVPKEVAV  ENVDFLAGLT  RLSFAILNPK  WREEMMGMVS  660
VIKPEMKMRY  YMDGSVNGHE  FTIEGEGTGR  PYEGHQEMTL  RVTMAEGGPM  PPAFDLVSHV  720
FCYGHRVFTK  YPEEIPDYFK  QAFPEGLSWE  RSLEFEDGGS  ASVSAHISLR  GNTFYHKSKF  780
TGVNFPADGP  IMQNQSVDWE  PSTEKITASD  GVLKGDVTMY  LKLEGGGNHK  CQFKTTYKAA  840
KEILEMPGDH  YIGHRLVRKT  EGNITEQVED  AVAHSEASMD  ELYK                    884

SEQ ID NO: 88           moltype = AA   length = 882
FEATURE                 Location/Qualifiers
REGION                  1..882
                        note = Synthetic
source                  1..882
                        mol_type = protein
                        organism = synthetic construct
SEQUENCE: 88
MKVPEAAISR  LITYLRILEE  LEAQGVHRTA  SEQLGELAQV  TAFQVDKDLS  YFGSYGTDGV  60
GYTVPVLKRE  LRHILGLNRK  WGLCIVGMGR  LGSALADWPG  FGESFELRGF  FDVDPGMVGR  120
PVRGGVIEHV  DLLPQRVPGR  IEIALLTVPR  EAAQKAADLL  VAAGIKGILN  FAPVVLEVPK  180
EVAVENVDIL  AGLTRLSFAI  LNPTWSAAGH  GMVSKGEELF  TGVVPILVEL  DGDVNGHKFS  240
VSGEGEGDAT  YGKLTLKFIC  TTGKLPVPWP  TLVTTLTYGV  QCFSRYPDHM  KQHDFFKSAM  300
PEGYVQERTI  FFKDDGNYKT  RAEVKFEGDT  LVNRIELKGI  DFKEDGNILG  HKLEYNYNSH  360
NVYIMADKQK  NGIKVNFKIR  HNIEDGSVQL  ADHYQQNTPI  GDGPVLLPDN  HYLSTQSKLS  420
KDPNEKRDHM  VLLEFVTAAG  ITLGMDELVP  EAAISRLITY  LRILEELEAQ  GVHRTASEQL  480
GELAQVTAFQ  VDEDLSYFGS  YGTDGVGYTV  PVLKRELRHI  LGLNRKWGLC  IVGMGRLGSA  540
LADWPGFGES  FELRGFFDVD  PGMVGRPVRG  GVIEHVDLLP  QRVPGRIEIA  LLTVPREAAQ  600
KAADLLVAAG  IKGILNFAPV  VLEVPKEVAV  ENVDFLAGLT  RLSFAILNPK  WREEMMVSVI  660
KPEMKMRYYM  DGSVNGHEFT  IEGEGTGRPY  EGHQEMTLRV  TMAEGGPMPF  AFDLVSHVFC  720
YGHRVFTKYP  EEIPDYFKQA  FPEGLSWERS  LEFEDGGSAS  VSAHISLRGN  TFYHKSKFTG  780
VNFPADGPIM  QNQSVDWEPS  TEKITASDGV  LKGDVTMYLK  LEGGGNHKCQ  FKTTYKAAKE  840
ILEMPGDHYI  GHRLVRKTEG  NITEQVEDAV  AHSEASMDEL  YK                      882

SEQ ID NO: 89           moltype = AA   length = 883
FEATURE                 Location/Qualifiers
REGION                  1..883
                        note = Synthetic
source                  1..883
                        mol_type = protein
                        organism = synthetic construct
SEQUENCE: 89
MKVPEAAISR  LITYLRILEE  LEAQGVHRTA  SEQLGELAQV  TAFQVDKDLS  YFGSYGTDGV  60
GYTVPVLKRE  LRHILGLNRK  WGLCIVGMGR  LGSALADWPG  FGESFELRGF  FDVDPGMVGR  120
PVRGGVIEHV  DLLPQRVPGR  IEIALLTVPR  EAAQKAADLL  VAAGIKGILN  FAPVVLEVPK  180
EVAVENVDIL  AGLTRLSFAI  LNPTWSAHGM  VSKGEELFTG  VVPILVELDG  DVNGHKFSVS  240
GEGEGDATYG  KLTLKFICTT  GKLPVPWPTL  VTTLTYGVQC  FSRYPDHMKQ  HDFFKSAMPE  300
GYVQERTIFF  KDDGNYKTRA  EVKFEGDTLV  NRIELKGIDF  KEDGNILGHK  LEYNYNSHNV  360
YIMADKQKNG  IKVNFKIRHN  IEDGSVQLAD  HYQQNTPIGD  GPVLLPDNHY  LSTQSKLSKD  420
PNEKRDHMVL  LEFVTAAGIT  LGMDELVPE  AAISRLITYL  RILEELEAQG  VHRTASEQLG  480
ELAQVTAFQV  DEDLSYFGSY  GTDGVGYTVP  VLKRELRHIL  GLNRKWGLCI  VGMGRLGSAL  540
ADWPGFGESF  ELRGFFDVDP  GMVGRPVRGG  VIEHVDLLPQ  RVPGRIEIAL  LTVPREAAQK  600
AADLLVAAGI  KGILNFAPVV  LEVPKEVAVE  NVDFLAGLTR  LSFAILNPKW  REEMMGMVSV  660
IKPEMKMRYY  MDGSVNGHEF  TIEGEGTGRP  YEGHQEMTLR  VTMAEGGPMP  FAFDLVSHVF  720
CYGHRVFTKY  PEEIPDYFKQ  AFPEGLSWER  SLEFEDGGSA  SVSAHISLRG  NTFYHKSKFT  780
GVNFPADGPI  MQNQSVDWEP  STEKITASDG  VLKGDVTMYL  KLEGGGNHKC  QFKTTYKAAK  840
EILEMPGDHY  IGHRLVRKTE  GNITEQVEDA  VAHSEASMDE  LYK                     883

SEQ ID NO: 90           moltype = AA   length = 880
FEATURE                 Location/Qualifiers
REGION                  1..880
                        note = Synthetic
source                  1..880
                        mol_type = protein
                        organism = synthetic construct
SEQUENCE: 90
MKVPEAAISR  LITYLRILEE  LEAQGVHRTA  SEQLGELAQV  TAFQVDKDLS  YFGSYGTDGV  60
GYTVPVLKRE  LRHILGLNRK  WGLCIVGMGR  LGSALADWPG  FGESFELRGF  FDVDPGMVGR  120
PVRGGVIEHV  DLLPQRVPGR  IEIALLTVPR  EAAQKAADLL  VAAGIKGILN  FAPVVLEVPK  180
EVAVENVDIL  AGLTRLSFAI  LNPTWSAAGH  GMVSKGEELF  TGVVPILVEL  DGDVNGHKFS  240
VSGEGEGDAT  YGKLTLKFIC  TTGKLPVPWP  TLVTTLTYGV  QCFSRYPDHM  KQHDFFKSAM  300
PEGYVQERTI  FFKDDGNYKT  RAEVKFEGDT  LVNRIELKGI  DFKEDGNILG  HKLEYNYNSH  360
NVYIMADKQK  NGIKVNFKIR  HNIEDGSVQL  ADHYQQNTPI  GDGPVLLPDN  HYLSTQSKLS  420
KDPNEKRDHM  VLLEFVTAAG  ITLGMDEPEA  AISRLITYL  ILEELEAQG  VHRTASEQLG  480
LAQVTAFQVD  EDLSYFGSYG  TDGVGYTVPV  LKRELRHILG  LNRKWGLCIV  GMGRLGSALA  540
DWPGFGESFE  LRGFFDVDPG  MVGRPVRGGV  IEHVDLLPQR  VPGRIEIALL  TVPREAAQKA  600
ADLLVAAGIK  GILNFAPVVL  EVPKEVAVEN  VDFLAGLTRL  SFAILNPKWR  EEMMVSVIKP  660
EMKMRYYMDG  SVNGHEFTIE  GEGTGRPYEG  HQEMTLRVTM  AEGGPMPFAF  DLVSHVFCYG  720
HRVFTKYPEE  IPDYFKQAFP  EGLSWERSLE  FEDGGSASVS  AHISLRGNTF  YHKSKFTGVN  780
FPADGPIMQN  QSVDWEPSTE  KITASDGVLK  GDVTMYLKLE  GGGNHKCQFK  TTYKAAKEIL  840
```

```
EMPGDHYIGH RLVRKTEGNI TEQVEDAVAH SEASMDELYK                          880

SEQ ID NO: 91           moltype = AA  length = 868
FEATURE                 Location/Qualifiers
REGION                  1..868
                        note = Synthetic
source                  1..868
                        mol_type = protein
                        organism = synthetic construct
SEQUENCE: 91
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWGMVSK GEELFTGVVP ILVELDGDVN GHKFSVSGEG    240
EGDATYGKLT LKFICTTGKL PVPWPTLVTT LTYGVQCFSR YPDHMKQHDF FKSAMPEGYV    300
QERTIFFKDD GNYKTRAEVK FEGDTLVNRI ELKGIDFKED GNILGHKLEY NYNSHNVYIM    360
ADKQKNGIKV NFKIRHNIED GSVQLADHYQ QNTPIGDGPV LLPDNHYLST QSKLSKDPNE    420
KRDHMVLLEF VTAAGITLGE AAISRLITYL RILEELEAQG VHRTASEQLG ELAQVTAFQV    480
DEDLSYFGSY GTDGVGYTVP VLKRELRHIL GLNRKWGLCI VGMGRLGSAL ADWPGFGESF    540
ELRGFFDVDP GMVGRPVRGG VIEHVDLLPQ RVPGRIEIAL LTVPREAAQK AADLLVAAGI    600
KGILNFAPVV LEVPKEVAVE NVDFLAGLTR LSFAILNPKW REESVIKPEM KMRYYMDGSV    660
NGHEFTIEGE GTGRPYEGHQ EMTLRVTMAE GGPMPFAFDL VSHVFCYGHR VFTKYPEEIP    720
DYFKQAFPEG LSWERSLEFE DGGSASVSAH ISLRGNTFYH KSKFTGVNFP ADGPIMQNQS    780
VDWEPSTEKI TASDGVLKGD VTMYLKLEGG GNHKCQFKTT YKAAKEILEM PGDHYIGHRL    840
VRKTEGNITE QVEDAVAHSE ASMDELYK                                      868

SEQ ID NO: 92           moltype = AA  length = 872
FEATURE                 Location/Qualifiers
REGION                  1..872
                        note = Synthetic
source                  1..872
                        mol_type = protein
                        organism = synthetic construct
SEQUENCE: 92
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTGEELFT GVVPILVELD GDVNGHKFSV SGEGEGDATY    240
GKLTLKFICT TGKLPVPWPT LVTTLTYGVQ CFSRYPDHMK QHDFFKSAMP EGYVQERTIF    300
FKDDGNYKTR AEVKFEGDTL VNRIELKGID FKEDGNILGH KLEYNYNSHN VYIMADKQKN    360
GIKVNFKIRH NIEDGSVQLA DHYQQNTPIG DGPVLLPDNH YLSTQSKLSK DPNEKRDHMV    420
LLEFVTAAGI TLGMDELYKV PEAAISRLIT YLRILEELEA QGVHRTASEQ LGELAQVTAF    480
QVDEDLSYFG SYGTDGVGYT VPVLKRELRH ILGLNRKWGL CIVGMGRLGS ALADWPGFGE    540
SFELRGFFDV DPGMVGRPVR GGVIEHVDLL PQRVPGRIEI ALLTVPREAA QKAADLLVAA    600
GIKGILNFAP VVLEVPKEVA VENVDFLAGL TRLSFAILNP KWREEMMSVI KPEMKMRYYM    660
DGSVNGHEFT IEGEGTGRPY EGHQEMTLRV TMAEGGPMPF AFDLVSHVFC YGHRVFTKYP    720
EEIPDYFKQA FPEGLSWERS LEFEDGGSAS VSAHISLRGN TFYHKSKFTG VNFPADGPIM    780
QNQSVDWEPS TEKITASDGV LKGDVTMYLK LEGGGNHKCQ FKTTYKAAKE ILEMPGDHYI    840
GHRLVRKTEG NITEQVEDAV AHSEASMDEL YK                                 872

SEQ ID NO: 93           moltype = AA  length = 866
FEATURE                 Location/Qualifiers
REGION                  1..866
                        note = Synthetic
source                  1..866
                        mol_type = protein
                        organism = synthetic construct
SEQUENCE: 93
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTSKGEEL FTGVVPILVE LDGDVNGHKF SVSGEGEGDA    240
TYGKLTLKFI CTTGKLPVPW PTLVTTLTYG VQCFSRYPDH MKQHDFFKSA MPEGYVQERT    300
IFFKDDGNYK TRAEVKFEGD TLVNRIELKG IDFKEDGNIL GHKLEYNYNS HNVYIMADKQ    360
KNGIKVNFKI RHNIEDGSVQ LADHYQQNTP IGDGPVLLPD NHYLSTQSKL SKDPNEKRDH    420
MVLLEFVTAA GITLGEAAIS RLITYLRILE ELEAQGVHRT ASEQLGELAQ VTAFQVDEDL    480
SYFGSYGTDG VGYTVPVLKR ELRHILGLNR KWGLCIVGMG RLGSALADWP GFGESFELRG    540
FFDVDPGMVG RPVRGGVIEH VDLLPQRVPG RIEIALLTVP REAAQKAADL LVAAGIKGIL    600
NFAPVVLEVP KEVAVENVDF LAGLTRLSFA ILNPKWREEM MSVIKPEMKM RYYMDGSVNG    660
HEFTIEGEGT GRPYEGHQEM TLRVTMAEGG PMPFAFDLVS HVFCYGHRVF TKYPEEIPDY    720
FKQAFPEGLS WERSLEFEDG GSASVSAHIS LRGNTFYHKS KFTGVNFPAD GPIMQNQSVD    780
WEPSTEKITA SDGVLKGDVT MYLKLEGGGN HKCQFKTTYK AAKEILEMPG DHYIGHRLVR    840
KTEGNITEQV EDAVAHSEAS MDELYK                                        866

SEQ ID NO: 94           moltype = AA  length = 872
FEATURE                 Location/Qualifiers
REGION                  1..872
                        note = Synthetic
source                  1..872
```

```
                        mol_type = protein
                        organism = synthetic construct
SEQUENCE: 94
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAGHG MVSKGEELFT GVVPILVELD GDVNGHKFSV   240
SGEGEGDATY GKLTLKFICT TGKLPVPWPT LVTTLTYGVQ CFSRYPDHMK QHDFFKSAMP   300
EGYVQERTIF FKDDGNYKTR AEVKFEGDTL VNRIELKGID FKEDGNILGH KLEYNYNSHN   360
VYIMADKQKN GIKVNFKIRH NIEDGSVQLA DHYQQNTPIG DGPVLLPDNH YLSTQSKLSK   420
DPNEKRDHMV LLEFVTAAGI TLGMDELYKK VPEAAISRLI TYLRILEELE AQGVHRTASE   480
QLGELAQVTA FQVDEDLSYF GSYGTDGVGY TVPVLKRELR HILGLNRKWG LCIVGMGRLG   540
SALADWPGFG ESFELRGFFD VDPGMVGRPV RGGVIEHVDL LPQRVPGRIE IALLTVPREA   600
AQKAADLLVA AGIKGILNFA PVVLEVPKEV AVENVDFLAG LTRLSFAILN PKEMKMRYYM   660
DGSVNGHEFT IEGEGTGRPY EGHQEMTLRV TMAEGGPMPF AFDLVSHVFC YGHRVFTKYP   720
EEIPDYFKQA FPEGLSWERS LEFEDGGSAS VSAHISLRGN TFYHKSKFTG VNFPADGPIM   780
QNQSVDWEPS TEKITASDGV LKGDVTMYLK LEGGGNHKCQ FKTTYKAAKE ILEMPGDHYI   840
GHRLVRKTEG NITEQVEDAV AHSEASMDEL YK                                 872

SEQ ID NO: 95           moltype = AA  length = 880
FEATURE                 Location/Qualifiers
REGION                  1..880
                        note = Synthetic
source                  1..880
                        mol_type = protein
                        organism = synthetic construct
SEQUENCE: 95
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMEAAI SRLITYLRIL EELEAQGVHR TASEQLGELA   480
QVTAFQVDED LSYFGSYGTD GVGYTVPVLK RELRHILGLN RKWGLCIVGM GRLGSALADW   540
PGFGESFELR GFFDVDPGMV GRPVRGGVIE HVDLLPQRVP GRIEIALLTV PREAAQKAAD   600
LLVAAGIKGI LNFAPVVLEV PKEVAVENVD FLAGLTRLSF AILNPKWREE MMGMVSVIKP   660
EMKMRYYMDG SVNGHEFTIE GEGTGRPYEG HQEMTLRVTM AEGGPMPFAF DLVSHVFCYG   720
HRVFTKYPEE IPDYFKQAFP EGLSWERSLE FEDGGSASVS AHISLRGNTF YHKSKFTGVN   780
FPADGPIMQN QSVDWEPSTE KITASDGVLK GDVTMYLKLE GGGNHKCQFK TTYKAAKEIL   840
EMPGDHYIGH RLVRKTEGNI TEQVEDAVAH SEASMDELYK                         880

SEQ ID NO: 96           moltype = AA  length = 869
FEATURE                 Location/Qualifiers
REGION                  1..869
                        note = Synthetic
source                  1..869
                        mol_type = protein
                        organism = synthetic construct
SEQUENCE: 96
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTSKGEEL FTGVVPILVE LDGDVNGHKF SVSGEGEGDA   240
TYGKLTLKFI CTTGKLPVPW PTLVTTLTYG VQCFSRYPDH MKQHDFFKSA MPEGYVQERT   300
IFFKDDGNYK TRAEVKFEGD TLVNRIELKG IDFKEDGNIL GHKLEYNYNS HNVYIMADKQ   360
KNGIKVNFKI RHNIEDGSVQ LADHYQQNTP IGDGPVLLPD NHYLSTQSKL SKDPNEKRDH   420
MVLLEFVTAA GITLGMDPEA AISRLITYLR ILEELEAQGV HRTASEQLGE LAQVTAFQVD   480
EDLSYFGSYG TDGVGYTVPV LKRELRHILG LNRKWGLCIV GMGRLGSALA DWPGFGESFE   540
LRGFFDVDPG MVGRPVRGGV IEHVDLLPQR VPGRIEIALL TVPREAAQKA ADLLVAAGIK   600
GILNFAPVVL EVPKEVAVEN VDFLAGLTRL SFAILNPKWR EEMMSVIKPE MKMRYYMDGS   660
VNGHEFTIEG EGTGRPYEGH QEMTLRVTMA EGGPMPFAFD LVSHVFCYGH RVFTKYPEEI   720
PDYFKQAFPE GLSWERSLEF EDGGSASVSA HISLRGNTFY HKSKFTGVNF PADGPIMQNQ   780
SVDWEPSTEK ITASDGVLKG DVTMYLKLEG GGNHKCQFKT TYKAAKEILE MPGDHYIGHR   840
LVRKTEGNIT EQVEDAVAHS EASMDELYK                                    869

SEQ ID NO: 97           moltype = AA  length = 883
FEATURE                 Location/Qualifiers
REGION                  1..883
                        note = Synthetic
source                  1..883
                        mol_type = protein
                        organism = synthetic construct
SEQUENCE: 97
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
```

```
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEVP EAAISRLITY LRILEELEAQ GVHRTASEQL   480
GELAQVTAFQ VDEDLSYFGS YGTDGVGYTV PVLKRELRHI LGLNRKWGLC IVGMGRLGSA   540
LADWPGFGES FELRGFFDVD PGMVGRPVRG GVIEHVDLLP QRVPGRIEIA LLTVPREAAQ   600
KAADLLVAAG IKGILNFAPV VLEVPKEVAV ENVDFLAGLT RLSFAILNPK WREEMMGVSV   660
IKPEMKMRYY MDGSVNGHEF TIEGEGTGRP YEGHQEMTLR VTMAEGGPMP FAFDLVSHVF   720
CYGHRVFTKY PEEIPDYFKQ AFPEGLSWER SLEFEDGGSA SVSAHISLRG NTFYHKSKFT   780
GVNFPADGPI MQNQSVDWEP STEKITASDG VLKGDVTMYL KLEGGGNHKC QFKTTYKAAK   840
EILEMPGDHY IGHRLVRKTE GNITEQVEDA VAHSEASMDE LYK                    883

SEQ ID NO: 98           moltype = AA  length = 884
FEATURE                 Location/Qualifiers
REGION                  1..884
                        note = Synthetic
source                  1..884
                        mol_type = protein
                        organism = synthetic construct
SEQUENCE: 98
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAHGM VSKGEELFTG VVPILVELDG DVNGHKFSVS   240
GEGEGDATYG KLTLKFICTT GKLPVPWPTL VTTLTYGVQC FSRYPDHMKQ HDFFKSAMPE   300
GYVQERTIFF KDDGNYKTRA EVKFEGDTLV NRIELKGIDF KEDGNILGHK LEYNYNSHNV   360
YIMADKQKNG IKVNFKIRHN IEDGSVQLAD HYQQNTPIGD GPVLLPDNHY LSTQSKLSKD   420
PNEKRDHMVL LEFVTAAGIT LGMDELYVPE AAISRLITYL RILEELEAQG VHRTASEQLG   480
ELAQVTAFQV DEDLSYFGSY GTDGVGYTVP VLKRELRHIL GLNRKWGLCI VGMGRLGSAL   540
ADWPGFGESF ELRGFFDVDP GMVGRPVRGG VIEHVDLLPQ RVPGRIEIAL LTVPREAAQK   600
AADLLVAAGI KGILNFAPVV LEVPKEVAVE NVDFLAGLTR LSFAILNPKW REEMMGSMVS   660
VIKPEMKMRY YMDGSVNGHE FTIEGEGTGR PYEGHQEMTL RVTMAEGGPM PFAFDLVSHV   720
FCYGHRVFTK YPEEIPDYFK QAFPEGLSWE RSLEFEDGGS ASVSAHISLR GNTFYHKSKF   780
TGVNFPADGP IMQNQSVDWE PSTEKITASD GVLKGDVTMY LKLEGGGNHK CQFKTTYKAA   840
KEILEMPGDH YIGHRLVRKT EGNITEQVED AVAHSEASMD ELYK                    884

SEQ ID NO: 99           moltype = AA  length = 878
FEATURE                 Location/Qualifiers
REGION                  1..878
                        note = Synthetic
source                  1..878
                        mol_type = protein
                        organism = synthetic construct
SEQUENCE: 99
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDPEA AISRLITYLR ILEELEAQGV HRTASEQLGE   480
LAQVTAFQVD EDLSYFGSYG TDGVGYTVPV LKRELRHILG LNRKWGLCIV GMGRLGSALA   540
DWPGFGESFE LRGFFDVDPG MVGRPVRGGV IEHVDLLPQR VPGRIEIALL TVPREAAQKA   600
ADLLVAAGIK GILNFAPVVL EVPKEVAVEN VDFLAGLTRL SFAILNPKWR EEMSVIKPEM   660
KMRYYMDGSV NGHEFTIEGE GTGRPYEGHQ EMTLRVTMAE GGPMPFAFDL VSHVFCYGHR   720
VFTKYPEEIP DYFKQAFPEG LSWERSLEFE DGGSASVSAH ISLRGNTFYH KSKFTGVNFP   780
ADGPIMQNQS VDWEPSTEKI TASDVLKGDV TMYLKLEGG GNHKCQFKTT YKAAKEILEM   840
PGDHYIGHRL VRKTEGNITE QVEDAVAHSE ASMDELYK                          878

SEQ ID NO: 100          moltype = AA  length = 880
FEATURE                 Location/Qualifiers
REGION                  1..880
                        note = Synthetic
source                  1..880
                        mol_type = protein
                        organism = synthetic construct
SEQUENCE: 100
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSGMVS KGEELFTGVV PILVELDGDV NGHKFSVSGE   240
GEGDATYGKL TLKFICTTGK LPVPWPTLVT TLTYGVQCFS RYPDHMKQHD FFKSAMPEGY   300
VQERTIFFKD DGNYKTRAEV KFEGDTLVNR IELKGIDFKE DGNILGHKLE YNYNSHNVYI   360
MADKQKNGIK VNFKIRHNIE DGSVQLADHY QQNTPIGDGP VLLPDNHYLS TQSKLSKDPN   420
EKRDHMVLLE FVTAAGITLG MDELYKVPEA AISRLITYLR ILEELEAQGV HRTASEQLGE   480
LAQVTAFQVD EDLSYFGSYG TDGVGYTVPV LKRELRHILG LNRKWGLCIV GMGRLGSALA   540
DWPGFGESFE LRGFFDVDPG MVGRPVRGGV IEHVDLLPQR VPGRIEIALL TVPREAAQKA   600
ADLLVAAGIK GILNFAPVVL EVPKEVAVEN VDFLAGLTRL SFAILNPKWR EEMMVSVIKP   660
```

```
EMKMRYYMDG  SVNGHEFTIE  GEGTGRPYEG  HQEMTLRVTM  AEGGPMPPAF  DLVSHVFCYG   720
HRVFTKYPEE  IPDYFKQAFP  EGLSWERSLE  FEDGGSASVS  AHISLRGNTF  YHKSKFTGVN   780
FPADGPIMQN  QSVDWEPSTE  KITASDGVLK  GDVTMYLKLE  GGGNHKCQFK  TTYKAAKEIL   840
EMPGDHYIGH  RLVRKTEGNI  TEQVEDAVAH  SEASMDELYK                           880

SEQ ID NO: 101              moltype = AA  length = 881
FEATURE                     Location/Qualifiers
REGION                      1..881
                            note = Synthetic
source                      1..881
                            mol_type = protein
                            organism = synthetic construct
SEQUENCE: 101
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTWSAAGG  HGMVSKGEEL  FTGVVPILVE  LDGDVNGHKF   240
SVSGEGEGDA  TYGKLTLKFI  CTTGKLPVPW  PTLVTTLTYG  VQCFSRYPDH  MKQHDFFKSA   300
MPEGYVQERT  IFFKDDGNYK  TRAEVKFEGD  TLVNRIELKG  IDFKEDGNIL  GHKLEYNYNS   360
HNVYIMADKQ  KNGIKVNFKI  RHNIEDGSVQ  LADHYQQNTP  IGDGPVLLPD  NHYLSTQSKL   420
SKDPNEKRDH  MVLLEFVTAA  GITLGMDEPE  AAISRLITYL  RILEELEAQG  VHRTASEQLG   480
ELAQVTAFQV  DEDLSYFGSY  GTDGVGYTVP  VLKRELRHIL  GLNRKWGLCI  VGMGRLGSAL   540
ADWPGFGESF  ELRGFFDVDP  GMVGRPVRGG  VIEHVDLLPQ  RVPGRIEIAL  LTVPREAAQK   600
AADLLVAAGI  KGILNFAPVV  LEVPKEVAVE  NVDFLAGLTR  LSFAILNPKW  REEMMVSVIK   660
PEMKMRYYMD  GSVNGHEFTI  EGEGTGRPYE  GHQEMTLRVT  MAEGGPMPFA  FDLVSHVFCY   720
GHRVFTKYPE  EIPDYFKQAF  PEGLSWERSL  EFEDGGSASV  SAHISLRGNT  FYHKSKFTGV   780
NFPADGPIMQ  NQSVDWEPST  EKITASDGVL  KGDVTMYLKL  EGGGNHKCQF  KTTYKAAKEI   840
LEMPGDHYIG  HRLVRKTEGN  ITEQVEDAVA  HSEASMDELY  K                        881

SEQ ID NO: 102              moltype = AA  length = 861
FEATURE                     Location/Qualifiers
REGION                      1..861
                            note = Synthetic
source                      1..861
                            mol_type = protein
                            organism = synthetic construct
SEQUENCE: 102
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTSKGEEL  FTGVVPILVE  LDGDVNGHKF  SVSGEGEGDA   240
TYGKLTLKFI  CTTGKLPVPW  PTLVTTLTYG  VQCFSRYPDH  MKQHDFFKSA  MPEGYVQERT   300
IFFKDDGNYK  TRAEVKFEGD  TLVNRIELKG  IDFKEDGNIL  GHKLEYNYNS  HNVYIMADKQ   360
KNGIKVNFKI  RHNIEDGSVQ  LADHYQQNTP  IGDGPVLLPD  NHYLSTQSKL  SKDPNEKRDH   420
MVLLEFVTAA  GITLAAISRL  ITYLRILEEL  EAQGVHRTAS  EQLGELAQVT  AFQVDEDLSY   480
FGSYGTDGVG  YTVPVLKREL  RHILGLNRKW  GLCIVGMGRL  GSALADWPGF  GESFELRGFF   540
DVDPGMVGRP  VRGGVIEHVD  LLPQRVPGRI  EIALLTVPRE  AAQKAADLLV  AAGIKGILNF   600
APVVLEVPKE  VAVENVDFLA  GLTRLSFAIL  NPKWREEVIK  PEMKMRYYMD  GSVNGHEFTI   660
EGEGTGRPYE  GHQEMTLRVT  MAEGGPMPFA  FDLVSHVFCY  GHRVFTKYPE  EIPDYFKQAF   720
PEGLSWERSL  EFEDGGSASV  SAHISLRGNT  FYHKSKFTGV  NFPADGPIMQ  NQSVDWEPST   780
EKITASDGVL  KGDVTMYLKL  EGGGNHKCQF  KTTYKAAKEI  LEMPGDHYIG  HRLVRKTEGN   840
ITEQVEDAVA  HSEASMDELY  K                                                861

SEQ ID NO: 103              moltype = AA  length = 881
FEATURE                     Location/Qualifiers
REGION                      1..881
                            note = Synthetic
source                      1..881
                            mol_type = protein
                            organism = synthetic construct
SEQUENCE: 103
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTWSAHGM  VSKGEELFTG  VVPILVELDG  DVNGHKFSVS   240
GEGEGDATYG  KLTLKFICTT  GKLPVPWPTL  VTTLTYGVQC  FSRYPDHMKQ  HDFFKSAMPE   300
GYVQERTIFF  KDDGNYKTRA  EVKFEGDTLV  NRIELKGIDF  KEDGNILGHK  LEYNYNSHNV   360
YIMADKQKNG  IKVNFKIRHN  IEDGSVQLAD  HYQQNTPIGD  GPVLLPDNHY  LSTQSKLSKD   420
PNEKRDHMVL  LEFVTAAGIT  LGMDELKVYP  EAAISRLITY  LRILEELEAQ  GVHRTASEQL   480
GELAQVTAFQ  VDEDLSYFGS  YGTDGVGYTV  PVLKRELRHI  LGLNRKWGLC  IVGMGRLGSA   540
LADWPGFGES  FELRGFFDVD  PGMVGRPVRG  GVIEHVDLLP  QRVPGRIEIA  LLTVPREAAQ   600
KAADLLVAAG  IKGILNFAPV  VLEVPKEVAV  ENVDFLAGLT  RLSFAILNPK  WREEMMVSIK   660
PEMKMRYYMD  GSVNGHEFTI  EGEGTGRPYE  GHQEMTLRVT  MAEGGPMPFA  FDLVSHVFCY   720
GHRVFTKYPE  EIPDYFKQAF  PEGLSWERSL  EFEDGGSASV  SAHISLRGNT  FYHKSKFTGV   780
NFPADGPIMQ  NQSVDWEPST  EKITASDGVL  KGDVTMYLKL  EGGGNHKCQF  KTTYKAAKEI   840
LEMPGDHYIG  HRLVRKTEGN  ITEQVEDAVA  HSEASMDELY  K                        881

SEQ ID NO: 104              moltype = AA  length = 877
FEATURE                     Location/Qualifiers
```

```
REGION                   1..877
                         note = Synthetic
source                   1..877
                         mol_type = protein
                         organism = synthetic construct
SEQUENCE: 104
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMPEAA ISRLITYLRI LEELEAQGVH RTASEQLGEL   480
AQVTAFQVDE DLSYFGSYGT DGVGYTVPVL KRELRHILGL NRKWGLCIVG MGRLGSALAD   540
WPGFGESFEL RGFFDVDPGM VGRPVRGGVI EHVDLLPQRV PGRIEIALLT VPREAAQKAA   600
DLLVAAGIKG ILNFAPVVLE VPKEVAVENV DFLAGLTRLS FAILNPKWRE EMSVIKPEMK   660
MRYYMDGSVN GHEFTIEGEG TGRPYEGHQE MTLRVTMAEG GPMPFAFDLV SHVFCYGHRV   720
FTKYPEEIPD YFKQAFPEGL SWERSLEFED GGSASVSAHI SLRGNTFYHK SKFTGVNFPA   780
DGPIMQNQSV DWEPSTEKIT ASDGVLKGDV TMYLKLEGGG NHKCQFKTTY KAAKEILEMP   840
GDHYIGHRLV RKTEGNITEQ VEDAVAHSEA SMDELYK                            877

SEQ ID NO: 105           moltype = AA  length = 869
FEATURE                  Location/Qualifiers
REGION                   1..869
                         note = Synthetic
source                   1..869
                         mol_type = protein
                         organism = synthetic construct
SEQUENCE: 105
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWGMVSK GEELFTGVVP ILVELDGDVN GHKFSVSGEG   240
EGDATYGKLT LKFICTTGKL PVPWPTLVTT LTYGVQCFSR YPDHMKQHDF FKSAMPEGYV   300
QERTIFFKDD GNYKTRAEVK FEGDTLVNRI ELKGIDFKED GNILGHKLEY NYNSHNVYIM   360
ADKQKNGIKV NFKIRHNIED GSVQLADHYQ QNTPIGDGPV LLPDNHYLST QSKLSKDPNE   420
KRDHMVLLEF VTAAGITLGE AAISRLITYL RILEELEAQG VHRTASEQLG ELAQVTAFQV   480
DEDLSYFGSY GTDGVGYTVP VLKRELRHIL GLNRKWGLCI VGMGRLGSAL ADWPGFGESF   540
ELRGFFDVDP GMVGRPVRGG VIEHVDLLPQ RVPGRIEIAL LTVPREAAQK AADLLVAAGI   600
KGILNFAPVV LEVPKEVAVE NVDFLAGLTR LSFAILNPKW REEMSVIKPE MKMRYYMDGS   660
VNGHEFTIEG EGTGRPYEGH QEMTLRVTMA EGGPMPFAFD LVSHVFCYGH RVFTKYPEEI   720
PDYFKQAFPE GLSWERSLEF EDGGSASVSA HISLRGNTFY HKSKFTGVNF PADGPIMQNQ   780
SVDWEPSTEK ITASDGVLKG DVTMYLKLEG GGNHKCQFKT TYKAAKEILE MPGDHYIGHR   840
LVRKTEGNIT EQVEDAVAHS EASMDELYK                                    869

SEQ ID NO: 106           moltype = AA  length = 889
FEATURE                  Location/Qualifiers
REGION                   1..889
                         note = Synthetic
source                   1..889
                         mol_type = protein
                         organism = synthetic construct
SEQUENCE: 106
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDELY KTKVPEAAIS RLITYLRILE ELEAQGVHRT   480
ASEQLGELAQ VTAFQVDEDL SYFGSYGTDG VGYTVPVLKR ELRHILGLNR KWGLCIVGMG   540
RLGSALADWP GFGESFELRG FFDVDPGMVG RPVRGGVIEH VDLLPQRVPG RIEIALLTVP   600
REAAQKAADL LVAAGIKGIL NFAPVVLEVP KEVAVENVDF LAGLTRLSFA ILNPKWREEM   660
MGMVSIKPE MKMRYYMDGS VNGHEFTIEG EGTGRPYEGH QEMTLRVTMA EGGPMPFAFD   720
LVSHVFCYGH RVFTKYPEEI PDYFKQAFPE GLSWERSLEF EDGGSASVSA HISLRGNTFY   780
HKSKFTGVNF PADGPIMQNQ SVDWEPSTEK ITASDGVLKG DVTMYLKLEG GGNHKCQFKT   840
TYKAAKEILE MPGDHYIGHR LVRKTEGNIT EQVEDAVAHS EASMDELYK               889

SEQ ID NO: 107           moltype = AA  length = 882
FEATURE                  Location/Qualifiers
REGION                   1..882
                         note = Synthetic
source                   1..882
                         mol_type = protein
                         organism = synthetic construct
SEQUENCE: 107
MKVPEAAISR LITYLRILEE LEAQGVHRTA SEQLGELAQV TAFQVDKDLS YFGSYGTDGV    60
```

```
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDEPE AAISRLITYL RILEELEAQG VHRTASEQLG    480
ELAQVTAFQV DEDLSYFGSY GTDGVGYTVP VLKRELRHIL GLNRKWGLCI VGMGRLGSAL    540
ADWPGFGESF ELRGFFDVDP GMVGRPVRGG VIEHVDLLPQ RVPGRIEIAL LTVPREAAQK    600
AADLLVAAGI KGILNFAPVV LEVPKEVAVE NVDFLAGLTR LSFAILNPKW REEMMGVSVI    660
KPEMKMRYYM DGSVNGHEFT IEGEGTGRPY EGHQEMTLRV TMAEGGPMPF AFDLVSHVFC    720
YGHRVFTKYP EEIPDYFKQA FPEGLSWERS LEFEDGGSAS VSAHISLRGN TFYHKSKFTG    780
VNFPADGPIM QNQSVDWEPS TEKITASDGV LKGDVTMYLK LEGGGNHKCQ FKTTYKAAKE    840
ILEMPGDHYI GHRLVRKTEG NITEQVEDAV AHSEASMDEL YK                      882

SEQ ID NO: 108         moltype = AA  length = 881
FEATURE                Location/Qualifiers
REGION                 1..881
                       note = Synthetic
source                 1..881
                       mol_type = protein
                       organism = synthetic construct
SEQUENCE: 108
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD    540
WPGFGESFEL RGFFDVDPGM VGRPVRGGVI EHVDLLPQRV PGRIEIALLT VPREAAQKAA    600
DLLVAAGIKG ILNFAPVVLE VPKEVAVENV DFLAGLTRLS FAILNPKWRE EMMGVSVIK     660
PEMKMRYYMD GSVNGHEFTI EGEGTGRPYE GHQEMTLRVT MAEGGPMPFA FDLVSHVFCY    720
GHRVFTKYPE EIPDYFKQAF PEGLSWERSL EFEDGGSASV SAHISLRGNT FYHKSKFTGV    780
NFPADGPIMQ NQSVDWEPST EKITASDGVL KGDVTMYLKL EGGGNHKCQF KTTYKAAKEI    840
LEMPGDHYIG HRLVRKTEGN ITEQVEDAVA HSEASMDELY K                       881

SEQ ID NO: 109         moltype = AA  length = 881
FEATURE                Location/Qualifiers
REGION                 1..881
                       note = Synthetic
source                 1..881
                       mol_type = protein
                       organism = synthetic construct
SEQUENCE: 109
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGH GMVSKGEELF TGVVPILVEL DGDVNGHKFS    240
VSGEGEGDAT YGKLTLKFIC TTGKLPVPWP TLVTTLTYGV QCFSRYPDHM KQHDFFKSAM    300
PEGYVQERTI FFKDDGNYKT RAEVKFEGDT LVNRIELKGI DFKEDGNILG HKLEYNYNSH    360
NVYIMADKQK NGIKVNFKIR HNIEDGSVQL ADHYQQNTPI GDGPVLLPDN HYLSTQSKLS    420
KDPNEKRDHM VLLEFVTAAG ITLGMDPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD    540
WPGFGESFEL RGFFDVDPGM VGRPVRGGVI EHVDLLPQRV PGRIEIALLT VPREAAQKAA    600
DLLVAAGIKG ILNFAPVVLE VPKEVAVENV DFLAGLTRLS FAILNPKWRE EMMGVSVIK     660
PEMKMRYYMD GSVNGHEFTI EGEGTGRPYE GHQEMTLRVT MAEGGPMPFA FDLVSHVFCY    720
GHRVFTKYPE EIPDYFKQAF PEGLSWERSL EFEDGGSASV SAHISLRGNT FYHKSKFTGV    780
NFPADGPIMQ NQSVDWEPST EKITASDGVL KGDVTMYLKL EGGGNHKCQF KTTYKAAKEI    840
LEMPGDHYIG HRLVRKTEGN ITEQVEDAVA HSEASMDELY K                       881

SEQ ID NO: 110         moltype = AA  length = 859
FEATURE                Location/Qualifiers
source                 1..859
                       mol_type = protein
                       organism = synthetic construct
SEQUENCE: 110
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLGM EAAISRLITY LRILEELEAQ GVHRTASEQL GELAQVTAFQ VDEDLSYFGS    480
YGTDGVGYTV PVLKRELRHI LGLNRKWGLC IVGMGRLGSA LADWPGFGES FELRGFFDVD    540
PGMVGRPVRG GVIEHVDLLP QRVPGRIEIA LLTVPREAAQ KAADLLVAAG IKGILNFAPV    600
```

```
VLEVPKEVAV ENVDFLAGLT RLSFAILNPK WREESVIKPE MKMRYYMDGS VNGHEFTIEG  660
EGTGRPYEGH QEMTLRVTMA EGGPMPFAFD LVSHVFCYGH RVFTKYPEEI PDYFKQAFPE  720
GLSWERSLEF EDGGSASVSA HISLRGNTFY HKSKFTGVNF PADGPIMQNQ SVDWEPSTEK  780
ITASDGVLKG DVTMYLKLEG GGNHKCQFKT TYKAAKEILE MPGDHYIGHR LVRKTEGNIT  840
EQVEDAVAHS EASMDELYK                                               859

SEQ ID NO: 111          moltype = AA  length = 879
FEATURE                 Location/Qualifiers
REGION                  1..879
                        note = Synthetic
source                  1..879
                        mol_type = protein
                        organism = synthetic construct
SEQUENCE: 111
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
VYIMADKQKN GIKVNFKIRH NIEDGSVQLA DHYQQNTPIG DGPVLLPDNH YLSTQSKLSK  420
DPNEKRDHMV LLEFVTAAGI TLGMDEPEAA ISRLITYLRI LEELEAQGVH RTASEQLGEL  480
AQVTAFQVDE DLSYFGSYGT DGVGYTVPVL KRELRHILGL NRKWGLCIVG MGRLGSALAD  540
WPGFGESFEL RGFFDVDPGM VGRPVRGGVI EHVDLLPQRV PGRIEIALLT VPREAAQKAA  600
DLLVAAGIKG ILNFAPVVLE VPKEVAVENV DFLAGLTRLS FAILNPKWRE EMMVSVIKPE  660
MKMRYYMDGS VNGHEFTIEG EGTGRPYEGH QEMTLRVTMA EGGPMPFAFD LVSHVFCYGH  720
RVFTKYPEEI PDYFKQAFPE GLSWERSLEF EDGGSASVSA HISLRGNTFY HKSKFTGVNF  780
PADGPIMQNQ SVDWEPSTEK ITASDGVLKG DVTMYLKLEG GGNHKCQFKT TYKAAKEILE  840
MPGDHYIGHR LVRKTEGNIT EQVEDAVAHS EASMDELYK                         879

SEQ ID NO: 112          moltype = AA  length = 880
FEATURE                 Location/Qualifiers
REGION                  1..880
                        note = Synthetic
source                  1..880
                        mol_type = protein
                        organism = synthetic construct
SEQUENCE: 112
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLGMEAAI SRLITYLRIL EELEAQGVHR TASEQLGELA  480
QVTAFQVDED LSYFGSYGTD GVGYTVPVLK RELRHILGLN RKWGLCIVGM GRLGSALADW  540
PGFGESFELR GFFDVDPGMV GRPVRGGVIE HVDLLPQRVP GRIEIALLTV PREAAQKAAD  600
LLVAAGIKGI LNFAPVVLEV PKEVAVENVD FLAGLTRLSF AILNPKWREE MMGMVSIKPE  660
MKMRYYMDGS VNGHEFTIEG EGTGRPYEGH QEMTLRVTMA EGGPMPFAFD LVSHVFCYGH  720
RVFTKYPEEI PDYFKQAFPE GLSWERSLEF EDGGSASVSA HISLRGNTFY HKSKFTGVNF  780
PADGPIMQNQ SVDWEPSTEK ITASDGVLKG DVTMYLKLEG GGNHKCQFKT TYKAAKEILE  840
MPGDHYIGHR LVRKTEGNIT EQVEDAVAHS EASMDELYK                         880

SEQ ID NO: 113          moltype = AA  length = 881
FEATURE                 Location/Qualifiers
REGION                  1..881
                        note = Synthetic
source                  1..881
                        mol_type = protein
                        organism = synthetic construct
SEQUENCE: 113
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLGMDPEA AISRLITYLR ILEELEAQGV HRTASEQLGE  480
LAQVTAFQVD EDLSYFGSYG TDGVGYTVPV LKRELRHILG LNRKWGLCIV GMGRLGSALA  540
DWPGFGESFE LRGFFDVDPG MVGRPVRGGV IEHVDLLPQR VPGRIEIALL TVPREAAQKA  600
ADLLVAAGIK GILNFAPVVL EVPKEVAVEN VDFLAGLTRL SFAILNPKWR EEMMGVSVIK  660
PEMKMRYYMD GSVNGHEFTI EGEGTGRPYE GHQEMTLRVT MAEGGPMPFA FDLVSHVFCY  720
GHRVFTKYPE EIPDYFKQAF PEGLSWERSL EFEDGGSASV SAHISLRGNT FYHKSKFTGV  780
NFPADGPIMQ NQSVDWEPST EKITASDGVL KGDVTMYLKL EGGGNHKCQF KTTYKAAKEI  840
LEMPGDHYIG HRLVRKTEGN ITEQVEDAVA HSEASMDELY K                      881

SEQ ID NO: 114          moltype = AA  length = 875
```

```
FEATURE                 Location/Qualifiers
REGION                  1..875
                        note = Synthetic
source                  1..875
                        mol_type = protein
                        organism = synthetic construct
SEQUENCE: 114
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPTEELFT GVVPILVELD GDVNGHKFSV SGEGEGDATY      240
GKLTLKFICT TGKLPVPWPT LVTTLTYGVQ CFSRYPDHMK QHDFFKSAMP EGYVQERTIF     300
FKDDGNYKTR AEVKFEGDTL VNRIELKGID FKEDGNILGH KLEYNYNSHN VYIMADKQKN     360
GIKVNFKIRH NIEDGSVQLA DHYQQNTPIG DGPVLLPDNH YLSTQSKLSK DPNEKRDHMV     420
LLEFVTAAGI TLGMDELVPE AAISRLITYL RILEELEAQG VHRTASEQLG ELAQVTAFQV     480
DEDLSYFGSY GTDGVGYTVP VLKRELRHIL GLNRKWGLCI VGMGRLGSAL ADWPGFGESF     540
ELRGFFDVDP GMVGRPVRGG VIEHVDLLPQ RVPGRIEIAL LTVPREAAQK AADLLVAAGI     600
KGILNFAPVV LEVPKEVAVE NVDFLAGLTR LSFAILNPKW REEMMGGSMV SVIKPEMKMR     660
YYMDGSVNGH EFTIEGEGTG RPYEGHQEMT LRVTMAEGGP MPFAFDLVSH VFCYGHRVFT     720
KYPEEIPDYF KQAFPEGLSW ERSLEFEDGG SASVSAHISL RGNTFYHKSK FTGVNFPADG     780
PIMQNQSVDW EPSTEKITAS DGVLKGDVTM YLKLEGGGNH KCQFKTTYKA AKEILEMPGD     840
HYIGHRLVRK TEGNITEQVE DAVAHSEASM DELYK                                875

SEQ ID NO: 115          moltype = AA  length = 877
FEATURE                 Location/Qualifiers
REGION                  1..877
                        note = Synthetic
source                  1..877
                        mol_type = protein
                        organism = synthetic construct
SEQUENCE: 115
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPTWSAHGM VSKGEELFTG VVPILVELDG DVNGHKFSVS     240
GEGEGDATYG KLTLKFICTT GKLPVPWPTL VTTLTYGVQC FSRYPDHMKQ HDFFKSAMPE     300
GYVQERTIFF KDDGNYKTRA EVKFEGDTLV NRIELKGIDF KEDGNILGHK LEYNYNSHNV     360
YIMADKQKNG IKVNFKIRHN IEDGSVQLAD HYQQNTPIGD GPVLLPDNHY LSTQSKLSKD     420
PNEKRDHMVL LEFVTAAGIT LGEAAISRLI TYLRILEELE AQGVHRTASE QLGELAQVTA     480
FQVDEDLSYF GSYGTDGVGY TVPVLKRELR HILGLNRKWG LCIVGMGRLG SALADWPGFG     540
ESFELRGFFD VDPGMVGRPV RGGVIEHVDL LPQRVPGRIE IALLTVPREA AQKAADLLVA     600
AGIKGILNFA PVVLEVPKEV AVENVDFLAG LTRLSFAILN PKWREEMMGS MVSVIKPEMK     660
MRYYMDGSVN GHEFTIEGEG TGRPYEGHQE MTLRVTMAEG GPMPFAFDLV SHVFCYGHRV     720
FTKYPEEIPD YFKQAFPEGL SWERSLEFED GGSASVSAHI SLRGNTFYHK SKFTGVNFPA     780
DGPIMQNQSV DWEPSTEKIT ASDGVLKGDV TMYLKLEGGG NHKCQFKTTY KAAKEILEMP     840
GDHYIGHRLV RKTEGNITEQ VEDAVAHSEA SMDELYK                              877

SEQ ID NO: 116          moltype = AA  length = 878
FEATURE                 Location/Qualifiers
REGION                  1..878
                        note = Synthetic
source                  1..878
                        mol_type = protein
                        organism = synthetic construct
SEQUENCE: 116
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPTWSAAGG HGMVSKGEEL FTGVVPILVE LDGDVNGHKF     240
SVSGEGEGDA TYGKLTLKFI CTTGKLPVPW PTLVTTLTYG VQCFSRYPDH MKQHDFFKSA     300
MPEGYVQERT IFFKDDGNYK TRAEVKFEGD TLVNRIELKG IDFKEDGNIL GHKLEYNYNS     360
HNVYIMADKQ KNGIKVNFKI RHNIEDGSVQ LADHYQQNTP IGDGPVLLPD NHYLSTQSKL     420
SKDPNEKRDH MVLLEFVTAA GITLGMDPEA AISRLITYLR ILEELEAQGV HRTASEQLGE     480
LAQVTAFQVD EDLSYFGSYG TDGVGYTVPV LKRELRHILG LNRKWGLCIV GMGRLGSALA     540
DWPGFGESFE LRGFFDVDPG MVGRPVRGGV IEHVDLLPQR VPGRIEIALL TVPREAAQKA     600
ADLLVAAGIK GILNFAPVVL EVPKEVAVEN VDFLAGLTRL SFAILNPKWR EEMSVIKPEM     660
KMRYYMDGSV NGHEFTIEGE GTGRPYEGHQ EMTLRVTMAE GGPMPFAFDL VSHVFCYGHR     720
VFTKYPEEIP DYFKQAFPEG LSWERSLEFE DGGSASVSAH ISLRGNTFYH KSKFTGVNFP     780
ADGPIMQNQS VDWEPSTEKI TASDGVLKGD VTMYLKLEGG GNHKCQFKTT YKAAKEILEM     840
PGDHYIGHRL VRKTEGNITE QVEDAVAHSE ASMDELYK                             878

SEQ ID NO: 117          moltype = AA  length = 882
FEATURE                 Location/Qualifiers
REGION                  1..882
                        note = Synthetic
source                  1..882
                        mol_type = protein
                        organism = synthetic construct
SEQUENCE: 117
```

```
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAAGG HGMVSKGEEL FTGVVPILVE LDGDVNGHKF  240
SVSGEGEGDA TYGKLTLKFI CTTGKLPVPW PTLVTTLTYG VQCFSRYPDH MKQHDFFKSA  300
MPEGYVQERT IFFKDDGNYK TRAEVKFEGD TLVNRIELKG IDFKEDGNIL GHKLEYNYNS  360
HNVYIMADKQ KNGIKVNFKI RHNIEDGSVQ LADHYQQNTP IGDGPVLLPD NHYLSTQSKL  420
SKDPNEKRDH MVLLEFVTAA GITLGMDPEA AISRLITYLR ILEELEAQGV HRTASEQLGE  480
LAQVTAFQVD EDLSYFGSYG TDGVGYTVPV LKRELRHILG LNRKWGLCIV GMGRLGSALA  540
DWPGFGESFE LRGFFDVDPG MVGRPVRGGV IEHVDLLPQR VPGRIEIALL TVPREAAQKA  600
ADLLVAAGIK GILNFAPVVL EVPKEVAVEN VDFLAGLTRL SFAILNPKWR EEMMGMVSVI  660
KPEMKMRYYM DGSVNGHEFT IEGEGTGRPY EGHQEMTLRV TMAEGGPMPF AFDLVSHVFC  720
YGHRVFTKYP EEIPDYFKQA FPEGLSWERS LEFEDGGSAS VSAHISLRGN TFYHKSKFTG  780
VNFPADGPIM QNQSVDWEPS TEKITASDGV LKGDVTMYLK LEGGGNHKCQ FKTTYKAAKE  840
ILEMPGDHYI GHRLVRKTEG NITEQVEDAV AHSEASMDEL YK                    882

SEQ ID NO: 118          moltype = AA  length = 879
FEATURE                 Location/Qualifiers
REGION                  1..879
                        note = Synthetic
source                  1..879
                        mol_type = protein
                        organism = synthetic construct
SEQUENCE: 118
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
VYIMADKQKN GIKVNFKIRH NIEDGSVQLA DHYQQNTPIG DGPVLLPDNH YLSTQSKLSK  420
DPNEKRDHMV LLEFVTAAGI TLGMPEAAIS RLITYLRILE ELEAQGVHRT ASEQLGELAQ  480
VTAFQVDEDL SYFGSYGTDG VGYTVPVLKR ELRHILGLNR KWGLCIVGMG RLGSALADWP  540
GFGESFELRG FFDVDPGMVG RPVRGGVIEH VDLLPQRVPG RIEIALLTVP REAAQKAADL  600
LVAAGIKGIL NFAPVVLEVP KEVAVENVDF LAGLTRLSFA ILNPKWREEM MGMVSVIKPE  660
MKMRYYMDGS VNGHEFTIEG EGTGRPYEGH QEMTLRVTMA EGGPMPFAFD LVSHVFCYGH  720
RVFTKYPEEI PDYFKQAFPE GLSWERSLEF EDGGSASVSA HISLRGNTFY HKSKFTGVNF  780
PADGPIMQNQ SVDWEPSTEK ITASDGVLKG DVTMYLKLEG GGNHKCQFKT TYKAAKEILE  840
MPGDHYIGHR LVRKTEGNIT EQVEDAVAHS EASMDELYK                         879

SEQ ID NO: 119          moltype = AA  length = 883
FEATURE                 Location/Qualifiers
REGION                  1..883
                        note = Synthetic
source                  1..883
                        mol_type = protein
                        organism = synthetic construct
SEQUENCE: 119
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
VYIMADKQKN GIKVNFKIRH NIEDGSVQLA DHYQQNTPIG DGPVLLPDNH YLSTQSKLSK  420
DPNEKRDHMV LLEFVTAAGI TLGMDEPEAA ISRLITYLRI LEELEAQGVH RTASEQLGEL  480
AQVTAFQVDE DLSYFGSYGT DGVGYTVPVL KRELRHILGL NRKWGLCIVG MGRLGSALAD  540
WPGFGESFEL RGFFDVDPGM VGRPVRGGVI EHVDLLPQRV PGRIEIALLT VPREAAQKAA  600
DLLVAAGIKG ILNFAPVVLE VPKEVAVENV DFLAGLTRLS FAILNPKWRE EMMGGSMVSV  660
IKPEMKMRYY MDGSVNGHEF TIEGEGTGRP YEGHQEMTLR VTMAEGGPMP FAFDLVSHVF  720
CYGHRVFTKY PEEIPDYFKQ AFPEGLSWER SLEFEDGGSA SVSAHISLRG NTFYHKSKFT  780
GVNFPADGPI MQNQSVDWEP STEKITASDG VLKGDVTMYL KLEGGGNHKC QFKTTYKAAK  840
EILEMPGDHY IGHRLVRKTE GNITEQVEDA VAHSEASMDE LYK                    883

SEQ ID NO: 120          moltype = AA  length = 875
FEATURE                 Location/Qualifiers
REGION                  1..875
                        note = Synthetic
source                  1..875
                        mol_type = protein
                        organism = synthetic construct
SEQUENCE: 120
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
VYIMADKQKN GIKVNFKIRH NIEDGSVQLA DHYQQNTPIG DGPVLLPDNH YLSTQSKLSK  420
```

```
DPNEKRDHMV LLEFVTAAGI TLGMEAAISR LITYLRILEE LEAQGVHRTA SEQLGELAQV    480
TAFQVDEDLS YFGSYGTDGV GYTVPVLKRE LRHILGLNRK WGLCIVGMGR LGSALADWPG    540
FGESFELRGF FDVDPGMVGR PVRGGVIEHV DLLPQRVPGR IEIALLTVPR EAAQKAADLL    600
VAAGIKGILN FAPVVLEVPK EVAVENVDFL AGLTRLSFAI LNPKWREEMM SVIKPEMKMR    660
YYMDGSVNGH EFTIEGEGTG RPYEGHQEMT LRVTMAEGGP MPFAFDLVSH VFCYGHRVFT    720
KYPEEIPDYF KQAFPEGLSW ERSLEFEDGG SASVSAHISL RGNTFYHKSK FTGVNFPADG    780
PIMQNQSVDW EPSTEKITAS DGVLKGDVTM YLKLEGGGNH KCQFKTTYKA AKEILEMPGD    840
HYIGHRLVRK TEGNITEQVE DAVAHSEASM DELYK                               875

SEQ ID NO: 121          moltype = AA   length = 873
FEATURE                 Location/Qualifiers
REGION                  1..873
                        note = Synthetic
source                  1..873
                        mol_type = protein
                        organism = synthetic construct
SEQUENCE: 121
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAGHG MVSKGEELFT GVVPILVELD GDVNGHKFSV    240
SGEGEGDATY GKLTLKFICT TGKLPVPWPT LVTTLTYGVQ CFSRYPDHMK QHDFFKSAMP    300
EGYVQERTIF FKDDGNYKTR AEVKFEGDTL VNRIELKGID FKEDGNILGH KLEYNYNSHN    360
VYIMADKQKN GIKVNFKIRH NIEDGSVQLA DHYQQNTPIG DGPVLLPDNH YLSTQSKLSK    420
DPNEKRDHMV LLEFVTAAGI TLGMEAAISR LITYLRILEE LEAQGVHRTA SEQLGELAQV    480
TAFQVDEDLS YFGSYGTDGV GYTVPVLKRE LRHILGLNRK WGLCIVGMGR LGSALADWPG    540
FGESFELRGF FDVDPGMVGR PVRGGVIEHV DLLPQRVPGR IEIALLTVPR EAAQKAADLL    600
VAAGIKGILN FAPVVLEVPK EVAVENVDFL AGLTRLSFAI LNPKWREESV IKPEMKMRYY    660
MDGSVNGHEF TIEGEGTGRP YEGHQEMTLR VTMAEGGPMP FAFDLVSHVF CYGHRVFTKY    720
PEEIPDYFKQ AFPEGLSWER SLEFEDGGSA SVSAHISLRG NTFYHKSKFT GVNFPADGPI    780
MQNQSVDWEP STEKITASDG VLKGDVTMYL KLEGGGNHKC QFKTTYKAAK EILEMPGDHY    840
IGHRLVRKTE GNITEQVEDA VAHSEASMDE LYK                                 873

SEQ ID NO: 122          moltype = AA   length = 888
FEATURE                 Location/Qualifiers
REGION                  1..888
                        note = Synthetic
source                  1..888
                        mol_type = protein
                        organism = synthetic construct
SEQUENCE: 122
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDELY KVPEAAISRL ITYLRILEEL EAQGVHRTAS    480
EQLGELAQVT AFQVDEDLSY FGSYGTDGVG YTVPVLKREL RHILGLNRKW GLCIVGMGRL    540
GSALADWPGF GESFELRGFF DVDPGMVGRP VRGGVIEHVD LLPQRVPGRI EIALLTVPRE    600
AAQKAADLLV AAGIKGILNF APVVLEVPKE VAVENVDFLA GLTRLSFAIL NPKWREEMMG    660
SMVSVIKPEM KMRYYMDGSV NGHEFTIEGE GTGRPYEGHQ EMTLRVTMAE GGPMPFAFDL    720
VSHVFCYGHR VFTKYPEEIP DYFKQAFPEG LSWERSLEFE DGGSASVSAH ISLRGNTFYH    780
KSKFTGVNFP ADGPIMQNQS VDWEPSTEKI TASDGVLKGD VTMYLKLEGG GNHKCQFKTT    840
YKAAKEILEM PGDHYIGHRL VRKTEGNITE QVEDAVAHSE ASMDELYK                 888

SEQ ID NO: 123          moltype = AA   length = 856
FEATURE                 Location/Qualifiers
REGION                  1..856
                        note = Synthetic
source                  1..856
                        mol_type = protein
                        organism = synthetic construct
SEQUENCE: 123
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLGE AAISRLITYL RILEELEAQG VHRTASEQLG ELAQVTAFQV DEDLSYFGSY    480
GTDGVGYTVP VLKRELRHIL GLNRKWGLCI VGMGRLGSAL ADWPGFGESF ELRGFFDVDP    540
GMVGRPVRGG VIEHVDLLPQ RVPGRIEIAL LTVPREAAQK AADLLVAAGI KGILNFAPVV    600
LEVPKEVAVE NVDFLAGLTR LSFAILNPKW REVIKPEMKM RYYMDGSVNG HEFTIEGEGT    660
GRPYEGHQEM TLRVTMAEGG PMPFAFDLVS HVFCYGHRVF TKYPEEIPDY FKQAFPEGLS    720
WERSLEFEDG GSASVSAHIS LRGNTFYHKS KFTGVNFPAD GPIMQNQSVD WEPSTEKITA    780
SDGVLKGDVT MYLKLEGGGN HKCQFKTTYK AAKEILEMPG DHYIGHRLVR KTEGNITEQV    840
```

-continued

```
EDAVAHSEAS MDELYK                                                               856

SEQ ID NO: 124          moltype = AA  length = 876
FEATURE                 Location/Qualifiers
REGION                  1..876
                        note = Synthetic
source                  1..876
                        mol_type = protein
                        organism = synthetic construct
SEQUENCE: 124
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPTWSAGHG MVSKGEELFT GVVPILVELD GDVNGHKFSV  240
SGEGEGDATY GKLTLKFICT TGKLPVPWPT LVTTLTYGVQ CFSRYPDHMK QHDFFKSAMP  300
EGYVQERTIF FKDDGNYKTR AEVKFEGDTL VNRIELKGID FKEDGNILGH KLEYNYNSHN  360
VYIMADKQKN GIKVNFKIRH NIEDGSVQLA DHYQQNTPIG DGPVLLPDNH YLSTQSKLSK  420
DPNEKRDHMV LLEFVTAAGI TLGMEAAISR LITYLRILEE LEAQGVHRTA SEQLGELAQV  480
TAFQVDEDLS YFGSYGTDGV GYTVPVLKRE LRHILGLNRK WGLCIVGMGR LGSALADWPG  540
FGESFELRGF FDVDPGMVGR PVRGGVIEHV DLLPQRVPGR IEIALLTVPR EAAQKAADLL  600
VAAGIKGILN FAPVVLEVPK EVAVENVDFL AGLTRLSFAI LNPKWREEMM VSVIKPEMKM  660
RYYMDGSVNG HEFTIEGEGT GRPYEGHQEM TLRVTMAEGG PMPFAFDLVS HVFCYGHRVF  720
TKYPEEIPDY FKQAFPEGLS WERSLEFEDG GSASVSAHIS LRGNTFYHKS KFTGVNFPAD  780
GPIMQNQSVD WEPSTEKITA SDGVLKGDVT MYLKLEGGGN HKCQFKTTYK AAKEILEMPG  840
DHYIGHRLVR KTEGNITEQV EDAVAHSEAS MDELYK                           876

SEQ ID NO: 125          moltype = AA  length = 867
FEATURE                 Location/Qualifiers
REGION                  1..867
                        note = Synthetic
source                  1..867
                        mol_type = protein
                        organism = synthetic construct
SEQUENCE: 125
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPLFTGVVP ILVELDGDVN GHKFSVSGEG EGDATYGKLT  240
LKFICTTGKL PVPWPTLVTT LTYGVQCFSR YPDHMKQHDF FKSAMPEGYV QERTIFFKDD  300
GNYKTRAEVK FEGDTLVNRI ELKGIDFKED GNILGHKLEY NYNSHNVYIM ADKQNGIKV   360
NFKIRHNIED GSVQLADHYQ QNTPIGDGPV LLPDNHYLST QSKLSKDPNE KRDHMVLLEF  420
VTAAGITLGM DELYKTKVPE AAISRLITYL RILEELEAQG VHRTASEQLG ELAQVTAFQV  480
DEDLSYFGSY GTDGVGYTVP VLKRELRHIL GLNRKWGLCI VGMRLGSAL ADWPGFGESF  540
ELRGFFDVDP GMVGRPVRGG VIEHVDLLPQ RVPGRIEIAL LTVPREAAQK AADLLVAAGI  600
KGILNFAPVV LEVPKEVAVE NVDFLAGLTR LSFAILNPKW REEVIKPEMK MRYYMDGSVN  660
GHEFTIEGEG TGRPYEGHQE MTLRVTMAEG GPMPFAFDLV SHVFCYGHRV FTKYPEEIPD  720
YFKQAFPEGL SWERSLEFED GGSASVSAHI SLRGNTFYHK SKFTGVNFPA DGPIMQNQSV  780
DWEPSTEKIT ASDGVLKGDV TMYLKLEGGG NHKCQFKTTY KAAKEILEMP GDHYIGHRLV  840
RKTEGNITEQ VEDAVAHSEA SMDELYK                                     867

SEQ ID NO: 126          moltype = AA  length = 859
FEATURE                 Location/Qualifiers
REGION                  1..859
                        note = Synthetic
source                  1..859
                        mol_type = protein
                        organism = synthetic construct
SEQUENCE: 126
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR  120
PVRGGVIEHV DLLPQRVPGR IEIALLTVPR EAAQKAADLL VAAGIKGILN FAPVVLEVPK  180
EVAVENVDIL AGLTRLSFAI LNPLFTGVVP ILVELDGDVN GHKFSVSGEG EGDATYGKLT  240
LKFICTTGKL PVPWPTLVTT LTYGVQCFSR YPDHMKQHDF FKSAMPEGYV QERTIFFKDD  300
GNYKTRAEVK FEGDTLVNRI ELKGIDFKED GNILGHKLEY NYNSHNVYIM ADKQKNGIKV  360
NFKIRHNIED GSVQLADHYQ QNTPIGDGPV LLPDNHYLST QSKLSKDPNE KRDHMVLLEF  420
VTAAGITLGM EAAISRLITY LRILEELEAQ GVHRTASEQL GELAQVTAFQ VDEDLSYFGS  480
YGTDGVGYTV PVLKRELRHI LGLNRKWGLC IVGMGRLGSA LADWPGFGES FELRGFFDVD  540
PGMVGRPVRG GVIEHVDLLP QRVPGRIEIA LLTVPREAAQ KAADLLVAAG IKGILNFAPV  600
VLEVPKEVAV ENVDFLAGLT RLSFAILNPK WREESVIKPE MKMRYYMDGS VNGHEFTIEG  660
EGTGRPYEGH QEMTLRVTMA EGGPMPFAFD LVSHVFCYGH RVFTKYPEEI PDYFKQAFPE  720
GLSWERSLEF EDGGSASVSA HISLRGNTFY HKSKFTGVNF PADGPIMQNQ SVDWEPSTEK  780
ITASDGVLKG DVTMYLKLEG GGNHKCQFKT TYKAAKEILE MPGDHYIGHR LVRKTEGNIT  840
EQVEDAVAHS EASMDELYK                                              859

SEQ ID NO: 127          moltype = AA  length = 874
FEATURE                 Location/Qualifiers
REGION                  1..874
                        note = Synthetic
source                  1..874
```

```
                              mol_type = protein
                              organism = synthetic construct
SEQUENCE: 127
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSHGMV SKGEELFTGV VPILVELDGD VNGHKFSVSG   240
EGEGDATYGK LTLKFICTTG KLPVPWPTLV TTLTYGVQCF SRYPDHMKQH DFFKSAMPEG   300
YVQERTIFFK DDGNYKTRAE VKFEGDTLVN RIELKGIDFK EDGNILGHKL EYNYNSHNVY   360
IMADKQKNGI KVNFKIRHNI EDGSVQLADH YQQNTPIGDG PVLLPDNHYL STQSKLSKDP   420
NEKRDHMVLL EFVTAAGITL GMPEAAISRL ITYLRILEEL EAQGVHRTAS EQLGELAQVT   480
AFQVDEDLSY FGSYGTDGVG YTVPVLKREL RHILGLNRKW GLCIVGMGRL GSALADWPGF   540
GESFELRGFF DVDPGMVGRP VRGGVIEHVD LLPQRVPGRI EIALLTVPRE AAQKAADLLV   600
AAGIKGILNF APVVLEVPKE VAVENVDFLA GLTRLSFAIL NPKWREEMMS VIKPEMKMRY   660
YMDGSVNGHE FTIEGEGTGR PYEGHQEMTL RVTMAEGGPM PFAFDLVSHV FCYGHRVFTK   720
YPEEIPDYFK QAFPEGLSWE RSLEFEDGGS ASVSAHISLR GNTFYHKSKF TGVNFPADGP   780
IMQNQSVDWE PSTEKITASD GVLKGDVTMY LKLEGGGNHK CQFKTTYKAA KEILEMPGDH   840
YIGHRLVRKT EGNITEQVED AVAHSEASMD ELYK                              874

SEQ ID NO: 128             moltype = AA  length = 856
FEATURE                    Location/Qualifiers
REGION                     1..856
                              note = Synthetic
source                     1..856
                              mol_type = protein
                              organism = synthetic construct
SEQUENCE: 128
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPLFTGVVP ILVELDGDVN GHKFSVSGEG EGDATYGKLT   240
LKFICTTGKL PVPWPTLVTT LTYGVQCFSR YPDHMKQHDF FKSAMPEGYV QERTIFFKDD   300
GNYKTRAEVK FEGDTLVNRI ELKGIDFKED GNILGHKLEY NYNSHNVYIM ADKQKNGIKV   360
NFKIRHNIED GSVQLADHYQ QNTPIGDGPV LLPDNHYLST QSKLSKDPNE KRDHMVLLEF   420
VTAAGITLGE AAISRLITYL RILEELEAQG VHRTASEQLG ELAQVTAFQV DEDLSYFGSY   480
GTDGVGYTVP VLKRELRHIL GLNRKWGLCI VGMGRLGSAL ADWPGFGESF ELRGFFDVDP   540
GMVGRPVRGG VIEHVDLLPQ RVPGRIEIAL LTVPREAAQK AADLLVAAGI KGILNFAPVV   600
LEVPKEVAVE NVDFLAGLTR LSFAILNPKW REVIKPEMKM RYYMDGSVNG HEFTIEGEGT   660
GRPYEGHQEM TLRVTMAEGG PMPFAFDLVS HVFCYGHRVF TKYPEEIPDY FKQAFPEGLS   720
WERSLEFEDG GSASVSAHIS LRGNTFYHKS KFTGVNFPAD GPIMQNQSVD WEPSTEKITA   780
SDGVLKGDVT MYLKLEGGGN HKCQFKTTYK AAKEILEMPG DHYIGHRLVR KTEGNITEQV   840
EDAVAHSEAS MDELYK                                                  856

SEQ ID NO: 129             moltype = AA  length = 882
FEATURE                    Location/Qualifiers
REGION                     1..882
                              note = Synthetic
source                     1..882
                              mol_type = protein
                              organism = synthetic construct
SEQUENCE: 129
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDEPE AAISRLITYL RILEELEAQG VHRTASEQLG   480
ELAQVTAFQV DEDLSYFGSY GTDGVGYTVP VLKRELRHIL GLNRKWGLCI VGMGRLGSAL   540
ADWPGFGESF ELRGFFDVDP GMVGRPVRGG VIEHVDLLPQ RVPGRIEIAL LTVPREAAQK   600
AADLLVAAGI KGILNFAPVV LEVPKEVAVE NVDFLAGLTR LSFAILNPKW REEMMGVSVI   660
KPEMKMRYYM DGSVNGHEFT IEGEGTGRPY EGHQEMTLRV TMAEGGPMPF AFDLVSHVFC   720
YGHRVFTKYP EEIPDYFKQA FPEGLSWERS LEFEDGGSAS VSAHISLRGN TFYHKSKFTG   780
VNFPADGPIM QNQSVDWEPS TEKITASDGV LKGDVTMYLK LEGGGNHKCQ FKTTYKAAKE   840
ILEMPGDHYI GHRLVRKTEG NITEQVEDAV AHSEASMDEL YK                     882

SEQ ID NO: 130             moltype = AA  length = 865
FEATURE                    Location/Qualifiers
REGION                     1..865
                              note = Synthetic
source                     1..865
                              mol_type = protein
                              organism = synthetic construct
SEQUENCE: 130
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWVSKGE ELFTGVVPIL VELDGDVNGH KFSVSGEGEG   240
```

```
DATYGKLTLK FICTTGKLPV PWPTLVTTLT YGVQCFSRYP DHMKQHDFFK SAMPEGYVQE   300
RTIFFKDDGN YKTRAEVKFE GDTLVNRIEL KGIDFKEDGN ILGHKLEYNY NSHNVYIMAD   360
KQKNGIKVNF KIRHNIEDGS VQLADHYQQN TPIGDGPVLL PDNHYLSTQS KLSKDPNEKR   420
DHMVLLEFVT AAGITLAAIS RLITYLRILE ELEAQGVHRT ASEQLGELAQ VTAFQVDEDL   480
SYFGSYGTDG VGYTVPVLKR ELRHILGLNR KWGLCIVGMG RLGSALADWP GFGESFELRG   540
FFDVDPGMVG RPVRGGVIEH VDLLPQRVPG RIEIALLTVP REAAQKAADL LVAAGIKGIL   600
NFAPVVLEVP KEVAVENVDF LAGLTRLSFA ILNPKWREEM SVIKPEMKMR YYMDGSVNGH   660
EFTIEGEGTG RPYEGHQEMT LRVTMAEGGP MPFAFDLVSH VFCYGHRVFT KYPEEIPDYF   720
KQAFPEGLSW ERSLEFEDGG SASVSAHISL RGNTFYHKSK FTGVNFPADG PIMQNQSVDW   780
EPSTEKITAS DGVLKGDVTM YLKLEGGGNH KCQFKTTYKA AKEILEMPGD HYIGHRLVRK   840
TEGNITEQVE DAVAHSEASM DELYK                                        865

SEQ ID NO: 131           moltype = AA  length = 881
FEATURE                  Location/Qualifiers
REGION                   1..881
                         note = Synthetic
source                   1..881
                         mol_type = protein
                         organism = synthetic construct
SEQUENCE: 131
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGMDPEA AISRLITYLR ILEELEAQGV HRTASEQLGE   480
LAQVTAFQVD EDLSYFGSYG TDGVGYTVPV LKRELRHILG LNRKWGLCIV GMGRLGSALA   540
DWPGFGESFE LRGFFDVDPG MVGRPVRGGV IEHVDLLPQR VPGRIEIALL TVPREAAQKA   600
ADLLVAAGIK GILNFAPVVL EVPKEVAVEN VDFLAGLTRL SFAILNPKWR EEMMGVSVIK   660
PEMKMRYYMD GSVNGHEFTI EGEGTGRPYE GHQEMTLRVT MAEGGPMPFA FDLVSHVFCY   720
GHRVFTKYPE EIPDYFKQAF PEGLSWERSL EFEDGGSASV SAHISLRGNT FYHKSKFTGV   780
NFPADGPIMQ NQSVDWEPST EKITASDGVL KGDVTMYLKL EGGGNHKCQF KTTYKAAKEI   840
LEMPGDHYIG HRLVRKTEGN ITEQVEDAVA HSEASMDELY K                      881

SEQ ID NO: 132           moltype = AA  length = 877
FEATURE                  Location/Qualifiers
REGION                   1..877
                         note = Synthetic
source                   1..877
                         mol_type = protein
                         organism = synthetic construct
SEQUENCE: 132
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAHGM VSKGEELFTG VVPILVELDG DVNGHKFSVS   240
GEGEGDATYG KLTLKFICTT GKLPVPWPTL VTTLTYGVQC FSRYPDHMKQ HDFFKSAMPE   300
GYVQERTIFF KDDGNYKTRA EVKFEGDTLV NRIELKGIDF KEDGNILGHK LEYNYNSHNV   360
YIMADKQKNG IKVNFKIRHN IEDGSVQLAD HYQQNTPIGD GPVLLPDNHY LSTQSKLSKD   420
PNEKRDHMVL LEFVTAAGIT LGEAAISRLI TYLRILEELE AQGVHRTASE QLGELAQVTA   480
FQVDEDLSYF GSYGTDGVGY TVPVLKRELR HILGLNRKWG LCIVGMGRLG SALADWPGFG   540
ESFELRGFFD VDPGMVGRPV RGGVIEHVDL LPQRVPGRIE IALLTVPREA AQKAADLLVA   600
AGIKGILNFA PVVLEVPKEV AVENVDFLAG LTRLSFAILN PKWREEMMGS MVSVIKPEMK   660
MRYYMDGSVN GHEFTIEGEG TGRPYEGHQE MTLRVTMAEG GPMPFAFDLV SHVFCYGHRV   720
FTKYPEEIPD YFKQAFPEGL SWERSLEFED GGSASVSAHI SLRGNTFYHK SKFTGVNFPA   780
DGPIMQNQSV DWEPSTEKIT ASDGVLKGDV TMYLKLEGGG NHKCQFKTTY KAAKEILEMP   840
GDHYIGHRLV RKTEGNITEQ VEDAVAHSEA SMDELYK                            877

SEQ ID NO: 133           moltype = AA  length = 865
FEATURE                  Location/Qualifiers
REGION                   1..865
                         note = Synthetic
source                   1..865
                         mol_type = protein
                         organism = synthetic construct
SEQUENCE: 133
MKVPEAAISR LITYLRILEE LEAQGVHRTA SEQLGELAQV TAFQVDKDLS YFGSYGTDGV   60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSGMVS KGEELFTGVV PILVELDGDV NGHKFSVSGE   240
GEGDATYGKL TLKFICTTGK LPVPWPTLVT TLTYGVQCFS RYPDHMKQHD FFKSAMPEGY   300
VQERTIFFKD DGNYKTRAEV KFEGDTLVNR IELKGIDFKE DGNILGHKLE YNYNSHNVYI   360
MADKQKNGIK VNFKIRHNIE DGSVQLADHY QQNTPIGDGP VLLPDNHYLS TQSKLSKDPN   420
EKRDHMVLLE FVTAAGITLA AISRLITYLR ILEELEAQGV HRTASEQLGE LAQVTAFQVD   480
EDLSYFGSYG TDGVGYTVPV LKRELRHILG LNRKWGLCIV GMGRLGSALA DWPGFGESFE   540
LRGFFDVDPG MVGRPVRGGV IEHVDLLPQR VPGRIEIALL TVPREAAQKA ADLLVAAGIK   600
GILNFAPVVL EVPKEVAVEN VDFLAGLTRL SFAILNPKWR EVIKPEMKMR YYMDGSVNGH   660
```

```
EFTIEGEGTG RPYEGHQEMT LRVTMAEGGP MPFAFDLVSH VFCYGHRVFT KYPEEIPDYF    720
KQAFPEGLSW ERSLEFEDGG SASVSAHISL RGNTFYHKSK FTGVNFPADG PIMQNQSVDW    780
EPSTEKITAS DGVLKGDVTM YLKLEGGGNH KCQFKTTYKA AKEILEMPGD HYIGHRLVRK    840
TEGNITEQVE DAVAHSEASM DELYK                                          865

SEQ ID NO: 134           moltype = AA  length = 880
FEATURE                  Location/Qualifiers
REGION                   1..880
                         note = Synthetic
source                   1..880
                         mol_type = protein
                         organism = synthetic construct
SEQUENCE: 134
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAGHG MVSKGEELFT GVVPILVELD GDVNGHKFSV    240
SGEGEGDATY GKLTLKFICT TGKLPVPWPT LVTTLTYGVQ CFSRYPDHMK QHDFFKSAMP    300
EGYVQERTIF FKDDGNYKTR AEVKFEGDTL VNRIELKGID FKEDGNILGH KLEYNYNSHN    360
VYIMADKQKN GIKVNFKIRH NIEDGSVQLA DHYQQNTPIG DGPVLLPDNH YLSTQSKLSK    420
DPNEKRDHMV LLEFVTAAGI TLGMDEPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD    540
WPGFGESFEL RGFFDVDPGM VGRPVRGGVI EHVDLLPQRV PGRIEIALLT VPREAAQKAA    600
DLLVAAGIKG ILNFAPVVLE VPKEVAVENV DFLAGLTRLS FAILNPKWRE EMMGVSVIKP    660
EMKMRYYMDG SVNGHEFTIE GEGTGRPYEG HQEMTLRVTM AEGGPMPAF  DLVSHVFCYG    720
HRVFTKYPEE IPDYFKQAFP EGLSWERSLE FEDGGSASVS AHISLRGNTF YHKSKFTGVN    780
FPADGPIMQN QSVDWEPSTE KITASDGVLK GDVTMYLKLE GGGNHKCQFK TTYKAAKEIL    840
EMPGDHYIGH RLVRKTEGNI TEQVEDAVAH SEASMDELYK                          880

SEQ ID NO: 135           moltype = AA  length = 864
FEATURE                  Location/Qualifiers
REGION                   1..864
                         note = Synthetic
source                   1..864
                         mol_type = protein
                         organism = synthetic construct
SEQUENCE: 135
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLGE AAISRLITYL RILEELEAQG VHRTASEQLG ELAQVTAFQV DEDLSYFGSY    480
GTDGVGYTVP VLKRELRHIL GLNRKWGLCI VGMGRLGSAL ADWPGFGESF ELRGFFDVDP    540
GMVGRPVRGG VIEHVDLLPQ RVPGRIEIAL LTVPREAAQK AADLLVAAGI KGILNFAPVV    600
LEVPKEVAVE NVDFLAGLTR LSFAILNPKW REEMMGSMVS VIKPEMKMRY YMDGSVNGHE    660
FTIEGEGTGR PYEGHQEMTL RVTMAEGGPM PFAFDLVSHV FCYGHRVFTK YPEEIPDYFK    720
QAFPEGLSWE RSLEFEDGGS ASVSAHISLR GNTFYHKSKF TGVNFPADGP IMQNQSVDWE    780
PSTEKITASD GVLKGDVTMY LKLEGGGNHK CQFKTTYKAA KEILEMPGDH YIGHRLVRKT    840
EGNITEQVED AVAHSEASMD ELYK                                           864

SEQ ID NO: 136           moltype = AA  length = 879
FEATURE                  Location/Qualifiers
REGION                   1..879
                         note = Synthetic
source                   1..879
                         mol_type = protein
                         organism = synthetic construct
SEQUENCE: 136
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMPEAA ISRLITYLRI LEELEAQGVH RTASEQLGEL    480
AQVTAFQVDE DLSYFGSYGT DGVGYTVPVL KRELRHILGL NRKWGLCIVG MGRLGSALAD    540
WPGFGESFEL RGFFDVDPGM VGRPVRGGVI EHVDLLPQRV PGRIEIALLT VPREAAQKAA    600
DLLVAAGIKG ILNFAPVVLE VPKEVAVENV DFLAGLTRLS FAILNPKWRE EMMVSVIKPE    660
MKMRYYMDGS VNGHEFTIEG EGTGRPYEGH QEMTLRVTMA EGGPMPFAFD LVSHVFCYGH    720
RVFTKYPEEI PDYFKQAFPE GLSWERSLEF EDGGSASVSA HISLRGNTFY HKSKFTGVNF    780
PADGPIMQNQ SVDWEPSTEK ITASDGVLKG DVTMYLKLEG GGNHKCQFKT TYKAAKEILE    840
MPGDHYIGHR LVRKTEGNIT EQVEDAVAHS EASMDELYK                           879

SEQ ID NO: 137           moltype = AA  length = 862
FEATURE                  Location/Qualifiers
```

```
REGION                  1..862
                        note = Synthetic
source                  1..862
                        mol_type = protein
                        organism = synthetic construct
SEQUENCE: 137
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPLFTGVVP ILVELDGDVN GHKFSVSGEG EGDATYGKLT   240
LKFICTTGKL PVPWPTLVTT LTYGVQCFSR YPDHMKQHDF FKSAMPEGYV QERTIFFKDD   300
GNYKTRAEVK FEGDTLVNRI ELKGIDFKED GNILGHKLEY NYNSHNVYIM ADKQKNGIKV   360
NFKIRHNIED GSVQLADHYQ QNTPIGDGPV LLPDNHYLST QSKLSKDPNE KRDHMVLLEF   420
VTAAGITLAA ISRLIAAISR LITYLRILEE LEAQGVHRTA SEQLGELAQV TAFQVDEDLS   480
YFGSYGTDGV GYTVPVLKRE LRHILGLNRK WGLCIVGMGR LGSALADWPG FGESFELRGF   540
FDVDPGMVGR PVRGGVIEHV DLLPQRVPGR IEIALLTVPR EAAQKAADLL VAAGIKGILN   600
FAPVVLEVPK EVAVENVDFL AGLTRLSFAI LNPKWREEVI KPEMKMRYYM DGSVNGHEFT   660
IEGEGTGRPY EGHQEMTLRV TMAEGGPMPF AFDLVSHVFC YGHRVFTKYP EEIPDYFKQA   720
FPEGLSWERS LEFEDGGSAS VSAHISLRGN TFYHKSKFTG VNFPADGPIM QNQSVDWEPS   780
TEKITASDGV LKGDVTMYLK LEGGGNHKCQ FKTTYKAAKE ILEMPGDHYI GHRLVRKTEG   840
NITEQVEDAV AHSEASMDEL YK                                           862

SEQ ID NO: 138          moltype = AA   length = 871
FEATURE                 Location/Qualifiers
REGION                  1..871
                        note = Synthetic
source                  1..871
                        mol_type = protein
                        organism = synthetic construct
SEQUENCE: 138
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSGMVS KGEELFTGVV PILVELDGDV NGHKFSVSGE   240
GEGDATYGKL TLKFICTTGK LPVPWPTLVT TLTYGVQCFS RYPDHMKQHD FFKSAMPEGY   300
VQERTIFFKD DGNYKTRAEV KFEGDTLVNR IELKGIDFKE DGNILGHKLE YNYNSHNVYI   360
MADKQKNGIK VNFKIRHNIE DGSVQLADHY QQNTPIGDGP VLLPDNHYLS TQSKLSKDPN   420
EKRDHMVLLE FVTAAGITLG MPEAAISRLI TYLRILEELE AQGVHRTASE QLGELAQVTA   480
FQVDEDLSYF GSYGTDGVGY TVPVLKRELR HILGLNRKWG LCIVGMGRLG SALADWPGFG   540
ESFELRGFFD VDPGMVGRPV RGGVIEHVDL LPQRVPGRIE IALLTVPREA AQKAADLLVA   600
AGIKGILNFA PVVLEVPKEV AVENVDFLAG LTRLSFAILN PKWREESVIK PEMKMRYYMD   660
GSVNGHEFTI EGEGTGRPYE GHQEMTLRVT MAEGGPMPFA FDLVSHVFCY GHRVFTKYPE   720
EIPDYFKQAF PEGLSWERSL EFEDGGSASV SAHISLRGNT FYHKSKFTGV NFPADGPIMQ   780
NQSVDWEPST EKITASDGVL KGDVTMYLKL EGGGNHKCQF KTTYKAAKEI LEMPGDHYIG   840
HRLVRKTEGN ITEQVEDAVA HSEASMDELY K                                 871

SEQ ID NO: 139          moltype = AA   length = 861
FEATURE                 Location/Qualifiers
REGION                  1..861
                        note = Synthetic
source                  1..861
                        mol_type = protein
                        organism = synthetic construct
SEQUENCE: 139
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPLFTGVVP ILVELDGDVN GHKFSVSGEG EGDATYGKLT   240
LKFICTTGKL PVPWPTLVTT LTYGVQCFSR YPDHMKQHDF FKSAMPEGYV QERTIFFKDD   300
GNYKTRAEVK FEGDTLVNRI ELKGIDFKED GNILGHKLEY NYNSHNVYIM ADKQKNGIKV   360
NFKIRHNIED GSVQLADHYQ QNTPIGDGPV LLPDNHYLST QSKLSKDPNE KRDHMVLLEF   420
VTAAGITLGM EAAISRLITY LRILEELEAQ GVHRTASEQL GELAQVTAFQ VDEDLSYFGS   480
YGTDGVGYTV PVLKRELRHI LGLNRKWGLC IVGMGRLGSA LADWPGFGES FELRGFFDVD   540
PGMVGRPVRG GVIEHVDLLP QRVPGRIEIA LLTVPREAAQ KAADLLVAAG IKGILNFAPV   600
VLEVPKEVAV ENVDFLAGLT RLSFAILNPK WREEMMSVIK PEMKMRYYMD GSVNGHEFTI   660
EGEGTGRPYE GHQEMTLRVT MAEGGPMPFA FDLVSHVFCY GHRVFTKYPE EIPDYFKQAF   720
PEGLSWERSL EFEDGGSASV SAHISLRGNT FYHKSKFTGV NFPADGPIMQ NQSVDWEPST   780
EKITASDGVL KGDVTMYLKL EGGGNHKCQF KTTYKAAKEI LEMPGDHYIG HRLVRKTEGN   840
ITEQVEDAVA HSEASMDELY K                                            861

SEQ ID NO: 140          moltype = AA   length = 865
FEATURE                 Location/Qualifiers
REGION                  1..865
                        note = Synthetic
source                  1..865
                        mol_type = protein
                        organism = synthetic construct
SEQUENCE: 140
MKVPEAAISR LITYLRILEE LEAQGVHRTA SEQLGELAQV TAFQVDKDLS YFGSYGTDGV    60
```

```
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLGM EAAISRLITY LRILEELEAQ GVHRTASEQL GELAQVTAFQ VDEDLSYFGS    480
YGTDGVGYTV PVLKRELRHI LGLNRKWGLC IVGMGRLGSA LADWPGFGES FELRGFFDVD    540
PGMVGRPVRG GVIEHVDLLP QRVPGRIEIA LLTVPREAAQ KAADLLVAAG IKGILNFAPV    600
VLEVPKEVAV ENVDFLAGLT RLSFAILNPK WREEMMGSMV SVIKPEMKMR YYMDGSVNGH    660
EFTIEGEGTG RPYEGHQEMT LRVTMAEGGP MPFAFDLVSH VFCYGHRVFT KYPEEIPDYF    720
KQAFPEGLSW ERSLEFEDGG SASVSAHISL RGNTFYHKSK FTGVNFPADG PIMQNQSVDW    780
EPSTEKITAS DGVLKGDVTM YLKLEGGGNH KCQFKTTYKA AKEILEMPGD HYIGHRLVRK    840
TEGNITEQVE DAVAHSEASM DELYK                                          865

SEQ ID NO: 141         moltype = AA  length = 860
FEATURE                Location/Qualifiers
REGION                 1..860
                       note = Synthetic
source                 1..860
                       mol_type = protein
                       organism = synthetic construct
SEQUENCE: 141
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLGM EAAISRLITY LRILEELEAQ GVHRTASEQL GELAQVTAFQ VDEDLSYFGS    480
YGTDGVGYTV PVLKRELRHI LGLNRKWGLC IVGMGRLGSA LADWPGFGES FELRGFFDVD    540
PGMVGRPVRG GVIEHVDLLP QRVPGRIEIA LLTVPREAAQ KAADLLVAAG IKGILNFAPV    600
VLEVPKEVAV ENVDFLAGLT RLSFAILNPK WREEMSVIKP EMKMRYYMDG SVNGHEFTIE    660
GEGTGRPYEG HQEMTLRVTM AEGGPMPFAF DLVSHVFCYG HRVFTKYPEE IPDYFKQAFP    720
EGLSWERSLE FEDGGSASVS AHISLRGNTF YHKSKFTGVN FPADGPIMQN QSVDWEPSTE    780
KITASDGVLK GDVTMYLKLE GGGNHKCQFK TTYKAAKEIL EMPGDHYIGH RLVRKTEGNI    840
TEQVEDAVAH SEASMDELYK                                                860

SEQ ID NO: 142         moltype = AA  length = 859
FEATURE                Location/Qualifiers
REGION                 1..859
                       note = Synthetic
source                 1..859
                       mol_type = protein
                       organism = synthetic construct
SEQUENCE: 142
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPLFTGVVP ILVELDGDVN GHKFSVSGEG EGDATYGKLT    240
LKFICTTGKL PVPWPTLVTT LTYGVQCFSR YPDHMKQHDF FKSAMPEGYV QERTIFFKDD    300
GNYKTRAEVK FEGDTLVNRI ELKGIDFKED GNILGHKLEY NYNSHNVYIM ADKQKNGIKV    360
NFKIRHNIED GSVQLADHYQ QNTPIGDGPV LLPDNHYLST QSKLSKDPNE KRDHMVLLEF    420
VTAAGITLEA AISRLITYLR ILEELEAQGV HRTASEQLGE LAQVTAFQVD EDLSYFGSYG    480
TDGVGYTVPV LKRELRHILG LNRKWGLCIV GMGRLGSALA DWPGFGESFE LRGFFDVDPG    540
MVGRPVRGGV IEHVDLLPQR VPGRIEIALL TVPREAAQKA ADLLVAAGIK GILNFAPVVL    600
EVPKEVAVEN VDFLAGLTRL SFAILNPKWR EEMMSVIKPE MKMRYYMDGS VNGHEFTIEG    660
EGTGRPYEGH QEMTLRVTMA EGGPMPFAFD LVSHVFCYGH RVFTKYPEEI PDYFKQAFPE    720
GLSWERSLEF EDGGSASVSA HISLRGNTFY HKSKFTGVNF PADGPIMQNQ SVDWEPSTEK    780
ITASDGVLKG DVTMYLKLEG GGNHKCQFKT TYKAAKEILE MPGDHYIGHR LVRKTEGNIT    840
EQVEDAVAHS EASMDELYK                                                 859

SEQ ID NO: 143         moltype = AA  length = 876
FEATURE                Location/Qualifiers
REGION                 1..876
                       note = Synthetic
source                 1..876
                       mol_type = protein
                       organism = synthetic construct
SEQUENCE: 143
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWGMVSK GEELFTGVVP ILVELDGDVN GHKFSVSGEG    240
EGDATYGKLT LKFICTTGKL PVPWPTLVTT LTYGVQCFSR YPDHMKQHDF FKSAMPEGYV    300
QERTIFFKDD GNYKTRAEVK FEGDTLVNRI ELKGIDFKED GNILGHKLEY NYNSHNVYIM    360
ADKQKNGIKV NFKIRHNIED GSVQLADHYQ QNTPIGDGPV LLPDNHYLST QSKLSKDPNE    420
KRDHMVLLEF VTAAGITLGM DEVPEAAISR LITYLRILEE LEAQGVHRTA SEQLGELAQV    480
```

```
TAFQVDEDLS YFGSYGTDGV GYTVPVLKRE LRHILGLNRK WGLCIVGMGR LGSALADWPG     540
FGESFELRGF FDVDPGMVGR PVRGGVIEHV DLLPQRVPGR IEIALLTVPR EAAQKAADLL     600
VAAGIKGILN FAPVVLEVPK EVAVENVDFL AGLTRLSFAI LNPKWREEMM VSVIKPEMKM     660
RYYMDGSVNG HEFTIEGEGT GRPYEGHQEM TLRVTMAEGG PMPFAFDLVS HVFCYGHRVF     720
TKYPEEIPDY FKQAPPEGLS WERSLEFEDG GSASVSAHIS LRGNTFYHKS KFTGVNFPAD     780
GPIMQNQSVD WEPSTEKITA SDGVLKGDVT MYLKLEGGGN HKCQFKTTYK AAKEILEMPG     840
DHYIGHRLVR KTEGNITEQV EDAVAHSEAS MDELYK                               876

SEQ ID NO: 144          moltype = AA  length = 858
FEATURE                 Location/Qualifiers
REGION                  1..858
                        note = Synthetic
source                  1..858
                        mol_type = protein
                        organism = synthetic construct
SEQUENCE: 144
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPLFTGVVP ILVELDGDVN GHKFSVSGEG EGDATYGKLT     240
LKFICTTGKL PVPWPTLVTT LTYGVQCFSR YPDHMKQHDF FKSAMPEGYV QERTIFFKDD     300
GNYKTRAEVK FEGDTLVNRI ELKGIDFKED GNILGHKLEY NYNSHNVYIM ADKQKNGIKV     360
NFKIRHNIED GSVQLADHYQ QNTPIGDGPV LLPDNHYLST QSKLSKDPNE KRDHMVLLEF     420
VTAAGITLEA AISRLITYLR ILEELEAQGV HRTASEQLGE LAQVTAFQVD EDLSYFGSYG     480
TDGVGYTVPV LKRELRHILG LNRKWGLCIV GMGRLGSALA DWPGFGESFE LRGFFDVDPG     540
MVGRPVRGGV IEHVDLLPQR VPGRIEIALL TVPREAAQKA ADLLVAAGIK GILNFAPVVL     600
EVPKEVAVEN VDFLAGLTRL SFAILNPKWR EEMSVIKPEM KMRYYMDGSV NGHEFTIEGE     660
GTGRPYEGHQ EMTLRVTMAE GGPMPFAFDL VSHVFCYGHR VFTKYPEEIP DYFKQAPPEG     720
LSWERSLEFE DGGSASVSAH ISLRGNTFYH KSKFTGVNFP ADGPIMQNQS VDWEPSTEKI     780
TASDGVLKGD VTMYLKLEGG GNHKCQFKTT YKAAKEILEM PGDHYIGHRL VRKTEGNITE     840
QVEDAVAHSE ASMDELYK                                                   858

SEQ ID NO: 145          moltype = AA  length = 871
FEATURE                 Location/Qualifiers
REGION                  1..871
                        note = Synthetic
source                  1..871
                        mol_type = protein
                        organism = synthetic construct
SEQUENCE: 145
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPLFTGVVP ILVELDGDVN GHKFSVSGEG EGDATYGKLT     240
LKFICTTGKL PVPWPTLVTT LTYGVQCFSR YPDHMKQHDF FKSAMPEGYV QERTIFFKDD     300
GNYKTRAEVK FEGDTLVNRI ELKGIDFKED GNILGHKLEY NYNSHNVYIM ADKQKNGIKV     360
NFKIRHNIED GSVQLADHYQ QNTPIGDGPV LLPDNHYLST QSKLSKDPNE KRDHMVLLEF     420
VTAAGITLGM DELVPEAAIS RLITYLRILE ELEAQGVHRT ASEQLGELAQ VTAFQVDEDL     480
SYFGSYGTDG VGYTVPVLKR ELRHILGLNR KWGLCIVGMG RLGSALADWP GFGESFELRG     540
FFDVDPGMVG RPVRGGVIEH VDLLPQRVPG RIEIALLTVP REAAQKAADL LVAAGIKGIL     600
NFAPVVLEVP KEVAVENVDF LAGLTRLSFA ILNPKWREEM MGGSMVSVIK PEMKMRYYMD     660
GSVNGHEFTI EGEGTGRPYE GHQEMTLRVT MAEGGPMPFA FDLVSHVFCY GHRVFTKYPE     720
EIPDYFKQAF PEGLSWERSL EFEDGGSASV SAHISLRGNT FYHKSKFTGV NFPADGPIMQ     780
NQSVDWEPST EKITASDGVL KGDVTMYLKL EGGGNHKCQF KTTYKAAKEI LEMPGDHYIG     840
HRLVRKTEGN ITEQVEDAVA HSEASMDELY K                                    871

SEQ ID NO: 146          moltype = AA  length = 863
FEATURE                 Location/Qualifiers
REGION                  1..863
                        note = Synthetic
source                  1..863
                        mol_type = protein
                        organism = synthetic construct
SEQUENCE: 146
MKVPEAAISR LITYLRILEE LEAQGVHRTA SEQLGELAQV TAFQVDKDLS YFGSYGTDGV      60
GYTVPVLKRE LRHILGLNRK WGLCIVGMGR LGSALADWPG FGESFELRGF FDVDPGMVGR     120
PVRGGVIEHV DLLPQRVPGR IEIALLTVPR EAAQKAADLL VAAGIKGILN FAPVVLEVPK     180
EVAVENVDIL AGLTRLSFAI LNPLFTGVVP ILVELDGDVN GHKFSVSGEG EGDATYGKLT     240
LKFICTTGKL PVPWPTLVTT LTYGVQCFSR YPDHMKQHDF FKSAMPEGYV QERTIFFKDD     300
GNYKTRAEVK FEGDTLVNRI ELKGIDFKED GNILGHKLEY NYNSHNVYIM ADKQKNGIKV     360
NFKIRHNIED GSVQLADHYQ QNTPIGDGPV LLPDNHYLST QSKLSKDPNE KRDHMVLLEF     420
VTAAGITLGE AAISRLITYL RILEELEAQG VHRTASEQLG ELAQVTAFQV DEDLSYFGSY     480
GTDGVGYTVP VLKRELRHIL GLNRKWGLCI VGMGRLGSAL ADWPGFGESF ELRGFFDVDP     540
GMVGRPVRGG VIEHVDLLPQ RVPGRIEIAL LTVPREAAQK AADLLVAAGI KGILNFAPVV     600
LEVPKEVAVE NVDFLAGLTR LSFAILNPKW REEMMGMVSV IKPEMKMRYY MDGSVNGHEF     660
TIEGEGTGRP YEGHQEMTLR VTMAEGGPMP FAFDLVSHVF CYGHRVFTKY PEEIPDYFKQ     720
AFPEGLSWER SLEFEDGGSA SVSAHISLRG NTFYHKSKFT GVNFPADGPI MQNQSVDWEP     780
STEKITASDG VLKGDVTMYL KLEGGGNHKC QFKTTYKAAK EILEMPGDHY IGHRLVRKTE     840
GNITEQVEDA VAHSEASMDE LYK                                             863
```

```
SEQ ID NO: 147            moltype = AA   length = 864
FEATURE                   Location/Qualifiers
REGION                    1..864
                          note = Synthetic
source                    1..864
                          mol_type = protein
                          organism = synthetic construct
SEQUENCE: 147
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPLFTGVVP ILVELDGDVN GHKFSVSGEG EGDATYGKLT   240
LKFICTTGKL PVPWPTLVTT LTYGVQCFSR YPDHMKQHDF FKSAMPEGYV QERTIFFKDD   300
GNYKTRAEVK FEGDTLVNRI ELKGIDFKED GNILGHKLEY NYNSHNVYIM ADKQKNGIKV   360
NFKIRHNIED GSVQLADHYQ QNTPIGDGPV LLPDNHYLST QSKLSKDPNE KRDHMVLLEF   420
VTAAGITLEA AISRLITYLR ILEELEAQGV HRTASEQLGE LAQVTAFQVD EDLSYFGSYG   480
TDGVGYTVPV LKRELRHILG LNRKWGLCIV GMGRLGSALA DWPGFGESFE LRGFFDVDPG   540
MVGRPVRGGV IEHVDLLPQR VPGRIEIALL TVPREAAQKA ADLLVAAGIK GILNFAPVVL   600
EVPKEVAVEN VDFLAGLTRL SFAILNPKWR EEMMGGSMVS VIKPEMKMRY YMDGSVNGHE   660
FTIEGEGTGR PYEGHQEMTL RVTMAEGGPM PFAFDLVSHV FCYGHRVFTK YPEEIPDYFK   720
QAFPEGLSWE RSLEFEDGGS ASVSAHISLR GNTFYHKSKF TGVNFPADGP IMQNQSVDWE   780
PSTEKITASD GVLKGDVTMY LKLEGGGNHK CQFKTTYKAA KEILEMPGDH YIGHRLVRKT   840
EGNITEQVED AVAHSEASMD ELYK                                         864

SEQ ID NO: 148            moltype = AA   length = 861
FEATURE                   Location/Qualifiers
REGION                    1..861
                          note = Synthetic
source                    1..861
                          mol_type = protein
                          organism = synthetic construct
SEQUENCE: 148
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPLFTGVVP ILVELDGDVN GHKFSVSGEG EGDATYGKLT   240
LKFICTTGKL PVPWPTLVTT LTYGVQCFSR YPDHMKQHDF FKSAMPEGYV QERTIFFKDD   300
GNYKTRAEVK FEGDTLVNRI ELKGIDFKED GNILGHKLEY NYNSHNVYIM ADKQKNGIKV   360
NFKIRHNIED GSVQLADHYQ QNTPIGDGPV LLPDNHYLST QSKLSKDPNE KRDHMVLLEF   420
VTAAGITLGM DEPEAAISRL ITYLRILEEL EAQGVHRTAS EQLGELAQVT AFQVDEDLSY   480
FGSYGTDGVG YTVPVLKREL RHILGLNRKW GLCIVGMGRL GSALADWPGF GESFELRGFF   540
DVDPGMVGRP VRGGVIEHVD LLPQRVPGRI EIALLTVPRE AAQKAADLLV AAGIKGILNF   600
APVVLEVPKE VAVENVDFLA GLTRLSFAIL NPKWREEVIK PEMKMRYYMD GSVNGHEFTI   660
EGEGTGRPYE GHQEMTLRVT MAEGGPMPFA FDLVSHVFCY GHRVFTKYPE EIPDYFKQAF   720
PEGLSWERSL EFEDGGSASV SAHISLRGNT FYHKSKFTGV NFPADGPIMQ NQSVDWEPST   780
EKITASDGVL KGDVTMYLKL EGGGNHKCQF KTTYKAAKEI LEMPGDHYIG HRLVRKTEGN   840
ITEQVEDAVA HSEASMDELY K                                            861

SEQ ID NO: 149            moltype = AA   length = 876
FEATURE                   Location/Qualifiers
REGION                    1..876
                          note = Synthetic
source                    1..876
                          mol_type = protein
                          organism = synthetic construct
SEQUENCE: 149
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSKGEEL FTGVVPILVE LDGDVNGHKF   240
SVSGEGEGDA TYGKLTLKFI CTTGKLPVPW PTLVTTLTYG VQCFSRYPDH MKQHDFFKSA   300
MPEGYVQERT IFFKDDGNYK TRAEVKFEGD TLVNRIELKG IDFKEDGNIL GHKLEYNYNS   360
HNVYIMADKQ KNGIKVNFKI RHNIEDGSVQ LADHYQQNTP IGDGPVLLPD NHYLSTQSKL   420
SKDPNEKRDH MVLLEFVTAA GITLGEAAIS RLITYLRILE ELEAQGVHRT ASEQLGELAQ   480
VTAFQVDEDL SYFGSYGTDG VGYTVPVLKR ELRHILGLNR KWGLCIVGMG RLGSALADWP   540
GFGESFELRG FFDVDPGMVG RPVRGGVIEH VDLLPQRVPG RIEIALLTVP REAAQKAADL   600
LVAAGIKGIL NFAPVVLEVP KEVAVENVDF LAGLTRLSFA ILNPKWREEM MSVIKPEMKM   660
RYYMDGSVNG HEFTIEGEGT GRPYEGHQEM TLRVTMAEGG PMPFAFDLVS HVFCYGHRVF   720
TKYPEEIPDY FKQAFPEGLS WERSLEFEDG GSASVSAHIS LRGNTFYHKS KFTGVNFPAD   780
GPIMQNQSVD WEPSTEKITA SDGVLKGDVT MYLKLEGGGN HKCQFKTTYK AAKEILEMPG   840
DHYIGHRLVR KTEGNITEQV EDAVAHSEAS MDELYK                             876

SEQ ID NO: 150            moltype = AA   length = 885
FEATURE                   Location/Qualifiers
REGION                    1..885
                          note = Synthetic
source                    1..885
                          mol_type = protein
```

```
                        organism = synthetic construct
SEQUENCE: 150
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGYNSHNVYI MADKQKNGIK VNFKIRHNIE   240
DGSVQLADHY QQNTPIGDGP VLLPDNHYLS TQSKLSKDPN EKRDHMVLLE FVTAAGITLG   300
MDELYKGGSG GMVSKEELF TGVVPILVEL DGDVNGHKFS VSGEGEGDAT YGKLTLKFIC   360
TTGKLPVPWP TLVTTLTYGV QCFSRYPDHM KQHDFFKSAM PEGYVQERTI FFKDDGNYKT   420
RAEVKFEGDT LVNRIELKGI DFKEDGNILG HKLEYNTKVP EAAISRLITY LRILEELEAQ   480
GVHRTASEQL GELAQVTAFQ VDEDLSYFGS YGTDGVGYTV PVLKRELRHI LGLNRKWGLC   540
IVGMGRLGSA LADWPGFGES FELRGFFDVD PGMVGRPVRG GVIEHVDLLP QRVPGRIEIA   600
LLTVPREAAQ KAADLLVAAG IKGILNFAPV VLEVPKEVAV ENVDFLAGLT RLSFAILNPK   660
WREEMMGMVS VIKPEMKMRY YMDGSVNGHE FTIEGEGTGR PYEGHQEMTL RVTMAEGGPM   720
PFAFDLVSHV FCYGHRVFTK YPEEIPDYFK QAFPEGLSWE RSLEFEDGGS ASVSAHISLR   780
GNTFYHKSKF TGVNFPADGP IMQNQSVDWE PSTEKITASD GVLKGDVTMY LKLEGGGNHK   840
CQFKTTYKAA KEILEMPGDH YIGHRLVRKT EGNITEQVED AVAHS                   885

SEQ ID NO: 151        moltype = AA  length = 885
FEATURE               Location/Qualifiers
REGION                1..885
                      note = Synthetic
source                1..885
                      mol_type = protein
                      organism = synthetic construct
SEQUENCE: 151
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGDGSVQLAD HYQQNTPIGD GPVLLPDNHY   240
LSTQSKLSKD PNEKRDHMVL LEFVTAAGIT LGMDELYKGG SGGMVSKEE LFTGVVPILV   300
ELDGDVNGHK FSVSGEGEGD ATYGKLTLKF ICTTGKLPVP WPTLVTTLTY GVQCFSRYPD   360
HMKQHDFFKS AMPEGYVQER TIFFKDDGNY KTRAEVKFEG DTLVNRIELK GIDFKEDGNI   420
LGHKLEYNYN SHNVYIMADK QKNGIKVNFK IRHNIETKVP EAAISRLITY LRILEELEAQ   480
GVHRTASEQL GELAQVTAFQ VDEDLSYFGS YGTDGVGYTV PVLKRELRHI LGLNRKWGLC   540
IVGMGRLGSA LADWPGFGES FELRGFFDVD PGMVGRPVRG GVIEHVDLLP QRVPGRIEIA   600
LLTVPREAAQ KAADLLVAAG IKGILNFAPV VLEVPKEVAV ENVDFLAGLT RLSFAILNPK   660
WREEMMGMVS VIKPEMKMRY YMDGSVNGHE FTIEGEGTGR PYEGHQEMTL RVTMAEGGPM   720
PFAFDLVSHV FCYGHRVFTK YPEEIPDYFK QAFPEGLSWE RSLEFEDGGS ASVSAHISLR   780
GNTFYHKSKF TGVNFPADGP IMQNQSVDWE PSTEKITASD GVLKGDVTMY LKLEGGGNHK   840
CQFKTTYKAA KEILEMPGDH YIGHRLVRKT EGNITEQVED AVAHS                   885

SEQ ID NO: 152        moltype = AA  length = 880
FEATURE               Location/Qualifiers
REGION                1..880
                      note = Synthetic
source                1..880
                      mol_type = protein
                      organism = synthetic construct
SEQUENCE: 152
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWSAAGG HGMVSVIKPE MKMRYYMDGS VNGHEFTIEG   240
EGTGRPYEGH QEMTLRVTMA EGGPMPFAFD LVSHVFCYGH RVFTKYPEEI PDYFKQAFPE   300
GLSWERSLEF EDGGSASVSA HISLRGNTFY HKSKFTGVNF PADGPIMQNQ SVDWEPSTEK   360
ITASDGVLKG DVTMYLKLEG GGNHKCQFKT TYKAAKEILE MPGDHYIGHR LVRKTEGNIT   420
EQVEDAVAHS TKVPEAAISR LITYLRILEE LEAQGVHRTA SEQLGELAQV TAFQVDEDLS   480
YFGSYGTDGV GYTVPVLKRE LRHILGLNRK WGLCIVGMGR LGSALADWPG FGESFELRGF   540
FDVDPGMVGR PVRGGVIEHV DLLPQRVPGR IEIALLTVPR EAAQKAADLL VAAGIKGILN   600
FAPVVLEVPK EVAVENVDFL AGLTRLSFAI LNPKWREEMM GMVSKEELF TGVVPILVEL   660
DGDVNGHKFS VSGEGEGDAT YGKLTLKFIC TTGKLPVPWP TLVTTLTYGV QCFSRYPDHM   720
KQHDFFKSAM PEGYVQERTI FFKDDGNYKT RAEVKFEGDT LVNRIELKGI DFKEDGNILG   780
HKLEYNYNSH NVYIMADKQK NGIKVNFKIR HNIEDGSVQL ADHYQQNTPI GDPVLLPDN   840
HYLSTQSKLS KDPNEKRDHM VLLEFVTAAG ITLGMDELYK                         880

SEQ ID NO: 153        moltype = AA  length = 871
FEATURE               Location/Qualifiers
REGION                1..871
                      note = Synthetic
source                1..871
                      mol_type = protein
                      organism = synthetic construct
SEQUENCE: 153
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
PVRGGVIEHV DLLPQRVPGR IEIALLTVPR EAAQKAADLL VAAGIKGILN FAPVVLEVPK   180
EVAVENVDIL AGLTRLSFAI LNPTWYNSHN VYIMADKQKN GIKVNFKIRH NIEDGSVQLA   240
DHYQQNTPIG DGPVLLPDNH YLSTQSKLSK DPNEKRDHMV LLEFVTAAGI TLGMDELYKG   300
```

```
GSGGMVSKGE  ELFTGVVPIL  VELDGDVNGH  KFSVSGEGEG  DATYGKLTLK  FICTTGKLPV   360
PWPTLVTTLT  YGVQCFSRYP  DHMKQHDFFK  SAMPEGYVQE  RTIFFKDDGN  YKTRAEVKFE   420
GDTLVNRIEL  KGIDFKEDGN  ILGHKLEYNT  KVPEAAISRL  ITYLRILEEL  EAQGVHRTAS   480
EQLGELAQVT  AFQVDEDLSY  FGSYGTDGVG  YTVPVLKREL  RHILGLNRKW  GLCIVGMGRL   540
GSALADWPGF  GESFELRGFF  DVDPGMVGRP  VRGGVIEHVD  LLPQRVPGRI  EIALLTVPRE   600
AAQKAADLLV  AAGIKGILNF  APVVLEVPKE  VAVENVDFLA  GLTRLSFAIL  NPKWREVIKP   660
EMKMRYYMDG  SVNGHEFTIE  GEGTGRPYEG  HQEMTLRVTM  AEGGPMPPAF  DLVSHVFCYG   720
HRVFTKYPEE  IPDYFKQAFP  EGLSWERSLE  FEDGGSASVS  AHISLRGNTF  YHKSKFTGVN   780
FPADGPIMQN  QSVDWEPSTE  KITASDGVLK  GDVTMYLKLE  GGGNHKCQFK  TTYKAAKEIL   840
EMPGDHYIGH  RLVRKTEGNI  TEQVEDAVAH  S                                   871

SEQ ID NO: 154            moltype = AA  length = 873
FEATURE                   Location/Qualifiers
REGION                    1..873
                          note = Synthetic
source                    1..873
                          mol_type = protein
                          organism = synthetic construct
SEQUENCE: 154
MKVPEAAISR  LITYLRILEE  LEAQGVHRTA  SEQLGELAQV  TAFQVDKDLS  YFGSYGTDGV    60
GYTVPVLKRE  LRHILGLNRK  WGLCIVGMGR  LGSALADWPG  FGESFELRGF  FDVDPGMVGR   120
PVRGGVIEHV  DLLPQRVPGR  IEIALLTVPR  EAAQKAADLL  VAAGIKGILN  FAPVVLEVPK   180
EVAVENVDIL  AGLTRLSFAI  LNPTWSGYNS  HNVYIMADKQ  KNGIKVNFKI  RHNIEDGSVQ   240
LADHYQQNTP  IGDGPVLLPD  NHYLSTQSKL  SKDPNEKRDH  MVLLEFVTAA  GITLGMDELY   300
KGGSGGMVSK  GEELFTGVVP  ILVELDGDVN  GHKFSVSGEG  EGDATYGKLT  LKFICTTGKL   360
PVPWPTLVTT  LTYGVQCFSR  YPDHMKQHDF  FKSAMPEGYV  QERTIFFKDD  GNYKTRAEVK   420
FEGDTLVNRI  ELKGIDFKED  GNILGHKLEY  NTKVPEAAIS  RLITYLRILE  ELEAQGVHRT   480
ASEQLGELAQ  VTAFQVDEDL  SYFGSYGTDG  VGYTVPVLKR  ELRHILGLNR  KWGLCIVGMG   540
RLGSALADWP  GFGESFELRG  FFDVDPGMVG  RPVRGGVIEH  VDLLPQRVPG  RIEIALLTVP   600
REAAQKAADL  LVAAGIKGIL  NFAPVVLEVP  KEVAVENVDF  LAGLTRLSFA  ILNPKWREVI   660
KPEMKMRYYM  DGSVNGHEFT  IEGEGTGRPY  EGHQEMTLRV  TMAEGGPMPF  AFDLVSHVFC   720
YGHRVFTKYP  EEIPDYFKQA  FPEGLSWERS  LEFEDGGSAS  VSAHISLRGN  TFYHKSKFTG   780
VNFPADGPIM  QNQSVDWEPS  TEKITASDGV  LKGDVTMYLK  LEGGGNHKCQ  FKTTYKAAKE   840
ILEMPGDHYI  GHRLVRKTEG  NITEQVEDAV  AHS                                 873

SEQ ID NO: 155            moltype = AA  length = 244
FEATURE                   Location/Qualifiers
REGION                    1..244
                          note = Synthetic
source                    1..244
                          mol_type = protein
                          organism = synthetic construct
SEQUENCE: 155
YNSHNVYIMA  DKQKNGIKVN  FKIRHNIEDG  SVQLADHYQQ  NTPIGDGPVL  LPDNHYLSTQ    60
SKLSKDPNEK  RDHMVLLEFV  TAAGITLGMD  ELYKGGSGGM  VSKGEELFTG  VVPILVELDG   120
DVNGHKFSVS  GEGEGDATYG  KLTLKFICTT  GKLPVPWPTL  VTTLTYGVQC  FSRYPDHMKQ   180
HDFFKSAMPE  GYVQERTIFF  KDDGNYKTRA  EVKFEGDTLV  NRIELKGIDF  KEDGNILGHK   240
LEYN                                                                    244

SEQ ID NO: 156            moltype = AA  length = 6
FEATURE                   Location/Qualifiers
REGION                    1..6
                          note = Synthetic
source                    1..6
                          mol_type = protein
                          organism = synthetic construct
SEQUENCE: 156
MDELYK                                                                    6

SEQ ID NO: 157            moltype = AA  length = 9
FEATURE                   Location/Qualifiers
REGION                    1..9
                          note = Synthetic
source                    1..9
                          mol_type = protein
                          organism = synthetic construct
SEQUENCE: 157
EASMDELYK                                                                 9

SEQ ID NO: 158            moltype = AA  length = 34
FEATURE                   Location/Qualifiers
REGION                    1..34
                          note = Synthetic
source                    1..34
                          mol_type = protein
                          organism = synthetic construct
SEQUENCE: 158
EASTSAWSHP  QFEKGGGSGG  GSGGSAWSHP  QFEK                                 34
```

| SEQ ID NO: 159 | moltype = DNA length = 2631 |
| --- | --- |
| FEATURE | Location/Qualifiers |
| misc_feature | 1..2631 |
| | note = Synthetic |
| source | 1..2631 |
| | mol_type = other DNA |
| | organism = synthetic construct |

SEQUENCE: 159
```
atgaaagttc ctgaggcagc catttccaga ctgattactt atctccgcat tctggaagag   60
ttggaggcac aaggtgtaca ccgcaccgcc tccgaacaac tcggagagct ggcccaggtc  120
accgcctttc aggttgataa ggacctgtcc tactttggca gttacggaac tgacggcgtg  180
ggatacactg taccagtcct caagagagaa ctcagacata tcctcggtct caacagaaaa  240
tggggcctgt gtatcgtggg gatgggacgc ctggatccg ctcttgctga ttggcctggt  300
ttcggcgaga gctttgagct gaggggtttc tttgatgtgg acccaggtat ggtcggtcgg  360
ccggttcgcg gtggtgtgat cgaacacgtg gatctgttgc cccaacgcgt acctggtaga  420
atcgaaatcg ctctgcttac ggtcccaaga gaggcagcac agaaagctgc cgacctgctg  480
gttgcagctg gcatcaaagg aatcctcaat ttcgctccag ttgtactcga ggttcccaaa  540
gaggtggcag ttgagaatgt ggacatcctt gccggtctta cgcgtctgag ctttgccatt  600
ctgaacccca cgtggagcgc agcaggtggg catggtatgt gagcaaggg cgaggagctg  660
ttcaccgggg tggtgcccat cctggtcgag ctggacggcg acgtaaacgg ccacaagttc  720
agcgtgtccg gcgagggcga gggcgatgcc acctacggca agctgaccct gaagttcatc  780
tgcaccaccg gcaagctgcc cgtgccctgg cccaccctcg tgaccaccct gacctacggc  840
gtgcagtgct tcagccgcta ccccgaccac atgaagcagc acgacttctt caagtccgcc  900
atgcccgaag gctacgtcca ggagcgcacc atcttcttca aggacgacgg caactacaag  960
acccgcgccg aggtgaagtt cgagggcgac accctggtga accgcatcga gctgaagggc 1020
atcgacttca aggaggacgg caacatcctg gggcacaagc tggagtacaa ctacaacagc 1080
cacaacgtct atatcatggc cgacaagcag aagaacggca tcaaggtgaa cttcaagatc 1140
cgccacaaca tcgaggacgg cagcgtgcag ctcgccgacc actaccagca gaacacccc 1200
atcggcgacg gccccgtgct gctgcccgac aaccactacc tgagcaccca gtccaagctg 1260
agcaaagacc ccaacgagaa gcgcgatcac atggtcctgc tggagtttgt gaccgccgcc 1320
gggatcactc tcggcatgga cgaggtacca gaagccgcta tcagccgctt gatcacatac 1380
ttgagaatct tggaggaact cgaagctcag ggagttcata gaactgcaag cgagcagttg 1440
ggcgaactcg cacaagttac agcattccaa gtggacgaag atctcagtta tttcggttcc 1500
tatggcaccg atggtgttgg ctatacagtc cctgttttga aacgcgagt gcgccacatt 1560
ttgggcctga atcgcaagtg gggattatgc attgttggca tgggcaggt aggtagtgca 1620
ctggcagact ggccgggctt tggtgaatct ttcgaactca gaggcttttt cgacgttgat 1680
cctggcatgg ttgggagacc tgtcagagga ggcgttattg agcatgttga cctcctgcca 1740
cagagagtcc cgggacgcat tgagattgcc ctcctgaccg ttcctcgcga agctgcccaa 1800
aaggcagcta atttactagt cgccgcaggt attaaggcga ttttgaactt tgccctgtg 1860
gttctggaag tgcctaagga agttgctgtc gaaaacgttg atttcctggc tggcttgacc 1920
cgcctttcct tcgcaatcct caatcctaag tggcgcgaag tgattaaacc agagatgaag 1980
atgaggtact acatggacgg ctccgtcaat gggcatgagt tcacaattga aggtgaaggc 2040
acaggcagac cttacgaggg acatcaagag tgcacactac gcgtcacaat ggccgaggc 2100
gggccaatgc ctttcgcgtt tgacttagtg tcacacgtgt tctgttacgg ccacagagta 2160
tttactaaat atccagaaga gataccagac tatttcaaac aagcatttcc tgaaggcctg 2220
tcatgggaaa ggtcgttgga gttcgaagat ggtgggtccg cttcagtcag tgcgcatata 2280
agccttagag gaaacacctt ctaccacaaa tccaaattta ctggggttaa cttttcctgc 2340
gatggtccta tcatgcaaaa ccaaagtgtt gattgggagc catcaaccga gaaaattact 2400
gccagcgacg gagttctgaa gggtgatgtt acgatgtacc taaaacttga aggaggcggc 2460
aatcacaaat gccaattcaa gactacttac aaggcggcaa agagattct tgaaatgcca 2520
ggagaccatt acatcggcca tcgcctcgtc aggaaaaccg aaggcaacat tactgagcag 2580
gtagaagatg cagtagctca ttccgaagct agcatgacg agctctacaa g            2631
```

| SEQ ID NO: 160 | moltype = DNA length = 2631 |
| --- | --- |
| FEATURE | Location/Qualifiers |
| misc_feature | 1..2631 |
| | note = Synthetic |
| source | 1..2631 |
| | mol_type = other DNA |
| | organism = synthetic construct |

SEQUENCE: 160
```
atgaaagttc ctgaggcagc catttccaga ctgattactt atctccgcat tctggaagag   60
ttggaggcac aaggtgtaca ccgcaccgcc tccgaacaac tcggagagct ggcccaggtc  120
accgcctttc aggttgataa ggacctgtcc tactttggca gttacggaac tgacggcgtg  180
ggatacactg taccagtcct caagagagaa ctcagacata tcctcggtct caacagaaaa  240
tggggcctgt gtatcgtggg gatgctcgc ctggatccg ctcttgctga ttggcctggt  300
ttcggcgaga gctttgagct gaggggtttc tttgatgtgg acccaggtat ggtcggtcgg  360
ccggttcgcg gtggtgtgat cgaacacgtg gatctgttgc cccaacgcgt acctggtaga  420
atcgaaatcg ctctgcttac ggtcccaaga gaggcagcac agaaagctgc cgacctgctg  480
gttgcagctg gcatcaaagg aatcctcaat ttcgctccag ttgtactcga ggttcccaaa  540
gaggtggcag ttgagaatgt ggacatcctt gccggtctta cgcgtctgag ctttgccatt  600
ctgaacccca cgtggagcgc agcaggtggg catggtatgt gagcaaggg cgaggagctg  660
ttcaccgggg tggtgcccat cctggtcgag ctggacggcg acgtaaacgg ccacaagttc  720
agcgtgtccg gcgagggcga gggcgatgcc acctacggca agctgaccct gaagttcatc  780
tgcaccaccg gcaagctgcc cgtgccctgg cccaccctcg tgaccaccct gacctacggc  840
gtgcagtgct tcagccgcta ccccgaccac atgaagcagc acgacttctt caagtccgcc  900
atgcccgaag gctacgtcca ggagcgcacc atcttcttca aggacgacgg caactacaag  960
acccgcgccg aggtgaagtt cgagggcgac accctggtga accgcatcga gctgaagggc 1020
atcgacttca aggaggacgg caacatcctg gggcacaagc tggagtacaa ctacaacagc 1080
```

-continued

```
cacaacgtct atatcatggc cgacaagcag aagaacggca tcaaggtgaa cttcaagatc  1140
cgccacaaca tcgaggacgg cagcgtgcag ctcgccgacc actaccagca gaacaccccc  1200
atcggcgacg gccccgtgct gctgcccgac aaccactacc tgagcaccca gtccaagctg  1260
agcaaagacc ccaacgagaa gcgcgatcac atggtcctgc tggagttcgt gaccgccgcc  1320
gggatcactc tcggcatgga cgaggtacca gaagccgcta tcagccgctt gatcacatac  1380
ttgagaatct tggaggaact cgaagctcag ggagttcata gaactgcaag cgagcagttg  1440
ggcgaactcg cacaagttac agcattccaa gtggacgaag atctcagtta tttcggttcc  1500
tatggcaccg atggtgttgg ctatacagtc cctgttttga aacgcgagtt gcgccacatt  1560
ttgggcctga atcgcaagtg gggattatgc attgttggca tggccaggtt aggtagtgca  1620
ctgcagact ggccgggctt tggtgaatct ttcgaactca gaggctttt cgacgttgat  1680
cctggcatgg ttgggagacc tgtcagagga ggcgttattg agcatgttga cctcctgcca  1740
cagagagtcc cgggacgcat tgagattgcc ctcctgaccg ttcctcgcga agctgcccaa  1800
aaggcagctg atttactagt cgccgcaggt attaagggca ttttgaactt tgcccctgtg  1860
gttctggaag tgcctaagga agttgctgtc gaaaacgtta atttcctggc tggcttgacc  1920
cgcctttcct tcgcaatcct caatcctaag tggcgcgaag tgattaaacc agagatgaag  1980
atgaggtact acatggacgg ctccgtcaat gggcatgagt tcacaattga aggtgaaggc  2040
acaggcgacc tacgaggg acatcaagag atgacactac gcgtcacaat ggccgagggc  2100
gggccaatgc ctttcgcgtt tgacttagtg tcacacgtgt tctgttacgg ccacagagta  2160
tttactaaat atccagaaga gataccagac tatttcaaac aagcatttcc tgaaggcctg  2220
tcatgggaaa ggtcgttgga gttcgaagat ggtgggtccg cttcagtcag tgcgcatata  2280
agccttagag gaaacacctt ctaccacaaa tccaaattta ctggggttaa cttcctgcc  2340
gatggtccta tcatgcaaaa ccaaagtgtt gattgggaag catcaaccga gaaaattact  2400
gccagcgacg gagttctgaa gggtgatgtt acgatgtacc taaaacttga aggaggcggc  2460
aatcacaaat gccaattcaa gactacttac aaggcggcaa aagagattct tgaaatgcca  2520
ggagaccatt acatcggcca tcgcctcgtc aggaaaaccg aaggcaacat tactgagcag  2580
gtagaagatg cagtagctca ttccgaagct agcatggacg agctctacaa g            2631
```

```
SEQ ID NO: 161         moltype = AA  length = 733
FEATURE                Location/Qualifiers
REGION                 1..733
                       note = Synthetic
source                 1..733
                       mol_type = protein
                       organism = synthetic construct
SEQUENCE: 161
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNSV DWEPSTEKIT ASDGVLKGDV TMYLKLEGGG NHKCQFKTTY    180
KAAKEILEMP GDHYIGHRLV RKTEGNITEQ VEDAVAHSNR KWGLCIVGMG RLGSALADYP   240
GFGESFELRG FFDVDPEKVG RPVRGGVIEH VDLLPQRVPG RIEIALLTVP REAAQKAADL   300
LVAAGIKGIL NFAPVVLEVP KEVAVENVDF SAYNSHNVYI MADKQNGIK VNFKIRHNIE    360
DGSVQLADHY QQNTPIGDGP VLLPDNHYLS TQSKLSKDPN EKRDHMVLLE FVTAAGITLG   420
MDELYKGGSG GMVSKGEELF TGVVPILVEL DGDVNGHKFS VSGEGEGDAT YGKLTLKFIC   480
TTGKLPVPWP TLVTTLTYGV QCFSRYPDHM KQHDFFKSAM PEGYVQERTI FFKDDGNYKT   540
RAEVKFEGDT LVNRIELKGI DFKEDGNILG HKLEYNGLAG LTRLSFAILN PKWREEMMGN   600
RKWGLCIVGM GRLGSALADY PGFGESFELR GFFDVDPEKV GRPVRGGVIE HVDLLPQRVP   660
GRIEIALLTV PREAAQKAAD LLVAAGIKGI LNFAPVVLEV PKEVAVENVD FLAGLTRLSF   720
AILNPKWREE MMG                                                      733

SEQ ID NO: 162         moltype = AA  length = 734
FEATURE                Location/Qualifiers
REGION                 1..734
                       note = Synthetic
source                 1..734
                       mol_type = protein
                       organism = synthetic construct
SEQUENCE: 162
MNRKWGLCIV GMGRLGSALA DYPGFGESFE LRGFFDVDPE KVGRPVRGGV IEHVDLLPQR    60
VPGRIEIALL TVPREAAQKA ADLLVAAGIK GILNFAPVVL EVPKEVAVEN VDFSAYNSHN   120
VYIMADKQKN GIKVNFKIRH NIEDGSVQLA DHYQQNTPIG DGPVLLPDNH YLSTQSKLSK   180
DPNEKRDHMV LLEFVTAAGI TLGMDELYKG SGGMVSKGE ELFTGVVPIL VELDGDVNGH    240
KFSVSGEGEG DATYGKLTLK FICTTGKLPV PWPTLVTTLT YGVQCFSRYP DHMKQHDFFK   300
SAMPEGYVQE RTIFFKDDGN YKTRAEVKFE GDTLVNRIEL KGIDFKEDGN ILGHKLEYNG   360
LAGLTRLSFA ILNPKWREEM MGNRKWGLCI VGMGRLGSAL ADYPGFGESF ELRGFFDVDP   420
EKVGRPVRGG VIEHVDLLPQ RVPGRIEIAL LTVPREAAQK AADLLVAAGI KGILNFAPVV   480
LEVPKEVAVE NVDFLAGLTR LSFAILNPKW REEMMGMVSV IKPEMKMRYY MDGSVNGHEF   540
TIEGEGTGRP YEGHQEMTLR VTMAEGGPMP FAFDLVSHVF CYGHRVFTKY PEEIPDYFKQ   600
APPEGLSWER SLEFEDGGSA SVSAHISLRG NTFYHKSKFT GVNFPADGPI MQNSVDWEP    660
STEKITASDG VLKGDVTMYL KLEGGGNHKC QFKTTYKAAK EILEMPGDHY IGHRLVRKTE   720
GNITEQVEDA VAHS                                                     734

SEQ ID NO: 163         moltype = AA  length = 733
FEATURE                Location/Qualifiers
REGION                 1..733
                       note = Synthetic
source                 1..733
                       mol_type = protein
                       organism = synthetic construct
SEQUENCE: 163
```

```
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNSV  DWEPSTEKIT ASDGVLKGDV TMYLKLEGGG NHKCQFKTTY   180
KAAKEILEMP GDHYIGHRLV RKTEGNITEQ VEDAVAHSNR KWGLCIVGMG RLGSALADYP   240
GFGESFELRG FFDVDPEKVG RPVRGGVIEH VDLLPQRVPG RIEIALLTVP REAAQKAADL   300
LVAAGIKGIL NFAPVVLEVP KEVAVENVDF LAGLTRLSFA ILNPKWREEM MGNRKWGLCI   360
VGMGRLGSAL ADYPGFGESF ELRGFFDVDP EKVGRPVRGG VIEHVDLLPQ RVPGRIEIAL   420
LTVPREAAQK AADLLVAAGI KGILNFAPVV LEVPKEVAVE NVDFSAYNSH NVYIMADKQK   480
NGIKVNFKIR HNIEDGSVQL ADHYQQNTPI GDGPVLLPDN HYLSTQSKLS KDPNEKRDHM   540
VLLEFVTAAG ITLGMDELYK GGSGGMVSKG EELFTGVVPI LVELDGDVNG HKFSVSGEGE   600
GDATYGKLTL KFICTTGKLP VPWPTLVTTL TYGVQCFSRY PDHMKQHDFF KSAMPEGYVQ   660
ERTIFFKDDG NYKTRAEVKF EGDTLVNRIE LKGIDFKEDG NILGHKLEYN GLAGLTRLSF   720
AILNPKWREE MMG                                                     733

SEQ ID NO: 164          moltype = AA  length = 734
FEATURE                 Location/Qualifiers
REGION                  1..734
                        note = Synthetic
source                  1..734
                        mol_type = protein
                        organism = synthetic construct
SEQUENCE: 164
MNRKWGLCIV GMGRLGSALA DYPGFGESFE LRGFFDVDPE KVGRPVRGGV IEHVDLLPQR    60
VPGRIEIALL TVPREAAQKA ADLLVAAGIK GILNFAPVVL EVPKEVAVEN VDFLAGLTRL   120
SFAILNPKWR EEMMGNRKWG LCIVGMGRLG SALADYPGFG ESFELRGFFD VDPEKVGRPV   180
RGGVIEHVDL LPQRVPGRIE IALLTVPREA AQKAADLLVA AGIKGILNFA PVVLEVPKEV   240
AVENVDFSAY NSHNVYIMAD KQKNGIKVNF KIRHNIEDGS VQLADHYQQN TPIGDGPVLL   300
PDNHYLSTQS KLSKDPNEKR DHMVLLEFVT AAGITLGMDE LYKGGSGGMV SKGEELFTGV   360
VPILVELDGD VNGHKFSVSG EGEGDATYGK LTLKFICTTG KLPVPWPTLV TTLTYGVQCF   420
SRYPDHMKQH DFFKSAMPEG YVQERTIFFK DDGNYKTRAE VKFEGDTLVN RIELKGIDFK   480
EDGNILGHKL EYNGLAGLTR LSFAILNPKW REEMMGMVSV IKPEMKMRYY MDGSVNGHEF   540
TIEGEGTGRP YEGHQEMTLR VTMAEGGPMP FAFDLVSHVF CYGHRVFTKY PEEIPDYFKQ   600
AFPEGLSWER SLEFEDGGSA SVSAHISLRG NTFYHKSKFT GVNFPADGPI MQNSVDWEP    660
STEKITASDG VLKGDVTMYL KLEGGGNHKC QFKTTYKAAK EILEMPGDHY IGHRLVRKTE   720
GNITEQVEDA VAHS                                                    734

SEQ ID NO: 165          moltype = AA  length = 733
FEATURE                 Location/Qualifiers
REGION                  1..733
                        note = Synthetic
source                  1..733
                        mol_type = protein
                        organism = synthetic construct
SEQUENCE: 165
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNSV  DWEPSTEKIT ASDGVLKGDV TMYLKLEGGG NHKCQFKTTY   180
KAAKEILEMP GDHYIGHRLV RKTEGNITEQ VEDAVAHSNR KWGLCIVGMG RLGSALADYP   240
GFGESFELRG FFDVDPEKVG RPVRGGVIEH VDLLPQRVPG RIEIALLTVP REAAQKAADL   300
LVAAGIKGIL NFAPVVLEVP KEVAVENVDF SADGSVQLAD HYQQNTPIGD GPVLLPDNHY   360
LSTQSKLSKD PNEKRDHMVL LEFVTAAGIT LGMDELYKGG SGGMVSKGEE LFTGVVPILV   420
ELDGDVNGHK FSVSGEGEGD ATYGKLTLKF ICTTGKLPVP WPTLVTTLTY GVQCFSRYPD   480
HMKQHDFFKS AMPEGYVQER TIFFKDDGNY KTRAEVKFEG DTLVNRIELK GIDFKEDGNI   540
LGHKLEYNYN SHNVYIMADK QKNGIKVNFK IRHNIEGLAG LTRLSFAILN PKWREEMMGN   600
RKWGLCIVGM GRLGSALADY PGFGESFELR GFFDVDPEKV GRPVRGGVIE HVDLLPQRVP   660
GRIEIALLTV PREAAQKAAD LLVAAGIKGI LNFAPVVLEV PKEVAVENVD FLAGLTRLSF   720
AILNPKWREE MMG                                                     733

SEQ ID NO: 166          moltype = AA  length = 734
FEATURE                 Location/Qualifiers
REGION                  1..734
                        note = Synthetic
source                  1..734
                        mol_type = protein
                        organism = synthetic construct
SEQUENCE: 166
MNRKWGLCIV GMGRLGSALA DYPGFGESFE LRGFFDVDPE KVGRPVRGGV IEHVDLLPQR    60
VPGRIEIALL TVPREAAQKA ADLLVAAGIK GILNFAPVVL EVPKEVAVEN VDFSADGSVQ   120
LADHYQQNTP IGDGPVLLPD NHYLSTQSKL SKDPNEKRDH MVLLEFVTAA GITLGMDELY   180
KGGSGGMVSK GEELFTGVVP ILVELDGDVN GHKFSVSGEG EGDATYGKLT LKFICTTGKL   240
PVPWPTLVTT LTYGVQCFSR YPDHMKQHDF FKSAMPEGYV QERTIFFKDD GNYKTRAEVK   300
FEGDTLVNRI ELKGIDFKED GNILGHKLEY NYNSHNVYIM ADKQKNGIKV NFKIRHNIEG   360
LAGLTRLSFA ILNPKWREEM MGNRKWGLCI VGMGRLGSAL ADYPGFGESF ELRGFFDVDP   420
EKVGRPVRGG VIEHVDLLPQ RVPGRIEIAL LTVPREAAQK AADLLVAAGI KGILNFAPVV   480
LEVPKEVAVE NVDFLAGLTR LSFAILNPKW REEMMGMVSV IKPEMKMRYY MDGSVNGHEF   540
TIEGEGTGRP YEGHQEMTLR VTMAEGGPMP FAFDLVSHVF CYGHRVFTKY PEEIPDYFKQ   600
AFPEGLSWER SLEFEDGGSA SVSAHISLRG NTFYHKSKFT GVNFPADGPI MQNSVDWEP    660
STEKITASDG VLKGDVTMYL KLEGGGNHKC QFKTTYKAAK EILEMPGDHY IGHRLVRKTE   720
GNITEQVEDA VAHS                                                    734
```

```
SEQ ID NO: 167           moltype = AA   length = 733
FEATURE                  Location/Qualifiers
REGION                   1..733
                         note = Synthetic
source                   1..733
                         mol_type = protein
                         organism = synthetic construct
SEQUENCE: 167
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNQSV DWEPSTEKIT ASDGVLKGDV TMYLKLEGGG NHKCQFKTTY   180
KAAKEILEMP GDHYIGHRLV RKTEGNITEQ VEDAVAHSNR KWGLCIVGMG RLGSALADYP   240
GFGESFELRG FFDVDPEKVG RPVRGGVIEH VDLLPQRVPG RIEIALLTVP REAAQKAADL   300
LVAAGIKGIL NFAPVVLEVP KEVAVENVDF LAGLTRLSFA ILNPKWREEM MGNRKWGLCI   360
VGMGRLGSAL ADYPGFGESF ELRGFFDVDP EKVGRPVRGG VIEHVDLLPQ RVPGRIEIAL   420
LTVPREAAQK AADLLVAAGI KGILNFAPVV LEVPKEVAVE NVDFSADGSV QLADHYQQNT   480
PIGDGPVLLP DNHYLSTQSK LSKDPNEKRD HMVLLEFVTA AGITLGMDEL YKGGSGGMVS   540
KGEELFTGVV PILVELDGDV NGHKFSVSGE GEGDATYGKL TLKFICTTGK LPVPWPTLVT   600
TLTYGVQCFS RYPDHMKQHD FFKSAMPEGY VQERTIFFKD DGNYKTRAEV KFEGDTLVNR   660
IELKGIDFKE DGNILGHKLE YNYNSHNVYI MADKQKNGIK VNFKIRHNIE GLAGLTRLSF   720
AILNPKWREE MMG                                                     733

SEQ ID NO: 168           moltype = AA   length = 734
FEATURE                  Location/Qualifiers
REGION                   1..734
                         note = Synthetic
source                   1..734
                         mol_type = protein
                         organism = synthetic construct
SEQUENCE: 168
MNRKWGLCIV GMGRLGSALA DYPGFGESFE LRGFFDVDPE KVGRPVRGGV IEHVDLLPQR    60
VPGRIEIALL TVPREAAQKA ADLLVAAGIK GILNFAPVVL EVPKEVAVEN VDFLAGLTRL   120
SFAILNPKWR EEMMGNRKWG LCIVGMGRLG SALADYPGFG ESFELRGFFD VDPEKVGRPV   180
RGGVIEHVDL LPQRVPGRIE IALLTVPREA AQKAADLLVA AGIKGILNFA PVVLEVPKEV   240
AVENVDFSAD GSVQLADHYQ QNTPIGDGPV LLPDNHYLST QSKLSKDPNE KRDHMVLLEF   300
VTAAGITLGM DELYKGGSGG MVSKGEELFT GVVPILVELD GDVNGHKFSV SGEGEGDATY   360
GKLTLKFICT TGKLPVPWPT LVTTLTYGVQ CFSRYPDHMK QHDFFKSAMP EGYVQERTIF   420
FKDDGNYKTR AEVKFEGDTL VNRIELKGID FKEDGNILGH KLEYNYNSHN VYIMADKQKN   480
GIKVNFKIRH NIEGLAGLTR LSFAILNPKW REEMMGMVSV IKPEMKMRYY MDGSVNGHEF   540
TIEGEGTGRP YEGHQEMTLR VTMAEGGPMP FAFDLVSHVF CYGHRVFTKY PEEIPDYFKQ   600
AFPEGLSWER SLEFEDGGSA SVSAHISLRG NTFYHKSKFT GVNFPADGPI MQNQSVDWEP   660
STEKITASDG VLKGDVTMYL KLEGGGNHKC QFKTTYKAAK EILEMPGDHY IGHRLVRKTE   720
GNITEQVEDA VAHS                                                    734

SEQ ID NO: 169           moltype = AA   length = 884
FEATURE                  Location/Qualifiers
REGION                   1..884
                         note = Synthetic
source                   1..884
                         mol_type = protein
                         organism = synthetic construct
SEQUENCE: 169
MVSVIKPEMK MRYYMDGSVN GHEFTIEGEG TGRPYEGHQE MTLRVTMAEG GPMPFAFDLV    60
SHVFCYGHRV FTKYPEEIPD YFKQAFPEGL SWERSLEFED GGSASVSAHI SLRGNTFYHK   120
SKFTGVNFPA DGPIMQNQSV DWEPSTEKIT ASDGVLKGDV TMYLKLEGGG NHKCQFKTTY   180
KAAKEILEMP GDHYIGHRLV RKTEGNITEQ VEDAVAHSKV PEAAISRLIT YLRILEELEA   240
QGVHRTASEQ LGELAQVTAF QVDKDLSYFG SYGTDGVGYT VPVLKRELRH ILGLNRKWGL   300
CIVGMGRLGS ALADWPGFGE SFELRGFFDV DPGMVGRPVR GGVIEHVDLL PQRVPGRIEI   360
ALLTVPREAA QKAADLLVAA GIKGILNFAP VVLEVPKEVA VENVDILAGL TRLSFAILNP   420
TWSAAGGHGY NSHNVYIMAD KQKNGIKVNF KIRHNIEDGS VQLADHYQQN TPIGDGPVLL   480
PDNHYLSTQS KLSKDPNEKR DHMVLLEFVT AAGITLGMDE LYKGGSGGMV SKGEELFTGV   540
VPILVELDGD VNGHKFSVSG EGEGDATYGK LTLKFICTTG KLPVPWPTLV TTLTYGVQCF   600
SRYPDHMKQH DFFKSAMPEG YVQERTIFFK DDGNYKTRAE VKFEGDTLVN RIELKGIDFK   660
EDGNILGHKL EYNTKVPEAA ISRLITYLRI LEELEAQGVH RTASEQLGEL AQVTAFQVDE   720
DLSYFGSYGT DGVGYTVPVL KRELRHILGL NRKWGLCIVG MGRLGSALAD WPGFGESFEL   780
RGFFDVDPGM VGRPVRGGVI EHVDLLPQRV PGRIEIALLT VPREAAQKAA DLLVAAGIKG   840
ILNFAPVVLE VPKEVAVENV DFLAGLTRLS FAILNPKWRE EMMG                    884

SEQ ID NO: 170           moltype = AA   length = 885
FEATURE                  Location/Qualifiers
REGION                   1..885
                         note = Synthetic
source                   1..885
                         mol_type = protein
                         organism = synthetic construct
SEQUENCE: 170
MKVPEAAISR LITYLRILEE LEAQGVHRTA SEQLGELAQV TAFQVDKDLS YFGSYGTDGV    60
GYTVPVLKRE LRHILGLNRK WGLCIVGMGR LGSALADWPG FGESFELRGF FDVDPGMVGR   120
```

```
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGYNSHNVYI MADKQKNGIK VNFKIRHNIE    240
DGSVQLADHY QQNTPIGDGP VLLPDNHYLS TQSKLSKDPN EKRDHMVLLE FVTAAGITLG    300
MDELYKGGSG GMVSKGEELF TGVVPILVEL DGDVNGHKFS VSGEGEGDAT YGKLTLKFIC    360
TTGKLPVPWP TLVTTLTYGV QCFSRYPDHM KQHDFFKSAM PEGYVQERTI FFKDDGNYKT    420
RAEVKFEGDT LVNRIELKGI DFKEDGNILG HKLEYNTKVP EAAISRLITY LRILEELEAQ    480
GVHRTASEQL GELAQVTAFQ VDEDLSYFGS YGTDGVGYTV PVLKRELRHI LGLNRKWGLC    540
IVGMGRLGSA LADWPGFGES FELRGFFDVD PGMVGRPVRG GVIEHVDLLP QRVPGRIEIA    600
LLTVPREAAQ KAADLLVAAG IKGILNFAPV VLEVPKEVAV ENVDFLAGLT RLSFAILNPK    660
WREEMMGMVS VIKPEMKMRY YMDGSVNGHE FTIEGEGTGR PYEGHQEMTL RVTMAEGGPM    720
PPFAFDLVSHV FCYGHRVFTK YPEEIPDYFK QAFPEGLSWE RSLEFEDGGS ASVSAHISLR    780
GNTFYHKSKF TGVNFPADGP IMQNQSVDWE PSTEKITASD GVLKGDVTMY LKLEGGGNHK    840
CQFKTTYKAA KEILEMPGDH YIGHRLVRKT EGNITEQVED AVAHS                   885

SEQ ID NO: 171           moltype = AA  length = 884
FEATURE                  Location/Qualifiers
REGION                   1..884
                         note = Synthetic
source                   1..884
                         mol_type = protein
                         organism = synthetic construct
SEQUENCE: 171
MVSVIKPEMK MRYYMDGSVN GHEFTIEGEG TGRPYEGHQE MTLRVTMAEG GPMPFAFDLV     60
SHVFCYGHRV FTKYPEEIPD YFKQAFPEGL SWERSLEFED GGSASVSAHI SLRGNTFYHK    120
SKFTGVNFPA DGPIMQNQSV DWEPSTEKIT ASDGVLKGDV TMYLKLEGGG NHKCQFKTTY    180
KAAKEILEMP GDHYIGHRLV RKTEGNITEQ VEDAVAHSKV PEAAISRLIT QYLRILEELEA   240
QGVHRTASEQ LGELAQVTAF QVDKDLSYFG SYGTDGVGYT VPVLKRELRH ILGLNRKWGL    300
CIVGMGRLGS ALADWPGFGE SFELRGFFDV DPGMVGRPVR GGVIEHVDLL PQRVPGRIEI    360
ALLTVPREAA QKAADLLVAA GIKGILNFAP VVLEVPKEVA VENVDILAGL TRLSFAILNP    420
TWSAAGGHGD GSVQLADHYQ QNTPIGDGPV LLPDNHYLST QSKLSKDPNE KRDHMVLLEF    480
VTAAGITLGM DELYKGGSGG MVSKGEELFT GVVPILVELD GDVNGHKFSV SGEGEGDATY    540
GKLTLKFICT TGKLPVPWPT LVTTLTYGVQ CFSRYPDHMK QHDFFKSAMP EGYVQERTIF    600
FKDDGNYKTR AEVKFEGDTL VNRIELKGID FKEDGNILGH KLEYNYNSHN VYIMADKQKN    660
GIKVNFKIRH NIETKVPEAA ISRLITYLRI LEELEAQGVH RTASEQLGEL AQVTAFQVDE    720
DLSYFGSYGT DGVGYTVPVL KRELRHILGL NRKWGLCIVG MGRLGSALAD WPGFGESFEL    780
RGFFDVDPGM VGRPVGGVI EHVDLLPQRV PGRIEIALLT VPREAAQKAA DLLVAAGIKG    840
ILNFAPVVLE VPKEVAVENV DFLAGLTRLS FAILNPKWRE EMMG                    884

SEQ ID NO: 172           moltype = AA  length = 885
FEATURE                  Location/Qualifiers
REGION                   1..885
                         note = Synthetic
source                   1..885
                         mol_type = protein
                         organism = synthetic construct
SEQUENCE: 172
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGDGSVQLAD HYQQNTPIGD GPVLLPDNHY    240
LSTQSKLSKD PNEKRDHMVL LEFVTAAGIT LGMDELYKGG SGGMVSKGEE LFTGVVPILV    300
ELDGDVNGHK FSVSGEGEGD ATYGKLTLKF ICTTGKLPVP WPTLVTTLTY GVQCFSRYPD    360
HMKQHDFFKS AMPEGYVQER TIFFKDDGNY KTRAEVKFEG DTLVNRIELK GIDFKEDGNI    420
LGHKLEYNYN SHNVYIMADK QKNGIKVNFK IRHNIETKVP EAAISRLITY LRILEELEAQ    480
GVHRTASEQL GELAQVTAFQ VDEDLSYFGS YGTDGVGYTV PVLKRELRHI LGLNRKWGLC    540
IVGMGRLGSA LADWPGFGES FELRGFFDVD PGMVGRPVRG GVIEHVDLLP QRVPGRIEIA    600
LLTVPREAAQ KAADLLVAAG IKGILNFAPV VLEVPKEVAV ENVDFLAGLT RLSFAILNPK    660
WREEMMGMVS VIKPEMKMRY YMDGSVNGHE FTIEGEGTGR PYEGHQEMTL RVTMAEGGPM    720
PPFAFDLVSHV FCYGHRVFTK YPEEIPDYFK QAFPEGLSWE RSLEFEDGGS ASVSAHISLR    780
GNTFYHKSKF TGVNFPADGP IMQNQSVDWE PSTEKITASD GVLKGDVTMY LKLEGGGNHK    840
CQFKTTYKAA KEILEMPGDH YIGHRLVRKT EGNITEQVED AVAHS                   885

SEQ ID NO: 173           moltype = AA  length = 879
FEATURE                  Location/Qualifiers
REGION                   1..879
                         note = Synthetic
source                   1..879
                         mol_type = protein
                         organism = synthetic construct
SEQUENCE: 173
MVSVIKPEMK MRYYMDGSVN GHEFTIEGEG TGRPYEGHQE MTLRVTMAEG GPMPFAFDLV     60
SHVFCYGHRV FTKYPEEIPD YFKQAFPEGL SWERSLEFED GGSASVSAHI SLRGNTFYHK    120
SKFTGVNFPA DGPIMQNQSV DWEPSTEKIT ASDGVLKGDV TMYLKLEGGG NHKCQFKTTY    180
KAAKEILEMP GDHYIGHRLV RKTEGNITEQ VEDAVAHSKV PEAAISRLIT YLRILEELEA    240
QGVHRTASEQ LGELAQVTAF QVDKDLSYFG SYGTDGVGYT VPVLKRELRH ILGLNRKWGL    300
CIVGMGRLGS ALADWPGFGE SFELRGFFDV DPGMVGRPVR GGVIEHVDLL PQRVPGRIEI    360
ALLTVPREAA QKAADLLVAA GIKGILNFAP VVLEVPKEVA VENVDILAGL TRLSFAILNP    420
TWSAAGGHGM VSKGEELFTG VVPILVELDG DVNGHKFSVS GEGEGDATYG KLTLKFICTT    480
GKLPVPWPTL VTTLTYGVQC FSRYPDHMKQ HDFFKSAMPE GYVQERTIFF KDDGNYKTRA    540
```

```
EVKFEGDTLV NRIELKGIDF KEDGNILGHK LEYNYNSHNV YIMADKQKNG IKVNFKIRHN    600
IEDGSVQLAD HYQQNTPIGD GPVLLPDNHY LSTQSKLSKD PNEKRDHMVL LEFVTAAGIT    660
LGMDELYKTK VPEAAISRLI TYLRILEELE AQGVHRTASE QLGELAQVTA FQVDEDLSYF    720
GSYGTDGVGY TVPVLKRELR HILGLNRKWG LCIVGMGRLG SALADWPGFG ESFELRGFFD    780
VDPGMVGRPV RGGVIEHVDL LPQRVPGRIE IALLTVPREA AQKAADLLVA AGIKGILNFA    840
PVVLEVPKEV AVENVDFLAG LTRLSFAILN PKWREEMMG                           879

SEQ ID NO: 174          moltype = AA  length = 880
FEATURE                 Location/Qualifiers
REGION                  1..880
                        note = Synthetic
source                  1..880
                        mol_type = protein
                        organism = synthetic construct
SEQUENCE: 174
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDELY KTKVPEAAIS RLITYLRILE ELEAQGVHRT    480
ASEQLGELAQ VTAFQVDEDL SYFGSYGTDG VGYTVPVLKR ELRHILGLNR KWGLCIVGMG    540
RLGSALADWP GFGESFELRG FFDVDPGMVG RPVRGGVIEH VDLLPQRVPG RIEIALLTVP    600
REAAQKAADL LVAAGIKGIL NFAPVVLEVP KEVAVENVDF LAGLTRLSFA ILNPKWREEM    660
MGMVSVIKPE MKMRYYMDGS VNGHEFTIEG EGTGRPYEGH QEMTLRVTMA EGGPMPFAFD    720
LVSHVFCYGH RVFTKYPEEI PDYFKQAFPE GLSWERSLEF EDGGSASVSA HISLRGNTFY    780
HKSKFTGVNF PADGPIMQNQ SVDWEPSTEK ITASDGVLKG DVTMYLKLEG GGNHKCQFKT    840
TYKAAKEILE MPGDHYIGHR LVRKTEGNIT EQVEDAVAHS                          880

SEQ ID NO: 175          moltype = AA  length = 879
FEATURE                 Location/Qualifiers
REGION                  1..879
                        note = Synthetic
source                  1..879
                        mol_type = protein
                        organism = synthetic construct
SEQUENCE: 175
MVSKGEELFT GVVPILVELD GDVNGHKFSV SGEGEGDATY GKLTLKFICT TGKLPVPWPT     60
LVTTLTYGVQ CFSRYPDHMK QHDFFKSAMP EGYVQERTIF FKDDGNYKTR AEVKFEGDTL    120
VNRIELKGID FKEDGNILGH KLEYNYNSHN VYIMADKQKN GIKVNFKIRH NIEDGSVQLA    180
DHYQQNTPIG DGPVLLPDNH YLSTQSKLSK DPNEKRDHMV LLEFVTAAGI TLGMDELYKK    240
VPEAAISRLI TYLRILEELE AQGVHRTASE QLGELAQVTA FQVDKDLSYF GSYGTDGVGY    300
TVPVLKRELR HILGLNRKWG LCIVGMGRLG SALADWPGFG ESFELRGFFD VDPGMVGRPV    360
RGGVIEHVDL LPQRVPGRIE IALLTVPREA AQKAADLLVA AGIKGILNFA PVVLEVPKEV    420
AVENVDILAG LTRLSFAILN PTWSAAGGHG MVSVIKPEMK MRYYMDGSVN GHEFTIEGEG    480
TGRPYEGHQE MTLRVTMAEG GPMPFAFDLV SHVFCYGHRV FTKYPEEIPD YFKQAFPEGL    540
SWERSLEFED GGSASVSAHI SLRGNTFYHK SKFTGVNFPA DGPIMQNQSV DWEPSTEKIT    600
ASDGVLKGDV TMYLKLEGGG NHKCQFKTTY KAAKEILEMP GDHYIGHRLV RKTEGNITEQ    660
VEDAVAHSTK VPEAAISRLI TYLRILEELE AQGVHRTASE QLGELAQVTA FQVDKDLSYF    720
GSYGTDGVGY TVPVLKRELR HILGLNRKWG LCIVGMGRLG SALADWPGFG ESFELRGFFD    780
VDPGMVGRPV RGGVIEHVDL LPQRVPGRIE IALLTVPREA AQKAADLLVA AGIKGILNFA    840
PVVLEVPKEV AVENVDFLAG LTRLSFAILN PKWREEMMG                           879

SEQ ID NO: 176          moltype = AA  length = 880
FEATURE                 Location/Qualifiers
REGION                  1..880
                        note = Synthetic
source                  1..880
                        mol_type = protein
                        organism = synthetic construct
SEQUENCE: 176
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSVIKPE MKMRYYMDGS VNGHEFTIEG    240
EGTGRPYEGH QEMTLRVTMA EGGPMPFAFD LVSHVFCYGH RVFTKYPEEI PDYFKQAFPE    300
GLSWERSLEF EDGGSASVSA HISLRGNTFY HKSKFTGVNF PADGPIMQNQ SVDWEPSTEK    360
ITASDGVLKG DVTMYLKLEG GGNHKCQFKT TYKAAKEILE MPGDHYIGHR LVRKTEGNIT    420
EQVEDAVAHS TKVPEAAISR LITYLRILEE LEAQGVHRTA SEQLGELAQV TAFQVDEDLS    480
YFGSYGTDGV GYTVPVLKRE LRHILGLNRK WGLCIVGMGR LGSALADWPG FGESFELRGF    540
FDVDPGMVGR PVRGGVIEHV DLLPQRVPGR IEIALLTVPR EAAQKAADLL VAAGIKGILN    600
FAPVVLEVPK EVAVENVDFL AGLTRLSFAI LNPKWREEMM GMVSKGEELF TGVVPILVEL    660
DGDVNGHKFS VSGEGEGDAT YGKLTLKFIC TTGKLPVPWP TLVTTLTYGV QCFSRYPDHM    720
KQHDFFKSAM PEGYVQERTI FFKDDGNYKT RAEVKFEGDT LVNRIELKGI DFKEDGNILG    780
HKLEYNYNSH NVYIMADKQK NGIKVNFKIR HNIEDGSVQL ADHYQQNTPI GDGPVLLPDN    840
HYLSTQSKLS KDPNEKRDHM VLLEFVTAAG ITLGMDELYK                          880
```

```
SEQ ID NO: 177          moltype = AA   length = 4
FEATURE                 Location/Qualifiers
REGION                  1..4
                        note = Synthetic
source                  1..4
                        mol_type = protein
                        organism = synthetic construct
SEQUENCE: 177
SAHG                                                                   4

SEQ ID NO: 178          moltype = AA   length = 5
FEATURE                 Location/Qualifiers
REGION                  1..5
                        note = Synthetic
source                  1..5
                        mol_type = protein
                        organism = synthetic construct
SEQUENCE: 178
SAGHG                                                                  5

SEQ ID NO: 179          moltype = AA   length = 6
FEATURE                 Location/Qualifiers
REGION                  1..6
                        note = Synthetic
source                  1..6
                        mol_type = protein
                        organism = synthetic construct
SEQUENCE: 179
SAAGHG                                                                 6

SEQ ID NO: 180          moltype = AA   length = 7
FEATURE                 Location/Qualifiers
REGION                  1..7
                        note = Synthetic
source                  1..7
                        mol_type = protein
                        organism = synthetic construct
SEQUENCE: 180
SAAGGHG                                                                7

SEQ ID NO: 181          moltype = AA   length = 4
FEATURE                 Location/Qualifiers
REGION                  1..4
                        note = Synthetic
source                  1..4
                        mol_type = protein
                        organism = synthetic construct
SEQUENCE: 181
KGEE                                                                   4

SEQ ID NO: 182          moltype = AA   length = 5
FEATURE                 Location/Qualifiers
REGION                  1..5
                        note = Synthetic
source                  1..5
                        mol_type = protein
                        organism = synthetic construct
SEQUENCE: 182
SKGEE                                                                  5

SEQ ID NO: 183          moltype = AA   length = 6
FEATURE                 Location/Qualifiers
REGION                  1..6
                        note = Synthetic
source                  1..6
                        mol_type = protein
                        organism = synthetic construct
SEQUENCE: 183
VSKGEE                                                                 6

SEQ ID NO: 184          moltype = AA   length = 7
FEATURE                 Location/Qualifiers
REGION                  1..7
                        note = Synthetic
source                  1..7
                        mol_type = protein
                        organism = synthetic construct
SEQUENCE: 184
MVSKGEE                                                                7
```

```
SEQ ID NO: 185          moltype = AA  length = 4
FEATURE                 Location/Qualifiers
REGION                  1..4
                        note = Synthetic
source                  1..4
                        mol_type = protein
                        organism = synthetic construct
SEQUENCE: 185
GMDE                                                                    4

SEQ ID NO: 186          moltype = AA  length = 5
FEATURE                 Location/Qualifiers
REGION                  1..5
                        note = Synthetic
source                  1..5
                        mol_type = protein
                        organism = synthetic construct
SEQUENCE: 186
GMDEL                                                                   5

SEQ ID NO: 187          moltype = AA  length = 6
FEATURE                 Location/Qualifiers
REGION                  1..6
                        note = Synthetic
source                  1..6
                        mol_type = protein
                        organism = synthetic construct
SEQUENCE: 187
GMDELY                                                                  6

SEQ ID NO: 188          moltype = AA  length = 7
FEATURE                 Location/Qualifiers
REGION                  1..7
                        note = Synthetic
source                  1..7
                        mol_type = protein
                        organism = synthetic construct
SEQUENCE: 188
GMDELYK                                                                 7

SEQ ID NO: 189          moltype = AA  length = 4
FEATURE                 Location/Qualifiers
REGION                  1..4
                        note = Synthetic
source                  1..4
                        mol_type = protein
                        organism = synthetic construct
SEQUENCE: 189
EMMG                                                                    4

SEQ ID NO: 190          moltype = AA  length = 4
FEATURE                 Location/Qualifiers
REGION                  1..4
                        note = Synthetic
source                  1..4
                        mol_type = protein
                        organism = synthetic construct
SEQUENCE: 190
MVSV                                                                    4

SEQ ID NO: 191          moltype = AA  length = 877
FEATURE                 Location/Qualifiers
source                  1..877
                        mol_type = protein
                        organism = synthetic construct
SEQUENCE: 191
MKVPEAAISR LITYLRILEE LEAQGVHRTA SEQLGELAQV TAFQVDKDLS YFGSYGTDGV  60
GYTVPVLKRE LRHILGLNRK WGLCIVGMGR LGSALADWPG FGESFELRGF FDVDPGMVGR 120
PVRGGVIEHV DLLPQRVPGR IEIALLTVPR EAAQKAADLL VAAGIKGILN FAPVVLEVPK 180
EVAVENVDIL AGLTRLSFAI LNPTWSAAGG HGMVSKGEEL FTGVVPILVE LDGDVNGHKF 240
SVSGEGEGDA TYGKLTLKFI CTTGKLPVPW PTLVTTLTYG VQCFSRYPDH MKQHDFFKSA 300
MPEGYVQERT IFFKDDGNYK TRAEVKFEGD TLVNRIELKG IDFKEDGNIL GHKLEYNYNS 360
HNVYIMADKQ KNGIKVNFKI RHNIEDGSVQ LADHYQQNTP IGDGPVLLPD NHYLSTQSKL 420
SKDPNEKRDH MVLLEFVTAA GITLGMDEVP EAAISRLITY LRILEELEAQ GVHRTASEQL 480
GELAQVTAFQ VDEDLSYFGS YGTDGVGYTV PVLKRELRHI LGLNRKWGLC IVGMGRLGSA 540
LADWPGFGES FELRGFFDVD PGMVGRPVRG GVIEHVDLLP QRVPGRIEIA LLTVPREAAQ 600
KAADLLVAAG IKGILNFAPV VLEVPKEVAV ENVDFLAGLT RLSFAILNPK WREVIKPEMK 660
MRYYMDGSVN GHEFTIEGEG TGRPYEGHQE MTLRVTMAEG GPMPFAFDLV SHVFCYGHRV 720
```

```
FTKYPEEIPD YFKQAFPEGL SWERSLEFED GGSASVSAHI SLRGNTFYHK SKFTGVNFPA    780
DGPIMQNQSV DWEPSTEKIT ASDGVLKGDV TMYLKLEGGG NHKCQFKTTY KAAKEILEMP    840
GDHYIGHRLV RKTEGNITEQ VEDAVAHSEA SMDELYK                             877

SEQ ID NO: 192             moltype = AA   length = 876
FEATURE                    Location/Qualifiers
source                     1..876
                           mol_type = protein
                           organism = synthetic construct
SEQUENCE: 192
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDEVP EAAISRLITY LRILEELEAQ GVHRTASEQL    480
GELAQVTAFQ VDEDLSYFGS YGTDGVGYTV PVLKRELRHI LGLNRKWGLC IVGMGRLGSA    540
LADWPGFGES FELRGFFDVD PGMVGRPVRG GVIEHVDLLP QRVPGRIEIA LLTVPREAAQ    600
KAADLLVAAG IKGILNFAPV VLEVPKEVAV ENVDFLAGLT RLSFAILNPK WRVIKPEMKM    660
RYYMDGSVNG HEFTIEGEGT GRPYEGHQEM TLRVTMAEGG PMPFAFDLVS HVFCYGRPYE    720
TKYPEEIPDY FKQAFPEGLS WERSLEFEDG GSASVSAHIS LRGNTFYHKS KFTGVNFPAD    780
GPIMQNQSVD WEPSTEKITA SDGVLKGDVT MYLKLEGGGN HKCQFKTTYK AAKEILEMPG    840
DHYIGHRLVR KTEGNITEQV EDAVAHSEAS MDELYK                              876

SEQ ID NO: 193             moltype = AA   length = 875
FEATURE                    Location/Qualifiers
source                     1..875
                           mol_type = protein
                           organism = synthetic construct
SEQUENCE: 193
MKVPEAAISR LITYLRILEE LEAQGVHRTA SEQLGELAQV TAFQVDKDLS YFGSYGTDGV     60
GYTVPVLKRE LRHILGLNRK WGLCIVGMGR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDEVP EAAISRLITY LRILEELEAQ GVHRTASEQL    480
GELAQVTAFQ VDEDLSYFGS YGTDGVGYTV PVLKRELRHI LGLNRKWGLC IVGMGRLGSA    540
LADWPGFGES FELRGFFDVD PGMVGRPVRG GVIEHVDLLP QRVPGRIEIA LLTVPREAAQ    600
KAADLLVAAG IKGILNFAPV VLEVPKEVAV ENVDFLAGLT RLSFAILNPK WVIKPEMKMR    660
YYMDGSVNGH EFTIEGEGTG RPYEGHQEMT LRVTMAEGGP MPFAFDLVSH VFCYGHRVFT    720
KYPEEIPDYF KQAFPEGLSW ERSLEFEDGG SASVSAHISL RGNTFYHKSK FTGVNFPADG    780
PIMQNQSVDW EPSTEKITAS DGVLKGDVTM YLKLEGGGNH KCQFKTTYKA AKEILEMPGD    840
HYIGHRLVRK TEGNITEQVE DAVAHSEASM DELYK                               875

SEQ ID NO: 194             moltype = AA   length = 877
FEATURE                    Location/Qualifiers
source                     1..877
                           mol_type = protein
                           organism = synthetic construct
SEQUENCE: 194
MKVPEAAISR LITYLRILEE LEAQGVHRTA SEQLGELAQV TAFQVDKDLS YFGSYGTDGV     60
GYTVPVLKRE LRHILGLNRK WGLCIVGMAR LGSALADWPG FGESFELRGF FDVDPGMVGR    120
PVRGGVIEHV DLLPQRVPGR IEIALLTVPR EAAQKAADLL VAAGIKGILN FAPVVLEVPK    180
EVAVENVDIL AGLTRLSFAI LNPTWSAAGG HGMVSKGEEL FTGVVPILVE LDGDVNGHKF    240
SVSGEGEGDA TYGKLTLKFI CTTGKLPVPW PTLVTTLTYG VQCFSRYPDH MKQHDFFKSA    300
MPEGYVQERT IFFKDDGNYK TRAEVKFEGD TLVNRIELKG IDFKEDGNIL GHKLEYNYNS    360
HNVYIMADKQ KNGIKVNFKI RHNIEDGSVQ LADHYQQNTP IGDGPVLLPD NHYLSTQSKL    420
SKDPNEKRDH MVLLEFVTAA GITLGMDEVP EAAISRLITY LRILEELEAQ GVHRTASEQL    480
GELAQVTAFQ VDEDLSYFGS YGTDGVGYTV PVLKRELRHI LGLNRKWGLC IVGMARLGSA    540
LADWPGFGES FELRGFFDVD PGMVGRPVRG GVIEHVDLLP QRVPGRIEIA LLTVPREAAQ    600
KAADLLVAAG IKGILNFAPV VLEVPKEVAV ENVDFLAGLT RLSFAILNPK WREVIKPEMK    660
MRYYMDGSVN GHEFTIEGEG TGRPYEGHQE MTLRVTMAEG GPMPFAFDLV SHVFCYGHRV    720
FTKYPEEIPD YFKQAFPEGL SWERSLEFED GGSASVSAHI SLRGNTFYHK SKFTGVNFPA    780
DGPIMQNQSV DWEPSTEKIT ASDGVLKGDV TMYLKLEGGG NHKCQFKTTY KAAKEILEMP    840
GDHYIGHRLV RKTEGNITEQ VEDAVAHSEA SMDELYK                             877

SEQ ID NO: 195             moltype = AA   length = 4
FEATURE                    Location/Qualifiers
source                     1..4
                           mol_type = protein
                           organism = synthetic construct
SEQUENCE: 195
KVPE                                                                   4
```

We claim:

1. A polynucleotide encoding a fusion protein, wherein the fusion protein comprises the amino acid sequence selected from the group consisting of:
   (a) residues 1-867 of SEQ ID NO: 13;
   (b) residues 1-861 of SEQ ID NO: 14;
   (c) residues 1-863 of SEQ ID NO: 15;
   (d) residues 1-862 of SEQ ID NO:16;
   (e) residues 1-865 of SEQ ID NO:20;
   (f) residues 1-853 of SEQ ID NO:24;
   (g) residues 1-868 of SEQ ID NO:191;
   (h) residues 1-867 of SEQ ID NO:192; and
   (i) residues 1-866 of SEQ ID NO:193.

2. An expression vector comprising the polynucleotide of claim 1 operatively linked to a promoter sequence capable of directing expression of the polynucleotide.

3. A host cell comprising the expression vector of claim 2.

4. A kit comprising:
   (a) the polynucleotide of claim 1; and
   (b) a control polynucleotide encoding a control fusion protein, wherein the control fusion protein comprises the amino acid sequence selected from the group consisting of:
      (i) residues 1-867 of SEQ ID NO:13 but having a G89A mutation relative to SEQ ID NO: 13;
      (ii) residues 1-861 of SEQ ID NO:14 but having a G89A mutation relative to SEQ ID NO: 14;
      (iii) residues 1-863 of SEQ ID NO:15 but having a G89A mutation relative to SEQ ID NO: 15;
      (iv) residues 1-862 of SEQ ID NO:16 but having a G89A mutation relative to SEQ ID NO: 16;
      (v) residues 1-865 of SEQ ID NO:20 but having a G89A mutation relative to SEQ ID NO:20;
      (vi) residues 1-853 of SEQ ID NO:24 but having a G89A mutation relative to SEQ ID NO:24;
      (vii) residues 1-868 of SEQ ID NO:191 but having a G89A mutation relative to SEQ ID NO: 191;
      (viii) residues 1-867 of SEQ ID NO:192 but having a G89A mutation relative to SEQ ID NO:192;
      (ix) residues 1-866 of SEQ ID NO:193 but having a G89A mutation relative to SEQ ID NO:193; and
      (x) residues 1-868 of SEQ ID NO:194.

5. The polynucleotide of claim 1, wherein the fusion protein comprises the amino acid sequence selected from the group consisting of SEQ ID NO:13-16, 20, 24, and 191-193.

6. The polynucleotide of claim 1, wherein the fusion protein comprises the amino acid sequence selected from the group consisting of:
   (g) residues 1-868 of SEQ ID NO:191;
   (h) residues 1-867 of SEQ ID NO: 192; and
   (i) residues 1-866 of SEQ ID NO: 193.

7. The polynucleotide of claim 1, wherein the fusion protein comprises the amino acid sequence of residues 1-868 of SEQ ID NO:191.

8. An expression vector comprising the polynucleotide of claim 5 operatively linked to a promoter sequence capable of directing expression of the polynucleotide.

9. An expression vector comprising the polynucleotide of claim 6 operatively linked to a promoter sequence capable of directing expression of the polynucleotide.

10. An expression vector comprising the polynucleotide of claim 7 operatively linked to a promoter sequence capable of directing expression of the polynucleotide.

11. The kit of claim 4, wherein
   (i) the polynucleotide comprises an expression vector comprising the polynucleotide operatively linked to a promoter sequence capable of directing expression of the polynucleotide; and
   (ii) the control polynucleotide comprises an expression vector comprising the control polynucleotide operatively linked to a promoter sequence capable of directing expression of the control polynucleotide.

12. A kit comprising:
(a) the polynucleotide of claim 6; and
(b) a control polynucleotide encoding a control fusion protein, wherein the control fusion protein comprises the amino acid sequence selected from the group consisting of:
   (i) residues 1-868 of SEQ ID NO:191 but having a G89A mutation relative to SEQ ID NO: 191;
   (ii) residues 1-867 of SEQ ID NO:192 but having a G89A mutation relative to SEQ ID NO:192;
   (iii) residues 1-866 of SEQ ID NO:193 but having a G89A mutation relative to SEQ ID NO:193; and
   (iv) residues 1-868 of SEQ ID NO:194.

13. A kit comprising:
(a) the polynucleotide of claim 7; and
(b) a control polynucleotide encoding a control fusion protein, wherein the control fusion protein comprises the amino acid sequence selected from the group consisting of:
   (i) residues 1-868 of SEQ ID NO:191 but having a G89A mutation relative to SEQ ID NO:191; and
   (ii) residues 1-868 of SEQ ID NO:194.

14. The kit of claim 12, wherein
(i) the polynucleotide comprises an expression vector comprising the polynucleotide operatively linked to a promoter sequence capable of directing expression of the polynucleotide; and
(ii) the control polynucleotide comprises an expression vector comprising the control polynucleotide operatively linked to a promoter sequence capable of directing expression of the control polynucleotide.

15. The kit of claim 13, wherein
(i) the polynucleotide comprises an expression vector comprising the polynucleotide operatively linked to a promoter sequence capable of directing expression of the polynucleotide; and
(ii) the control polynucleotide comprises an expression vector comprising the control polynucleotide operatively linked to a promoter sequence capable of directing expression of the control polynucleotide.

* * * * *